US010370366B2

(12) United States Patent
Cole et al.

(10) Patent No.: US 10,370,366 B2
(45) Date of Patent: *Aug. 6, 2019

(54) PYRIDAZINONE COMPOUNDS AND METHODS FOR THE TREATMENT OF CYSTIC FIBROSIS

(71) Applicant: Flatley Discovery Lab, LLC, Charlestown, MA (US)

(72) Inventors: Bridget M. Cole, Quincy, MA (US); Richard A. Nugent, Ashland, MA (US); Andrew Kolodziej, Winchester, MA (US); Karen Handley, Londonderry, NH (US); Yevgen Barsukov, Brookline, MA (US)

(73) Assignee: Flatley Discovery Lab, LLC, Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,813

(22) Filed: Oct. 6, 2017

(65) Prior Publication Data

US 2018/0093976 A1   Apr. 5, 2018

Related U.S. Application Data

(62) Division of application No. 14/210,277, filed on Mar. 13, 2014, now Pat. No. 9,783,529.

(Continued)

(51) Int. Cl.
| | | |
|---|---|---|
| C07D 413/12 | (2006.01) |
| A61K 31/502 | (2006.01) |
| A61K 45/06 | (2006.01) |
| C07D 413/14 | (2006.01) |
| C07D 498/04 | (2006.01) |
| A61K 31/38 | (2006.01) |
| A61K 31/4245 | (2006.01) |
| A61K 31/443 | (2006.01) |
| A61K 31/47 | (2006.01) |
| A61K 31/5025 | (2006.01) |
| A61K 31/506 | (2006.01) |
| A61K 31/519 | (2006.01) |
| C07D 237/32 | (2006.01) |
| C07D 401/04 | (2006.01) |
| C07D 401/06 | (2006.01) |
| C07D 405/04 | (2006.01) |
| C07D 405/12 | (2006.01) |
| C07D 405/14 | (2006.01) |
| C07D 487/04 | (2006.01) |
| A61K 31/5377 | (2006.01) |

(Continued)

(52) U.S. Cl.
CPC ............ C07D 413/12 (2013.01); A61K 31/38 (2013.01); A61K 31/4245 (2013.01); A61K 31/443 (2013.01); A61K 31/47 (2013.01); A61K 31/502 (2013.01); A61K 31/506 (2013.01); A61K 31/5025 (2013.01); A61K 31/519 (2013.01); A61K 31/5377 (2013.01); A61K 45/06 (2013.01); C07D 237/32 (2013.01); C07D 401/04 (2013.01); C07D 401/06 (2013.01); C07D 401/12 (2013.01); C07D 401/14 (2013.01); C07D 403/04 (2013.01); C07D 405/04 (2013.01); C07D 405/12 (2013.01); C07D 405/14 (2013.01); C07D 413/14 (2013.01); C07D 417/14 (2013.01); C07D 487/04 (2013.01); C07D 495/14 (2013.01); C07D 498/04 (2013.01); C07D 519/00 (2013.01)

(58) Field of Classification Search
CPC ..... A61K 31/38; C07D 413/12; C07D 487/04
USPC .......................... 544/224, 235; 514/247, 248
See application file for complete search history.

(56) References Cited

U.S. PATENT DOCUMENTS

| 8,937,178 B2* | 1/2015 | Cole | C07D 413/12 |
| | | | 544/238 |
| 9,682,969 B2* | 6/2017 | Cole | C07D 413/12 |

(Continued)

FOREIGN PATENT DOCUMENTS

| EP | 0634404 A1 | 1/1995 |
| WO | 98/38168 A1 | 9/1998 |

OTHER PUBLICATIONS

Deeb, O., et al., "Exploring QSARs for Inhibitory Activity of Non-peptide HIV-1 Protease Inhibitors by GA-PLS and GA-SVM," Chem. Biol. Drug Des., 75: 506-514 (2010).

*Primary Examiner* — Golam M Shameem
(74) *Attorney, Agent, or Firm* — Elmore Patent Law Group, P.C.; Edgar W. Harlan; Carolyn S. Elmore

(57) ABSTRACT

The invention relates to a compound of having the following formulae and methods of treating cystic fibrosis:

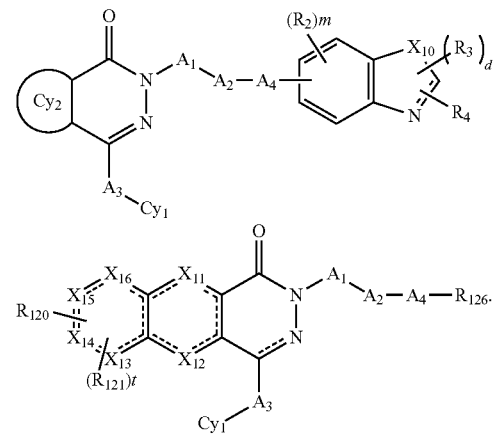

11 Claims, No Drawings

Related U.S. Application Data

(60) Provisional application No. 61/778,870, filed on Mar. 13, 2013.

(51) Int. Cl.
*C07D 401/12* (2006.01)
*C07D 401/14* (2006.01)
*C07D 403/04* (2006.01)
*C07D 417/14* (2006.01)
*C07D 495/14* (2006.01)
*C07D 519/00* (2006.01)

(56) References Cited

U.S. PATENT DOCUMENTS 9,783,529 B2 * 10/2017 Cole .................... C07D 413/12
9,790,215 B2 * 10/2017 Cole .................... C07D 413/12

* cited by examiner

PYRIDAZINONE COMPOUNDS AND METHODS FOR THE TREATMENT OF CYSTIC FIBROSIS

RELATED APPLICATIONS

This application is a divisional of U.S. application Ser. No. 14/210,277, filed on Mar. 13, 2014, which claims the benefit of U.S. Provisional Application No. 61/778,870, filed on Mar. 13, 2013. The entire teachings of the above applications are incorporated herein by reference.

BACKGROUND

Cystic fibrosis (CF) is a lethal, recessive, genetic disease affecting approximately 1 in 2500 live births among Caucasians. (Cohen-Cymberknoh M, Shoseyov D, Kerem E. Managing cystic fibrosis: strategies that increase life expectancy and improve quality of life. Am J Respir Crit Care Med (2011); 183: 1463-1471; Boat T F, Welsh M J and Beaudet A L. Cystic fibrosis. (1989) IN "The Metabolic Basis of Inherited Disease" (C L Scriver, A L Beaudet, W S Sly and D Valee, eds.), $6^{th}$ Ed., pp. 2649-2680. McGraw-Hill, New York. Approximately 1 in 25 persons are carriers of the genetic defect associated with disease. The major symptoms of cystic fibrosis include chronic pulmonary disease, pancreatic exocrine insufficiency, infertility in males, and elevated sweat electrolyte levels. The symptoms are consistent with cystic fibrosis being an exocrine disorder. (Hantash F: U.S. Patent Application No. 20060057593. Method for detecting cystic fibrosis).

The CF gene codes for a cAMP/PKA-dependent, ATP-requiring, membrane-bound chloride ion channel known as CFTR (cystic fibrosis transmembrane conductance regulator), and is, generally localized to the apical membranes of many secreting. There are currently over 1700 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cutbert A W. New horizons in the treatment of cystic fibrosis. British J Pharm, (2011), 163: 173-183).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, Deficiency in bicarbonate secretion due to loss of CFTR function also results in a lower pH at the airway surface which impairs anti-bacterial killing activity and increases susceptibility to infection. An exaggerated inflammatory response in response to chronic lung infections leads to the development of bronchiectasis and progressive obstructive airways disease. Pulmonary insufficiency is responsible for most CF-related deaths. (Cohen-Cymberknoh M, Shoseyov D, Kerem E. Managing cystic fibrosis: strategies that increase life expectancy and improve quality of life. Am J Respir Crit Care Med (2011); 183: 1463-1471).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C, Smyth A. Treatment strategies for cystic fibrosis: what's in the pipeline? Pharmacotherapy (2009), 10: 1191-1202).

SUMMARY

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I to a patient in need thereof:

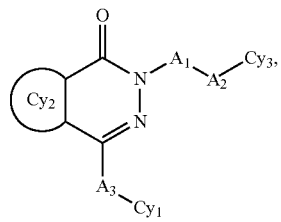

Formula I $A_1$ is absent, —[C(R100)(R101)]n-, —C(O)—, —C(S)—, —S(O)—, —C(O)N($R_{100}$)—, —S(O)$_2$—, carbocycle, substituted carbocycle, heterocycle, substituted heterocycle, aromatic, substituted aromatic, heteroaromatic or substituted heteroaromatic;

wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —[C(R100)(R101)]n-, —C(O)—, —C(S)—, —S(O)—, —C(O)N($R_{100}$)—, —C(O)N($R_{100}$)($R_{101}$), N($R_{100}$)($R_{101}$), —S(O)$_2$—, —S(O)$_2$$R_{100}$, —S(O)$R_{100}$, —S(O)$_2$N($R_{100}$)$R_{101}$);

$A_3$ is a bond or —[C(R100)(R101)]n-, —C(O)—, —C(S)—, —S(O)—, —C(O)N($R_{100}$)—, —C(O)N($R_{100}$)($R_{101}$), N($R_{100}$)($R_{101}$), —S(O)$_2$—, S(O)$_2$$R_{100}$, S(O)$R_{100}$, S(O)$_2$N($R_{100}$)$R_{101}$);

$Cy_1$ is absent, an aryl, substituted aryl, carbocycle, substituted carbocycle, heterocyclyl, substituted heterocyclyl, heteroaryl, or substituted heteroaryl group having one, two or three rings;

Cy₂ is an aryl, substituted aryl, carbocycle, substituted carbocycle, heterocyclyl, substituted heterocyclyl, heteroaryl, or substituted heteroaryl group having one, two or three rings; and Cy₃ is absent, an aryl, substituted aryl, carbocycle, substituted carbocycle, heterocyclyl, substituted heterocyclyl, heteroaryl, or substituted heteroaryl group having one, two or three rings.

DETAILED DESCRIPTION OF THE INVENTION

The invention relates to a compound of Formula I and methods of treating cystic fibrosis comprising the step of administering a therapeutically effective amount of a compound of Formula I to a patient in need thereof:

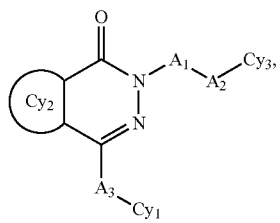

Formula I $A_1$ is absent, —[C($R_{100}$)($R_{101}$)]$_n$—, —C(O)—, —C(S)—, —S(O)—, —C(O)N($R_{100}$)—, —S(O)₂N($R_{100}$)—, —S(O)₂—, carbocycle, substituted carbocycle, heterocycle, substituted heterocycle, aromatic, substituted aromatic, heteroaromatic or substituted heteroaromatic;

wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —[C(R100)(R101)]n-, —C(O)—, —C(S)—, —S(O)—, —C(O)N($R_{100}$)—, —C(O)N($R_{100}$)($R_{101}$), N($R_{100}$)($R_{101}$), —S(O)₂—, —S(O)₂$R_{100}$, —S(O)$R_{100}$, —S(O)₂N($R_{100}$)$R_{101}$);

$A_3$ is absent or —[C(R100)(R101)]n-, —C(O)—, —C(S)—, —S(O)—, —C(O)N($R_{100}$)—, —C(O)N($R_{100}$)($R_{101}$), N($R_{100}$)($R_{101}$), —S(O)₂—, S(O)₂$R_{100}$, S(O)$R_{100}$, S(O)₂N($R_{100}$)($R_{101}$);

Cy₁ is absent, an aryl, substituted aryl, carbocycle, substituted carbocycle, heterocyclyl, substituted heterocyclyl, heteroaryl, or substituted heteroaryl group having one, two or three rings;

Cy₂ is an aryl, substituted aryl, carbocycle, substituted carbocycle, heterocyclyl, substituted heterocyclyl, heteroaryl, or substituted heteroaryl group having one, two or three rings; and Cy₃ is absent, an aryl, substituted aryl, carbocycle, substituted carbocycle, heterocyclyl, substituted heterocyclyl, heteroaryl, or substituted heteroaryl group having one, two or three rings.

In a preferred embodiment, the invention relates to a compound having the formula:

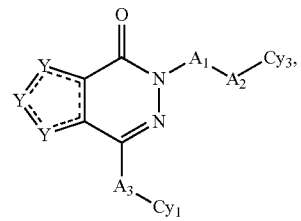

wherein each X is independently, —C$R_{100}$— or —N—.

In a preferred embodiment, the invention relates to a compound wherein X is —C($R_{100}$) and wherein $R_{100}$ is preferred as H, halogen, alkoxy or alkyl.

In a preferred embodiment, the invention relates to a compound having the formula:

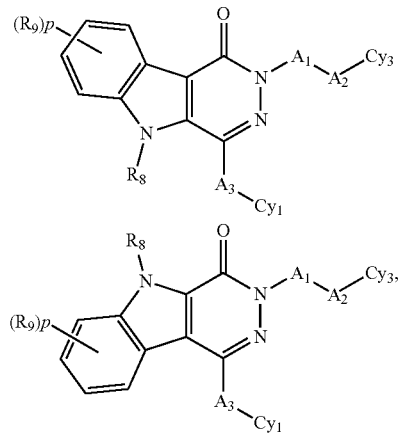

wherein each Y is independently —C$R_{100}$—, —N$R_{100}$, —N, —O or —S.

In a preferred embodiment, the invention relates to a compound having the formula:

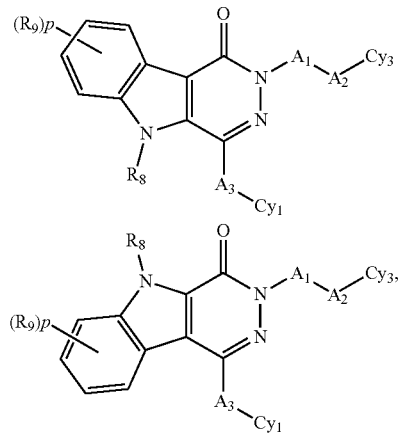

wherein p is 0, 1, 2, 3 or 4; and wherein $R_8$ is hydrogen, deuterium, alkyl, substituted alkyl, alkenyl, substituted alkenyl, alkynyl, substituted alkynyl, aliphatic, substituted aliphatic, carbocycle, substituted carbocycle, aryl, substituted aryl, heterocyclyl, substituted heterocyclyl, heteroaryl, or substituted heteroaryl; and $R_9$ is independently selected from hydrogen, deuterium, halo, alkyl, substituted alkyl, alkenyl, substituted alkenyl, alkynyl, substituted alkynyl, aliphatic, substituted aliphatic, carbocycle, substituted carbocycle, aryl, substituted aryl, heterocyclyl, substituted heterocyclyl, heteroaryl, or substituted heteroaryl —O$R_{100}$, —N$R_{100}R_{101}$, —C(O)$R_{100}$, —C(O)O$R_{100}$, —C(O)N$R_{100}R_{101}$, —N($R_{100}$)C(O)$R_{101}$, —S(O)₂$R_{100}$, —S(O)$R_{100}$, —S$R_{100}$, —S(O)₂N($R_{100}$)$R_{101}$, —CF₃, —CN, —NO₂, —N₃.

In a preferred embodiment, the invention relates to a compound wherein $R_8$ is $C_1$-$C_4$ alkyl.

In a preferred embodiment, the invention relates to a compound wherein $R_9$ is H, alkyl, alkoxy or halogen.

In a preferred embodiment, the invention relates to a compound, wherein $A_3$ is H and $Cy_1$ is absent.

In a preferred embodiment, the invention relates to a compound having the formula:

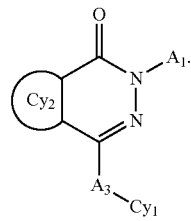

In a preferred embodiment, the invention relates to a compound wherein $A_1$ is carbocycle, substituted carbocycle, heterocycle, substituted heterocycle, aromatic, substituted aromatic, heteroaromatic, substituted heteroaromatic.

In a preferred embodiment, the invention relates to a compound having the formula:

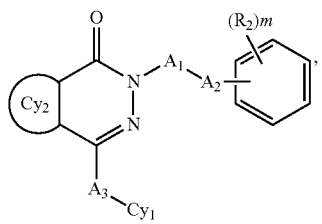

wherein m is 0, 1, 2, 3, 4 or 5; and each $R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group.

In a preferred embodiment, the invention relates to a compound having the formula:

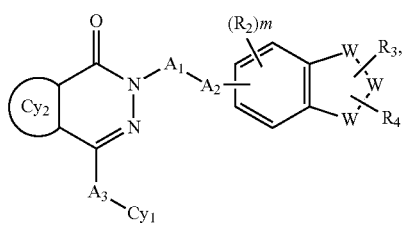

wherein each W is independently CH, $CR_{100}$, C(O), N, $NR_{100}$, O, S, SO, or $SO_2$;

each R3 and R4 is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$—$SR_{100}$, —$S(O)_2N(R_{100})R_{101}$, —$CF_3$, —CN, —$NO_2$, —$N_3$; and wherein ----- represents a single or double bond.

In a preferred embodiment, the invention relates to a compound wherein $A_1$ is $C(R_{100})(R_{101})$ and $A_2$ is —$C(O)N(R_{100})$—.

In a preferred embodiment, the invention relates to a compound wherein $A_3$ is absent, —[C(R100)(R101)]n—, —C(O)—, —$C(O)N(R_{100})$— or —$C(O)N(R_{100})(R_{101})$.

In a preferred embodiment, the invention relates to a compound wherein $Cy_1$ is selected from:

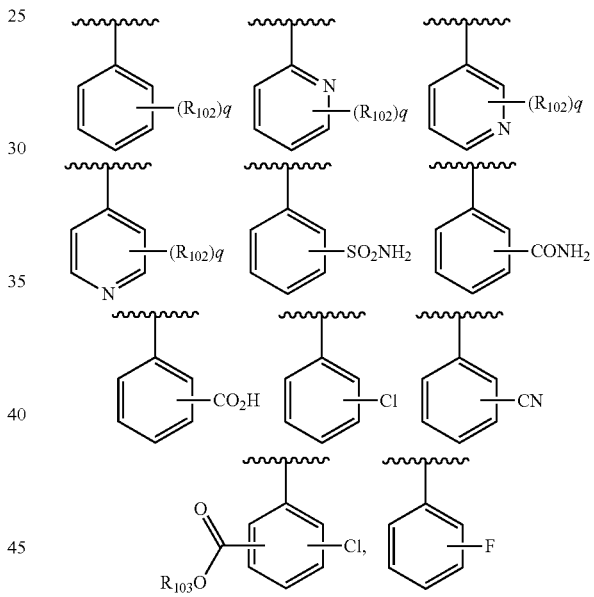

wherein q is 0, 1, 2, 3, 4 or 5; each $R_{102}$ is hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$ —$CF_3$, —CN, —$NO_2$, —$N_3$; alternatively two of $R_{102}$ groups together with the atoms to which they are attached and any intervening atoms may form an additional optionally substituted 3, 4, 5, 6 or 7 membered ring; and $R_{103}$ is hydrogen, deuterium, alkyl, substituted alkyl, alkenyl, substituted alkenyl, alkynyl, substituted alkynyl, aliphatic, substituted aliphatic, aryl and substituted aryl.

In a preferred embodiment, the invention relates to a compound wherein Cy2 is selected from:

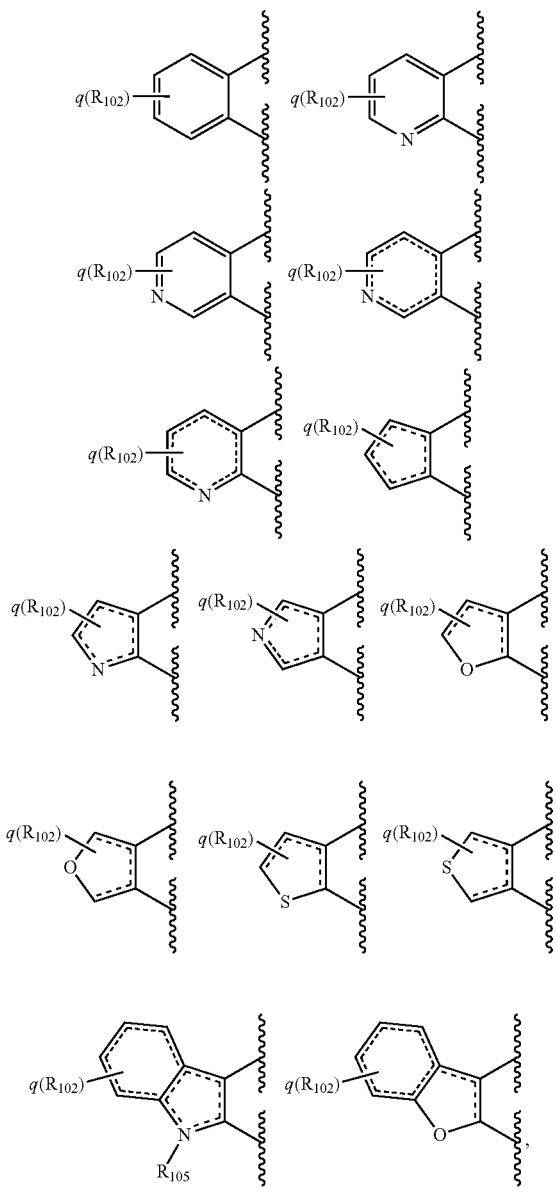

wherein q is 0, 1, 2, 3, 4 or 5;

each $R_{102}$ is independently hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two of $R_{102}$ groups together with the atoms to which they are attached and any intervening atoms may form an additional optionally substituted 3, 4, 5, 6 or 7 membered ring; and $R_{105}$ is hydrogen, deuterium, alkyl, substituted alkyl, alkenyl, substituted alkenyl, alkynyl, substituted alkynyl, aliphatic, substituted aliphatic, aryl and substituted aryl.

In one embodiment, the invention relates to a compound of Formula II:

Formula II or a pharmaceutically acceptable salt, ester or prodrug thereof;

wherein ----- represents a single or double bond;

m is 0, 1, 2, 3 or 4;

d is 0, 1 or 2;

$X_{10}$ is CH, $CH_2$, S, N or O;

$Cy_1$ is absent, an aryl, substituted aryl, carbocycle, substituted carbocycle, heterocyclyl, substituted heterocyclyl, heteroaryl, or substituted heteroaryl group having one, two or three rings;

$Cy_2$ is an aryl, substituted aryl, carbocycle, substituted carbocycle, heterocyclyl, substituted heterocyclyl, heteroaryl, or substituted heteroaryl group having one, two or three rings; preferably, $Cy_2$ is a $C_5$-$C_7$ aryl or heteroaryl; Preferably $Cy_2$ is substituted with —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl;

$A_1$ is absent, —$[C(R_{100})(R_{101})]_n$—, —C(O)—, —C(S)—, —S(O)—, —$C(O)N(R_{100})$—, —$S(O)_2N(R_{100})$—, —$S(O)_2$—, —$[C(R_{25})(R_{26})]_n$—, —$[C(R_{25})(R_{26})]$n-C≡C—$[C(R_{27})(R_{28})]$p, or —$[C(R_{25})(R_{26})]$n-C≡C—$[C(R_{27})(R_{28})]$p, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring; Preferably each $R_{100}$ and $R_{101}$ is independently selected from $C_1$-$C_8$ alkyl, $C_2$-$C_8$ alkenyl, $C_2$-$C_8$ alkynyl and $C_3$-$C_8$ cycloalkyl;

$A_2$ is absent or —$[C(R_{100})(R_{101})]$n-, —C(O)—, —C(S)—, —S(O)—, —$C(O)N(R_{100})$—, —$C(O)N(R_{100})(R_{101})$, $N(R_{100})(R_{101})$, —$S(O)_2$—, —$S(O)_2R_{100}$, —$S(O)R_{100}$, —$S(O)_2N(R_{100})R_{101}$, —$[C(R_{25})(R_{26})]$n-, —$[C(R_{25})(R_{26})]$n-C≡C—$[C(R_{27})(R_{28})]$p, or —$[C(R_{25})(R_{26})]$n-C≡C—$[C(R_{27})(R_{28})]$p;

$A_3$ is absent or —$[C(R100)(R101)]$n-, —C(O)—, —C(S)—, —S(O)—, —$C(O)N(R_{100})$—, —$C(O)N(R_{100})(R_{101})$, $N(R_{100})(R_{101})$, —$S(O)_2$—, $S(O)_2R_{100}$, $S(O)R_{100}$, $S(O)_2N(R_{100})(R_{101})$, —$[C(R_{25})(R_{26})]$n-, —$[C(R_{25})(R_{26})]$n-C≡C—$[C(R_{27})(R_{28})]$p, or —$[C(R_{25})(R_{26})]$n-C≡C—$[C(R_{27})(R_{28})]$p;

$A_4$ is absent or —$[C(R_{25})(R_{26})]$n-, —$[C(R_{25})(R_{26})]$n-C≡C—$[C(R_{27})(R_{28})]$p, or —$[C(R_{25})(R_{26})]$n-C≡C—$[C(R_{27})(R_{28})]$p;

wherein each $R_{25}$, $R_{26}$, $R_{27}$ and $R_{28}$ is independently selected hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{25}$, $R_{26}$, $R_{27}$ and $R_{28}$ groups together with the atoms to which they are attached and any intervening atoms may form an additional optionally substituted, 3, 4, 5, 6 or 7 membered ring; preferably a cyclopropyl group;

p is 0, 1, 2, 3, 4, 5, 6, or 7;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group; and, each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$.

In one embodiment, the invention relates to a compound of Formula IIA:

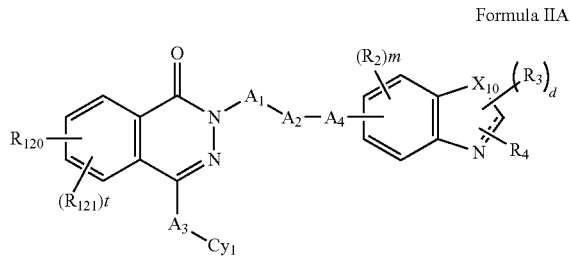

Formula IIA or a pharmaceutically acceptable salt, ester or prodrug thereof;

wherein ===== represents a single or double bond;

m is 0, 1, 2, 3 or 4;

t is 0, 1, 2 or 3;

$X_{10}$ is CH, $CH_2$, O, N or S;

$Cy_1$ is absent, an aryl, substituted aryl, carbocycle, substituted carbocycle, heterocyclyl, substituted heterocyclyl, heteroaryl, or substituted heteroaryl group having one, two or three rings;

$A_1$ is absent, —$[C(R_{100})(R_{101})]_n$—, —C(O)—, —C(S)—, —S(O)—, —$C(O)N(R_{100})$—, —$S(O)_2N(R_{100})$—, —$S(O)_2$—, —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, —$S(O)_2R_{100}$, —$S(O)R_{100}$, —$S(O)_2N(R_{100})R_{101}$, —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

$A_3$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, $S(O)_2R_{100}$, $S(O)R_{100}$, $S(O)_2N(R_{100})(R_{101})$, —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

$A_4$ is absent or —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

wherein each $R_{25}$, $R_{26}$, $R_{27}$ and $R_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{25}$, $R_{26}$, $R_{27}$ and R28 groups together with the atoms to which they are attached and any intervening atoms may form an additional optionally substituted, 3, 4, 5, 6 or 7 membered ring; preferably a cyclopropyl group;

p is 0, 1, 2, 3, 4, 5, 6, or 7;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two R2 together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group;

each R3 and R4 is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{120}$ is selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; and, each $R_{121}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$.

In one embodiment, the invention relates to a compound of Formula IIB:

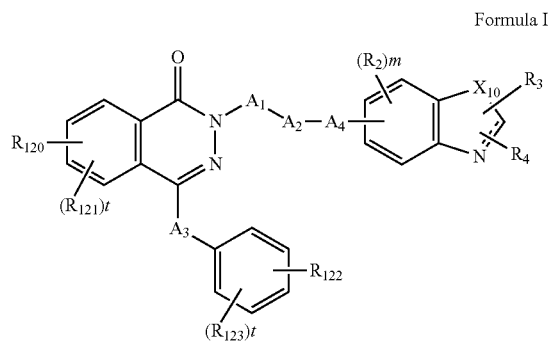

Formula IIB or a pharmaceutically acceptable salt, ester or prodrug thereof;

wherein ===== represents a single or double bond;

m is 0, 1, 2, 3 or 4;

t is 0, 1, 2 or 3;

$X_{10}$ is CH, $CH_2$, N, S or O;

$A_1$ is absent, —$[C(R_{100})(R_{101})]_n$—, —C(O)—, —C(S)—, —S(O)—, —$C(O)N(R_{100})$—, —$S(O)_2N(R_{100})$—, —$S(O)_2$—, —$[C(R_{25})(R_{26})]_n$—, —$[C(R_{25})(R_{26})]n$-C═C—$[C(R_{27})(R_{28})]p$, or —$[C(R_{25})(R_{26})]n$-C≡C—$[C(R_{27})(R_{28})]p$, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, —$S(O)_2R_{100}$, —$S(O)R_{100}$, —$S(O)_2N(R_{100})R_{101}$, —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

$A_3$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, $S(O)_2R_{100}$, $S(O)R_{100}$, $S(O)_2N(R_{100})(R_{101})$, —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

$A_4$ is absent or —$[C(R_{25})(R_{26})]n$-, —$[C(R_{25})(R_{26})]n$-C═C—$[C(R_{27})(R_{28})]p$, or —$[C(R_{25})(R_{26})]n$-C≡C—$[C(R_{27})(R_{28})]p$;

wherein each $R_{25}$, $R_{26}$, $R_{27}$ and $R_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{25}$, $R_{26}$, $R_{27}$ and R28 groups together with the atoms to which they are attached and any intervening atoms may form an additional optionally substituted, 3, 4, 5, 6 or 7 membered ring; preferably a cyclopropyl group;

p is 0, 1, 2, 3, 4, 5, 6, or 7;

R2 is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two R2 together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group;

each R3 and R4 is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{120}$ is selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

each $R_{121}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{122}$ is halogen or —CN; and, each $R_{123}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$.

In one embodiment, the invention relates to a compound of Formula IIC:

Formula IIC

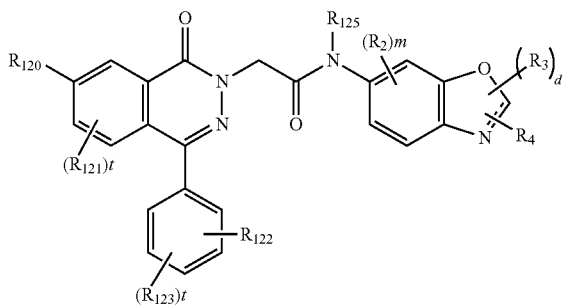

or a pharmaceutically acceptable salt, ester or prodrug thereof;

wherein ===== represents a single or double bond;

m is 0, 1, 2, 3 or 4;

t is 0, 1, 2 or 3;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two R2 together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group;

each R3 and R4 is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{120}$ is selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

each $R_{121}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{122}$ is halogen or —CN; and, each $R_{123}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{125}$ is alkyl or substituted alkyl;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring.

In one embodiment, the invention relates to a compound of Formula IID:

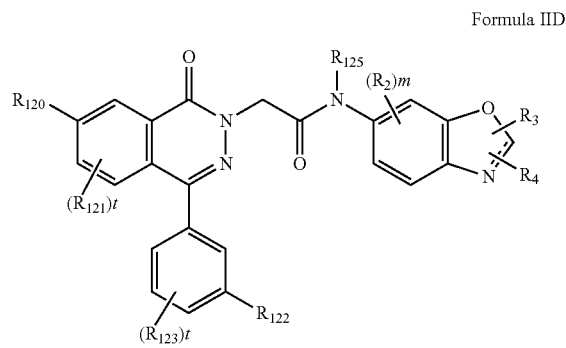

Formula IID or a pharmaceutically acceptable salt, ester or prodrug thereof;

wherein ===== represents a single or double bond;

m is 0, 1, 2, 3 or 4;

t is 0, 1, 2 or 3;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group;

each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{120}$ is selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

each $R_{121}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

$R_{122}$ is halogen, —CN, $SO_2NH_2$, $CONH_2$, $CO_2H$, —$CH_3$, $OCH_3$, —$OR_{100}$;

each $R_{123}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; and, R125 is alkyl or substituted alkyl;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring.

In one embodiment, the invention relates to a compound of Formula IV:

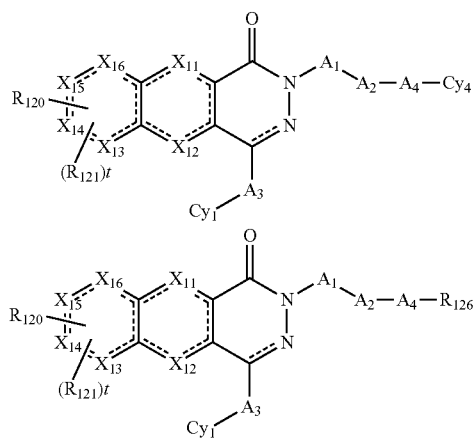

or a pharmaceutically acceptable salt, ester or prodrug thereof;
wherein ===== represents a single or double bond;
m is 0, 1, 2, 3 or 4;
$Cy_1$ is absent, an aryl, substituted aryl, carbocycle, substituted carbocycle, heterocyclyl, substituted heterocyclyl, heteroaryl, or substituted heteroaryl group having one, two or three rings;

$Cy_2$ is an aryl, substituted aryl, carbocycle, substituted carbocycle, heterocyclyl, substituted heterocyclyl, heteroaryl, or substituted heteroaryl group having one, two or three rings;

$Cy_4$ is an aryl, substituted aryl, carbocycle, substituted carbocycle, heterocyclyl, substituted heterocyclyl, heteroaryl, or substituted heteroaryl group having one, two or three rings;

$A_1$ is absent, —[$C(R_{100})(R_{101})]_n$—, —C(O)—, —C(S)—, —S(O)—, —$C(O)N(R_{100})$—, —$S(O)_2N(R_{100})$—, —$S(O)_2$—, —[$C(R_{25})(R_{26})$]n-, —[$C(R_{25})(R_{26})$]n-C=C—[$C(R_{27})(R_{28})$]p, or —[$C(R_{25})(R_{26})$]n-C≡C—[$C(R_{27})(R_{28})$]p, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted ary,1 —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —[$C(R_{100})(R_{101})$]n-, —C(O)—, —C(S)—, —S(O)—, —$C(O)N(R_{100})$—, —$C(O)N(R_{100})(R_{101})$, $N(R_{100})(R_{101})$, —$S(O)_2$—, —$S(O)_2R_{100}$, —$S(O)R_{100}$, —$S(O)_2N(R_{100})R_{101}$, —[$C(R_{25})(R_{26})$]n-, —[$C(R_{25})(R_{26})$]n-C=C—[$C(R_{27})(R_{28})$]p, or —[$C(R_{25})(R_{26})$]n-C≡C—[$C(R_{27})(R_{28})$]p;

$A_3$ is absent or —[$C(R_{100})(R_{101})$]n-, —C(O)—, —C(S)—, —S(O)—, —$C(O)N(R_{100})$—, —$C(O)N(R_{100})(R_{101})$, $N(R_{100})(R_{101})$, —$S(O)_2$—, $S(O)_2R_{100}$, $S(O)R_{100}$, $S(O)_2N(R_{100})(R_{101})$, —[$C(R_{25})(R_{26})$]n-, —[$C(R_{25})(R_{26})$]n-C=C—[$C(R_{27})(R_{28})$]p, or —[$C(R_{25})(R_{26})$]n-C≡C—[$C(R_{27})(R_{28})$]p;

$A_4$ is absent or —[$C(R_{100})(R_{101})$]n-, —[$C(R_{25})(R_{26})$]n-, —[$C(R_{25})(R_{26})$]n-C=C—[$C(R_{27})(R_{28})$]p, or —[$C(R_{25})(R_{26})$]n-C≡C—[$C(R_{27})(R_{28})$]p;

wherein each $R_{25}$, $R_{26}$, $R_{27}$ and $R_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{25}$, $R_{26}$, $R_{27}$ and R28 groups together with the atoms to which they are attached and any intervening atoms may form an additional optionally substituted, 3, 4, 5, 6 or 7 membered ring; preferably a cyclopropyl group;

$R_{126}$ is selected from hydrogen, halogen, optionally substituted $C_1$-$C_8$ alkyl, —$OR_{100}$, —$SR_{100}$, $N(R_{100})(R_{101})$ and $S(O)_2C_{1-8}$alkyl;

p is 0, 1, 2, 3, 4, 5, 6, or 7;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two R2 together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group;

each R3 and R4 is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;

each $X_{11}$ and $X_{12}$ is selected from absent, —$C(R_{110})(R_{111})$—, —$N(R_{110})$, —S—, —O—, and $S(O)_2$; wherein at least one of $X_{11}$ and $X_{12}$ is present; each $R_{110}$ and $R_{111}$ is independently selected from absent, hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; and, each $X_{13}$, $X_{14}$, $X_{15}$, and $X_{16}$ is independently selected from —C— and —N—.

In one embodiment, the invention relates to a compound of Formula IVA, IVB, IVC, IVD or IVE:

Formula IVA

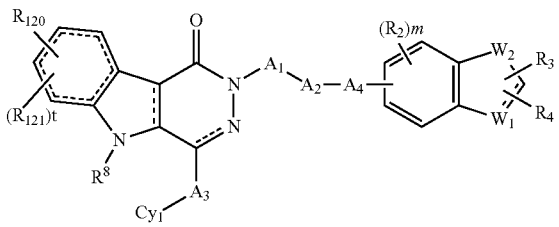

Formula IVB

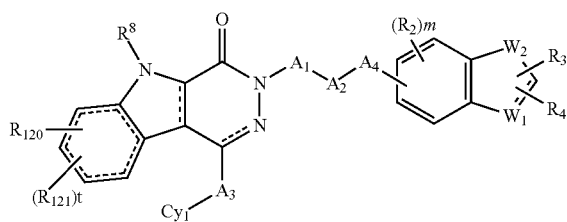

Formula IVC

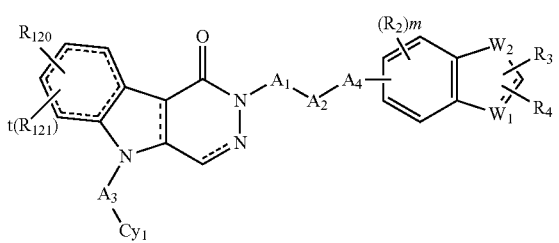

Formula IVD

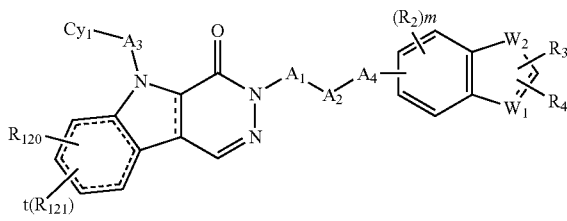

Formula IVE

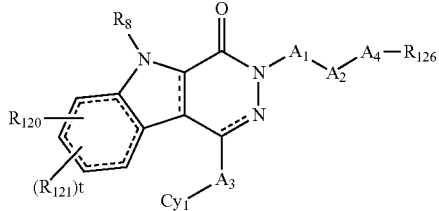

or a pharmaceutically acceptable salt, ester or prodrug thereof;

wherein ===== represents a single or double bond;

m is 0, 1, 2, 3 or 4;

$W_1$ is CH, $CH_2$, $CR_{100}$, C(O), N, $NR_{100}$, O, S, SO, or $SO_2$; preferably O or N; more preferably $W_1$ is N;

$W_2$ is O, S, N, CH, $CH_2$; preferably S or O; more preferably $W_2$ is O;

$Cy_1$ is absent, an aryl, substituted aryl, carbocycle, substituted carbocycle, heterocyclyl, substituted heterocyclyl, heteroaryl, or substituted heteroaryl group having one, two or three rings;

$Cy_2$ is an aryl, substituted aryl, carbocycle, substituted carbocycle, heterocyclyl, substituted heterocyclyl, heteroaryl, or substituted heteroaryl group having one, two or three rings;

$A_1$ is absent, —$[C(R_{100})(R_{101})]_n$—, —C(O)—, —C(S)—, —S(O)—, —$C(O)N(R_{100})$—, —$S(O)_2N(R_{100})$—, —$S(O)_2$—, —$[C(R_{25})(R_{26})]_n$—, —$[C(R_{25})(R_{26})]n$-C=C—$[C(R_{27})(R_{28})]p$, or —$[C(R_{25})(R_{26})]n$-C≡C—$[C(R_{27})(R_{28})]p$, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{200}$, —$SR_{200}$, —$C(O)R_{200}$, —$C(O)N(R_{200})_2$, —$NC(O)R_{200}$, —$S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, —$S(O)_2R_{100}$, —$S(O)R_{100}$, —$S(O)_2N(R_{100})R_{101}$, —$[C(R_{25})(R_{26})]n$-, —$[C(R_{25})(R_{26})]n$-C=C—$[C(R_{27})(R_{28})]p$, or —$[C(R_{25})(R_{26})]n$-C≡C—$[C(R_{27})(R_{28})]p$;

$A_3$ is absent or —$[C(R_{100})(R_{101})]n$-, —C(O)—, —C(S)—, —S(O)—, —$C(O)N(R_{100})$—, —$C(O)N(R_{100})(R_{101})$, $N(R_{100})(R_{101})$, —$S(O)_2$—, $S(O)_2R_{100}$, $S(O)R_{100}$, $S(O)_2N(R_{100})(R_{101})$, —$[C(R_{25})(R_{26})]n$-, —$[C(R_{25})(R_{26})]n$-C=C—$[C(R_{27})(R_{28})]p$, or —$[C(R_{25})(R_{26})]n$-C≡C—$[C(R_{27})(R_{28})]p$;

$A_4$ is absent or —$[C(R_{25})(R_{26})]n$-, —$[C(R_{25})(R_{26})]n$-C=C—$[C(R_{27})(R_{28})]p$, or —$[C(R_{25})(R_{26})]n$-C≡C—$[C(R_{27})(R_{28})]p$;

wherein each $R_{25}$, $R_{26}$, $R_{27}$ and $R_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl, substituted aryl, —$OR_{100}$, —$SR_{100}$, —$NR_{100}R_{101}$, —C(O)

$R_{100}$, —C(O)O$R_{100}$, —C(O)N$R_{100}R_{101}$, —N($R_{100}$)C(O)$R_{101}$, —S(O)$_2R_{100}$, —S(O)$R_{100}$, —S$R_{100}$, —S(O)$_2$N($R_{100}$)$R_{101}$, —CF$_3$, —CN, —NO$_2$, and —N$_3$; alternatively two of $R_{25}$, $R_{26}$, $R_{27}$ and $R_{28}$ groups together with the atoms to which they are attached and any intervening atoms may form an additional optionally substituted, 3, 4, 5, 6 or 7 membered ring; preferably a cyclopropyl group;

$R_{126}$ is selected from hydrogen, halogen, optionally substituted $C_1$-$C_8$ alkyl, —O$R_{100}$, —S$R_{100}$, N($R_{100}$)($R_{101}$) and S(O)$_2C_{1-8}$ alkyl;

p is 0, 1, 2, 3, 4, 5, 6, or 7;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —O$R_{100}$, —S$R_{100}$, —N$R_{100}R_{101}$, —C(O)$R_{100}$, —C(O)O$R_{100}$, —C(O)N$R_{100}R_{101}$, —N($R_{100}$)C(O)$R_{101}$, —S(O)$_2R_{100}$, —S(O)$R_{100}$, —S$R_{100}$, —S(O)$_2$N($R_{100}$)$R_{101}$, —CF$_3$, —CN, —NO$_2$, —N$_3$; alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group; and, each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —O$R_{100}$, —S$R_{100}$, —N$R_{100}R_{101}$, —C(O)$R_{100}$, —C(O)O$R_{100}$, —C(O)N$R_{100}R_{101}$, —N($R_{100}$)C(O)$R_{101}$, —S(O)$_2R_{100}$, —S(O)$R_{100}$, —S$R_{100}$, —S(O)$_2$N($R_{100}$)$R_{101}$, —CF$_3$, —CN, —NO$_2$, —N$_3$.

In one embodiment, the invention relates to a compound of Formula V:

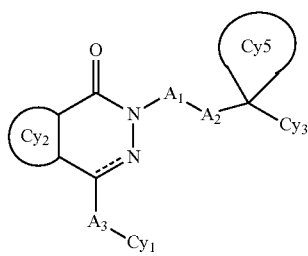

Formula V or a pharmaceutically acceptable salt, ester or prodrug thereof;

wherein ===== represents a single or double bond;

m is 0, 1, 2, 3 or 4;

Cy$_1$ is absent, an aryl, substituted aryl, carbocycle, substituted carbocycle, heterocyclyl, substituted heterocyclyl, heteroaryl, or substituted heteroaryl group having one, two or three rings;

Cy$_2$ is an aryl, substituted aryl, carbocycle, substituted carbocycle, heterocyclyl, substituted heterocyclyl, heteroaryl, or substituted heteroaryl group having one, two or three rings;

A$_1$ is absent, —[C($R_{100}$)($R_{101}$)]$_n$—, —C(O)—, —C(S)—, —S(O)—, —C(O)N($R_{100}$)—, —S(O)$_2$N($R_{100}$)—, —S(O)$_2$—, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; preferably, Cy$_2$ is a $C_5$-$C_7$ aryl or heteroaryl; Preferably Cy$_2$ is substituted with —O$R_{200}$, —S$R_{200}$, —C(O)$R_{200}$, —C(O)N($R_{200}$)$_2$, —NC(O)$R_{200}$, —S(O)$_2R_{200}$ wherein $R_{200}$ is hydrogen, $C_1$-$C_6$ alkyl, $C_2$-$C_6$ alkenyl, or $C_2$-$C_6$ alkynyl;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —O$R_{200}$, —S$R_{200}$, —C(O)$R_{200}$, —C(O)N($R_{200}$)$_2$, —NC(O)$R_{200}$, —S(O)$_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;

Cy$_3$ is absent, an aryl, substituted aryl, carbocycle, substituted carbocycle, heterocyclyl, substituted heterocyclyl, heteroaryl, or substituted heteroaryl group having one, two or three rings;

Cy$_5$ is a spiro attached $C_3$-$C_6$ carbocycle, preferably cyclopropyl or cyclobutyl;

A$_2$ is absent or —[C($R_{100}$)($R_{101}$)]n-, —C(O)—, —C(S)—, —S(O)—, —C(O)N($R_{100}$)—, —C(O)N($R_{100}$)($R_{101}$), N($R_{100}$)($R_{101}$), —S(O)$_2$—, —S(O)$_2R_{100}$, —S(O)$R_{100}$, —S(O)$_2$N($R_{100}$)$R_{101}$);

A$_3$ is absent or —[C($R_{100}$)($R_{101}$)]n-, —C(O)—, —C(S)—, —S(O)—, —C(O)N($R_{100}$)—, —C(O)N($R_{100}$)($R_{101}$), N($R_{100}$)($R_{101}$), —S(O)$_2$—, S(O)$_2R_{100}$, S(O)$R_{100}$, S(O)$_2$N($R_{100}$)($R_{101}$);

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —O$R_{100}$, —S$R_{100}$, —N$R_{100}R_{101}$, —C(O)$R_{100}$, —C(O)O$R_{100}$, —C(O)N$R_{100}R_{101}$, —N($R_{100}$)C(O)$R_{101}$, —S(O)$_2R_{100}$, —S(O)$R_{100}$, —S$R_{100}$, —S(O)$_2$N($R_{100}$)$R_{101}$, —CF$_3$, —CN, —NO$_2$, —N$_3$;

alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group; and, each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —O$R_{100}$, —S$R_{100}$, —N$R_{100}R_{101}$, —C(O)$R_{100}$, —C(O)O$R_{100}$, —C(O)N$R_{100}R_{101}$, —N($R_{100}$)C(O)$R_{101}$, —S(O)$_2R_{100}$, —S(O)$R_{100}$, —S$R_{100}$, —S(O)$_2$N($R_{100}$)$R_{101}$, —CF$_3$, —CN, —NO$_2$, —N$_3$.

In one embodiment, the invention relates to a compound of Formula V, having the formula:

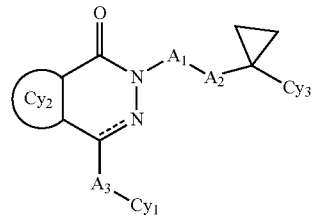

or a pharmaceutically acceptable salt thereof.

In one embodiment, the invention relates to a compound of Formula VI:

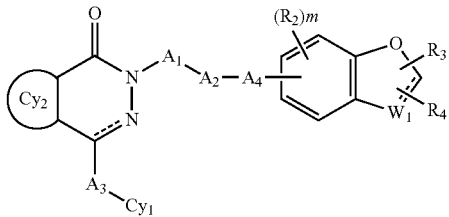

Formula VI or a pharmaceutically acceptable salt, ester or prodrug thereof;
wherein ===== represents a single or double bond;
wherein $W_1$ is CH, $CH_2$, $CR_{100}$, C(O), O, S, SO, or $SO_2$;
m is 0, 1, 2, 3 or 4;
$Cy_1$ is absent, an aryl, substituted aryl, carbocycle, substituted carbocycle, heterocyclyl, substituted heterocyclyl, heteroaryl, or substituted heteroaryl group having one, two or three rings;
$Cy_2$ is an aryl, substituted aryl, carbocycle, substituted carbocycle, heterocyclyl, substituted heterocyclyl, heteroaryl, or substituted heteroaryl group having one, two or three rings;
$A_1$ is absent, $-[C(R_{100})(R_{101})]_n-$, $-C(O)-$, $-C(S)-$, $-S(O)-$, $-C(O)N(R_{100})-$, $-S(O)_2N(R_{100})-$, $-S(O)_2-$, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, $-OR_{200}$, $-SR_{200}$, $-C(O)R_{200}$, $-C(O)N(R_{200})_2$, $-NC(O)R_{200}$, $-S(O)_2R_{200}$ wherein $R_{200}$ is hydrogen, $C_1$-$C_6$ alkyl, $C_2$-$C_6$ alkenyl, or $C_2$-$C_6$ alkynyl; alternatively two of $R_{100}$ and $R_{101}$ groups together with the atoms to which they are attached and any intervening atoms may form an additional optionally substituted, 3, 4, 5, 6 or 7 membered ring;
$A_2$ is absent or $-[C(R100)(R101)]n-$, $-C(O)-$, $-C(S)-$, $-S(O)-$, $-C(O)N(R_{100})-$, $-C(O)N(R_{100})(R_{101})$, $N(R_{100})(R_{101})$, $-S(O)_2-$, $-S(O)_2R_{100}$, $-S(O)R_{100}$, $-S(O)_2N(R_{100})R_{101}$);
$A_3$ is absent or $-[C(R100)(R101)]r-$, $-C(O)-$, $-C(S)-$, $-S(O)-$, $-C(O)N(R_{100})-$, $-C(O)N(R_{100})(R_{101})$, $N(R_{100})(R_{101})$, $-S(O)_2-$, $S(O)_2R_{100}$, $S(O)R_{100}$, $S(O)_2N(R_{100})(R_{101})$;
$A_4$ is $-[C(R_{25})(R_{26})]r-$, $-[C(R_{25})(R_{26})]r-C≡C-[C(R_{27})(R_{28})]p$, or $-[C(R_{25})(R_{26})]r-C≡C-[C(R_{27})(R_{28})]p$;
wherein each $R_{25}$, $R_{26}$, $R_{27}$ and $R_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl, substituted aryl, $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, and $-N_3$; alternatively two of $R_{25}$, $R_{26}$, $R_{27}$ and $R_{28}$ groups together with the atoms to which they are attached and any intervening atoms may form an additional optionally substituted, 3, 4, 5, 6 or 7 membered ring; preferably a cyclopropyl group;
p is 0, 1, 2, 3, 4, 5, 6, or 7;
r is 1, 2, 3, 4, 5, 6, or 7;
$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$; alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group; and,
each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$.

In one embodiment, the invention relates to a compound of Formula VII:

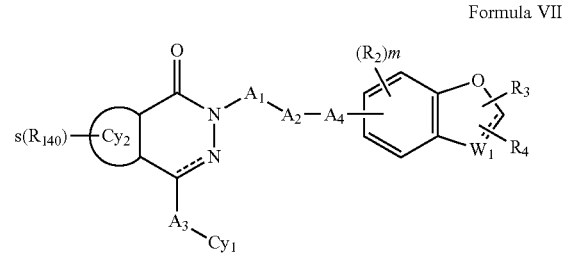

Formula VII or a pharmaceutically acceptable salt, ester or prodrug thereof;
wherein ===== represents a single or double bond;
wherein $W_1$ is CH, $CH_2$, $CR_{100}$, C(O), O, S, SO, or $SO_2$;
m is 0, 1, 2, 3 or 4;
s is 1, 2, 3 or 4;
$Cy_1$ is absent, an aryl, substituted aryl, carbocycle, substituted carbocycle, heterocyclyl, substituted heterocyclyl, heteroaryl, or substituted heteroaryl group having one, two or three rings;
$Cy_2$ is an aryl, substituted aryl, carbocycle, substituted carbocycle, heterocyclyl, substituted heterocyclyl, heteroaryl, or substituted heteroaryl group having one, two or three rings;
$A_1$ is absent, $-[C(R_{100})(R_{101})]_n-$, $-C(O)-$, $-C(S)-$, $-S(O)-$, $-C(O)N(R_{100})-$, $-S(O)_2N(R_{100})-$, $-S(O)_2-$, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7; wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —OR$_{200}$, —SR$_{200}$, —C(O)R$_{200}$, —C(O)N(R$_{200}$)$_2$, —NC(O)R$_{200}$, —S(O)$_2$R$_{200}$ wherein R$_{200}$ is hydrogen, C$_1$-C$_6$ alkyl, C$_2$-C$_6$ alkenyl, or C$_2$-C$_6$ alkynyl; alternatively two of R$_{100}$ and R$_{101}$ groups together with the atoms to which they are attached and any intervening atoms may form an additional optionally substituted, 3, 4, 5, 6 or 7 membered ring;

A$_2$ is absent or —[C(R100)(R101)]n-, —C(O)—, —C(S)—, —S(O)—, —C(O)N(R$_{100}$)—, —C(O)N(R$_{100}$)(R$_{101}$), N(R$_{100}$)(R$_{101}$), —S(O)$_2$—, —S(O)$_2$R$_{100}$, —S(O)R$_{100}$, —S(O)$_2$N(R$_{100}$)R$_{101}$);

A$_3$ is absent or —[C(R100)(R101)]r-, —C(O)—, —C(S)—, —S(O)—, —C(O)N(R$_{100}$)—, —C(O)N(R$_{100}$)(R$_{101}$), N(R$_{100}$)(R$_{101}$), —S(O)$_2$—, S(O)$_2$R$_{100}$, S(O)R$_{100}$, S(O)$_2$N(R$_{100}$)(R$_{101}$);

A$_4$ is absent, —[C(R$_{25}$)(R$_{26}$)]r-, —[C(R$_{25}$)(R$_{26}$)]r-C═C—[C(R$_{27}$)(R$_{28}$)]p, or —[C(R$_{25}$)(R$_{26}$)]r-C≡C—[C(R$_{27}$)(R$_{28}$)]p;

wherein each R$_{25}$, R$_{26}$, R$_{27}$ and R$_{28}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl, substituted aryl, —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, and —N$_3$; alternatively two of R$_{25}$, R$_{26}$, R$_{27}$ and R$_{28}$ groups together with the atoms to which they are attached and any intervening atoms may form an additional optionally substituted, 3, 4, 5, 6 or 7 membered ring; preferably a cyclopropyl group;

p is 0, 1, 2, 3, 4, 5, 6, or 7;

r is 1, 2, 3, 4, 5, 6, or 7;

R$_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$; alternatively two R$_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group; and, each R$_3$ and R$_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$; and, each R$_{140}$ is independently selected from halogen, —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$.

In one embodiment, the invention relates to a compound of Formula V-VII wherein Cy$_2$ is selected from:

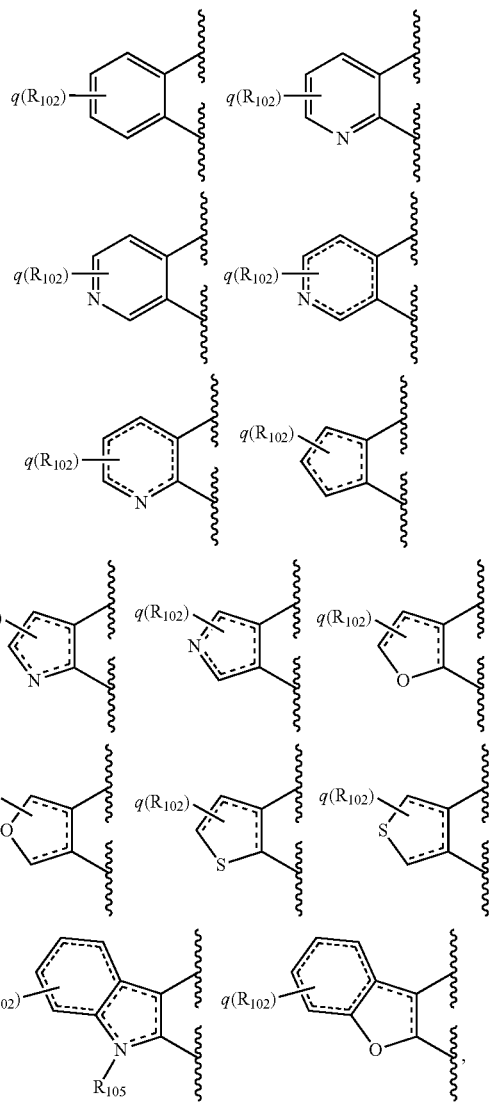

wherein q is 0, 1, 2, 3, 4 or 5;

each R$_{102}$ is independently hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$ —CF$_3$, —CN, —NO$_2$, —N$_3$; alternatively two of R$_{102}$ groups together with the atoms to which they are attached and any intervening atoms may form an additional optionally substituted 3, 4, 5, 6 or 7 membered ring; and R$_{105}$ is hydrogen, deuterium, alkyl, substituted alkyl, alkenyl, substituted alkenyl, alkynyl, substituted alkynyl, aliphatic, substituted aliphatic, aryl and substituted aryl.

In one embodiment, the invention relates to a compound of Formula V-VII wherein Cy1 is selected from:

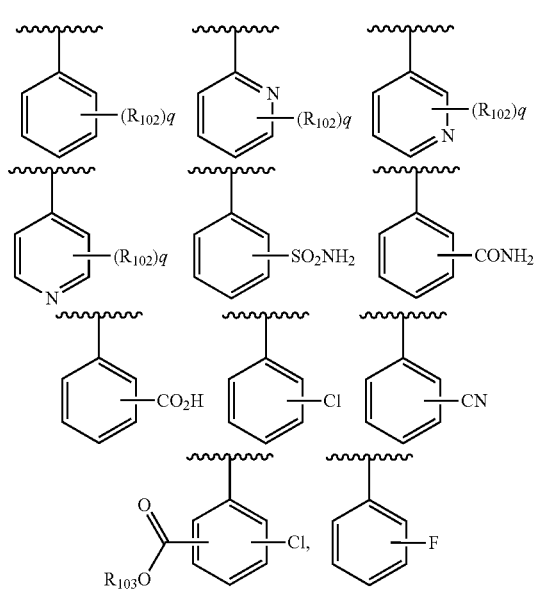

wherein q is 0, 1, 2, 3, 4 or 5; each $R_{102}$ is hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$ —$CF_3$, —CN, —$NO_2$, —$N_3$; alternatively two of $R_{102}$ groups together with the atoms to which they are attached and any intervening atoms may form an additional optionally substituted 3, 4, 5, 6 or 7 membered ring; and, $R_{103}$ is hydrogen, deuterium, alkyl, substituted alkyl, alkenyl, substituted alkenyl, alkynyl, substituted alkynyl, aliphatic, substituted aliphatic, aryl and substituted aryl.

In one embodiment, the invention relates to a compound of Formula V wherein $Cy_3$ is selected from:

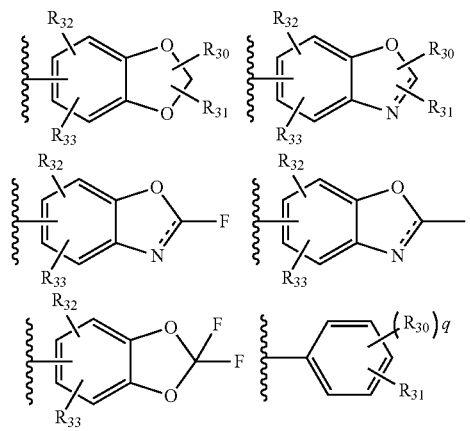

each $R_{30}$, $R_{31}$, $R_{32}$ and $R_{33}$ is independently selected from hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$ —$CF_3$, —CN, —$NO_2$, —$N_3$; alternatively two of $R_{30}$, $R_{31}$, $R_{32}$ or $R_{33}$ groups together with the atoms to which they are attached and any intervening atoms may form an additional optionally substituted 3, 4, 5, 6 or 7 membered ring; and, q is 0, 1, 2, 3, 4 or 5.

In a more preferred embodiment, a compound of formula I is selected from Table A:

TABLE A

Structure structure structure structure structure

TABLE A-continued

Structure

TABLE A-continued
Structure
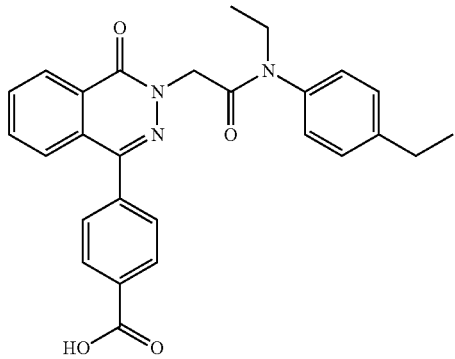 [SMILES: CCc1ccc(N(CC)C(=O)Cn2nc(-c3ccc(C(=O)O)cc3)c3ccccc3c2=O)cc1]
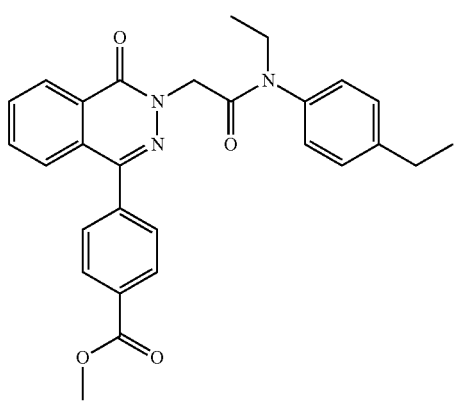 [SMILES: CCc1ccc(N(CC)C(=O)Cn2nc(-c3ccc(C(=O)OC)cc3)c3ccccc3c2=O)cc1]

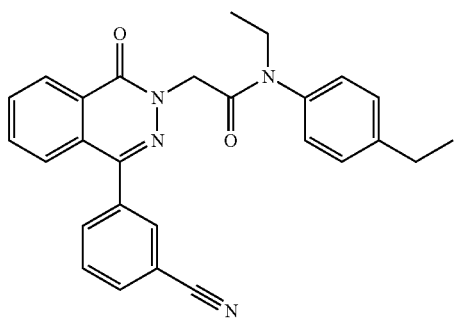 [SMILES: CCc1ccc(N(CC)C(=O)Cn2nc(-c3cccc(C#N)c3)c3ccccc3c2=O)cc1]
TABLE A-continued
Structure
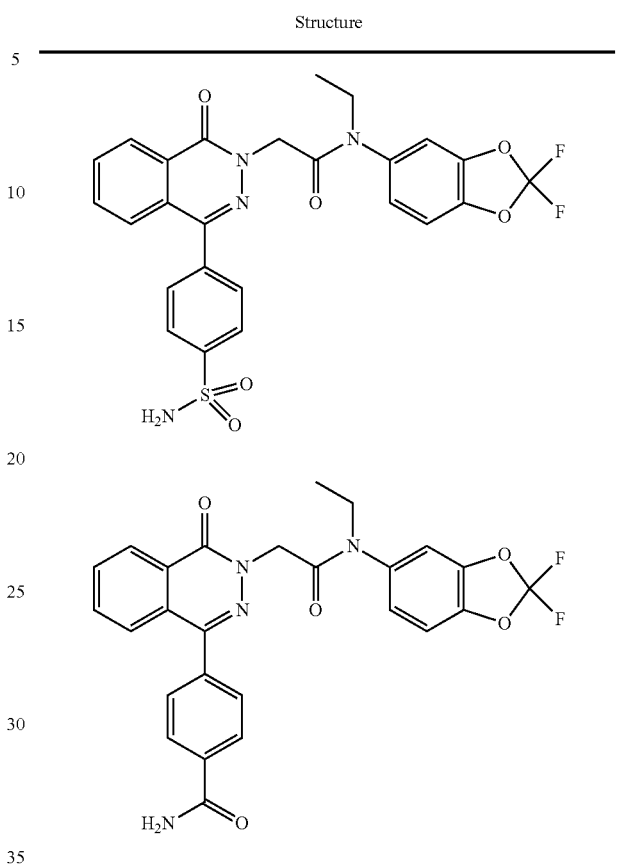
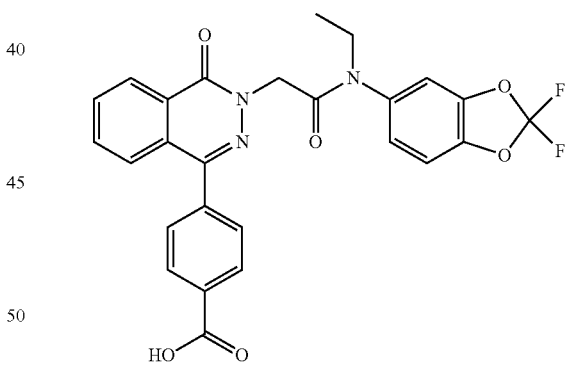
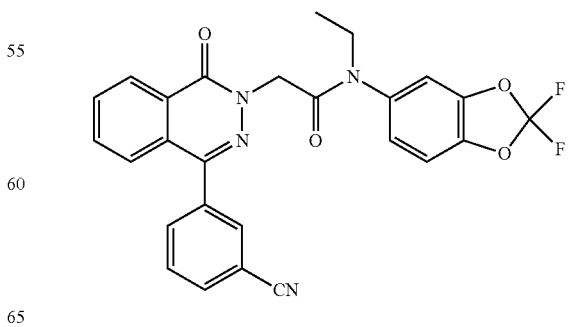

TABLE A-continued
| Structure |
|---|
| 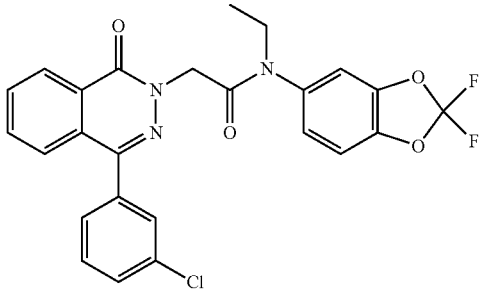 [SMILES: CCN(C(=O)Cn1nc(-c2cccc(F)c2)c2ccccc2c1=O)c1ccc2c(c1)OC(F)(F)O2] |
| 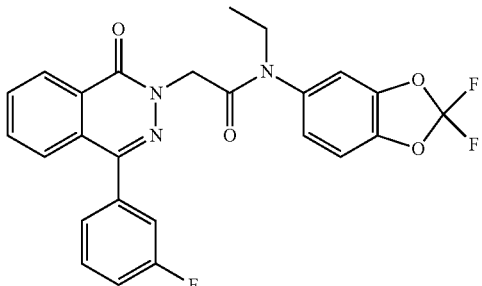 [SMILES: CCN(C(=O)Cn1nc(-c2cccnc2)c2ccccc2c1=O)c1ccc2c(c1)OC(F)(F)O2] |
| 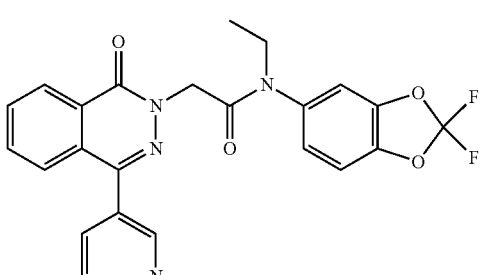 |
| 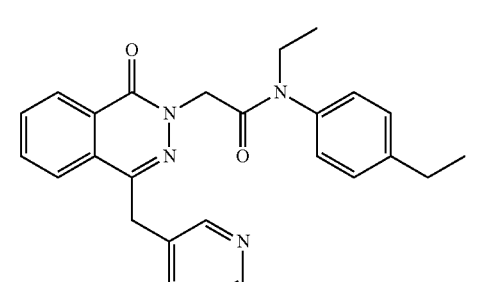 |
| 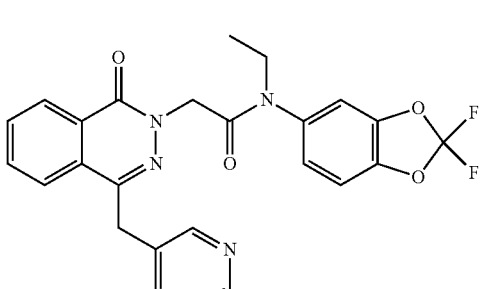 |
TABLE A-continued
| Structure |
|---|
| 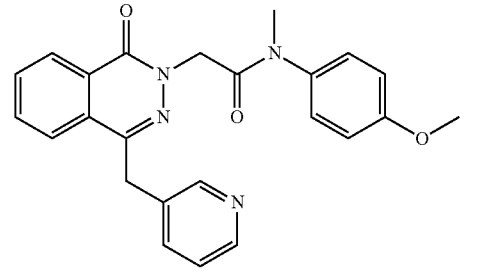 [SMILES: COc1ccc(N(C)C(=O)Cn2nc(Cc3cccnc3)c3ccccc3c2=O)cc1] |
| 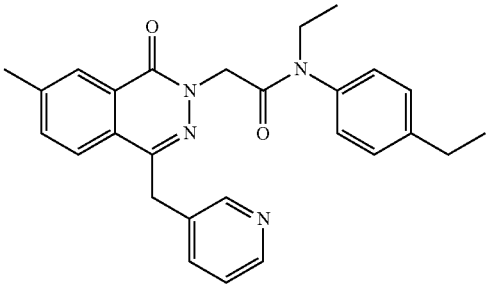 [SMILES: CCc1ccc(N(CC)C(=O)Cn2nc(Cc3cccnc3)c3ccc(C)cc3c2=O)cc1] |
| 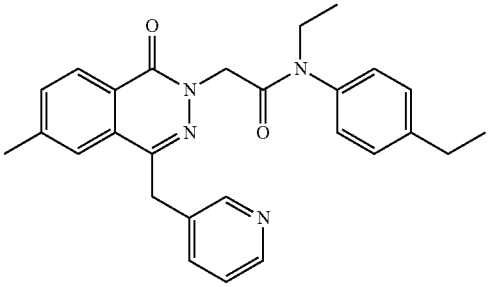 [SMILES: CCc1ccc(N(CC)C(=O)Cn2nc(Cc3cccnc3)c3cc(C)ccc3c2=O)cc1] |
| 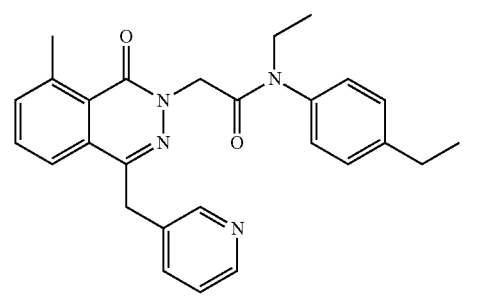 [SMILES: CCc1ccc(N(CC)C(=O)Cn2nc(Cc3cccnc3)c3cccc(C)c3c2=O)cc1] |
| 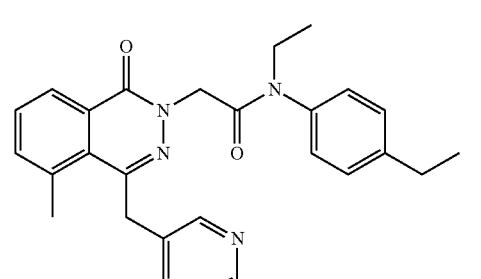 |

TABLE A-continued

| Structure |
|---|
| (chemical structures) |

TABLE A-continued
| Structure |
|---|
| 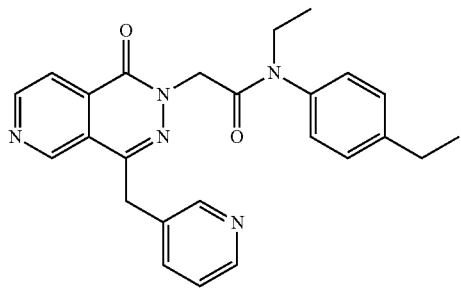 [SMILES: CCc1ccc(N(CC)C(=O)Cn2nc(Cc3cccnc3)c3cnccc3c2=O)cc1] |
| 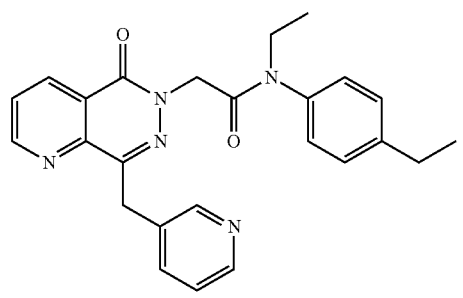 [SMILES: CCc1ccc(N(CC)C(=O)Cn2nc(Cc3cccnc3)c3ncccc3c2=O)cc1] |
| 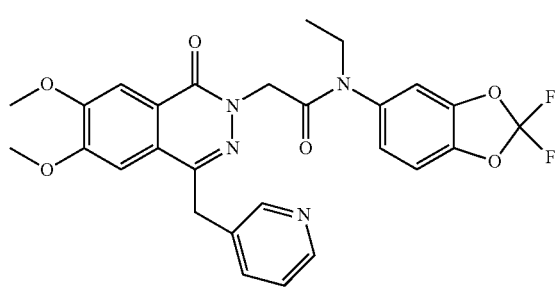 [SMILES: CCN(C(=O)Cn1nc(Cc2cccnc2)c2cc(OC)c(OC)cc2c1=O)c1ccc2c(c1)OC(F)(F)O2] |
| 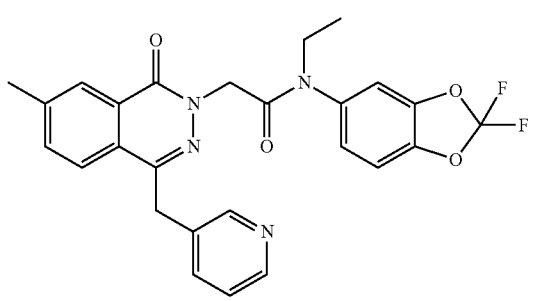 [SMILES: CCN(C(=O)Cn1nc(Cc2cccnc2)c2ccc(C)cc2c1=O)c1ccc2c(c1)OC(F)(F)O2] |
| 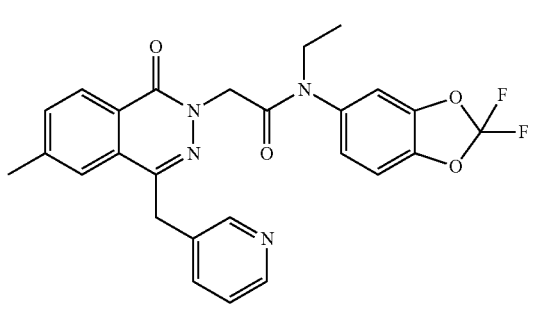 [SMILES: CCN(C(=O)Cn1nc(Cc2cccnc2)c2cc(C)ccc2c1=O)c1ccc2c(c1)OC(F)(F)O2] |
TABLE A-continued
| Structure |
|---|
| 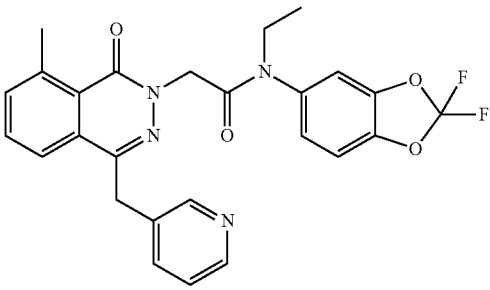 [SMILES: CCN(C(=O)Cn1nc(Cc2cccnc2)c2cccc(C)c2c1=O)c1ccc2c(c1)OC(F)(F)O2] |
| 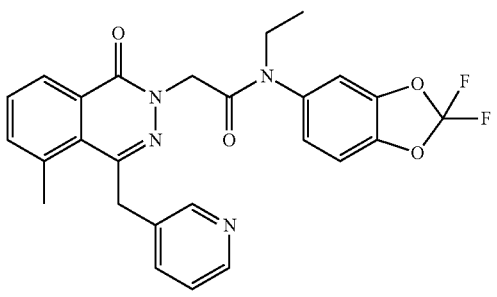 [SMILES: CCN(C(=O)Cn1nc(Cc2cccnc2)c2c(C)cccc2c1=O)c1ccc2c(c1)OC(F)(F)O2] |
| 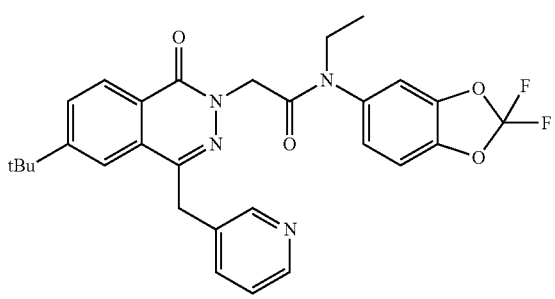 [SMILES: CCN(C(=O)Cn1nc(Cc2cccnc2)c2cc(C(C)(C)C)ccc2c1=O)c1ccc2c(c1)OC(F)(F)O2] |
| 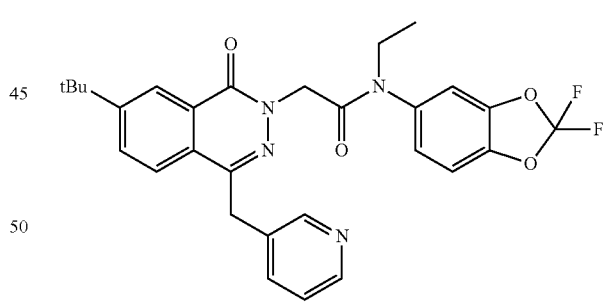 |
| 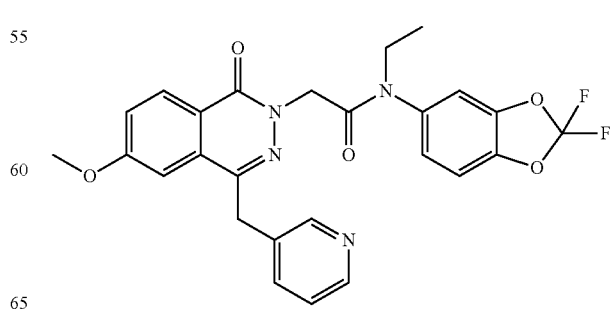 |

TABLE A-continued

Structure

TABLE A-continued
Structure
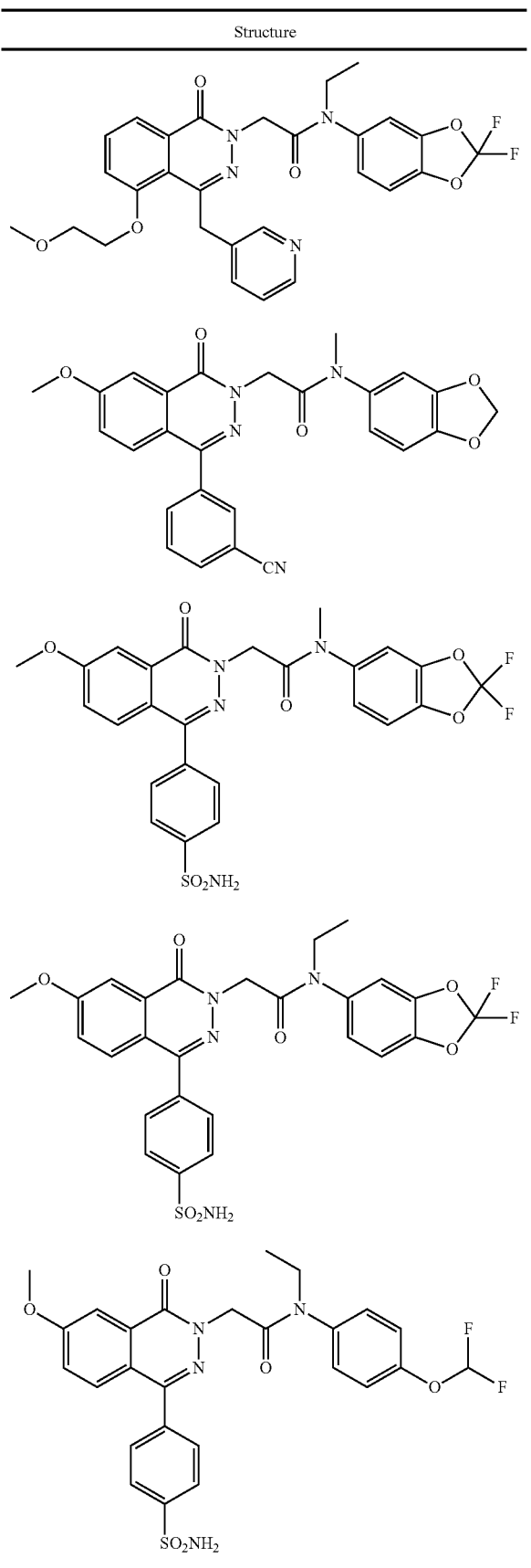
TABLE A-continued
Structure
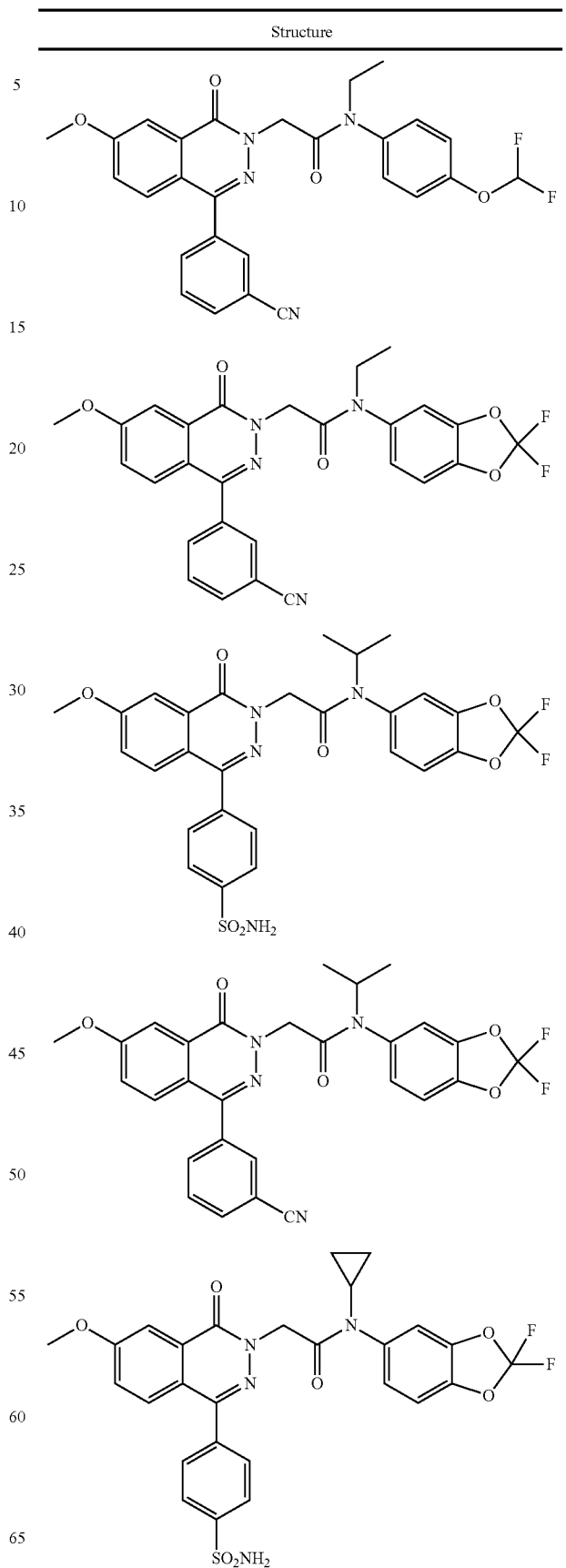

TABLE A-continued
| Structure |
|---|
| 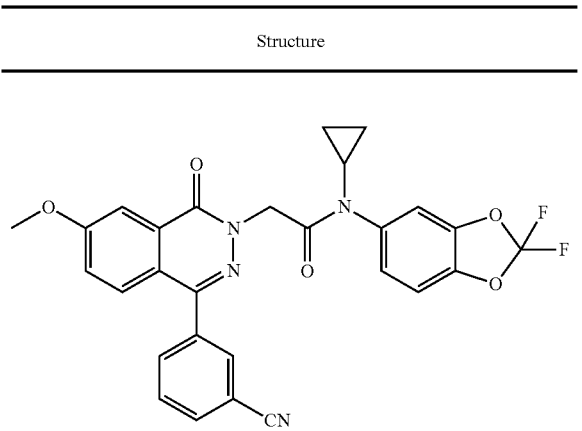 |
| 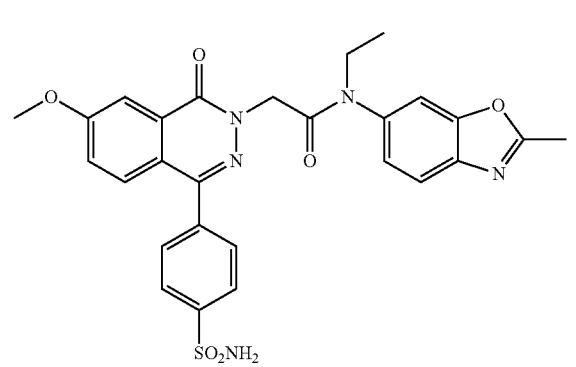 |
| 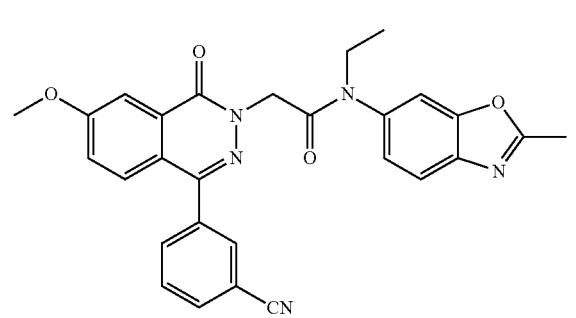 |
| 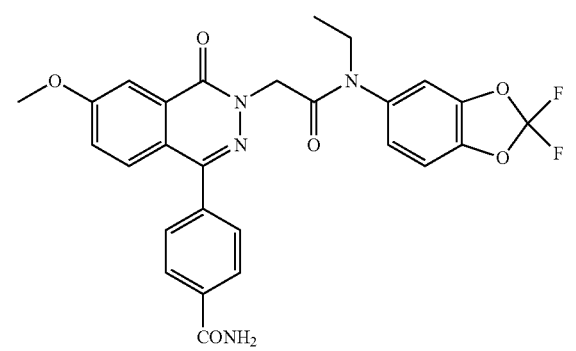 [SMILES: CCN(C(=O)Cn1nc(-c2ccc(C(N)=O)cc2)c2ccc(OC)cc2c1=O)c1ccc2c(c1)OC(F)(F)O2] |
TABLE A-continued
| Structure |
|---|
| 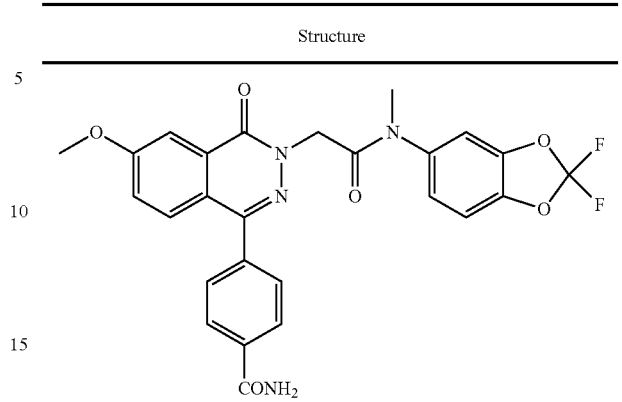 |
| 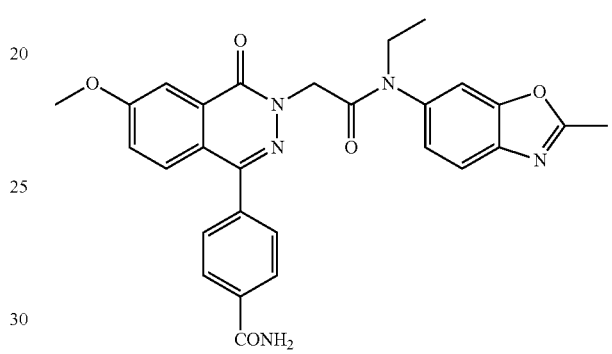 |
| 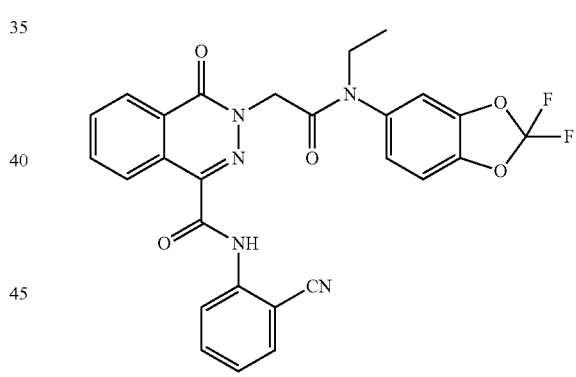 |
| 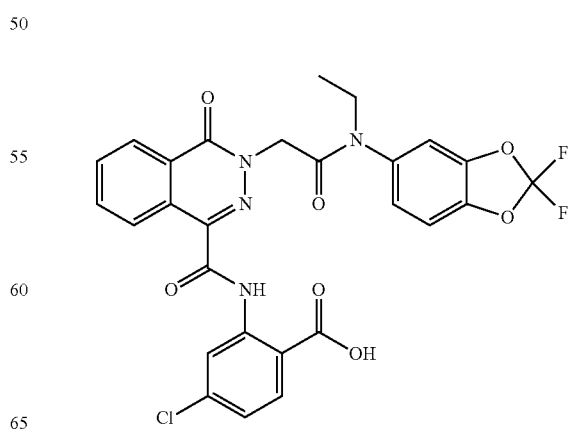 |

TABLE A-continued
Structure
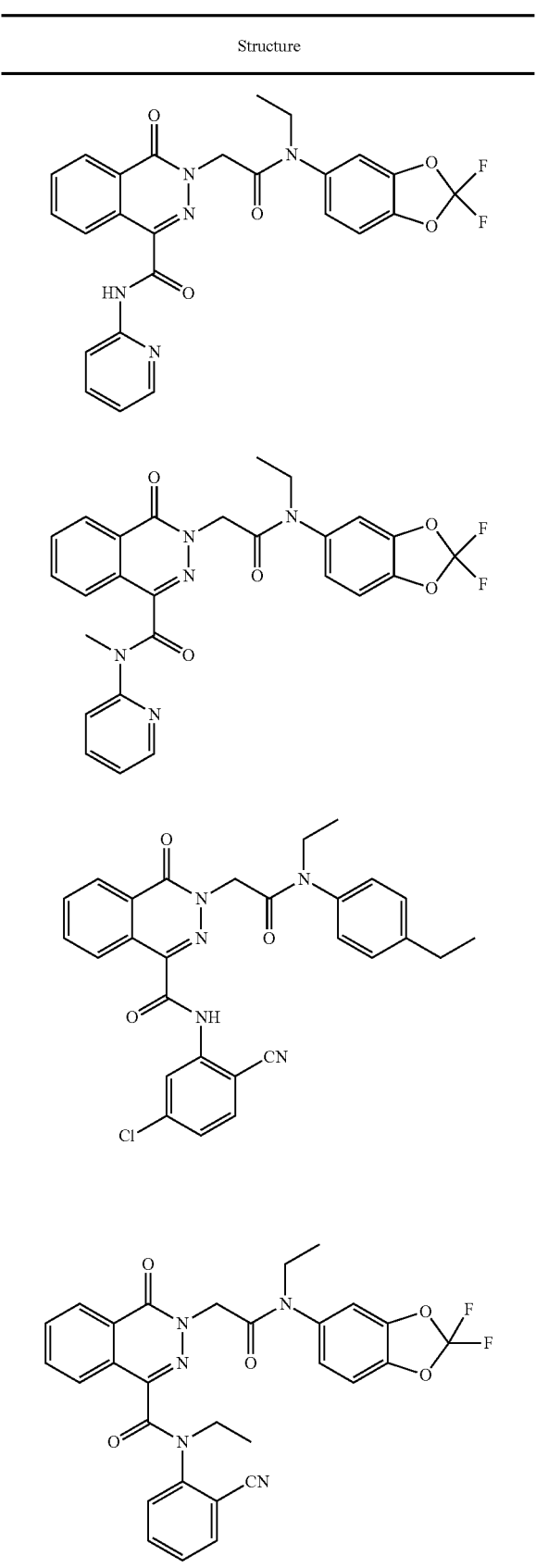
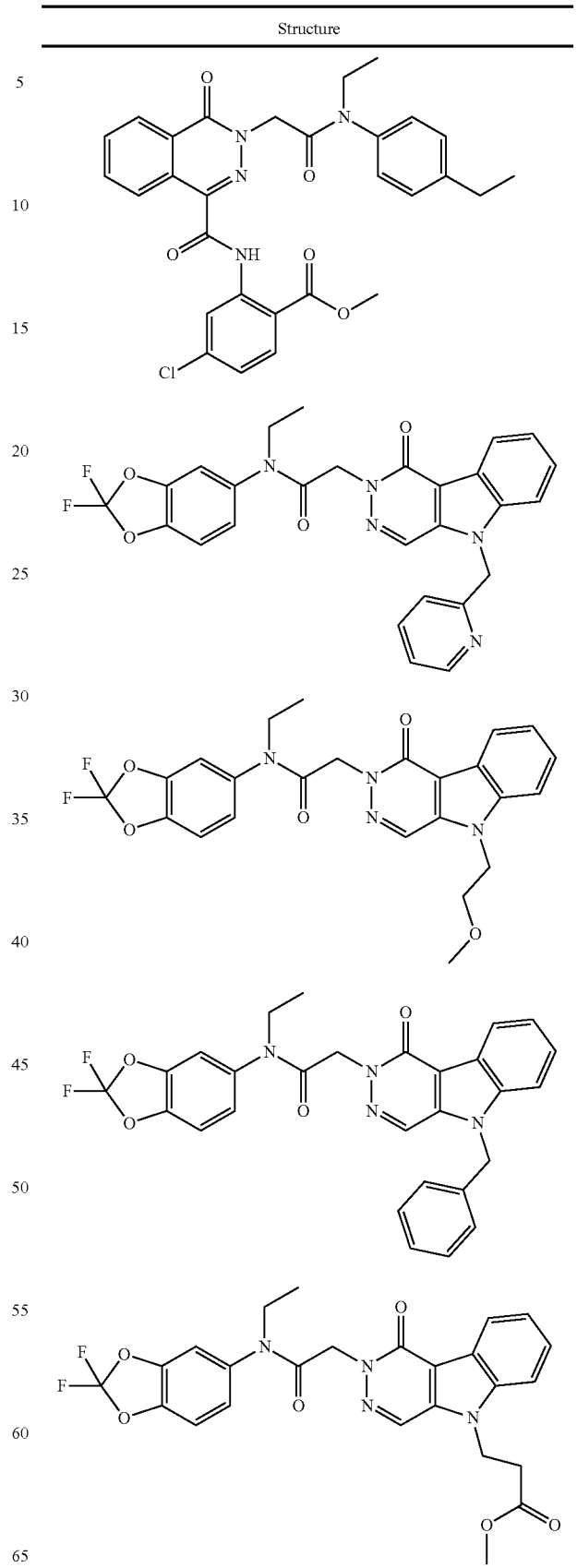

TABLE A-continued

Structure

TABLE A-continued

Structure (chemical structures)

TABLE A-continued

Structure

TABLE A-continued

Structure

TABLE A-continued
| Structure |
|---|
| 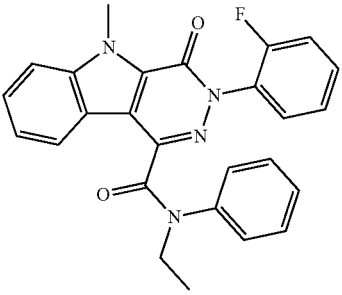 [SMILES: CCN(C(=O)c1nn(-c2ccccc2F)c(=O)c2c1c1ccccc1n2C)c1ccccc1] |
| 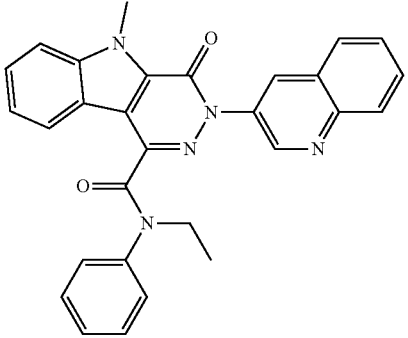 [SMILES: CCN(C(=O)c1nn(-c2cnc3ccccc3c2)c(=O)c2c1c1ccccc1n2C)c1ccccc1] |
| 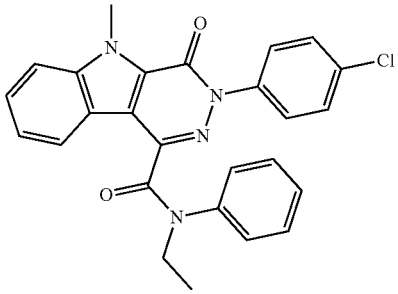 [SMILES: CCN(C(=O)c1nn(-c2ccc(Cl)cc2)c(=O)c2c1c1ccccc1n2C)c1ccccc1] |
| 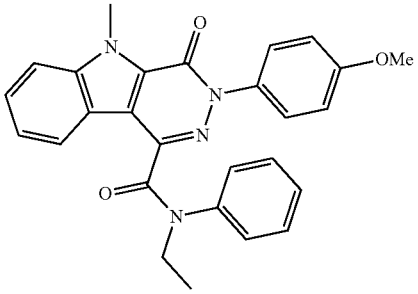 [SMILES: CCN(C(=O)c1nn(-c2ccc(OC)cc2)c(=O)c2c1c1ccccc1n2C)c1ccccc1] |
| 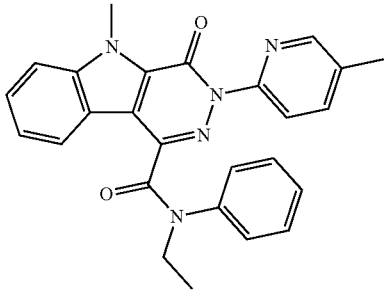 [SMILES: CCN(C(=O)c1nn(-c2ccc(C)cn2)c(=O)c2c1c1ccccc1n2C)c1ccccc1] |
TABLE A-continued
| Structure |
|---|
| 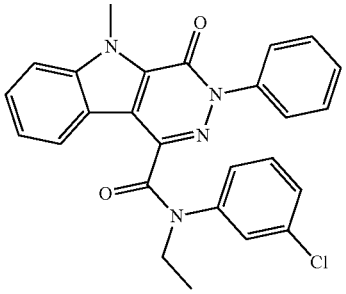 [SMILES: CCN(C(=O)c1nn(-c2ccccc2)c(=O)c2c1c1ccccc1n2C)c1cccc(Cl)c1] |
| 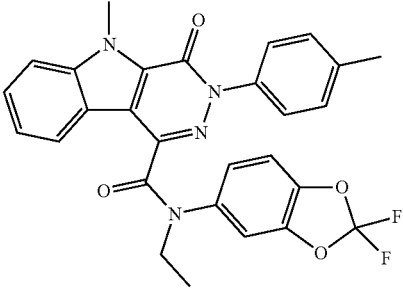 [SMILES: CCN(C(=O)c1nn(-c2ccc(C)cc2)c(=O)c2c1c1ccccc1n2C)c1ccc2c(c1)OC(F)(F)O2] |
| 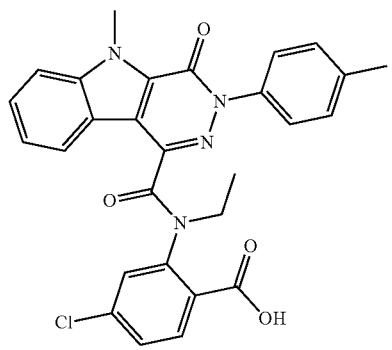 [SMILES: CCN(C(=O)c1nn(-c2ccc(C)cc2)c(=O)c2c1c1ccccc1n2C)c1cc(Cl)ccc1C(=O)O] |
| 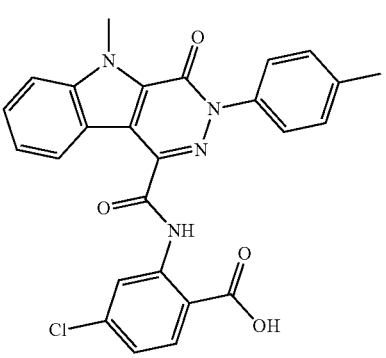 [SMILES: Cc1ccc(-n2nc(C(=O)Nc3cc(Cl)ccc3C(=O)O)c3c4ccccc4n(C)c3c2=O)cc1] |

TABLE A-continued
| Structure |
|---|
| 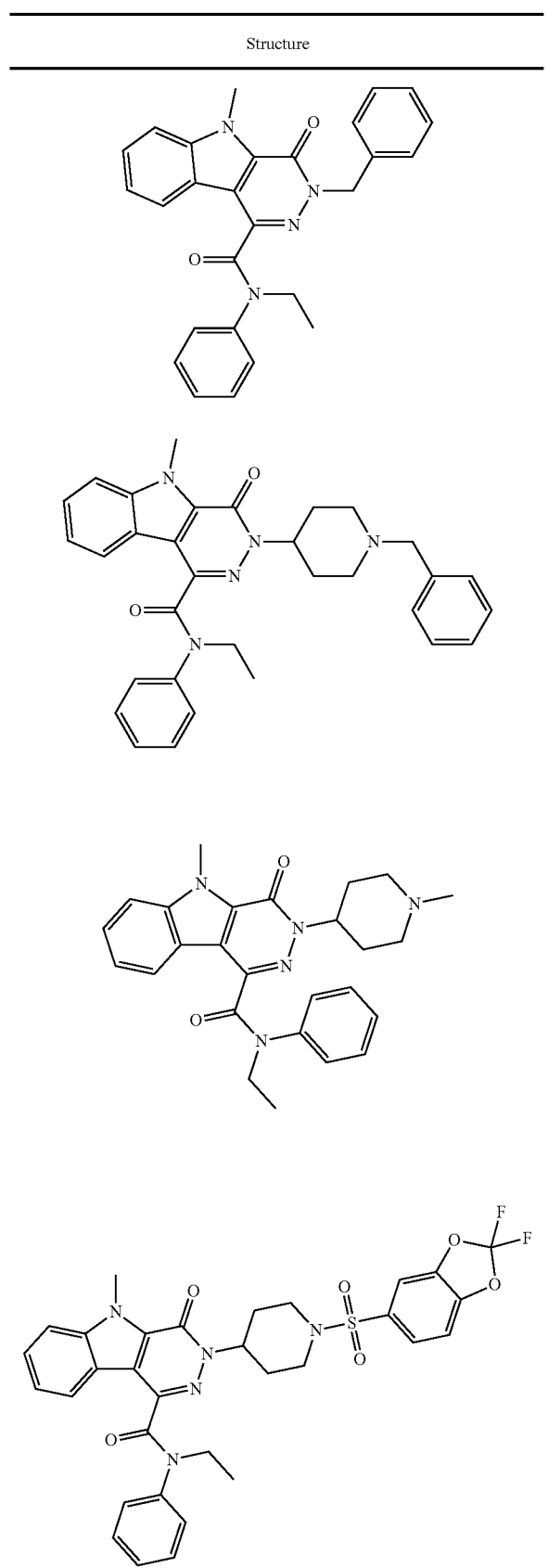 |
TABLE A-continued
| Structure |
|---|
| 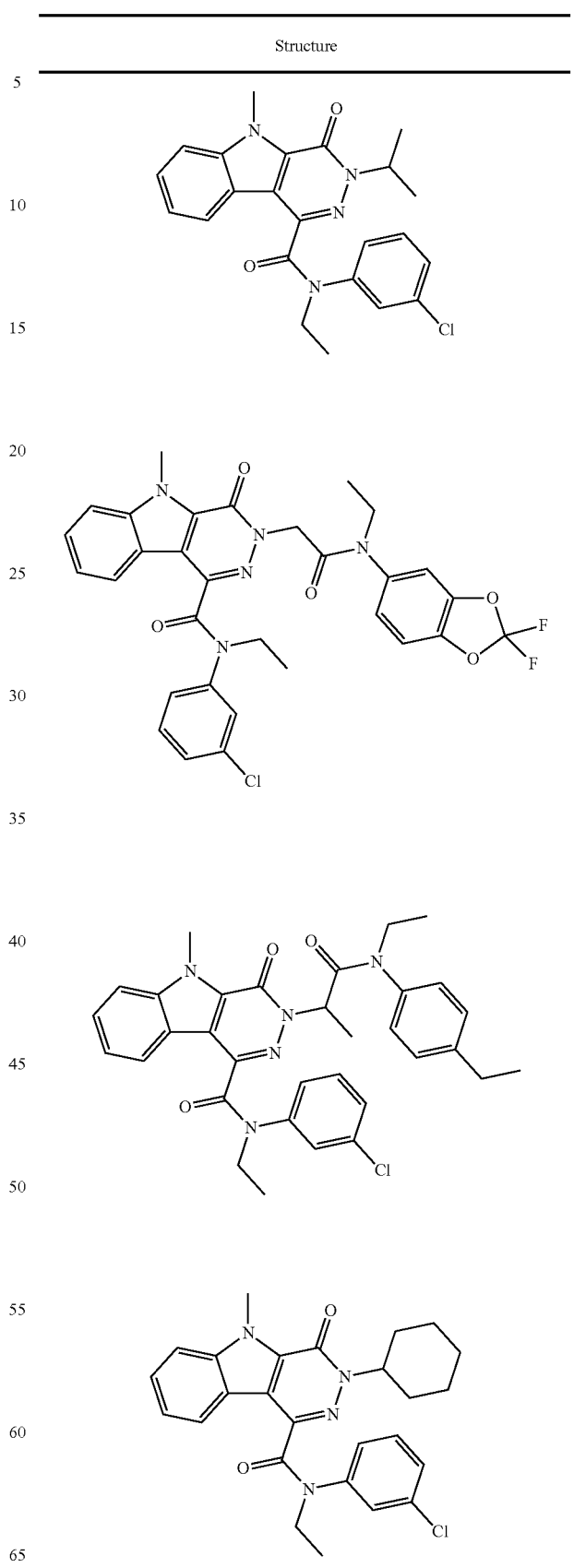 |

TABLE A-continued
| Structure |
|---|
| 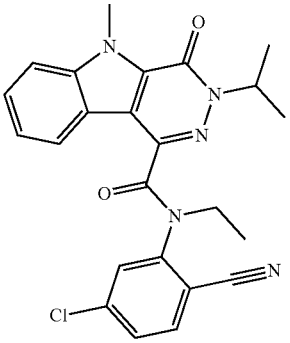 [SMILES: CCN(C(=O)c1nn(C(C)C)c(=O)c2c1c1ccccc1n2C)c1cc(Cl)ccc1C#N] |
| 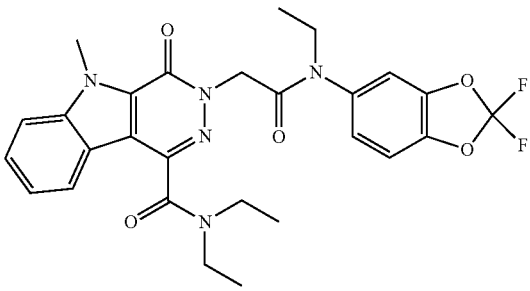 [SMILES: CCN(CC)C(=O)c1nn(CC(=O)N(CC)c2ccc3c(c2)OC(F)(F)O3)c(=O)c2c1c1ccccc1n2C] |
| 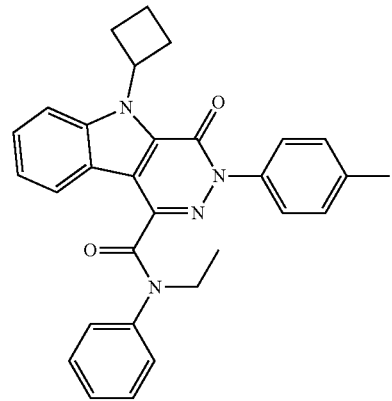 [SMILES: CCN(C(=O)c1nn(-c2ccc(C)cc2)c(=O)c2c1c1ccccc1n2C1CCC1)c1ccccc1] |
| 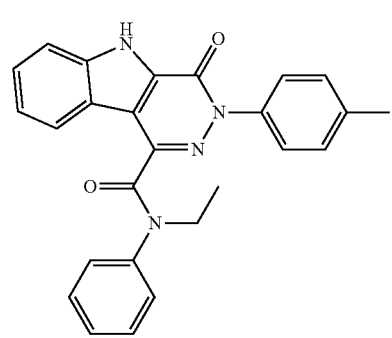 [SMILES: CCN(C(=O)c1nn(-c2ccc(C)cc2)c(=O)c2[nH]c3ccccc3c12)c1ccccc1] |
TABLE A-continued
| Structure |
|---|
| 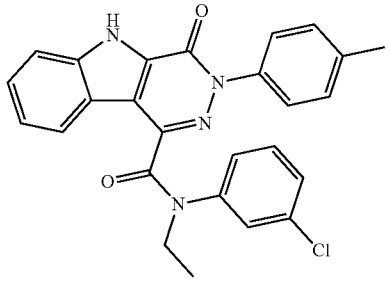 [SMILES: CCN(C(=O)c1nn(-c2ccc(C)cc2)c(=O)c2[nH]c3ccccc3c12)c1cccc(Cl)c1] |
| 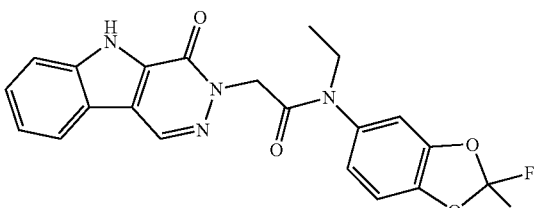 |
| 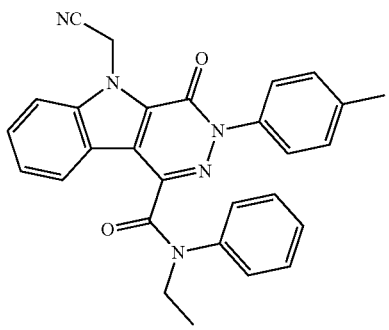 [SMILES: CCN(C(=O)c1nn(-c2ccc(C)cc2)c(=O)c2c1c1ccccc1n2CC#N)c1ccccc1] |
| 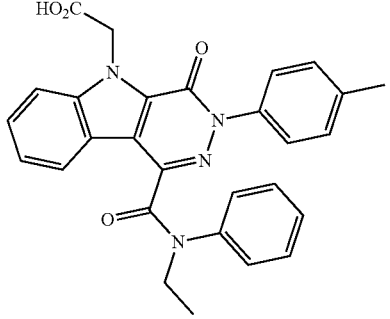 [SMILES: CCN(C(=O)c1nn(-c2ccc(C)cc2)c(=O)c2c1c1ccccc1n2CC(=O)O)c1ccccc1] |
| 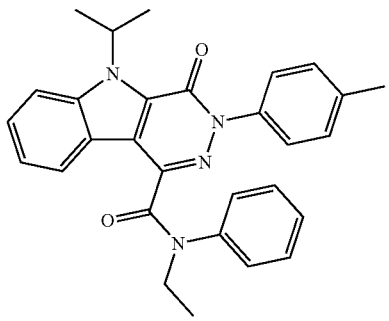 [SMILES: CCN(C(=O)c1nn(-c2ccc(C)cc2)c(=O)c2c1c1ccccc1n2C(C)C)c1ccccc1] |

TABLE A-continued

Structure

[chemical structure]

[chemical structure]

[chemical structure]

[chemical structure]

[chemical structure]

TABLE A2

[chemical structure]

[chemical structure]

[chemical structure]

[chemical structure]

[chemical structure]

In a preferred embodiment, the invention relates to a compound selected from Table A2 or a pharmaceutically acceptable salt thereof:

TABLE A2-continued
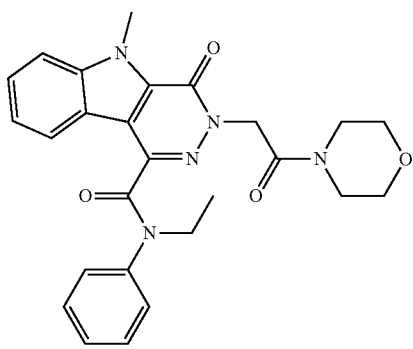 [SMILES: CCN(C(=O)c1nn(CC(=O)N2CCOCC2)c(=O)c2c1c1ccccc1n2C)c1ccccc1]
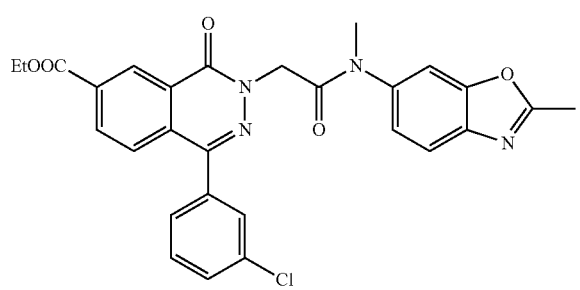 [SMILES: CCOC(=O)c1ccc2c(-c3cccc(Cl)c3)nn(CC(=O)N(C)c3ccc4nc(C)oc4c3)c(=O)c2c1]
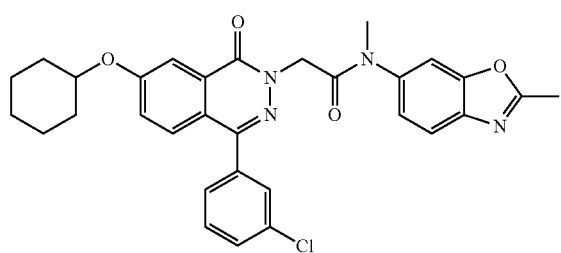
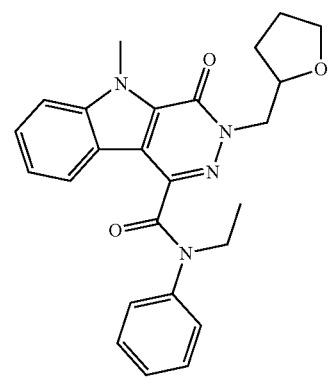 [SMILES: CCN(C(=O)c1nn(CC2CCCO2)c(=O)c2c1c1ccccc1n2C)c1ccccc1]
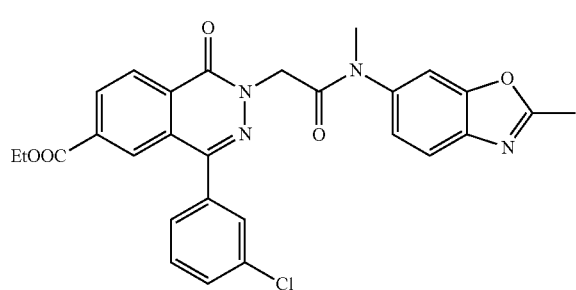 [SMILES: CCOC(=O)c1ccc2c(=O)n(CC(=O)N(C)c3ccc4nc(C)oc4c3)nc(-c3cccc(Cl)c3)c2c1]
TABLE A2-continued
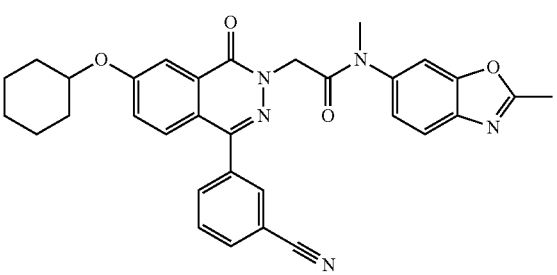 [SMILES: Cc1nc2ccc(N(C)C(=O)Cn3nc(-c4cccc(C#N)c4)c4ccc(OC5CCCCC5)cc4c3=O)cc2o1]
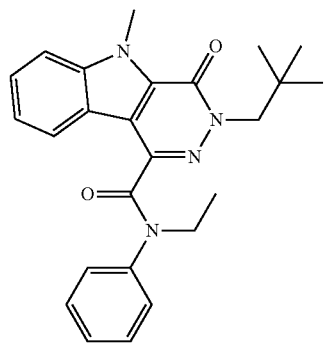 [SMILES: CCN(C(=O)c1nn(CC(C)(C)C)c(=O)c2c1c1ccccc1n2C)c1ccccc1]
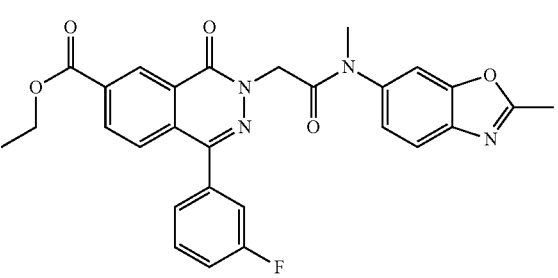 [SMILES: CCOC(=O)c1ccc2c(-c3cccc(F)c3)nn(CC(=O)N(C)c3ccc4nc(C)oc4c3)c(=O)c2c1]
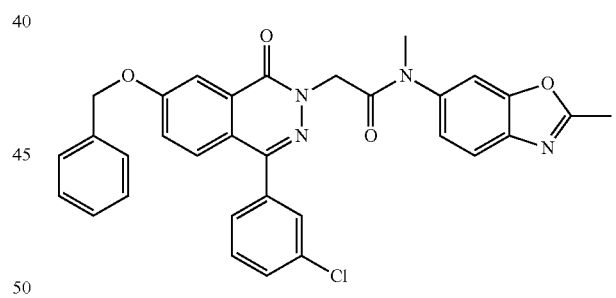
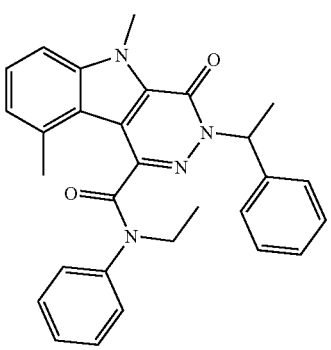 [SMILES: CCN(C(=O)c1nn(C(C)c2ccccc2)c(=O)c2c1c1c(C)cccc1n2C)c1ccccc1]

TABLE A2-continued
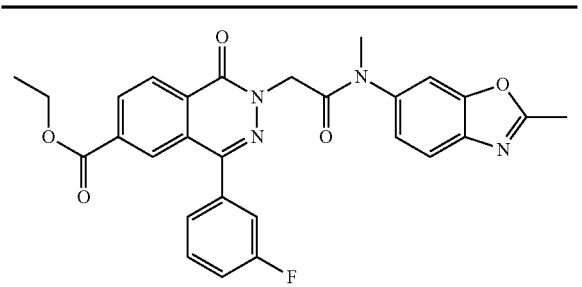
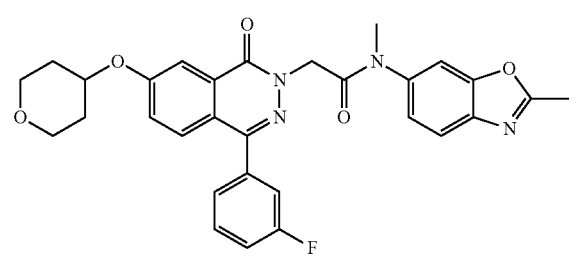
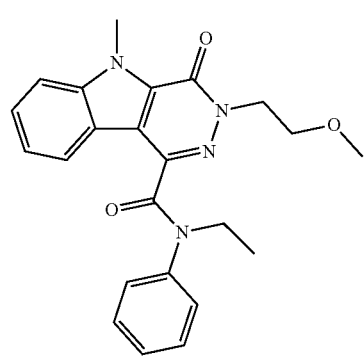 [SMILES: CCN(C(=O)c1nn(CCOC)c(=O)c2c1c1ccccc1n2C)c1ccccc1]
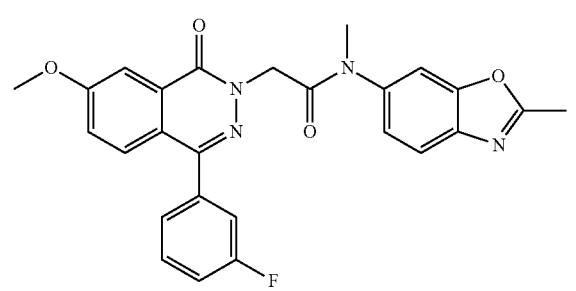
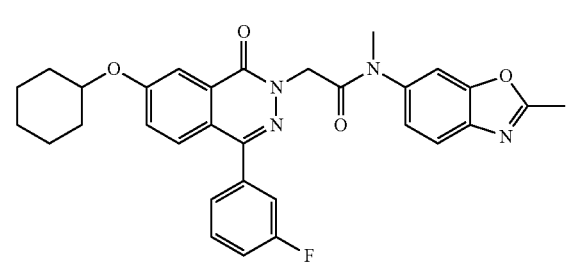 [SMILES: Cc1nc2ccc(N(C)C(=O)Cn3nc(-c4cccc(F)c4)c4ccc(OC5CCCCC5)cc4c3=O)cc2o1]
TABLE A2-continued
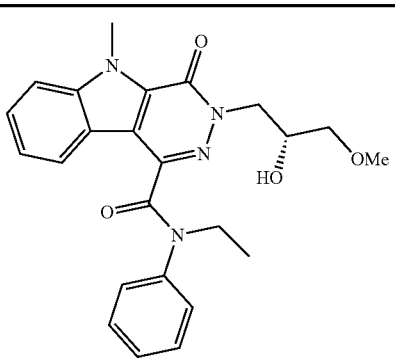
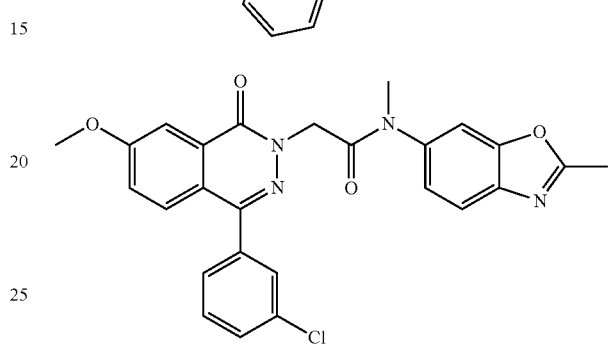
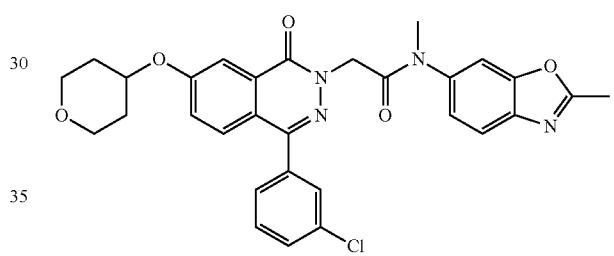
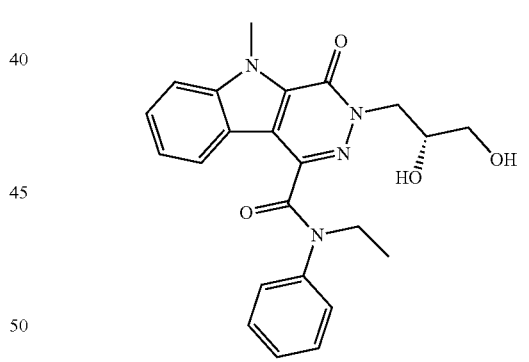
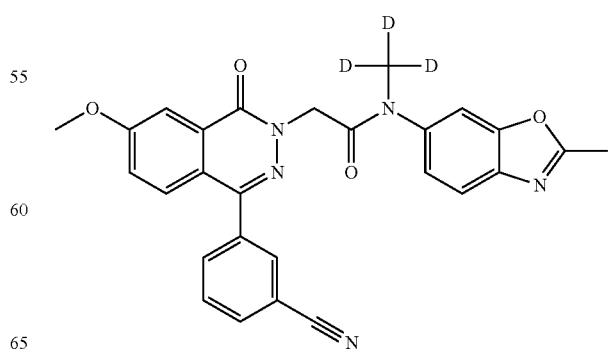

TABLE A2-continued
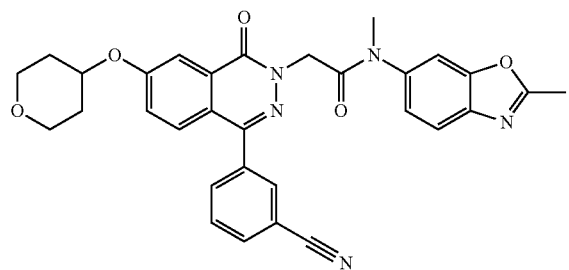 [SMILES: Cc1nc2ccc(N(C)C(=O)Cn3nc(-c4cccc(C#N)c4)c4ccc(OC5CCOCC5)cc4c3=O)cc2o1]
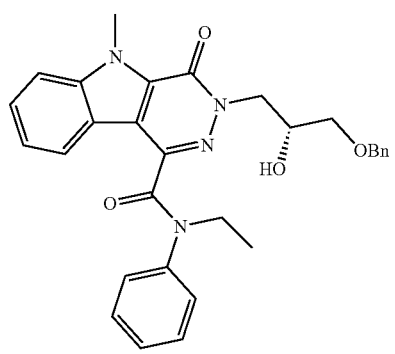 [SMILES: CCN(C(=O)c1nn(C[C@@H](O)COCc2ccccc2)c(=O)c2c1c1ccccc1n2C)c1ccccc1]
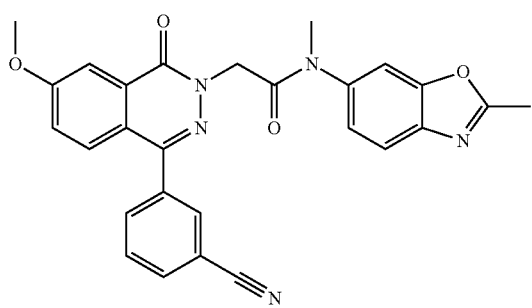 [SMILES: COc1ccc2c(-c3cccc(C#N)c3)nn(CC(=O)N(C)c3ccc4nc(C)oc4c3)c(=O)c2c1]
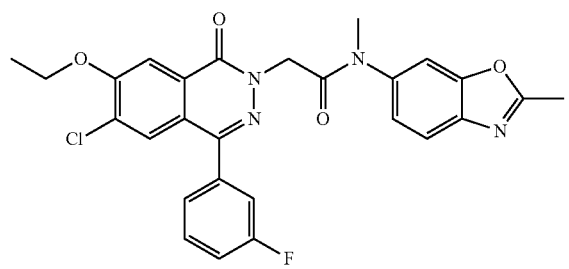
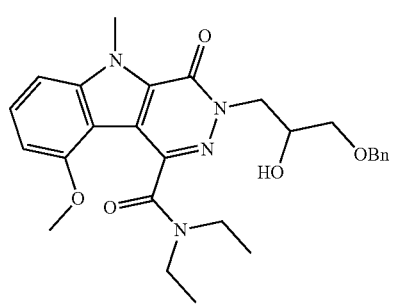 [SMILES: CCN(CC)C(=O)c1nn(CC(O)COCc2ccccc2)c(=O)c2c1c1c(OC)cccc1n2C]
TABLE A2-continued
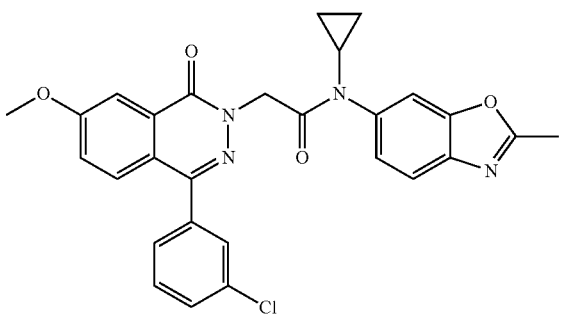
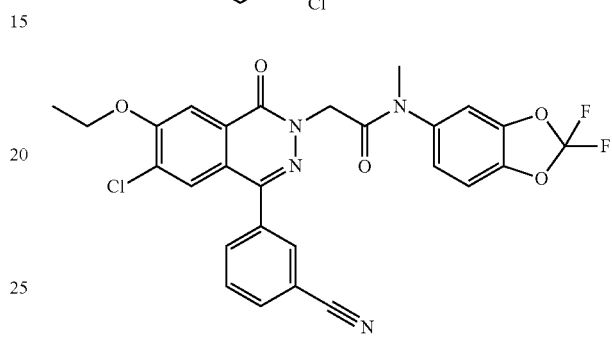
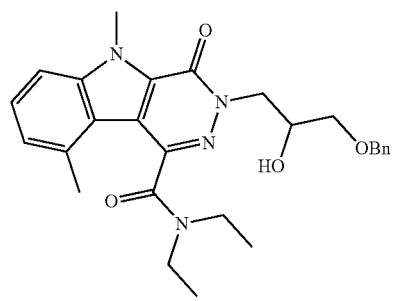 [SMILES: CCN(CC)C(=O)c1nn(CC(O)COCc2ccccc2)c(=O)c2c1c1c(C)cccc1n2C]
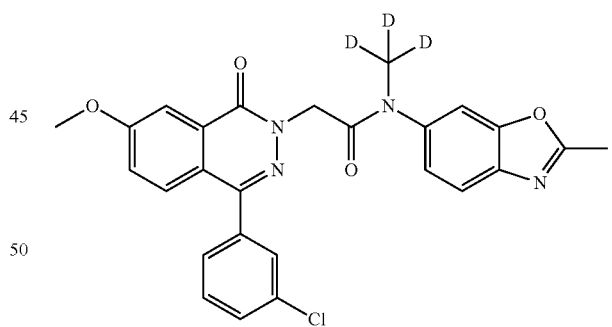
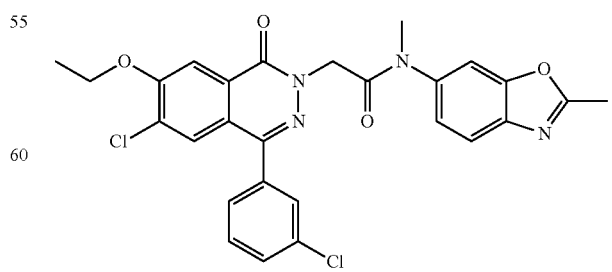

TABLE A2-continued
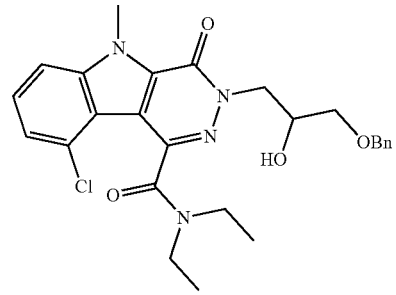 [SMILES: CCN(CC)C(=O)c1nn(CC(O)COCc2ccccc2)c(=O)c2c1c1c(Cl)cccc1n2C]
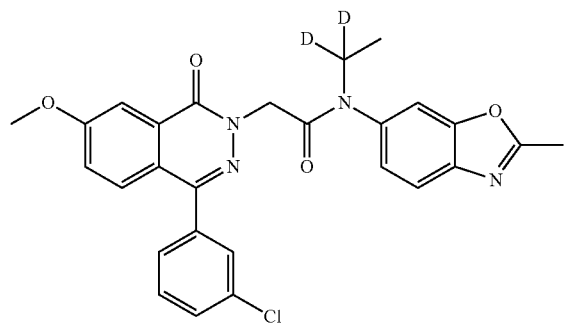
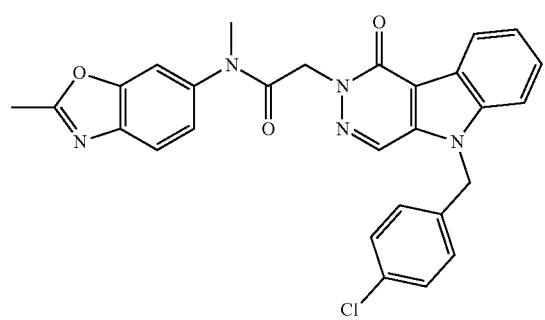
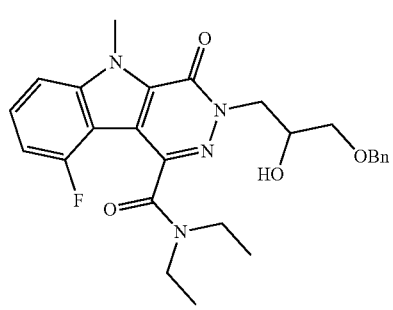
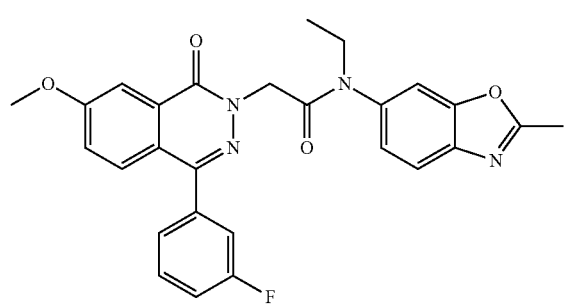
TABLE A2-continued
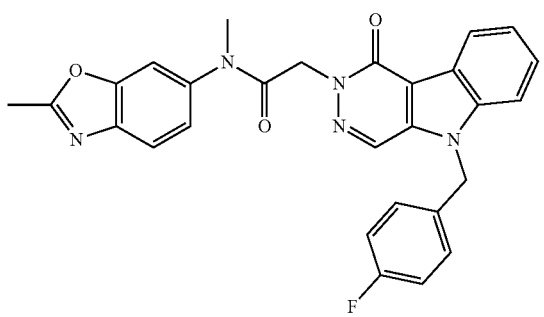 [SMILES: Cc1nc2ccc(N(C)C(=O)Cn3ncc4c(c3=O)c3ccccc3n4Cc3ccc(F)cc3)cc2o1]
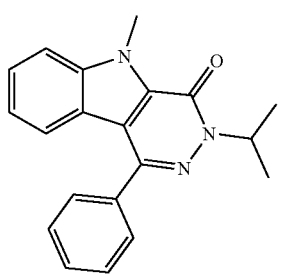 [SMILES: CC(C)n1nc(-c2ccccc2)c2c3ccccc3n(C)c2c1=O]
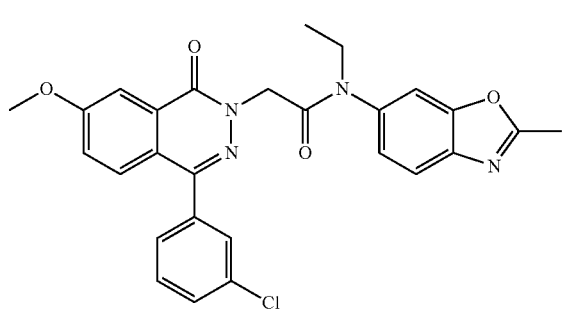
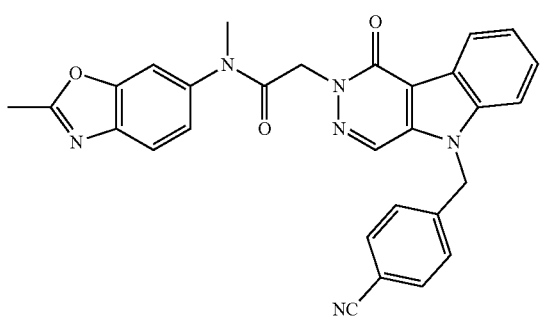 [SMILES: Cc1nc2ccc(N(C)C(=O)Cn3ncc4c(c3=O)c3ccccc3n4Cc3ccc(C#N)cc3)cc2o1]
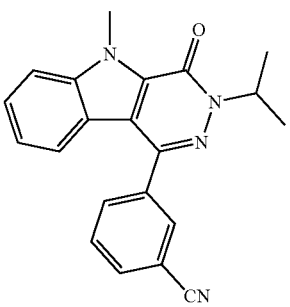 [SMILES: CC(C)n1nc(-c2cccc(C#N)c2)c2c3ccccc3n(C)c2c1=O]

TABLE A2-continued
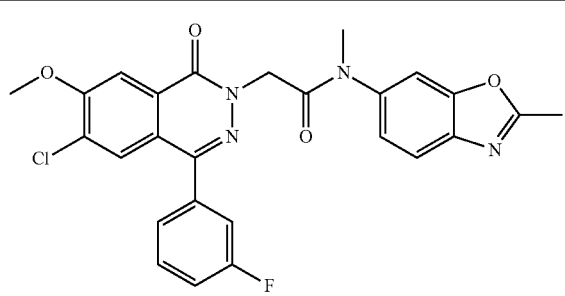
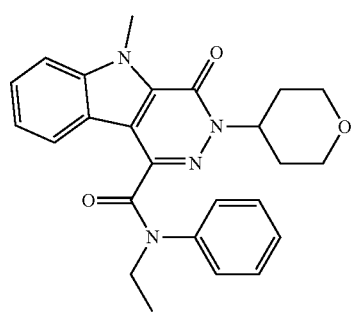 [SMILES: CCN(C(=O)c1nn(C2CCOCC2)c(=O)c2c1c1ccccc1n2C)c1ccccc1]
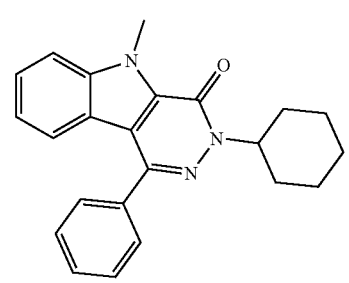 [SMILES: Cn1c2ccccc2c2c(-c3ccccc3)nn(C3CCCCC3)c(=O)c21]
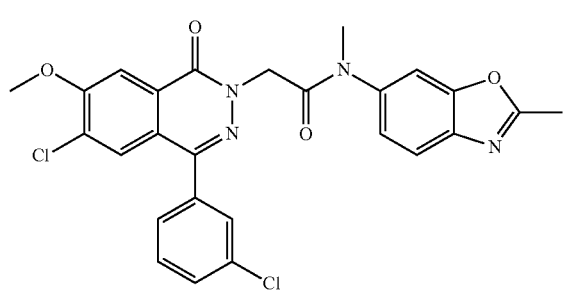
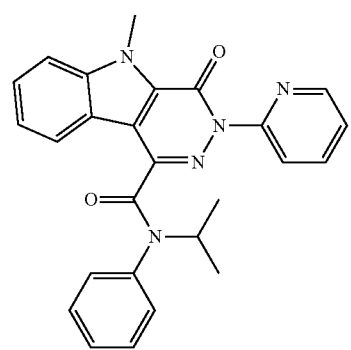 [SMILES: CC(C)N(C(=O)c1nn(-c2ccccn2)c(=O)c2c1c1ccccc1n2C)c1ccccc1]
TABLE A2-continued
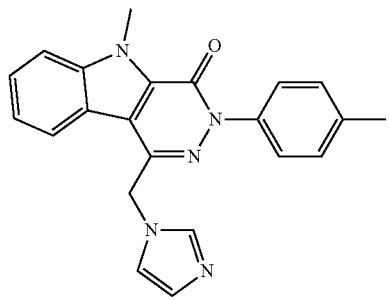 [SMILES: Cc1ccc(-n2nc(Cn3ccnc3)c3c4ccccc4n(C)c3c2=O)cc1]
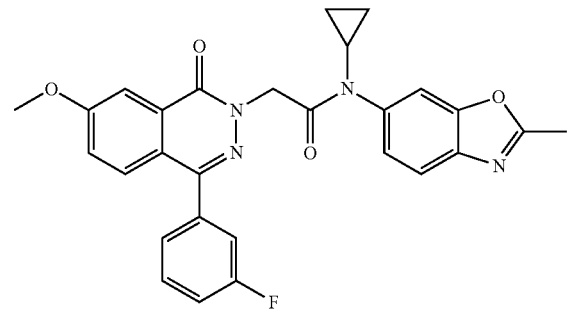
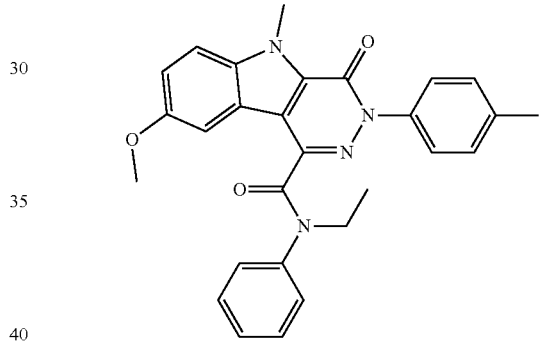
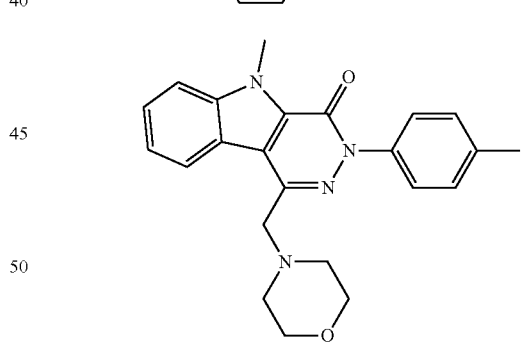
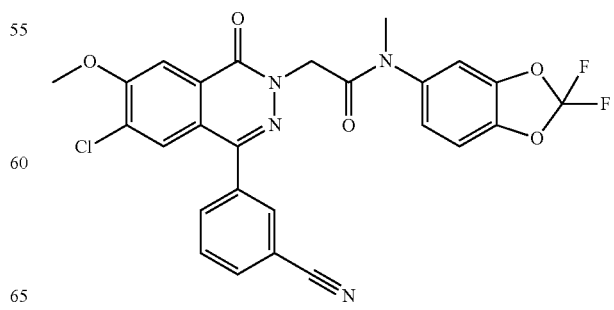

TABLE A2-continued
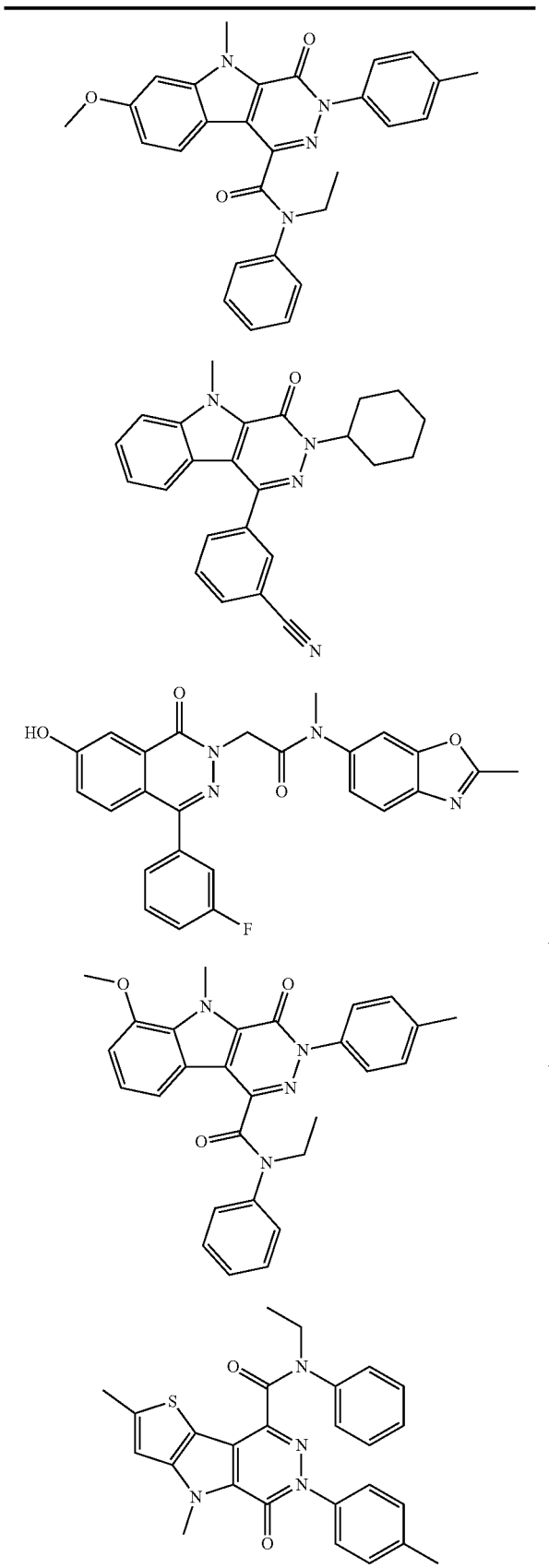
TABLE A2-continued
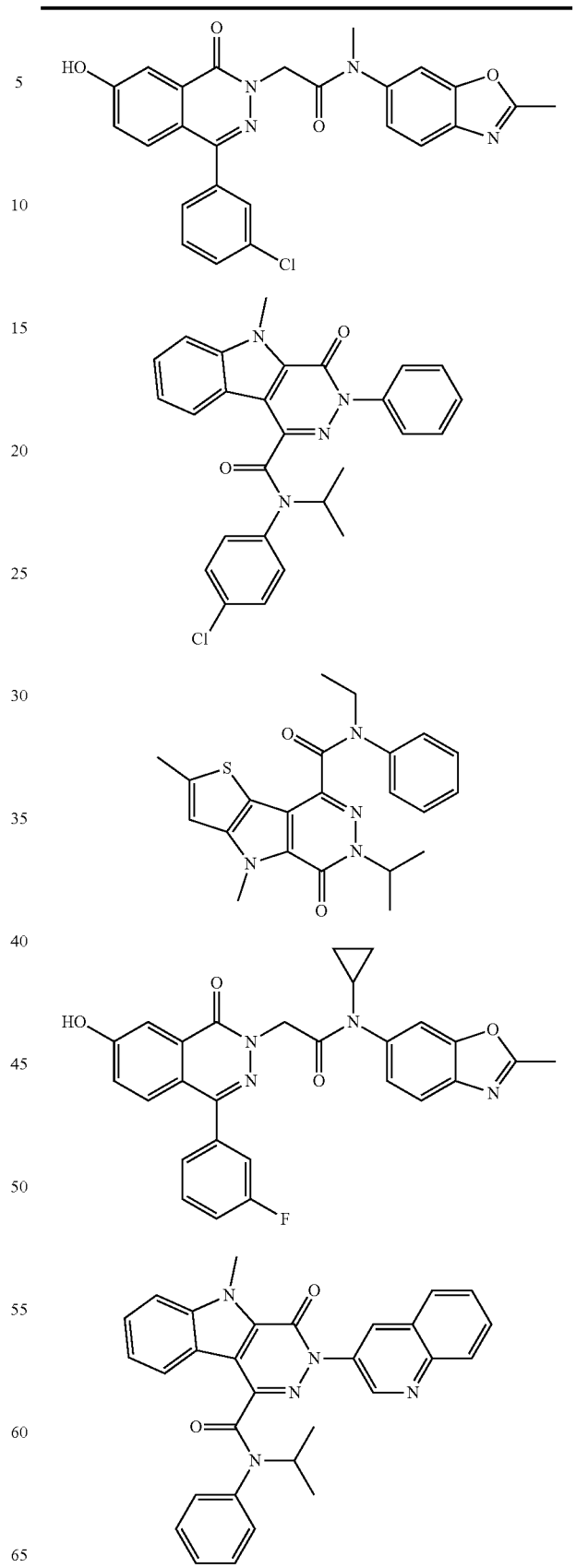

TABLE A2-continued
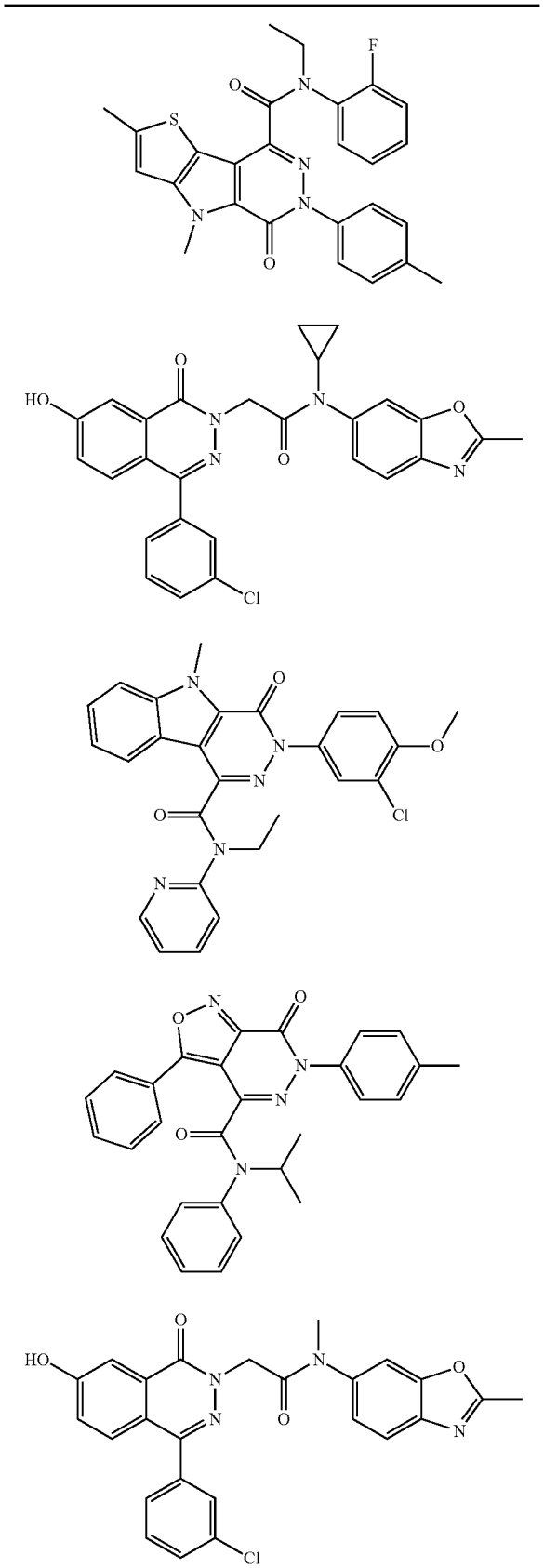
TABLE A2-continued
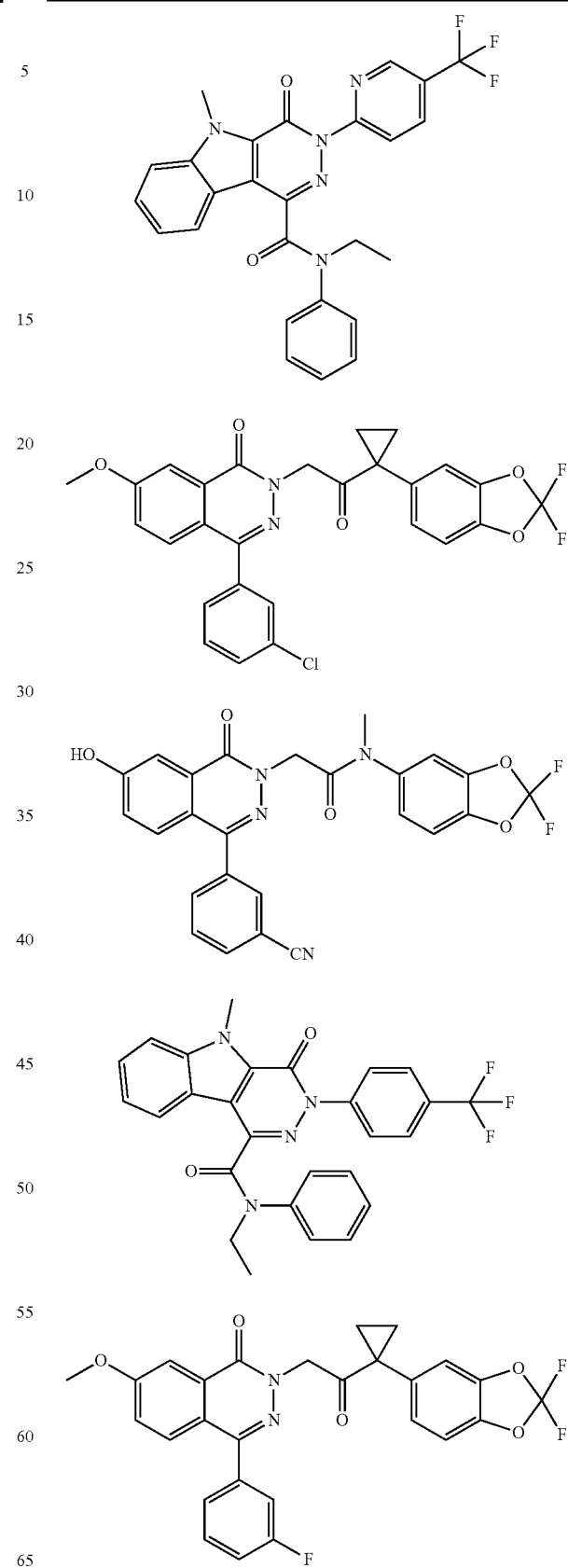

TABLE A2-continued
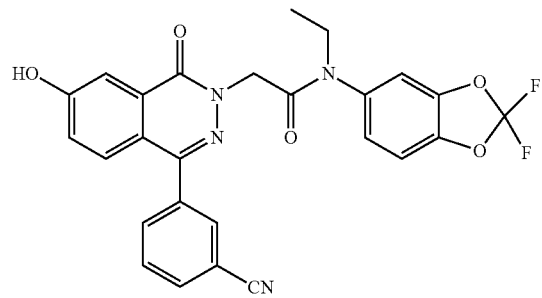 [SMILES: CCN(C(=O)Cn1nc(-c2cccc(C#N)c2)c2ccc(O)cc2c1=O)c1ccc2c(c1)OC(F)(F)O2]
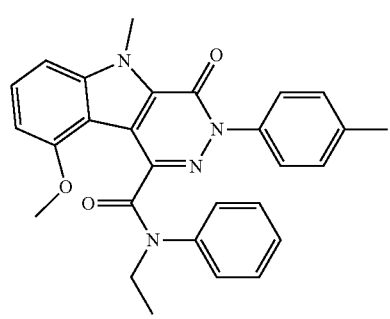 [SMILES: CCN(C(=O)c1nn(-c2ccc(C)cc2)c(=O)c2c1c1c(OC)cccc1n2C)c1ccccc1]
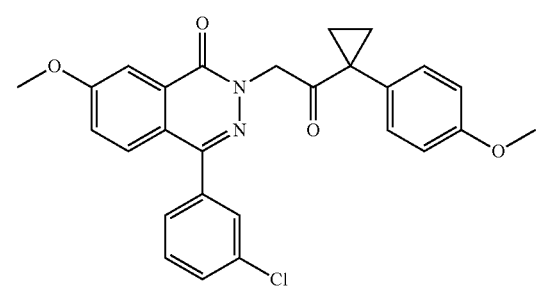
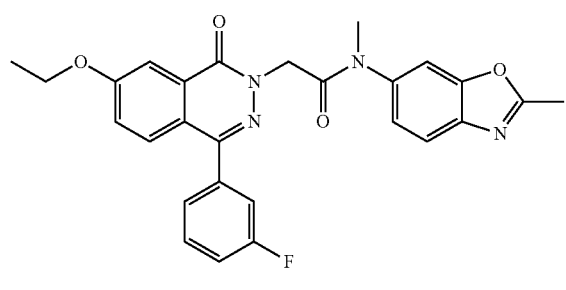 [SMILES: CCOc1ccc2c(-c3cccc(F)c3)nn(CC(=O)N(C)c3ccc4nc(C)oc4c3)c(=O)c2c1]
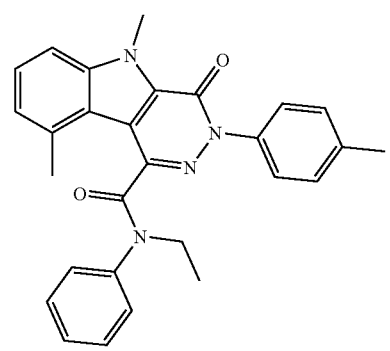 [SMILES: CCN(C(=O)c1nn(-c2ccc(C)cc2)c(=O)c2c1c1c(C)cccc1n2C)c1ccccc1]
TABLE A2-continued
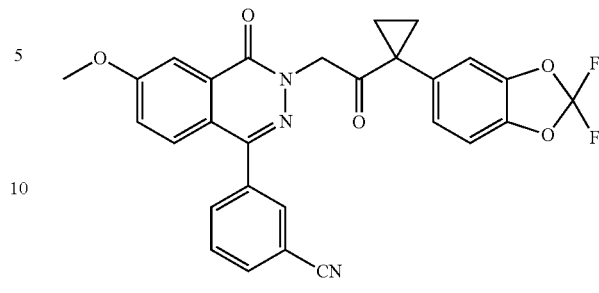
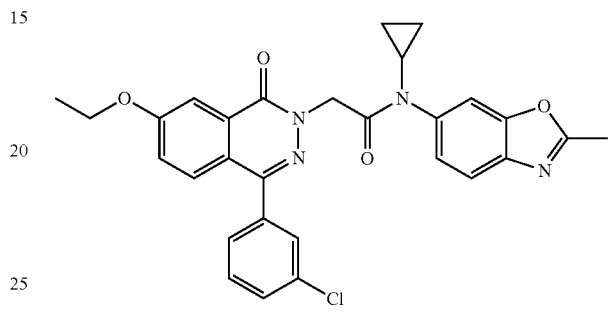
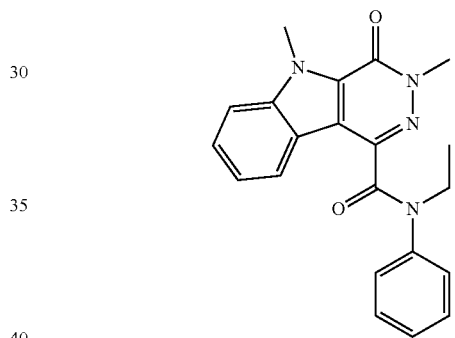
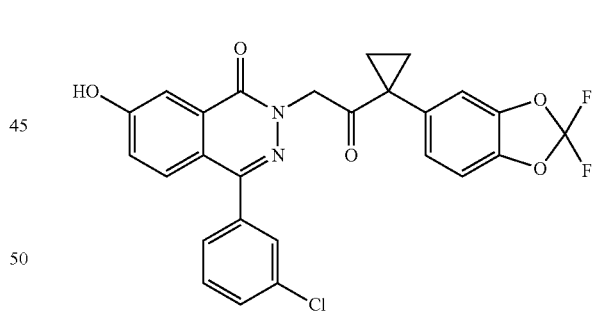
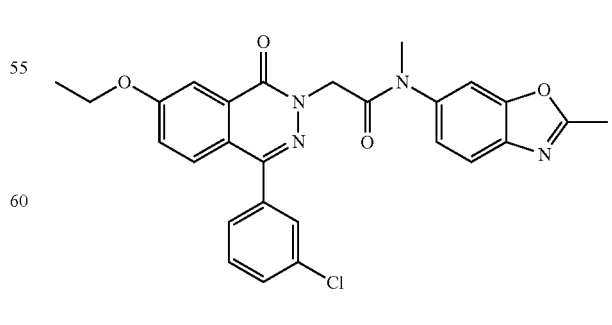

TABLE A2-continued
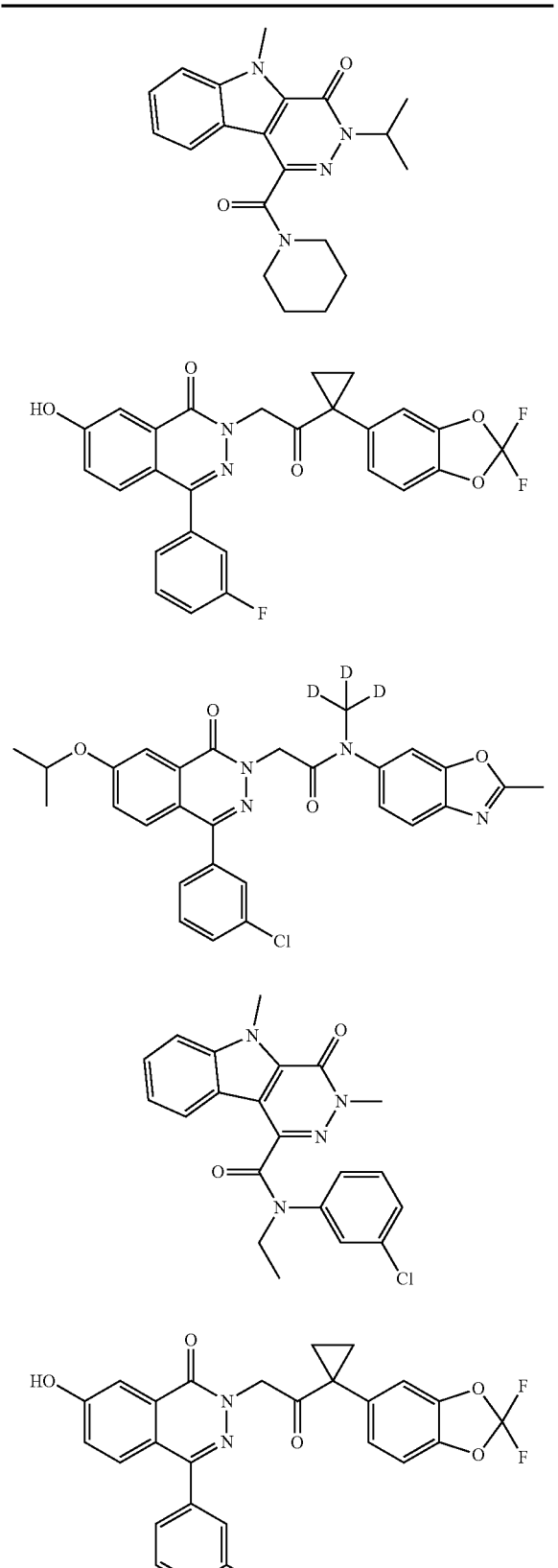
TABLE A2-continued
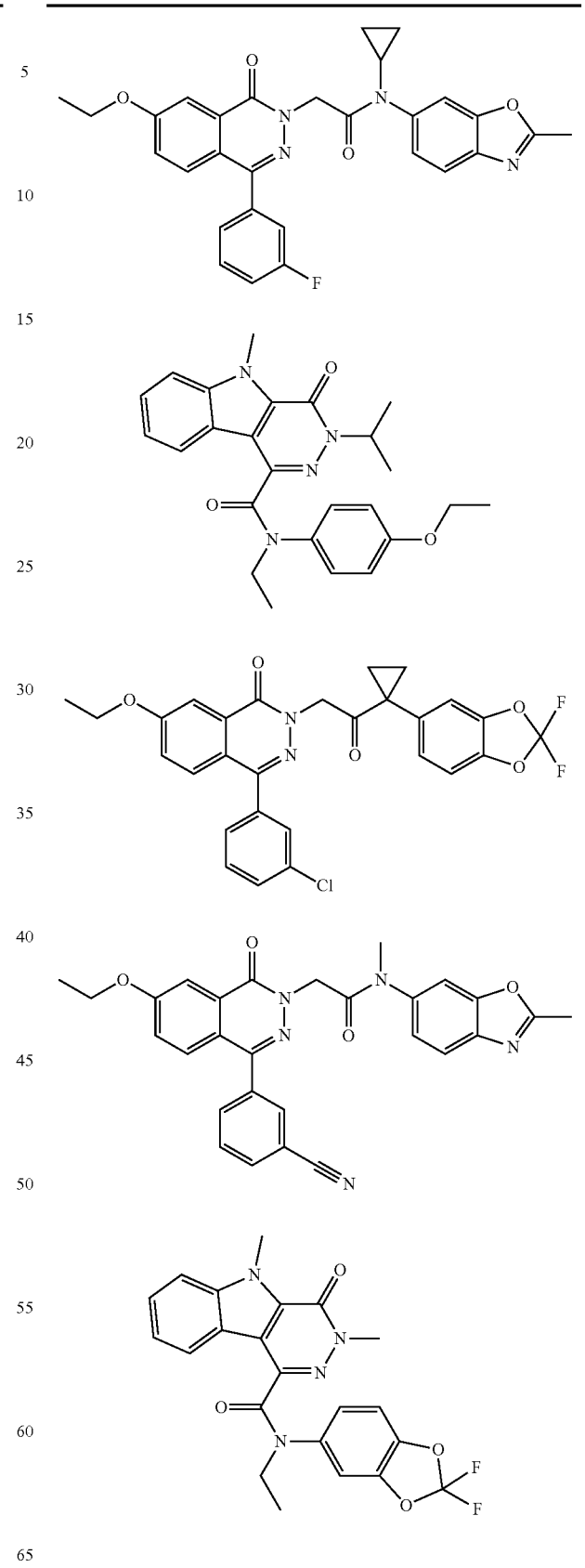

TABLE A2-continued
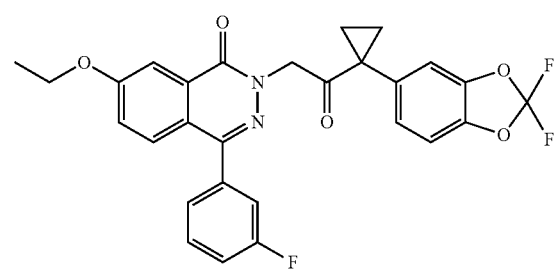 [SMILES: CCOc1ccc2c(-c3cccc(F)c3)nn(CC(=O)C3(c4ccc5c(c4)OC(F)(F)O5)CC3)c(=O)c2c1]
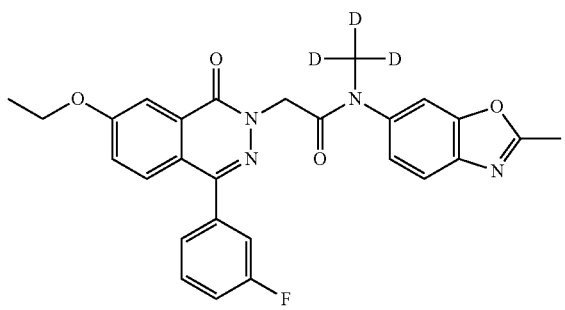 [SMILES: [2H]C([2H])([2H])N(C(=O)Cn1nc(-c2cccc(F)c2)c2ccc(OCC)cc2c1=O)c1ccc2nc(C)oc2c1]
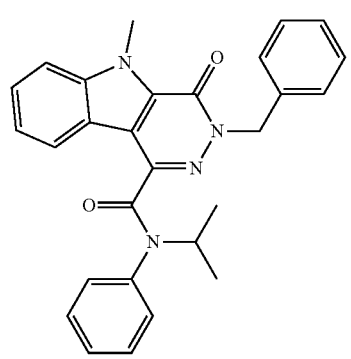 [SMILES: CC(C)N(C(=O)c1nn(Cc2ccccc2)c(=O)c2c1c1ccccc1n2C)c1ccccc1]
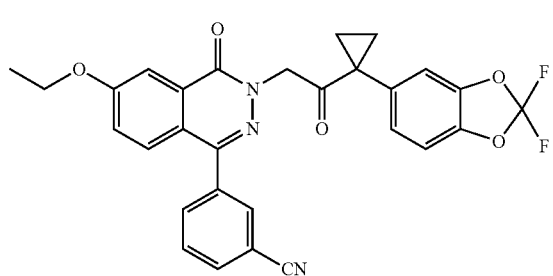 [SMILES: CCOc1ccc2c(-c3cccc(C#N)c3)nn(CC(=O)C3(c4ccc5c(c4)OC(F)(F)O5)CC3)c(=O)c2c1]
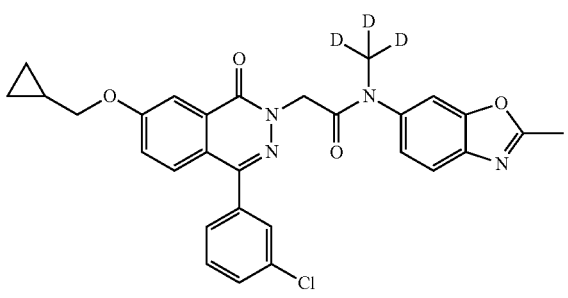 [SMILES: [2H]C([2H])([2H])N(C(=O)Cn1nc(-c2cccc(Cl)c2)c2ccc(OCC3CC3)cc2c1=O)c1ccc2nc(C)oc2c1]
TABLE A2-continued
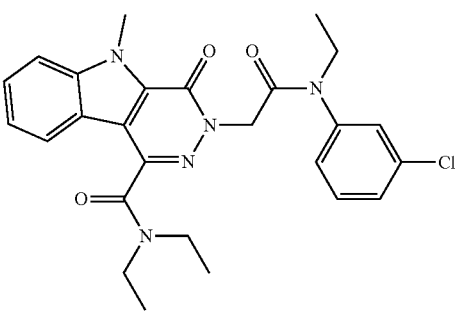 [SMILES: CCN(CC)C(=O)c1nn(CC(=O)N(CC)c2cccc(Cl)c2)c(=O)c2c1c1ccccc1n2C]
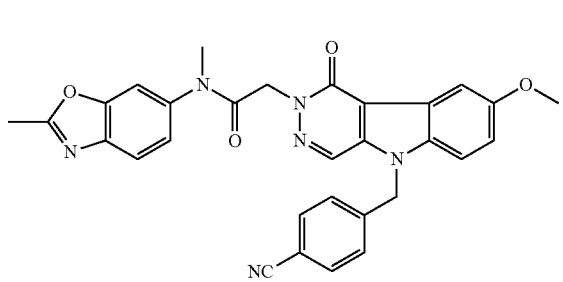
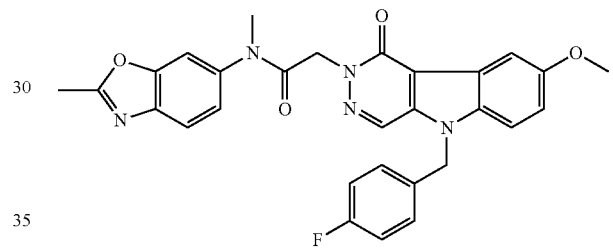
The compounds of this invention may be prepared by methods known in the art. Exemplary synthetic routes to prepare compounds of this invention are illustrated below:
Scheme 1:
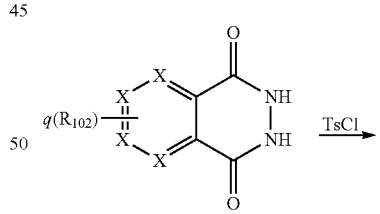
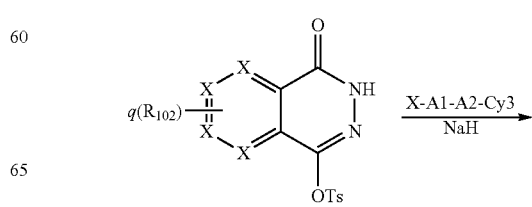

Scheme 2:
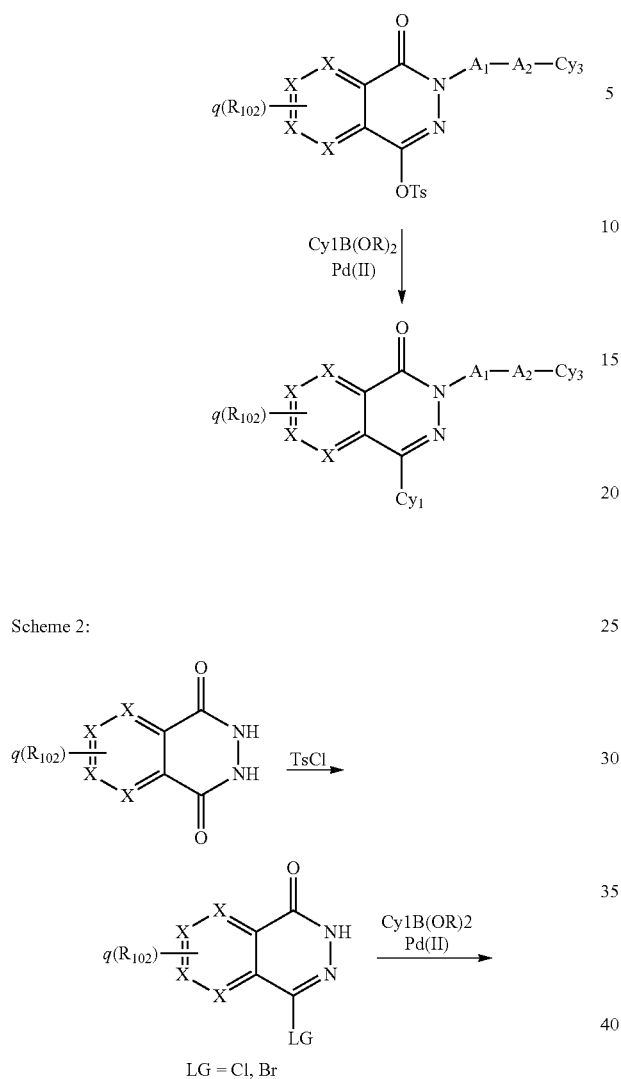
Scheme 3:
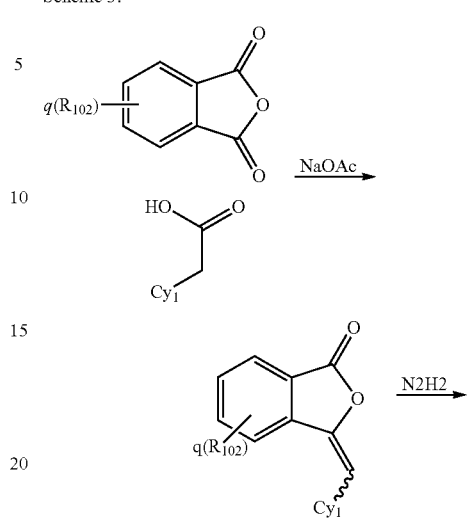
Scheme 4:
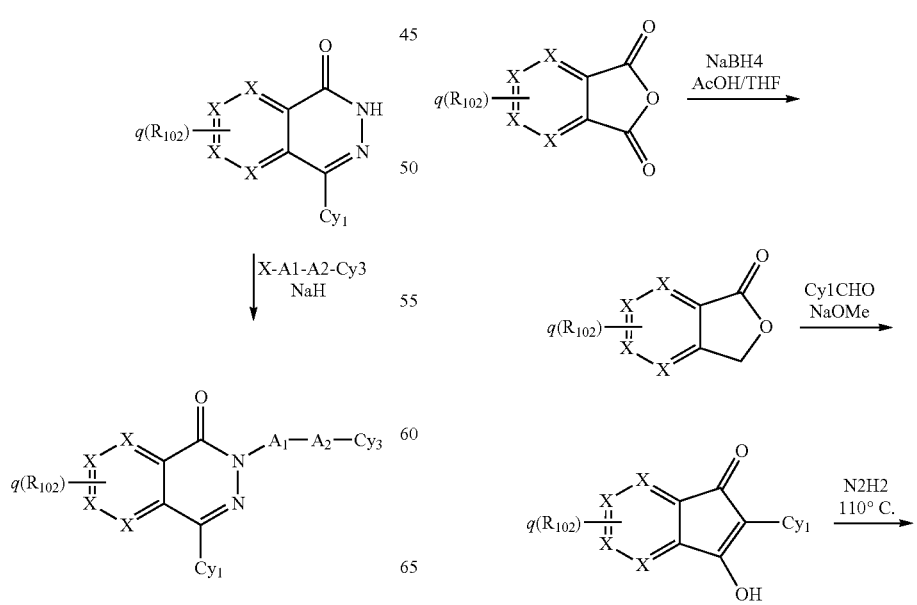

83
-continued
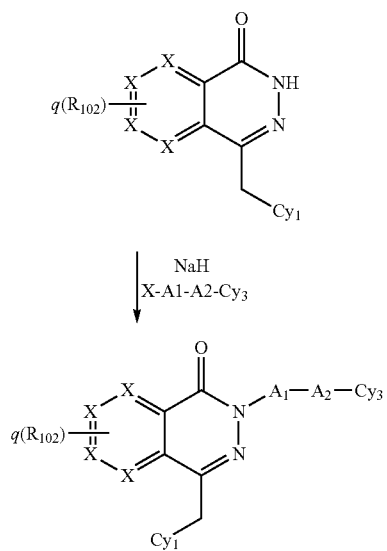
Scheme 5:
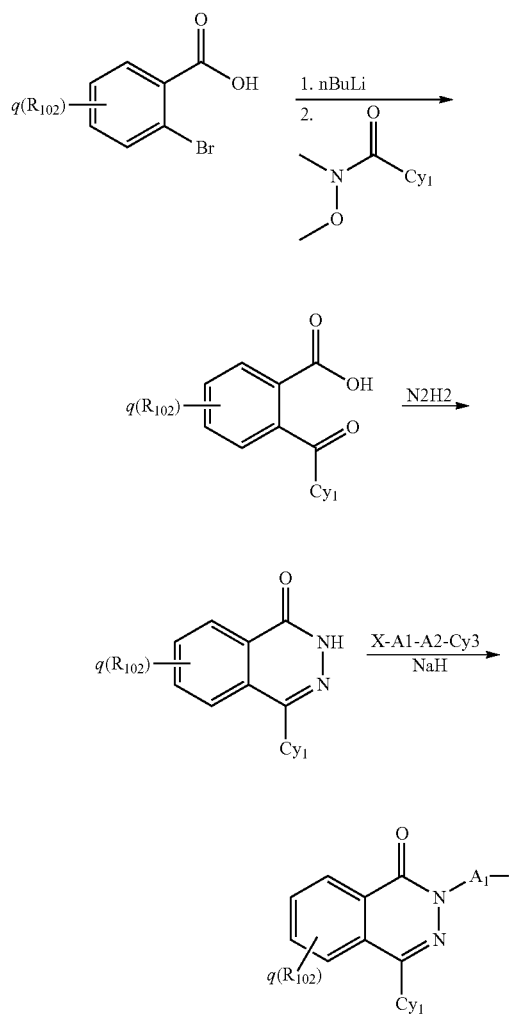
84
Scheme 6
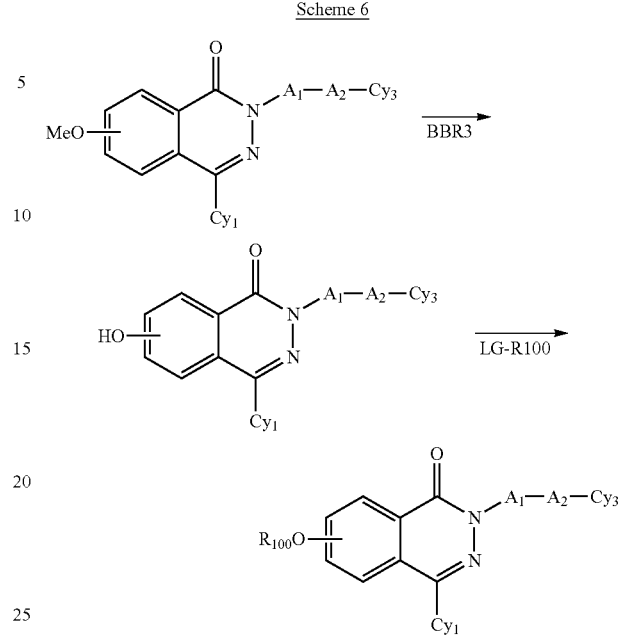
Scheme 7
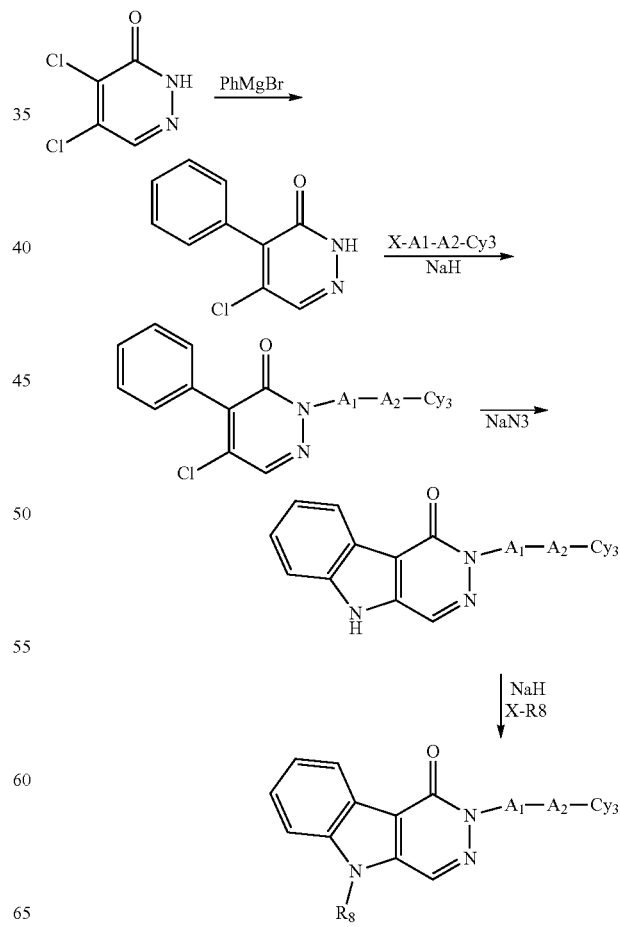

Scheme 8
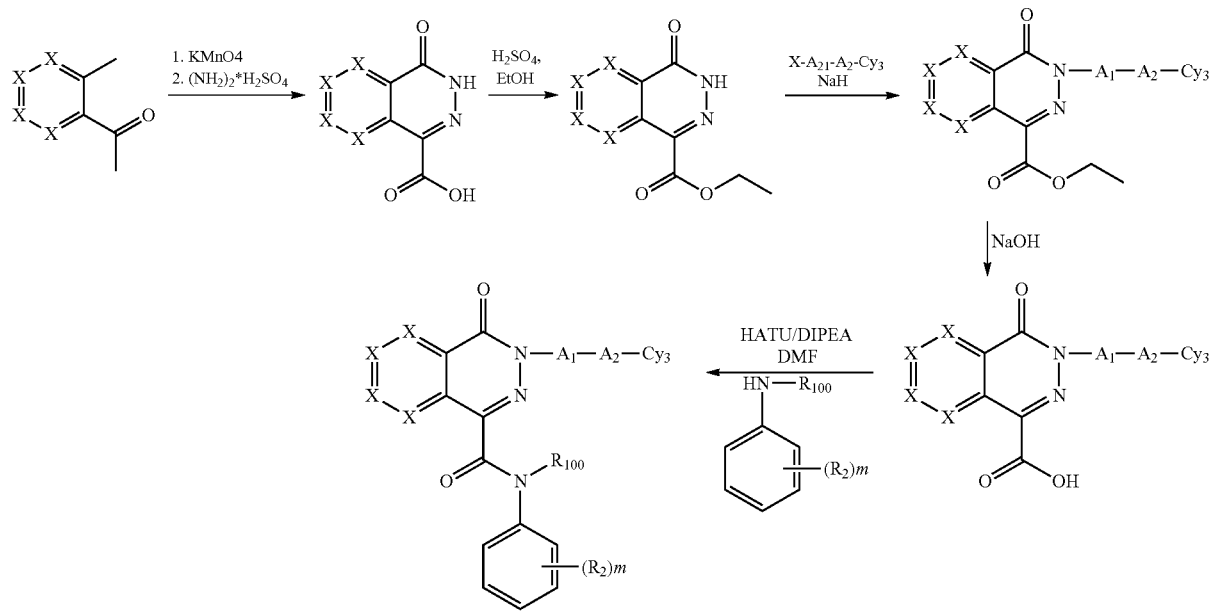
Scheme 9
Scheme 10
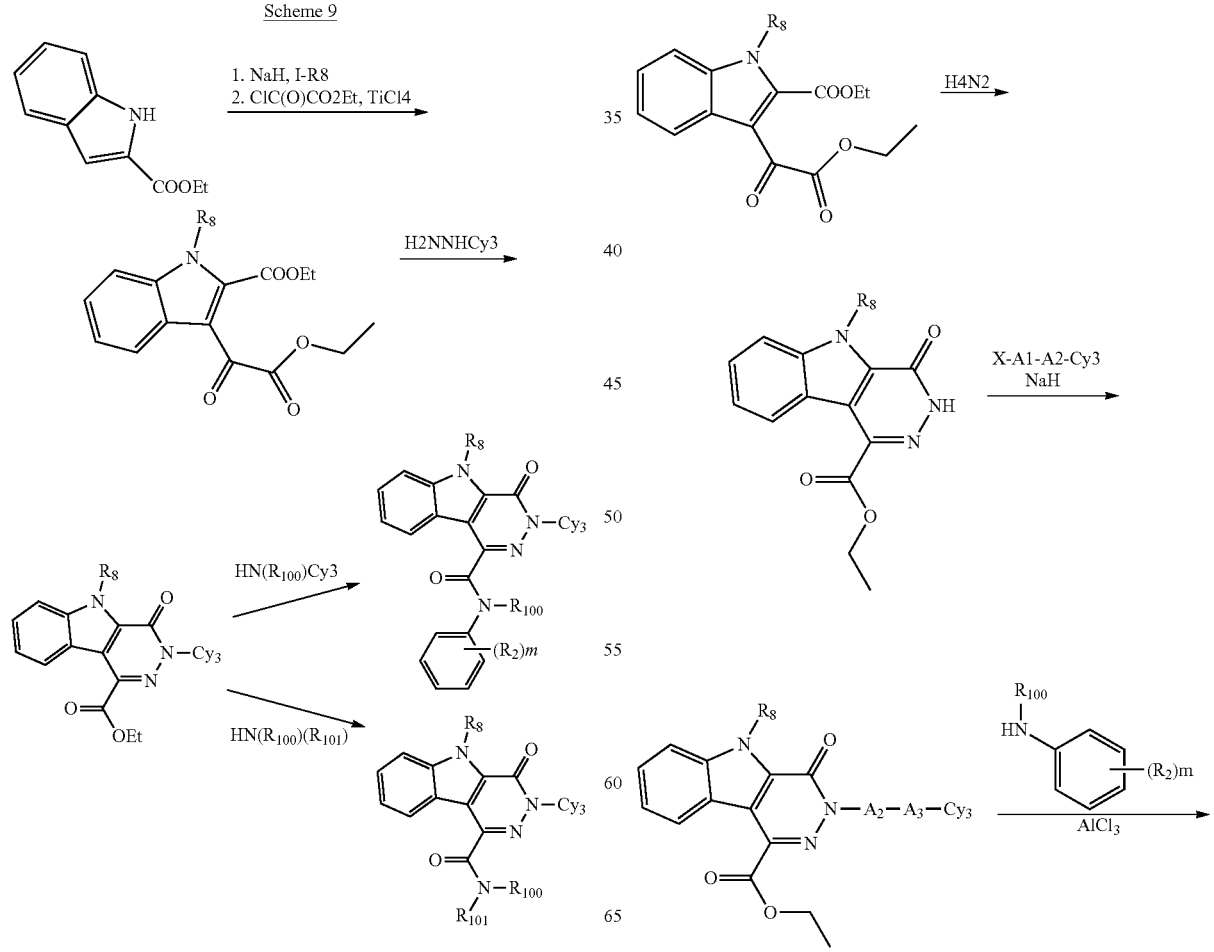

Scheme 11
Scheme 12
Scheme 13
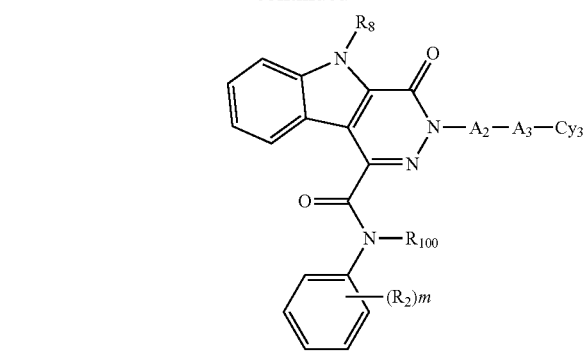
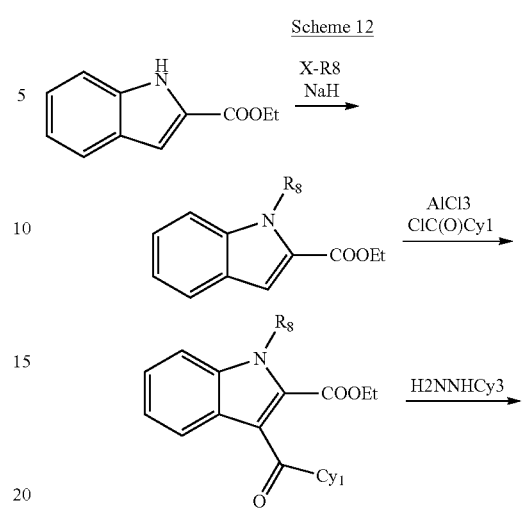
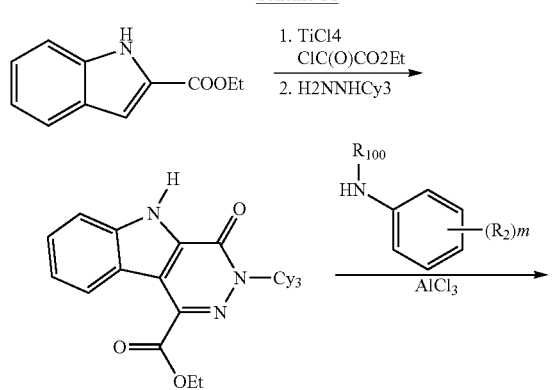
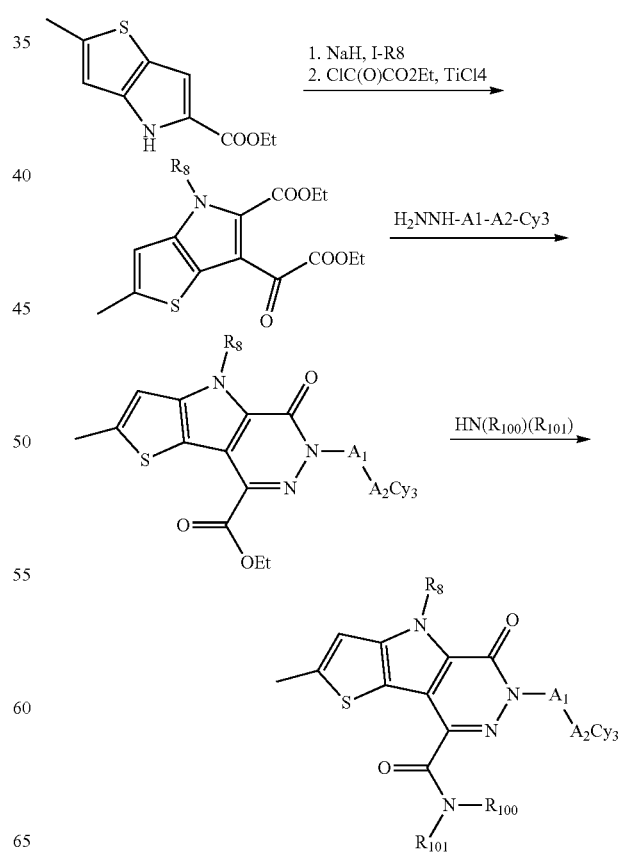

Scheme 14

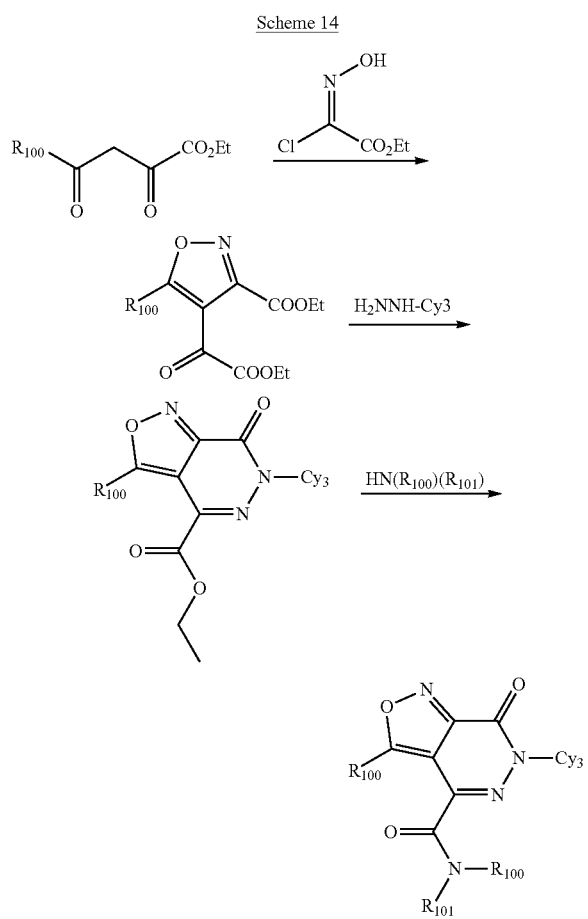

Scheme 15

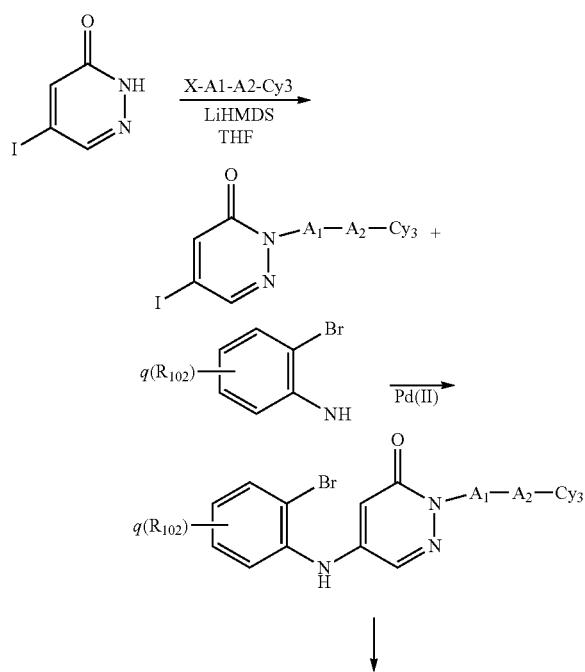

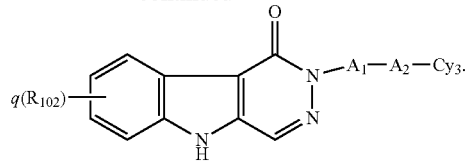

Compounds of the invention are useful as modulators of CFTR and treating diseases or disorders mediated by CFTR such as for the treatment of disease, disorders or conditions such as cystic fibrosis, hereditary emphysema, hereditary hemochromatosis, coagulation-fibrinolysis deficiencies, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's disease, Spinocerebullar ataxia type I, Spinal and bulbar muscular atrophy, Dentororubal pallidoluysian, and Myotic dystrophy, as well as, spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1, 3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1, 3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches.

The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1, 2, 4-triazolyl, 1H-1, 2, 3-triazolyl, 2H-1, 2, 3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1, 5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1, 2, 4-oxadiazolyl, 1, 3, 4-oxadiazolyl, 1, 2, 5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1, 2, 4-thiadiazolyl, 1, 3, 4-thiadiazolyl, 1, 2, 5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N, N-alkylamino, such as N-methylamino, N-ethylamino, N, N-dimethylamino, N, N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. CH₃—CH₂—), or in other instances, a bivalent linking moiety can be "alkyl," in which case those skilled in the art will understand the alkyl to be a divalent radical (e.g., —CH₂—CH₂—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

Example 1

Synthesis of N-ethyl-N-(4-ethylphenyl)-2-(1-oxo-4-phenylphthalazin-2(1H)-yl)acetamide

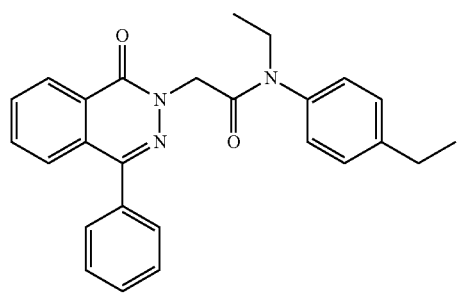 [SMILES: CCc1ccc(N(CC)C(=O)Cn2nc(-c3ccccc3)c3ccccc3c2=O)cc1]

2-bromo-N-ethyl-N-(4-ethylphenyl)acetamide

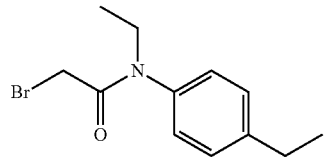

4-Ethylaniline (5.13 mL, 41.3 mmol) in THF (44 mL) was cooled to 0° C. and treated with a solution of acetaldehyde (2.55 mL, 45.4 mmol) and H₂SO₄ (3.09 mL, 12.38 mmol) in THF (117 mL). The resulting white slurry was stirred for 10 min, then treated with NaBH₄ (1.03 g, 27.2 mmol). After 4 hrs, additional NaBH₄ (0.390 g, 10.32 mmol) was added and stirring maintained overnight. The reaction was quenched with sat'd NH₄Cl and extracted with Et₂O. The organic phase was washed with brine, dried over MgSO₄ and evaporated to dryness. The crude product was purified by silica gel chromatography (10-20% EtOAc/hexane) to yield 3.0 g (48%) of N,4-diethylaniline. A solution of N,4-diethylaniline (0.5 g, 2.95 mmol), DMAP (0.018 g, 0.147 mmol), and 2-bromoacetic acid (0.975 g, 7.02 mmol) in DCM (29.5 mL) was treated with EDC.HCl (1.35 g, 7.08 mmol) and stirred at rt for 12 hrs. The reaction was diluted with DCM, washed with brine and 2N NaOH, dried over MgSO₄ and evaporated to dryness. The crude product was purified by silica gel chromatography (10-20% EtOAc/pet ether) to yield 2-bromo-N-ethyl-N-(4-ethylphenyl)acetamide (650 mg).

4-oxo-3, 4-dihydrophthalazin-1-yl 4-methylbenzenesulfonate

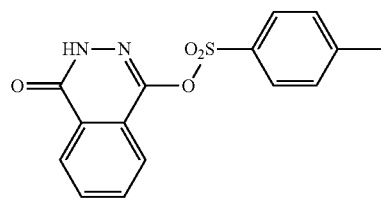 [SMILES: Cc1ccc(S(=O)(=O)Oc2n[nH]c(=O)c3ccccc23)cc1]

A solution of 2, 3-dihydrophthalazine-1,4-dione (10 g, 61.7 mmol) in pyridine (190 mL) under N₂ was treated with tosyl chloride (11.76 g, 61.7 mmol), heated to reflux for 3 hrs, and then stirred at rt overnight. The reaction was concentrated and dissolved in 1:1 EtOAc and sat'd NaHCO₃. The precipitate was filtered, washed with water, EtOAc, and sat'd NaHCO₃, and then dried overnight to yield 4-oxo-3, 4-dihydrophthalazin-1-yl 4-methylbenzenesulfonate (12.9 g, 66%) (MS: ESI+ve, 317 [M+H]).

3-(2-(ethyl(4-ethylphenyl)amino)-2-oxoethyl)-4-oxo-3, 4-dihydrophthalazin-1-yl 4-methylbenzenesulfonate Example 1

N-ethyl-N-(4-ethylphenyl)-2-(1-oxo-4-phenyl-phthalazin-2(1H)-yl)acetamide

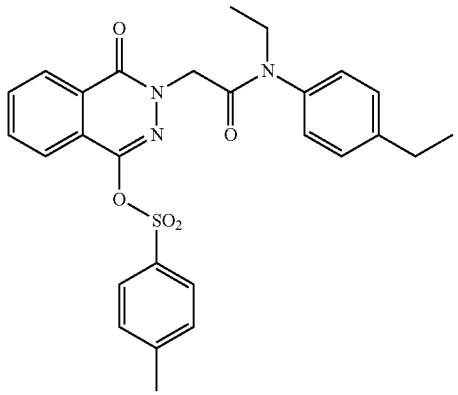 [SMILES: CCc1ccc(N(CC)C(=O)Cn2nc(OS(=O)(=O)c3ccc(C)cc3)c3ccccc3c2=O)cc1]

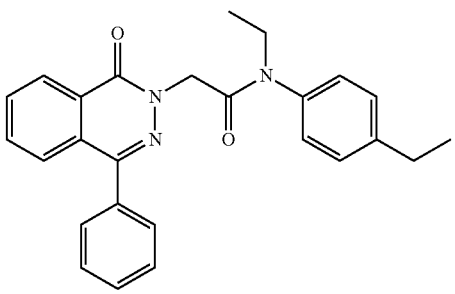 [SMILES: CCc1ccc(N(CC)C(=O)Cn2nc(-c3ccccc3)c3ccccc3c2=O)cc1]

NaH (60%) (0.306 g, 7.64 mmol) was suspended in DMF (66 mL) and treated with 4-oxo-3,4-dihydrophthalazin-1-yl 4-methylbenzenesulfonate (2.10 g, 6.65 mmol) in portions over ~1 min. When the bubbling had subsided, 2-bromo-N-ethyl-N-(4-ethylphenyl)acetamide (1.5 g, 6.65 mmol) and NaI (0.50 g, 3.32 mmol) were added. After stirring overnight, the reaction was quenched by addition of ice, then diluted with DCM. The aq. layer was extracted with DCM (2×), and the combined organic layers were washed 4×5% LiCl (aq) and brine, dried with $MgSO_4$, and evaporated onto silica gel. The material was chromatographed (20% EtOAc/pet ether) to yield 3-(2-(ethyl(4-ethylphenyl)amino)-2-oxoethyl)-4-oxo-3, 4-dihydrophthalazin-1-yl 4-methylbenzenesulfonate (1.62 g, 48%), (MS: ESI+ve, 506 [M+H]).

A microwave vial containing 3-(2-(ethyl(4-ethylphenyl)amino)-2-oxoethyl)-4-oxo-3, 4-dihydrophthalazin-1-yl 4-methylbenzenesulfonate (50 mg, 0.099 mmol), phenylboronic acid (24.12 mg, 0.198 mmol), $Na_2CO_3$ (26.2 mg, 0.247 mmol), and bis(triphenylphosphine)palladium (II) chloride (4.86 mg, 6.92 µmol) was flushed with $N_2$, then treated with THF (1.5 mL) and water (0.5 mL). The mixture was heated in the microwave at 155° C. for 45 min. It was filtered and the product extracted 3×EtOAc. The combined organic layers were washed with water and brine, dried over $MgSO_4$, and evaporated to dryness. The resulting material was purified by reverse phase HPLC to deliver N-ethyl-N-(4-ethylphenyl)-2-(1-oxo-4-phenylphthalazin-2(1H)-yl)acetamide (8.8 mg), (MS: ESI+ve, 412 [M+H]).

Representative compounds of the invention were prepared in a similar manner to example 1 (scheme 1) using the appropriate alkylating agent and commercially available boronic acid or boronic ester.

| Example No. | Structure | IUPAC Name | LCMS m/z |
|---|---|---|---|
| 2. | 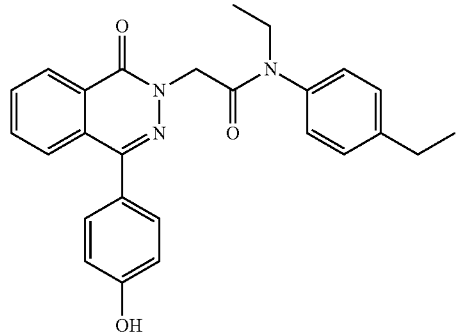 [SMILES: CCc1ccc(N(CC)C(=O)Cn2nc(-c3ccc(O)cc3)c3ccccc3c2=O)cc1] | N-ethyl-N-(4-ethylphenyl)-2-(4-(4-hydroxyphenyl)-1-oxophthalazin-2(1H)-yl)acetamide: | 428 [M + H] |
| 3. | 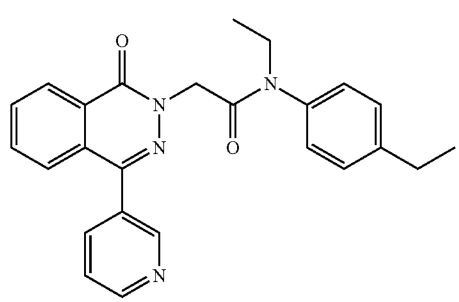 | N-ethyl-N-(4-ethylphenyl)-2-(1-oxo-4-(pyridin-3-yl)phthalazin-2(1H)-yl)acetamide | 413 [M + H] |

-continued

| Example No. | Structure | IUPAC Name | LCMS m/z |
| --- | --- | --- | --- |
| 4. | 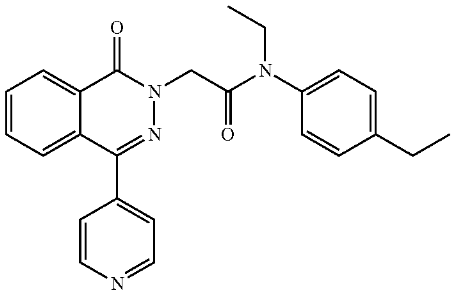 [SMILES: CCc1ccc(N(CC)C(=O)Cn2nc(-c3ccncc3)c3ccccc3c2=O)cc1] | N-ethyl-N-(4-ethylphenyl)-2-(1-oxo-4-(pyridin-4-yl)phthalazin-2(1H)-yl)acetamide | 413 [M + H] |
| 5. | 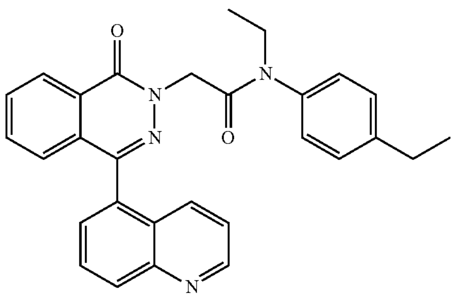 [SMILES: CCc1ccc(N(CC)C(=O)Cn2nc(-c3cccc4ncccc34)c3ccccc3c2=O)cc1] | N-ethyl-N-(4-ethylphenyl)-2-(1-oxo-4-(quinolin-5-yl)phthalazin-2(1H)-yl)acetamide | 463 [M + H] |
| 6. | 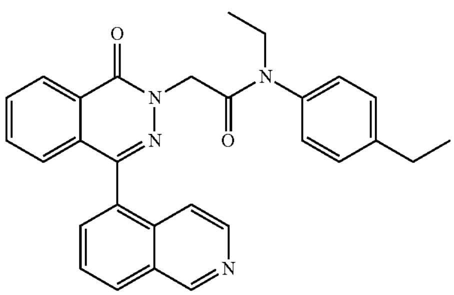 [SMILES: CCc1ccc(N(CC)C(=O)Cn2nc(-c3cccc4cnccc34)c3ccccc3c2=O)cc1] | N-ethyl-N-(4-ethylphenyl)-2-(4-(isoquinolin-5-yl)-1-oxophthalazin-2(1H)-yl)acetamide | 463 [M + H] |
| 7. | 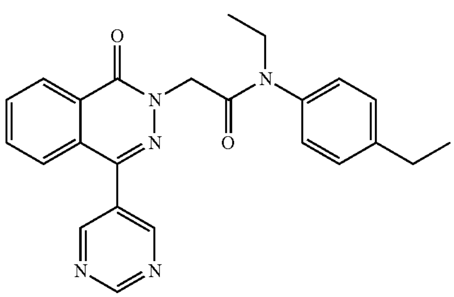 [SMILES: CCc1ccc(N(CC)C(=O)Cn2nc(-c3cncnc3)c3ccccc3c2=O)cc1] | N-ethyl-N-(4-ethylphenyl)-2-(1-oxo-4-(pyrimidin-5-yl)phthalazin-2(1H)-yl)acetamide | 414 [M + H] |
| 8. | 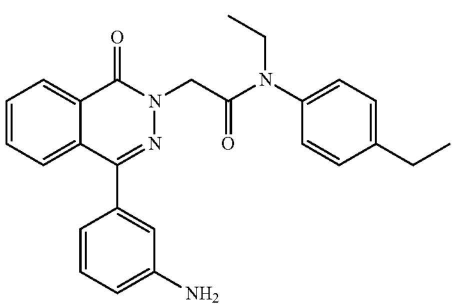 [SMILES: CCc1ccc(N(CC)C(=O)Cn2nc(-c3cccc(N)c3)c3ccccc3c2=O)cc1] | 2-(4-(3-aminophenyl)-1-oxophthalazin-2(1H)-yl)-N-ethyl-N-(4-ethylphenyl)acetamide | 427 [M + H] |

-continued

| Example No. | Structure | IUPAC Name | LCMS m/z |
|---|---|---|---|
| 9. | 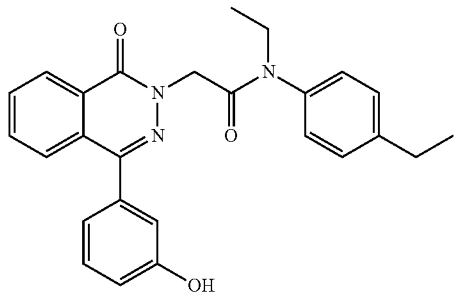 [SMILES: CCc1ccc(N(CC)C(=O)Cn2nc(-c3cccc(O)c3)c3ccccc3c2=O)cc1] | N-ethyl-N-(4-ethylphenyl)-2-(4-(3-hydroxyphenyl)-1-oxophthalazin-2(1H)-yl)acetamide | 428 [M + H] |
| 10. | 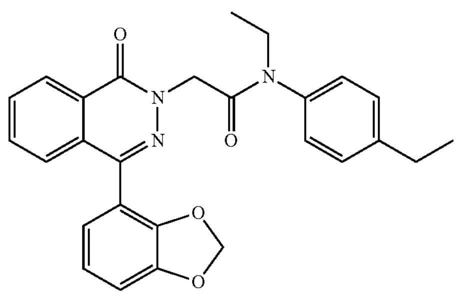 [SMILES: CCc1ccc(N(CC)C(=O)Cn2nc(-c3cccc4c3OCO4)c3ccccc3c2=O)cc1] | 2-(4-(benzo[d][1,3]dioxol-4-yl)-1-oxophthalazin-2(1H)-yl)-N-ethyl-N-(4-ethylphenyl)acetamide | 456 [M + H] |
| 11. | 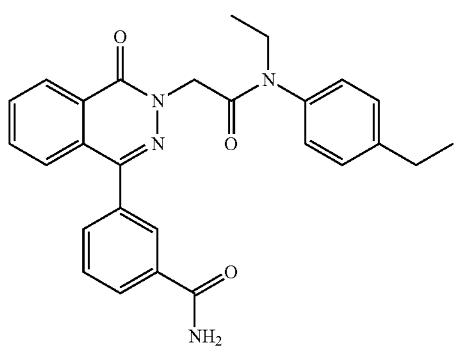 [SMILES: CCc1ccc(N(CC)C(=O)Cn2nc(-c3cccc(C(N)=O)c3)c3ccccc3c2=O)cc1] | 3-(3-(2-(ethyl(4-ethylphenyl)amino)-2-oxoethyl)-4-oxo-3,4-dihydrophthalazin-1-yl)benzamide | 455 [M + H] |
| 12. | 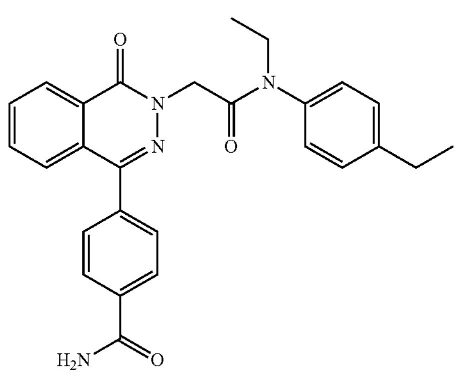 [SMILES: CCc1ccc(N(CC)C(=O)Cn2nc(-c3ccc(C(N)=O)cc3)c3ccccc3c2=O)cc1] | 4-(3-(2-(ethyl(4-ethylphenyl)amino)-2-oxoethyl)-4-oxo-3,4-dihydrophthalazin-1-yl)benzamide | 455 [M + H] |

| Example No. | Structure | IUPAC Name | LCMS m/z |
|---|---|---|---|
| 13. | 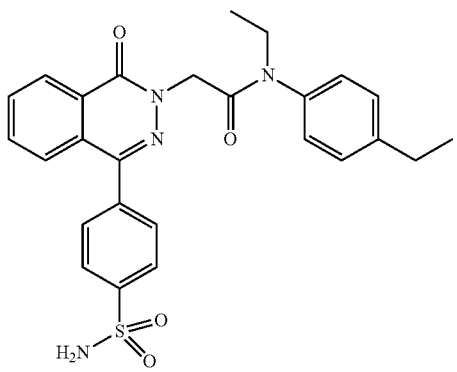 [SMILES: CCc1ccc(N(CC)C(=O)Cn2nc(-c3ccc(S(N)(=O)=O)cc3)c3ccccc3c2=O)cc1] | N-ethyl-N-(4-ethylphenyl)-2-(1-oxo-4-(4-sulfamoylphenyl)phthalazin-2(1H)-yl)acetamide | 491 [M + H] |
| 14. | 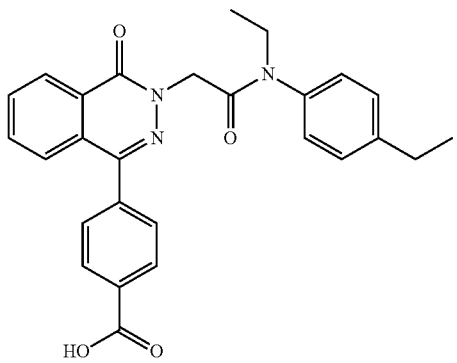 [SMILES: CCc1ccc(N(CC)C(=O)Cn2nc(-c3ccc(C(=O)O)cc3)c3ccccc3c2=O)cc1] | 4-(3-(2-(ethyl(4-ethylphenyl)amino)-2-oxoethyl)-4-oxo-3,4-dihydrophthalazin-1-yl)benzoic acid | 456 [M + H] |
| 15. | 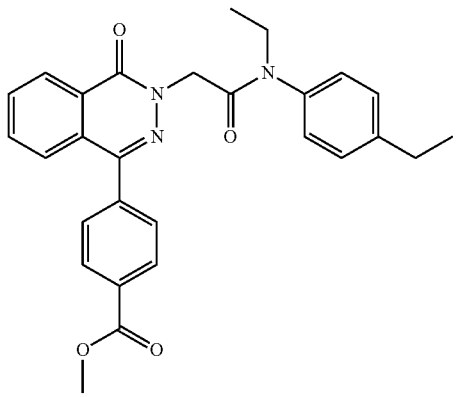 [SMILES: CCc1ccc(N(CC)C(=O)Cn2nc(-c3ccc(C(=O)OC)cc3)c3ccccc3c2=O)cc1] | methyl 4-(3-(2-(ethyl(4-ethylphenyl)amino)-2-oxoethyl)-4-oxo-3,4-dihydrophthalazin-1-yl)benzoate | 470 [M + H] |
| 16. | 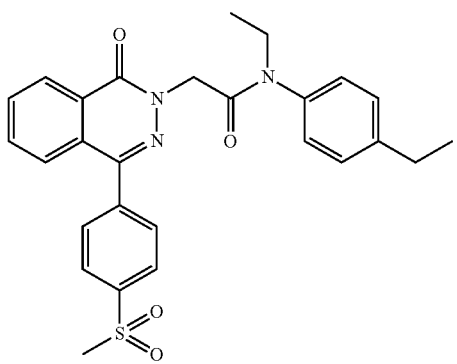 [SMILES: CCc1ccc(N(CC)C(=O)Cn2nc(-c3ccc(S(C)(=O)=O)cc3)c3ccccc3c2=O)cc1] | N-ethyl-N-(4-ethylphenyl)-2-(4-(4-(methylsulfanoyl)phenyl)-1-oxophthalazin-2(1H)-yl)acetamide | 490 [M + H] |

| Example No. | Structure | IUPAC Name | LCMS m/z |
| --- | --- | --- | --- |
| 17. | 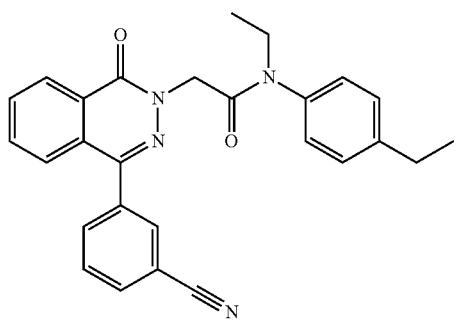 [SMILES: CCc1ccc(N(CC)C(=O)Cn2nc(-c3cccc(C#N)c3)c3ccccc3c2=O)cc1] | 2-(4-(3-cyanophenyl)-1-oxophthalazin-2(1H)-yl)-N-ethyl-N-(4-ethylphenyl)acetamide | 437 [M + H] |
| 18. | 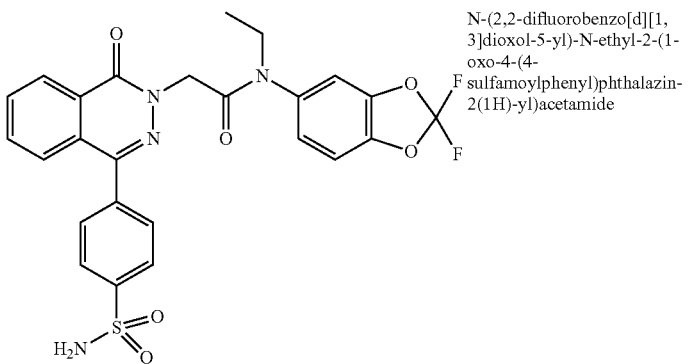 | N-(2,2-difluorobenzo[d][1,3]dioxol-5-yl)-N-ethyl-2-(1-oxo-4-(4-sulfamoylphenyl)phthalazin-2(1H)-yl)acetamide | 543 [M + H] |
| 19. | 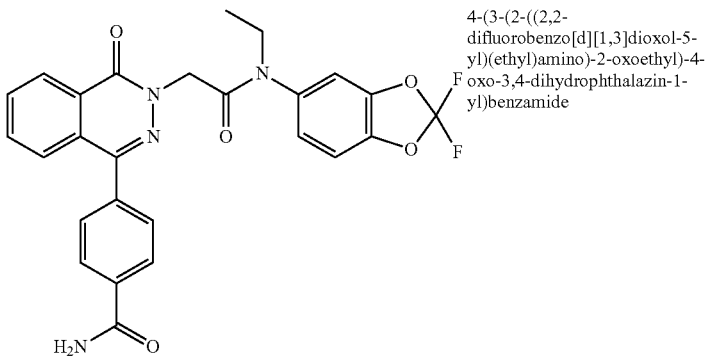 | 4-(3-(2-((2,2-difluorobenzo[d][1,3]dioxol-5-yl)(ethyl)amino)-2-oxoethyl)-4-oxo-3,4-dihydrophthalazin-1-yl)benzamide | 507 [M + H] |
| 20. | 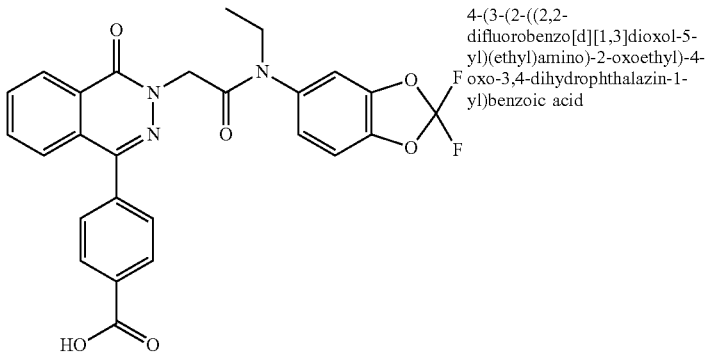 | 4-(3-(2-((2,2-difluorobenzo[d][1,3]dioxol-5-yl)(ethyl)amino)-2-oxoethyl)-4-oxo-3,4-dihydrophthalazin-1-yl)benzoic acid | 508 [M + H] |

-continued

| Example No. | Structure | IUPAC Name | LCMS m/z |
|---|---|---|---|
| 21. | 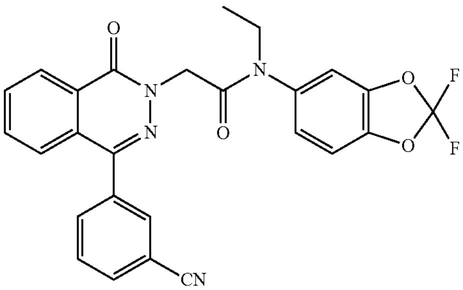 [SMILES: CCN(C(=O)Cn1nc(-c2cccc(C#N)c2)c2ccccc2c1=O)c1ccc2c(c1)OC(F)(F)O2] | 2-(4-(3-cyanophenyl)-1-oxophthalazin-2(1H)-yl)-N-(2,2-difluorobenzo[d][1,3]dioxol-5-yl)-N-ethylacetamide | 489 [M + H] |
| 22. | 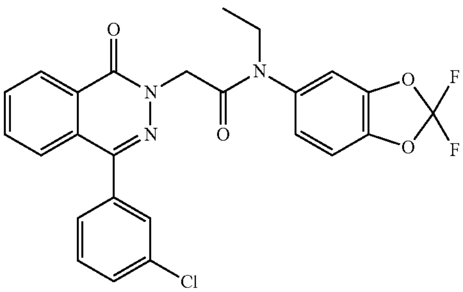 [SMILES: CCN(C(=O)Cn1nc(-c2cccc(Cl)c2)c2ccccc2c1=O)c1ccc2c(c1)OC(F)(F)O2] | 2-(4-(3-cyanophenyl)-1-oxophthalazin-2(1H)-yl)-N-(2,2-difluorobenzo[d][1,3]dioxol-5-yl)-N-ethylacetamide | |
| 23. | 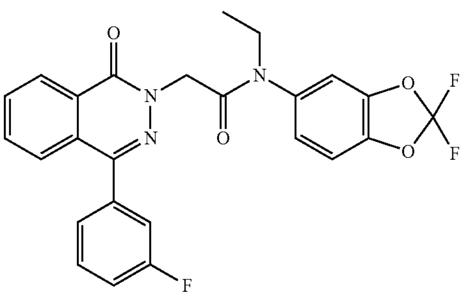 [SMILES: CCN(C(=O)Cn1nc(-c2cccc(F)c2)c2ccccc2c1=O)c1ccc2c(c1)OC(F)(F)O2] | N-(2,2-difluorobenzo[d][1,3]dioxol-5-yl)-N-ethyl-2-(4-(3-fluorophenyl)-1-oxophthalazin-2(1H)-yl)acetamide | |
| 24. | 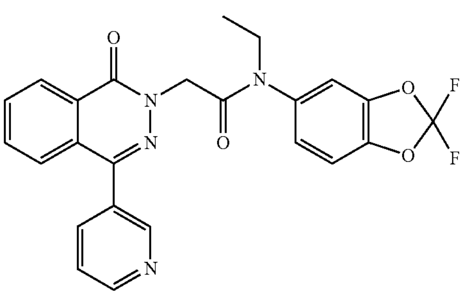 [SMILES: CCN(C(=O)Cn1nc(-c2cccnc2)c2ccccc2c1=O)c1ccc2c(c1)OC(F)(F)O2] | N-(2,2-difluorobenzo[d][1,3]dioxol-5-yl)-N-ethyl-2-(1-oxo-4-(pyridin-3-yl)phthalazin-2(1H)-yl)acetamide | |

N-ethyl-2, 2-difluorobenzo[d][1, 3]dioxol-5-amine

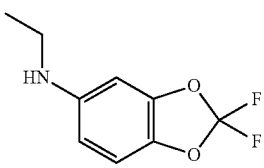

To a solution of 2, 2-difluoro-5-aminobenzo[d][1, 3]dioxole (7.45 g, 43.0 mmol) in DMF (60 mL) was added $K_2CO_3$ (17.8 g, 129 mmol), and the reaction mixture was stirred at rt for 1 hr. The reaction was cooled to 0° C. and EtI (3.52 mL, 43.0 mmol) added dropwise. After stirring at rt overnight, the reaction mixture was diluted with water (500 mL) and the product extracted with EtOAc (3×100 mL). The combined organics were washed with brine (200 mL), dried over $Na_2SO_4$, and concentrated. The crude product was purified by chromatography (0-10% EtOAc/hexane) to yield N-ethyl-2, 2-difluorobenzo[d][1, 3]dioxol-5-amine (5.98 g), (MS: ESI+ve, 202 [M+H]).

111

2-Bromo-N-(2, 2-difluorobenzo[d][1, 3]dioxol-5-yl)-N-ethylacetamide

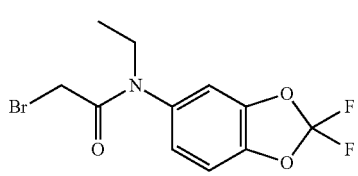 [SMILES: CCN(C(=O)CBr)c1ccc2c(c1)OC(F)(F)O2]

A solution of N-ethyl-2, 2-difluorobenzo[d][1, 3]dioxol-5-amine (8.0 g, 3.9 mmol) in DCM (100 mL) was treated with 2-bromoacetic acid (13.2 g, 9.4 mmol), EDC.HCL (14.8 g, 93.6 mmol), and DMAP (238 mg, 19.5 mmol), then stirred at rt overnight. The reaction mixture was diluted with water (500 mL) and the product extracted with DCM (3×100 mL). The combined organics were washed with brine, dried over $Na_2SO_4$, and concentrated. The crude product was purified by chromatography (0-7% EtOAc/hexane) to yield 2-bromo-N-(2, 2-difluorobenzo[d][1, 3]dioxol-5-yl)-N-ethylacetamide (11.0 g), (MS: ESI+ve, 322 [M+H]). $^1$H NMR: (400 MHz, DMSO) δ: 1.03-1.00 (t, J=14.4, 3H), 3.68-3.63 (m, 2H), 4.03 (s, 2H) 7.26-7.23 (d, J=8.4, 1H), 7.53-7.50 (d, J=8.4, 1H), 7.57 (s, 1H).

3-(2-((2, 2-difluorobenzo[d][1, 3]dioxol-5-yl)(ethyl)amino)-2-oxoethyl)-4-oxo-3, 4-dihydrophthalazin-1-yl 4-methylbenzenesulfonate

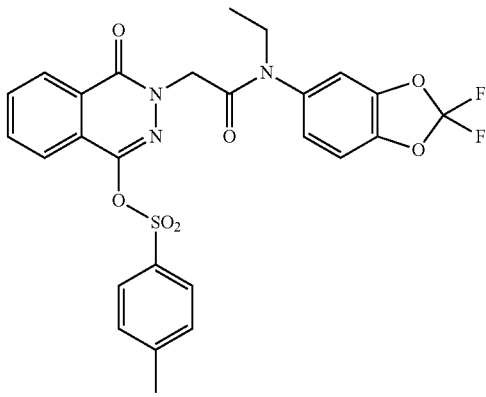 [SMILES: CCN(C(=O)Cn1nc(OS(=O)(=O)c2ccc(C)cc2)c2ccccc2c1=O)c1ccc2c(c1)OC(F)(F)O2]

A 0° C. solution of 4-oxo-3, 4-dihydrophthalazin-1-yl 4-methylbenzenesulfonate (0.37 g, 1.2 mmol) in DMF (6 mL) was treated with NaHMDS (2M in THF) (0.65 mL, 1.30 mmol). After stirring for 20 min, a solution of 2-bromo-N-(2, 2-difluorobenzo[d][1, 3]dioxol-5-yl)-N-ethylacetamide (0.458 g, 1.423 mmol) in DMF (1.0 mL) was added and the mixture stirred overnight at rt. The reaction was quenched with 5% LiCl (aq) and extracted with EtOAc. The combined organics were dried over $MgSO_4$ and concentrated. The crude product was purified by chromatography (10-100% EtOAc/pet ether) to yield 3-(2-((2, 2-difluorobenzo[d][1, 3]dioxol-5-yl)(ethyl)amino)-2-oxoethyl)-4-oxo-3, 4-dihydrophthalazin-1-yl 4-methylbenzenesulfonate (479 mg), (MS: ESI+ve, 558[M+H]).

112

3-(pyridin-3-ylmethylene)isobenzofuran-1(3H)-one

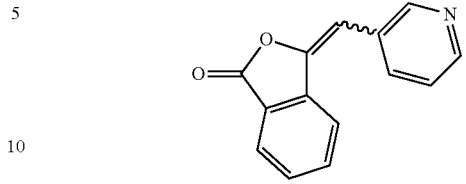

A mixture of 3-(carboxymethyl)pyridin-1-ium chloride (13 g, 75 mmol), isobenzofuran-1, 3-dione (11.09 g, 75 mmol), and NaOAc (0.246 g, 3.00 mmol) was placed into a round bottom flask and warmed to 190° C. for 30 minutes. The mixture was extracted with DCM and washed with $NaHCO_3$ (aq). The organic phase was dried over $MgSO_4$ and evaporated to give 3-(pyridin-3-ylmethylene) isobenzofuran-1 (3H)-one (8.5 g).

4-(pyridin-3-ylmethyl)phthalazin-1(2H)-one

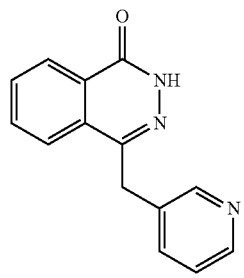 [SMILES: O=c1[nH]nc(Cc2cccnc2)c2ccccc12]

Two microwave vials containing 3-(pyridin-3-ylmethylene)isobenzofuran-1 (3H)-one (1.5 g, 6.72 mmol), hydrazine sulfate (0.874 g, 6.72 mmol), water (6.5 mL), EtOH (1.9 mL) and 2M NaOH (1.9 mL) were flushed with $N_2$, then heated in a microwave to 180° C. for 15 min. The resulting mixtures were cooled to rt and placed in the freezer. The solids were filtered, washed with water, and dried to yield 4-(pyridin-3-ylmethyl)phthalazin-1(2H)-one (2.36 g), (MS: ESI+ve, 238 [M+H]).

Example 25

N-ethyl-N-(4-ethylphenyl)-2-(1-oxo-4-(pyridin-3-ylmethyl)phthalazin-2(1H)-yl)acetamide

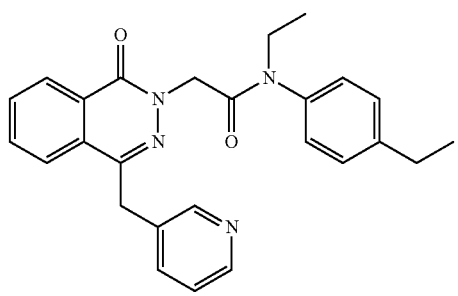 [SMILES: CCc1ccc(N(CC)C(=O)Cn2nc(Cc3cccnc3)c3ccccc3c2=O)cc1]

A 0° C. vial of NaH (60%) (6.49 mg, 0.162 mmol) and DMF (738 µL) was treated with a solution of 4-(pyridin-3-ylmethyl)phthalazin-1(2H)-one (35 mg, 0.148 mmol) in DMF (369 µL). After 10 min, 2-bromo-N-ethyl-N-(4-ethylphenyl)acetamide (39.9 mg, 0.148 mmol) in DMF (369 µL) was added and the reaction stirred at rt overnight. Sat'd NH₄Cl was added and the product extracted with EtOAc. The organic phase was washed with brine, dried over MgSO₄, and evaporated. The crude product was purified by chromatography (0-5% MeOH/EtOAc) to give N-ethyl-N-(4-ethylphenyl)-2-(1-oxo-4-(pyridin-3-ylmethyl)phthalazin-2(1H)-yl)acetamide (20 mg), (MS: ESI+ve, 427 [M+H])

The following compounds were prepared in a similar manner to example 25 (scheme 3).

Preparation of 6-methylisobenzofuran-1(3H)-one and 5-methylisobenzofuran-1(3H)-one

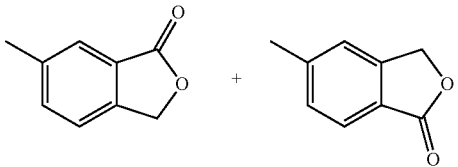

| Example No. | Structure | IUPAC Name | LCMS m/z |
|---|---|---|---|
| 26. | 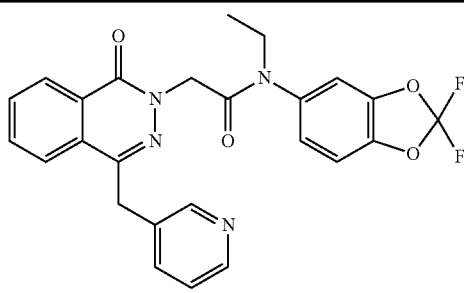 | N-(2,2-difluorobenzo[d][1,3]dioxol-5-yl)-N-ethyl-2-(1-oxo-4-(pyridin-3-ylmethyl)phthalazin-2(1H)-yl)acetamide | 479 [M + H] |
| 27. | 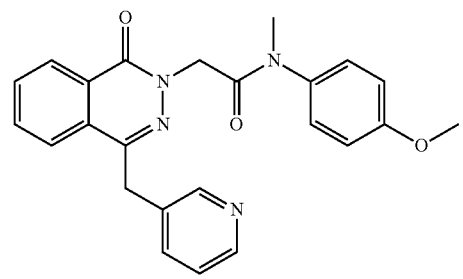 [SMILES: COc1ccc(N(C)C(=O)Cn2nc(Cc3cccnc3)c3ccccc3c2=O)cc1] | N-(4-methoxyphenyl)-N-methyl-2-(1-oxo-4-(pyridin-3-ylmethyl)phthalazin-2(1H)-yl)acetamide | 415 [M + H] |

2-chloro-N-(4-methoxyphenyl)-N-methylacetamide

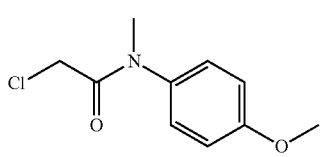

A solution of DMAP (0.022 g, 0.182 mmol) and 4-methoxy-N-methylaniline (0.5 g, 3.64 mmol) in DCM (36 mL) under N₂ was treated with 2-chloroacetic acid (1.20 g, 8.67 mmol) and EDC.HCl (1.67 g, 8.75 mmol), then stirred overnight at rt. The reaction was diluted with DCM, then washed with brine and 2 M NaOH. The organic layer was dried over MgSO₄, and evaporated to dryness. The crude product was purified by chromatography (10-20% EtOAc/pet ether) to give 2-chloro-N-(4-methoxyphenyl)-N-methylacetamide (446 mg).

A solution of 4-methyl phthalic anhydride (5.0 g, 30.8 mmol) in THF (35 mL) at 15° C. was treated with HOAc (3.43 mL, 61.6 mmol) and NaBH₄ (1.13 g, 30.8 mmol). Stirring was maintained at 15° C. for 30 min and then at rt for 4 hr. The reaction was concentrated under vacuum. HOAc (15 mL) and Ac₂O (15 mL) were added and the mixture heated at 110° C. for 3 hr. The mixture was concentrated, quenched with sat'd NH₄Cl (500 mL) and then extracted with EtOAc (2×250 mL). The organic layer was washed with brine, dried over Na₂SO₄, and concentrated. The crude product was purified by chromatography (0-15% EtOAc/hexane) to obtain a mixture of 6-methylisobenzofuran-1(3H)-one and 5-methylisobenzofuran-1(3H)-one (2.0 g), (MS: ESI+ve, 149 [M+H]).

3-hydroxy-6-methyl-2-(pyridin-3-yl)-1H-inden-1-one

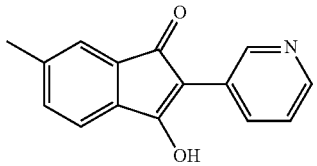 [SMILES: Cc1ccc2c(c1)C(=O)C(c1cccnc1)=C2O]

The mixture of 6-methylisobenzofuran-1(3H)-one and 5-methylisobenzofuran-1(3H)-one (2.0 g, 13.5 mmol) was dissolved in EtOAc (10 mL) and MeOH (20 mL), then treated with 3-pyridine carboxaldehyde (1.44 g, 13.5 mmol) and NaOMe (2.18 g, 40.0 mmol) portionwise at 0° C. The reaction mixture was stirred for 30 min at 0° C. and then heated to 60° C. for 3 h. The reaction mixture was concentrated under vacuum, diluted with water (50 mL), and acidified with acetic acid (10 mL). The resulting precipitate was filtered and dried to obtain 3-hydroxy-6-methyl-2-(pyridin-3-yl)-1-H-inden-1-one (1.54 g), (MS: ESI+ve, 238 [M+H]). $^1$H NMR: (400 MHz, DMSO) δ: 2.35 (s, 3H), 7.20-7.14 (t, 1H), 7.22 (s, 1H), 7.81-7.77 (d, J=8.8 Hz, 1H), 8.22-8.20 (d, J=7.6, 1H), 9.47-9.44 (d, J=11.6 Hz, 1H), 9.73 (s, 1H), 14.91 (s, 1H).

7-methyl-4-(pyridin-3-ylmethyl)phthalazin-1(2H)-one and 6-methyl-4-(pyridin-3-ylmethyl)phthalazin-1(2H)-one

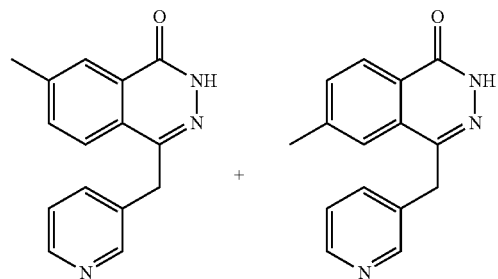 [SMILES: Cc1ccc2c(Cc3cccnc3)n[nH]c(=O)c2c1 ; Cc1ccc2c(=O)[nH]nc(Cc3cccnc3)c2c1]

A solution of 3-hydroxy-6-methyl-2-(pyridin-3-yl)-1-H-inden-1-one (1.2 g, 5.0 mmol) in hydrazine hydrate (10 mL) was heated at 110° C. overnight. The reaction mixture was diluted with water (50 mL) and the resulting precipitate filtered and dried to obtain 7-methyl-4-(pyridin-3-yl-methyl)-phthalazine-1(2H)-one and 6-methyl-4-(pyridin-3-yl-methyl)-phthalazine-1(2H)-one (5.01 g, (MS: ESI+ve, 252 [M+H]) as a 1:1 isomeric mixture. $^1$H NMR: (400 MHz, DMSO) δ: 2.48 (s, 6H), 4.30-4.32 (d, J=2, 4H), 7.34-7.29 (m, 2H), 7.74-7.66 (m, 5H), 7.85 (s, 1H), 7.92-7.89 (d, J=8.4, 1H), 8.16-8.14 (d, J=8, 1H), 8.41-8.41 (m, 1H), 8.43-8.42 (m, 2H), 8.60-8.43 (m, 2H), 12.51 (s, 2H).

Examples 28 and 29

N-ethyl-N-(4-ethylphenyl)-2-(7-methyl-1-oxo-4-(pyridin-3-ylmethyl)phthalazin-2(1H)-yl)acetamide and N-ethyl-N-(4-ethylphenyl)-2-(6-methyl-1-oxo-4-(pyridin-3-ylmethyl)phthalazin-2(1H)-yl)acetamide Example 28

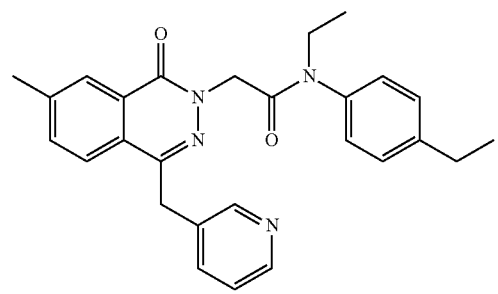

Example 29

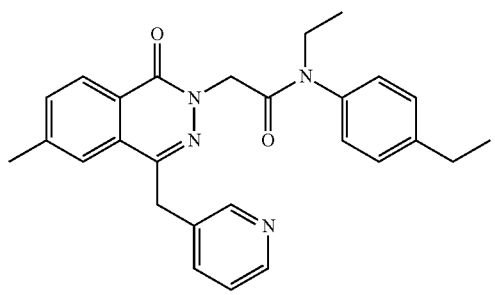

A solution of 7-methyl-4-(pyridin-3-yl-methyl)-phthalazine-1(2H)-one and 6-methyl-4-(pyridin-3-yl-methyl)-phthalazine-1(2H)-one (0.5 g, 1.9 mmol) in THF (15 mL) was treated with NaH (60%) (0.087 g, 2.1 mmol) portionwise at 0° C. and then for 30 min at 0° C. A solution of 2-bromo-N-ethyl-N-(4-ethylphenyl)acetamide (0.537 g, 1.9 mmol) in THF (5 mL) was added dropwise and the reaction mixture warmed to rt overnight. The reaction was diluted with sat'd NH$_4$Cl (25 mL) and extracted with EtOAc (2×50 mL). The organics were washed with brine (50 mL), dried over Na$_2$SO$_4$, and concentrated to give crude which was purified by preparative HPLC to obtain the separable isomers, Example 28: N-ethyl-N-(4-ethylphenyl)-2-(7-methyl-1-oxo4-(pyridine-3-ylmethyl)-phthalazine-2(1H)-yl)acetamide (0.024 g), (MS: ESI+ve, 441 [M+H]); $^1$H NMR: (400 MHz, DMSO) δ: 1.05-1.00 (m, 3H), 1.23-1.19 (t, 3H), 2.51-2.48 (m, 3H), 2.69-2.63 (m, 2H), 3.68-3.63 (m, 2H), 4.31 (s, 2H), 4.55 (s, 2H), 7.36-7.28 (m, 5H), 7.72-7.66 (m, 2H), 7.87-7.85 (d, J=8.4, 1H), 8.03 (s, 1H), 8.15 (s, 1H), 8.59-8.40 (m, 1H), 8.60 (s, 1H); Example 29: N-ethyl-N-(4-ethylphenyl)-2-(6-methyl-1-oxo4-(pyridine-3-ylmethyl)-phthalazine-2(1H)-yl)acetamide (0.034 g), (MS: ESI+ve, 441 [M+H]); $^1$H NMR: (400 MHz, DMSO) δ: 1.04-1.00 (t, 3H), 1.23-1.19 (t, 3H), 2.50 (s, 3H), 2.69-2.63 (m, 2H), 3.68-3.63 (m, 2H), 4.32 (s, 2H), 4.54 (s, 2H), 7.36-7.29 (m, 5H), 7.71-7.66 (m, 2H), 7.80 (s, 1H), 8.14-8.12 (d, J=8, 1H), 8.43-8.41 (m, 1H), 8.62-8.61 (d, J=1.6, 1H).

Representative compounds of the invention were prepared in a similar manner to examples 28 and 29 from the corresponding phthalic anhydride or isobenzofuran-1(3H)-one and the appropriate alkylating agent (scheme 4).

| Example No. | Structure | IUPAC Name | LCMS m/z |
|---|---|---|---|
| 30. | 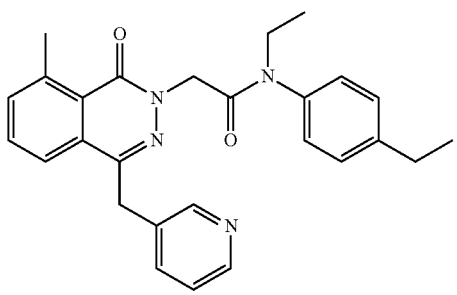 [SMILES: CCc1ccc(N(CC)C(=O)Cn2nc(Cc3cccnc3)c3cccc(C)c3c2=O)cc1] | N-ethyl-N-(4-ethylphenyl)-2-(8-methyl-1-oxo-4-(pyridin-3-ylmethyl)phthalazin-2(1H)-yl)acetamide | 441 [M + H] |
| 31. | 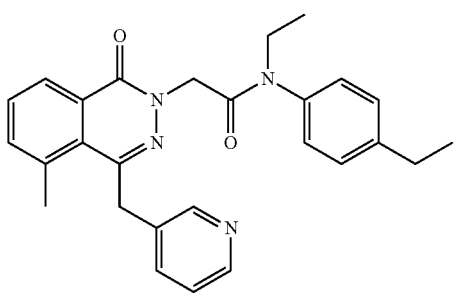 [SMILES: CCc1ccc(N(CC)C(=O)Cn2nc(Cc3cccnc3)c3c(C)cccc3c2=O)cc1] | N-ethyl-N-(4-ethylphenyl)-2-(5-methyl-1-oxo-4-(pyridin-3-ylmethyl)phthalazin-2(1H)-yl)acetamide | 441 [M + H] |
| 32. | 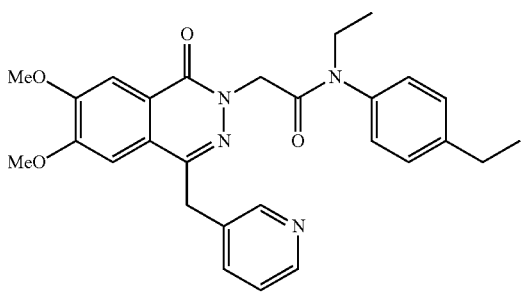 [SMILES: CCc1ccc(N(CC)C(=O)Cn2nc(Cc3cccnc3)c3cc(OC)c(OC)cc3c2=O)cc1] | 2-(6,7-dimethoxy-1-oxo-4-(pyridin-3-ylmethyl)phthalazin-2(1H)-yl)-N-ethyl-N-(4-ethylphenyl)acetamide | 487 [M + H] |
| 33. | 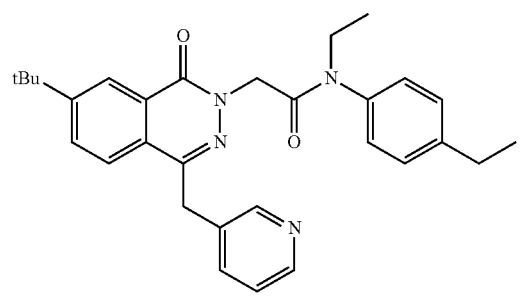 [SMILES: CCc1ccc(N(CC)C(=O)Cn2nc(Cc3cccnc3)c3ccc(C(C)(C)C)cc3c2=O)cc1] | 2-(7-(tert-butyl)-1-oxo-4-(pyridin-3-ylmethyl)phthalazin-2(1H)-yl)-N-ethyl-N-(4-ethylphenyl)acetamide | 483 [M + H] |
| 34. | 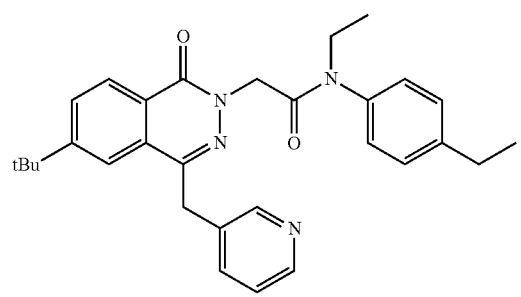 [SMILES: CCc1ccc(N(CC)C(=O)Cn2nc(Cc3cccnc3)c3cc(C(C)(C)C)ccc3c2=O)cc1] | 2-(6-(tert-butyl)-1-oxo-4-(pyridin-3-ylmethyl)phthalazin-2(1H)-yl)-N-ethyl-N-(4-ethylphenyl)acetamide | 483 [M + H] |

| Example No. | Structure | IUPAC Name | LCMS m/z |
|---|---|---|---|
| 35. | 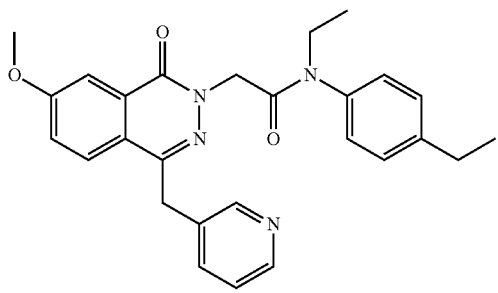 [SMILES: CCc1ccc(N(CC)C(=O)Cn2nc(Cc3cccnc3)c3ccc(OC)cc3c2=O)cc1] | N-ethyl-N-(4-ethylphenyl)-2-(7-methoxy-1-oxo-4-(pyridin-3-ylmethyl)phthalazin-2(1H)-yl)acetamide | 457 [M + H] |
| 36. | 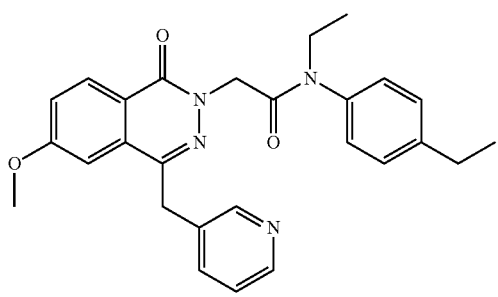 [SMILES: CCc1ccc(N(CC)C(=O)Cn2nc(Cc3cccnc3)c3cc(OC)ccc3c2=O)cc1] | N-ethyl-N-(4-ethylphenyl)-2-(6-methoxy-1-oxo-4-(pyridin-3-ylmethyl)phthalazin-2(1H)-yl)acetamide | 457 [M + H] |
| 37. | 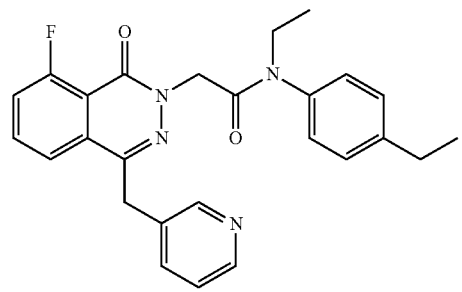 | N-ethyl-N-(4-ethylphenyl)-2-(8-fluoro-1-oxo-4-(pyridin-3-ylmethyl)phthalazin-2(1H)-yl)acetamide | 445 [M + H] |
| 38. | 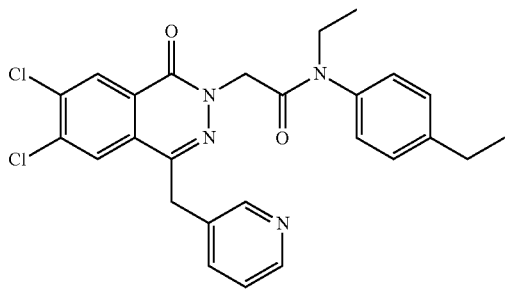 [SMILES: CCc1ccc(N(CC)C(=O)Cn2nc(Cc3cccnc3)c3cc(Cl)c(Cl)cc3c2=O)cc1] | 2-(6,7-dichloro-1-oxo-4-(pyridin-3-ylmethyl)phthalazin-2(1H)-yl)-N-ethyl-N-(4-ethylphenyl)acetamide | 495 [M + H] |
| 39. | 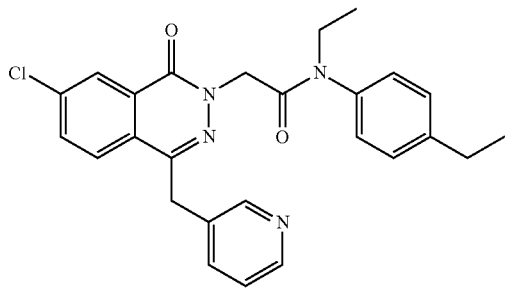 [SMILES: CCc1ccc(N(CC)C(=O)Cn2nc(Cc3cccnc3)c3ccc(Cl)cc3c2=O)cc1] | 2-(7-chloro-1-oxo-4-(pyridin-3-ylmethyl)phthalazin-2(1H)-yl)-N-ethyl-N-(4-ethylphenyl)acetamide | 461 [M + H] |

| Example No. | Structure | IUPAC Name | LCMS m/z |
|---|---|---|---|
| 40. | 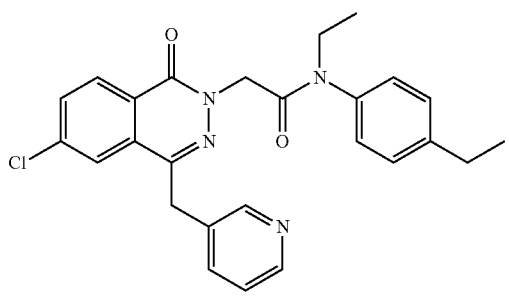 [SMILES: CCc1ccc(N(CC)C(=O)Cn2nc(Cc3cccnc3)c3cc(Cl)ccc3c2=O)cc1] | 2-(6-chloro-1-oxo-4-(pyridin-3-ylmethyl)phthalazin-2(1H)-yl)-N-ethyl-N-(4-ethylphenyl)acetamide | 461 [M + H] |
| 41. | 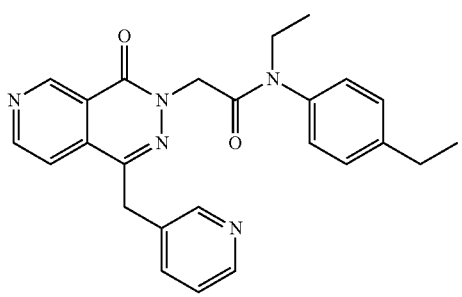 [SMILES: CCc1ccc(N(CC)C(=O)Cn2nc(Cc3cccnc3)c3ccncc3c2=O)cc1] | N-ethyl-N-(4-ethylphenyl)-2-(4-oxo-1-(pyridin-3-ylmethyl)pyrido[3,4-d]pyridazin-3(4H)-yl)acetamide | 428 [M + H] |
| 42. | 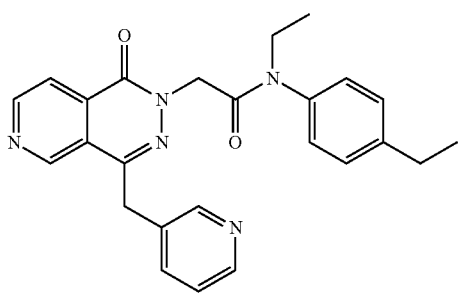 [SMILES: CCc1ccc(N(CC)C(=O)Cn2nc(Cc3cccnc3)c3cnccc3c2=O)cc1] | N-ethyl-N-(4-ethylphenyl)-2-(1-oxo-4-(pyridin-3-ylmethyl)pyrido[3,4-d]pyridazin-2(1H)-yl)acetamide | 428 [M + H] |
| 43. | 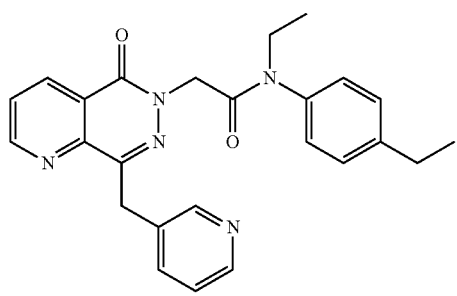 [SMILES: CCc1ccc(N(CC)C(=O)Cn2nc(Cc3cccnc3)c3ncccc3c2=O)cc1] | N-ethyl-N-(4-ethylphenyl)-2-(5-oxo-8-(pyridin-3-ylmethyl)pyrido[2,3-d]pyridazin-6(5H)-yl)acetamide | 428 [M + H] |
| 44. | 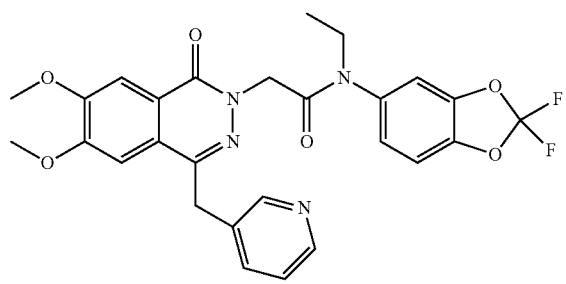 [SMILES: CCN(C(=O)Cn1nc(Cc2cccnc2)c2cc(OC)c(OC)cc2c1=O)c1ccc2c(c1)OC(F)(F)O2] | N-(2,2-difluorobenzo[d][1,3]dioxol-5-yl)-2-(6,7-dimethoxy-1-oxo-4-(pyridin-3-ylmethyl)phthalazin-2(1H)-yl)-N-ethylacetamide | 539 [M + H] |

| Example No. | Structure | IUPAC Name | LCMS m/z |
|---|---|---|---|
| 45. | 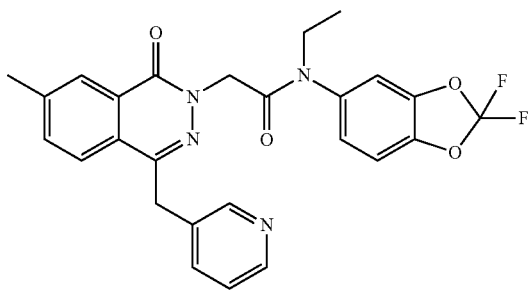 [SMILES: CCN(C(=O)Cn1nc(Cc2cccnc2)c2ccc(C)cc2c1=O)c1ccc2c(c1)OC(F)(F)O2] | N-(2,2-difluorobenzo[d][1,3]dioxol-5-yl)-N-ethyl-2-(7-methyl-1-oxo-4-(pyridin-3-ylmethyl)phthalazin-2(1H)-yl)acetamide | 493 [M + H] |
| 46. | 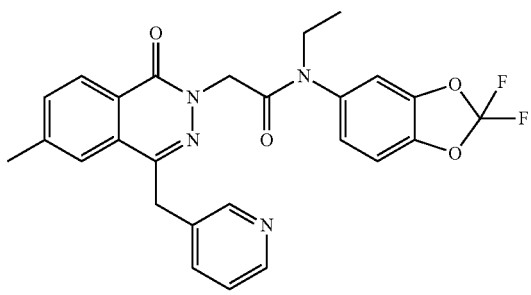 [SMILES: CCN(C(=O)Cn1nc(Cc2cccnc2)c2cc(C)ccc2c1=O)c1ccc2c(c1)OC(F)(F)O2] | N-(2,2-difluorobenzo[d][1,3]dioxol-5-yl)-N-ethyl-2-(6-methyl-1-oxo-4-(pyridin-3-ylmethyl)phthalazin-2(1H)-yl)acetamide | 493 [M + H] |
| 47. | 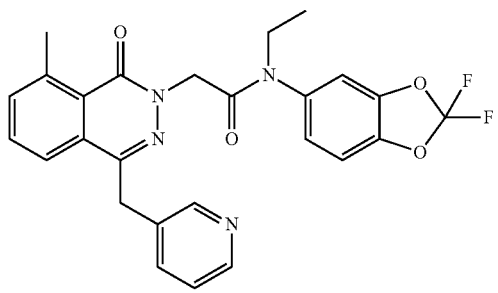 [SMILES: CCN(C(=O)Cn1nc(Cc2cccnc2)c2cccc(C)c2c1=O)c1ccc2c(c1)OC(F)(F)O2] | N-(2,2-difluorobenzo[d][1,3]dioxol-5-yl)-N-ethyl-2-(8-methyl-1-oxo-4-(pyridin-3-ylmethyl)phthalazin-2(1H)-yl)acetamide | 493 [M + H] |
| 48. | 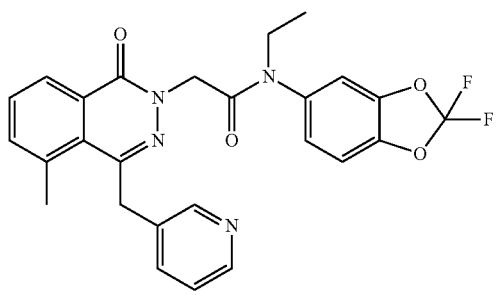 [SMILES: CCN(C(=O)Cn1nc(Cc2cccnc2)c2c(C)cccc2c1=O)c1ccc2c(c1)OC(F)(F)O2] | N-(2,2-difluorobenzo[d][1,3]dioxol-5-yl)-N-ethyl-2-(5-methyl-1-oxo-4-(pyridin-3-ylmethyl)phthalazin-2(1H)-yl)acetamide | 493 [M + H] |
| 49. | 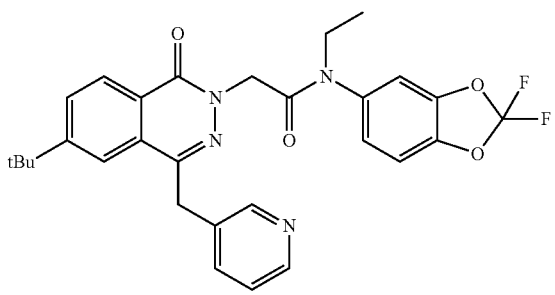 [SMILES: CCN(C(=O)Cn1nc(Cc2cccnc2)c2cc(C(C)(C)C)ccc2c1=O)c1ccc2c(c1)OC(F)(F)O2] | 2-(6-(tert-butyl)-1-oxo-4-(pyridin-3-ylmethyl)phthalazin-2(1H)-yl)-N-(2,2-difluorobenzo[d][1,3]dioxol-5-yl)-N-ethylacetamide | 535 [M + H] |

-continued

| Example No. | Structure | IUPAC Name | LCMS m/z |
|---|---|---|---|
| 50. | 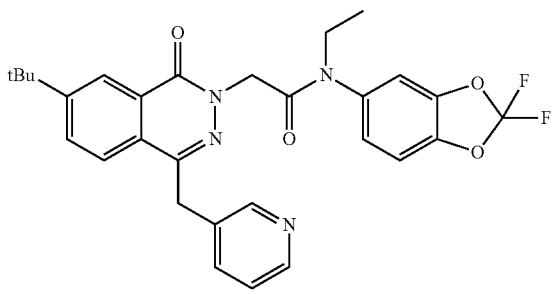 [SMILES: CCN(C(=O)Cn1nc(Cc2cccnc2)c2ccc(C(C)(C)C)cc2c1=O)c1ccc2c(c1)OC(F)(F)O2] | 2-(7-(tert-butyl)-1-oxo-4-(pyridin-3-ylmethyl)phthalazin-2(1H)-yl)-N-(2,2-difluorobenzo[d][1,3]dioxol-5-yl)-N-ethylacetamide | 535 [M + H] |
| 51. | 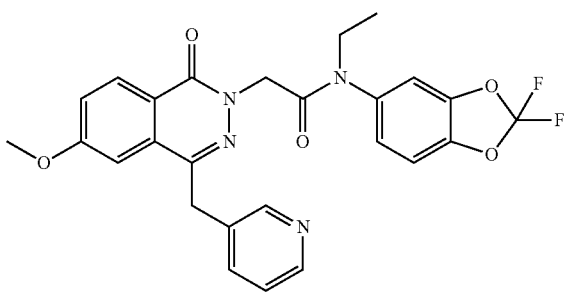 [SMILES: CCN(C(=O)Cn1nc(Cc2cccnc2)c2cc(OC)ccc2c1=O)c1ccc2c(c1)OC(F)(F)O2] | N-(2,2-difluorobenzo[d][1,3]dioxol-5-yl)-N-ethyl-2-(6-methoxy-1-oxo-4-(pyridin-3-ylmethyl)phthalazin-2(1H)-yl)acetamide | 509 [M + H] |
| 52. | 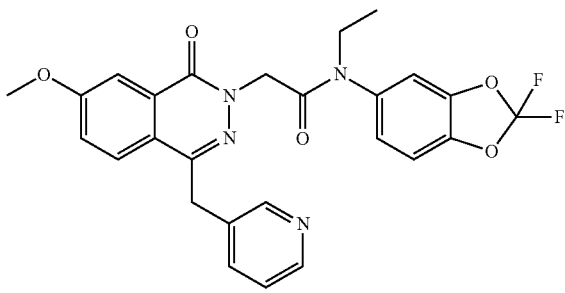 [SMILES: CCN(C(=O)Cn1nc(Cc2cccnc2)c2ccc(OC)cc2c1=O)c1ccc2c(c1)OC(F)(F)O2] | N-(2,2-difluorobenzo[d][1,3]dioxol-5-yl)-N-ethyl-2-(7-methoxy-1-oxo-4-(pyridin-3-ylmethyl)phthalazin-2(1H)-yl)acetamide | 509 [M + H] |
| 53. | 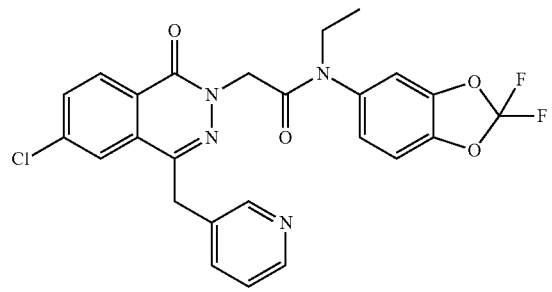 [SMILES: CCN(C(=O)Cn1nc(Cc2cccnc2)c2cc(Cl)ccc2c1=O)c1ccc2c(c1)OC(F)(F)O2] | 2-(6-chloro-1-oxo-4-(pyridin-3-ylmethyl)phthalazin-2(1H)-yl)-N-(2,2-difluorobenzo[d][1,3]dioxol-5-yl)-N-ethylacetamide | 513 [M + H] |
| 54. | 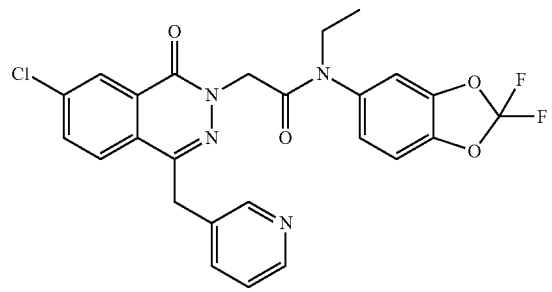 [SMILES: CCN(C(=O)Cn1nc(Cc2cccnc2)c2ccc(Cl)cc2c1=O)c1ccc2c(c1)OC(F)(F)O2] | 2-(7-chloro-1-oxo-4-(pyridin-3-ylmethyl)phthalazin-2(1H)-yl)-N-(2,2-difluorobenzo[d][1,3]dioxol-5-yl)-N-ethylacetamide | 513 [M + H] |

| Example No. | Structure | IUPAC Name | LCMS m/z |
|---|---|---|---|
| 55. | 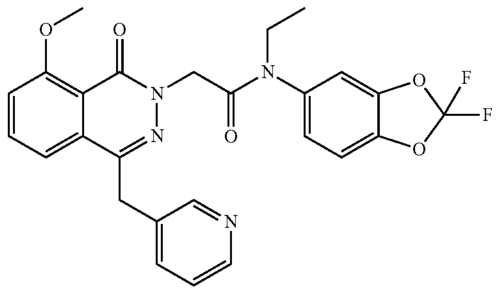 [SMILES: CCN(C(=O)Cn1nc(Cc2cccnc2)c2cccc(OC)c2c1=O)c1ccc2c(c1)OC(F)(F)O2] | N-(2,2-difluorobenzo[d][1,3]dioxol-5-yl)-N-ethyl-2-(8-methoxy-1-oxo-4-(pyridin-3-ylmethyl)phthalazin-2(1H)-yl)acetamide | 509 [M + H] |
| 56. | 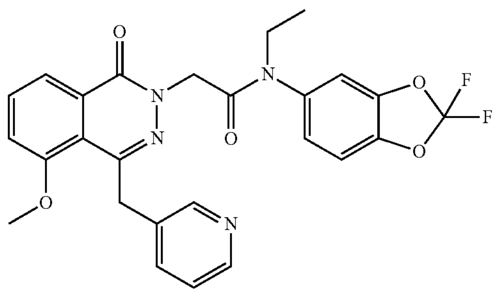 [SMILES: CCN(C(=O)Cn1nc(Cc2cccnc2)c2c(OC)cccc2c1=O)c1ccc2c(c1)OC(F)(F)O2] | N-(2,2-difluorobenzo[d][1,3]dioxol-5-yl)-N-ethyl-2-(5-methoxy-1-oxo-4-(pyridin-3-ylmethyl)phthalazin-2(1H)-yl)acetamide | 509 [M + H] |
| 57. | 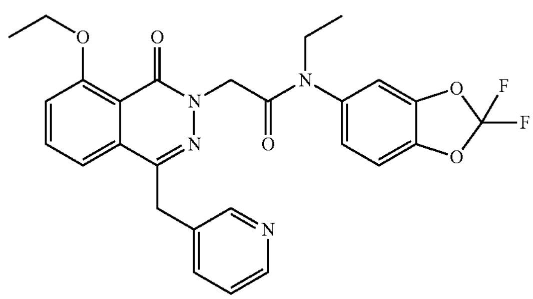 [SMILES: CCOc1cccc2c(Cc3cccnc3)nn(CC(=O)N(CC)c3ccc4c(c3)OC(F)(F)O4)c(=O)c12] | N-(2,2-difluorobenzo[d][1,3]dioxol-5-yl)-N-ethyl-2-(8-ethoxy-1-oxo-4-(pyridin-3-ylmethyl)phthalazin-2(1H)-yl)acetamide | 523 [M + H] |
| 58. | 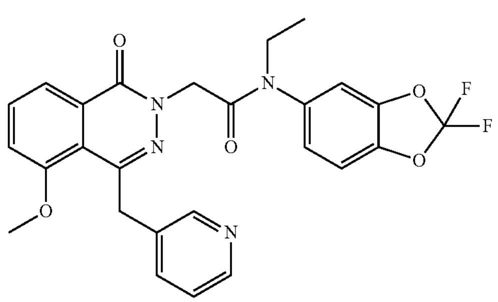 | N-(2,2-difluorobenzo[d][1,3]dioxol-5-yl)-N-ethyl-2-(5-ethoxy-1-oxo-4-(pyridin-3-ylmethyl)phthalazin-2(1H)-yl)acetamide | 523 [M + H] |
| 59. | 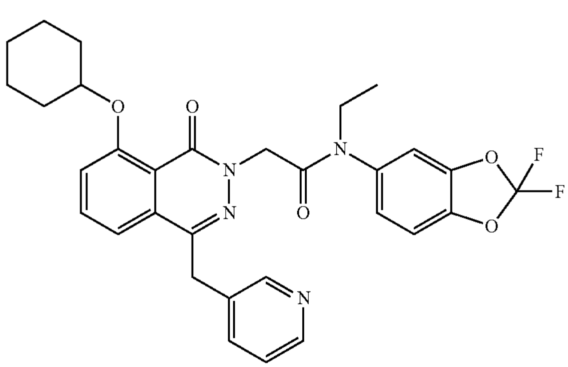 [SMILES: CCN(C(=O)Cn1nc(Cc2cccnc2)c2cccc(OC3CCCCC3)c2c1=O)c1ccc2c(c1)OC(F)(F)O2] | 2-(8-(cyclohexyloxy)-1-oxo-4-(pyridin-3-ylmethyl)phthalazin-2(1H)-yl)-N-(2,2-difluorobenzo[d][1,3]dioxol-5-yl)-N-ethylacetamide | 577 [M + H] |

| Example No. | Structure | IUPAC Name | LCMS m/z |
|---|---|---|---|
| 60. | 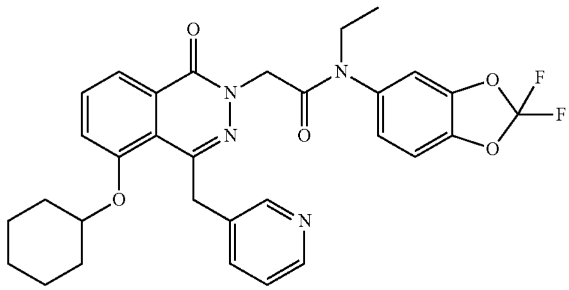 [SMILES: CCN(C(=O)Cn1nc(Cc2cccnc2)c2c(OC3CCCCC3)cccc2c1=O)c1ccc2c(c1)OC(F)(F)O2] | 2-(5-(cyclohexyloxy)-1-oxo-4-(pyridin-3-ylmethyl)phthalazin-2(1H)-yl)-N-(2,2-difluorobenzo[d][1,3]dioxol-5-yl)-N-ethylacetamide | 577 [M + H] |
| 61. | 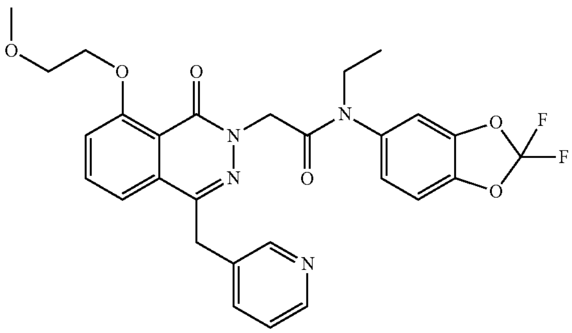 [SMILES: CCN(C(=O)Cn1nc(Cc2cccnc2)c2cccc(OCCOC)c2c1=O)c1ccc2c(c1)OC(F)(F)O2] | N-(2,2-difluorobenzo[d][1,3]dioxol-5-yl)-N-ethyl-2-(8-(2-methoxyethoxy)-1-oxo-4-(pyridin-3-ylmethyl)phthalazin-2(1H)-yl)acetamide | 553 [M + H] |
| 62. | 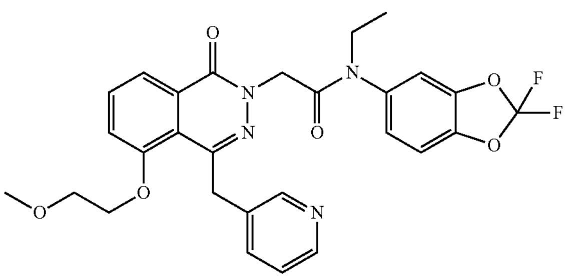 [SMILES: CCN(C(=O)Cn1nc(Cc2cccnc2)c2c(OCCOC)cccc2c1=O)c1ccc2c(c1)OC(F)(F)O2] | N-(2,2-difluorobenzo[d][1,3]dioxol-5-yl)-N-ethyl-2-(5-(2-methoxyethoxy)-1-oxo-4-(pyridin-3-ylmethyl)phthalazin-2(1H)-yl)acetamide | 553 [M + H] |

4-hydroxyisobenzofuran-1(3H)-one

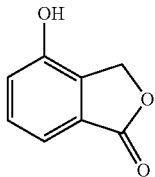

4-methoxyisobenzofuran-1(3H)-one and 7-methoxyisobenzofuran-1(3H)-one

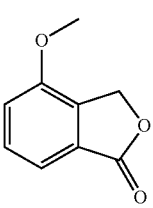 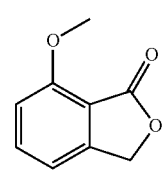

A solution of 3-hydroxy benzoic acid (1.0 g, 7.24 mmol) in 40% formaldehyde (20 mL) was treated with conc. HCl (20 mL) and conc. H₂SO₄ (1 mL) at rt, then stirred overnight. The reaction mixture was concentrated, treated with sat'd NH₄Cl (50 mL) and extracted with EtOAc (2×25 mL). The organic layer was washed with brine, dried over Na₂SO₄, and concentrated. The crude product was purified by silica gel chromatography (0-25% EtOAc/hexane) to give 6-hydroxyisobenzofuran-1(3H)-one (0.850 g), (MS: ESI+ve, 151 [M+H]). ¹H NMR (400 MHz, DMSO) δ: 5.31 (s, 2H), 7.28-7.30 (d, J=7.2, 1H), 7.39-7.43 (t, 1H), 7.46-7.48 (dd, J=4.0, 1H), 10.25 (s, 1H).

To a solution of 6-hydroxyisobenzofuran-1(3H)-one (4.0 g, 26.0 mmol) in acetone (40 mL) was added K₂CO₃ (14.7 g, 107 mmol) at rt. The mixture was stirred under N₂ for 30 min, then dimethyl sulfate (11 mL, 106.6 mmol) was added and the reaction mixture stirred overnight at rt. It was concentrated, treated with sat'd NH₄Cl (500 mL), and extracted with EtOAc (2×50 mL). The organic layer was washed with brine, dried over Na₂SO₄, and concentrated. The crude product was purified by silica gel chromatography (0-60% EtOAc/hexane) to give a mixture of 4-methoxyisobenzofuran-1 (3H)-one and 7-methoxyisobenzofuran-1 (3H)-one (3.5 g), (MS: ESI+ve, 165 [M+H]).

4-ethoxyisobenzofuran-1(3H)-one

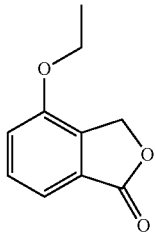

To a solution of 6-hydroxyisobenzofuran-1(3H)-one (4.0 g, 26.0 mmol) in acetone (40 mL) was added K₂CO₃ (14.7 g, 106.6 mmol) at rt. The mixture was stirred at rt under N₂ for 30 min, then diethylsulfate (14 mL, 106.6 mmol) was added and the reaction stirred at rt overnight. It was concentrated, treated with sat'd NH₄Cl (500 mL), and extracted with EtOAc (2×50 mL). The organic layer was washed with brine, dried over Na₂SO₄, and concentrated. The crude product was purified by silica gel chromatography (0-60% EtOAc/hexane) to give 4-ethoxyisobenzofuran-1(3H)-one (3.5 g), (MS: ESI+ve, 179 [M+H]).

4-(cyclohexyloxy)isobenzofuran-1(3H)-one

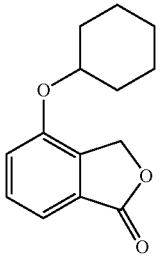 [SMILES: O=C1OCc2c(OC3CCCCC3)cccc21]

To a solution of 6-hydroxyisobenzofuran-1(3H)-one (4.0 g, 26.6 mmol) in DMSO (30 mL) was added K-OtBu (8.9 g, 79.9 mmol) at rt and the mixture stirred for 30 min. Cyclohexyl bromide (20.0 mL, 159.9 mmol) was added and stirring continued at 110° C. overnight. The reaction mixture was concentrated, treated with sat'd NH₄Cl (500 mL), and extracted with EtOAc (2×100 mL). The organic layer was washed with brine, dried over Na₂SO₄, and concentrated. The crude product was purified by silica gel chromatography (0-5% EtOAc/hexane) to give 4-(cyclohexyloxy)isobenzofuran-1(3H)-one (2.0 g), (MS: ESI+ve, 233 [M+H]).

4-(2-methoxyethoxy)isobenzofuran-1(3H)-one

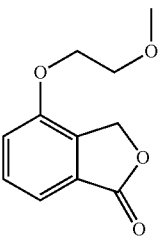

To a solution of 6-hydroxyisobenzofuran-1(3H)-one (3.0 g, 20.0 mmol) in DMF (50 mL) was added NaH (60%) (1.44 g, 20.0 mmol). The mixture was stirred for 30 min, then 2-bromo ethyl methyl ether (3.0 g, 20.0 mmol) was added and stirring continued overnight. The reaction mixture was concentrated, treated with sat'd NH₄Cl (500 mL), and extracted with EtOAc (2×100 mL). The organic layer was washed with brine, dried over Na₂SO₄, and concentrated. The crude product was purified by silica gel chromatography (0-20% EtOAc/hexane) to give 4-(2-methoxyethoxy)isobenzofuran-1(3H)-one (3.2 g), (MS: ESI+ve, 209 [M+H]).

4-(3-chlorophenyl)phthalazin-1(2H)-one

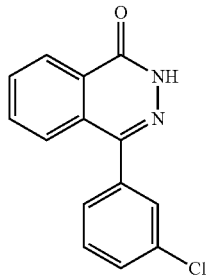 [SMILES: O=c1[nH]nc(-c2cccc(Cl)c2)c2ccccc12]

A solution of 1-chlorophthalazine-4-one (1.0 g, 5.5 mmol), 3-chlorophenyl boronic acid (1.3 g, 8.3 mmol), tricyclohexyphosphine (0.058 g, 0.27 mmol), and K₃PO₄ (2.3 g, 11.0 mmol) in THF (20 mL) and water (5 mL) was degassed with N₂ for 30 min then treated with tri(dibenzylideneacetone)-dipalladium (0.050 g, 0.05 mmol) and heated at reflux overnight. The reaction mixture was diluted with water (100 mL) and the product extracted with EtOAc (2×100 mL). The organics were washed with brine, dried over Na₂SO₄, and concentrated to give 4-(3-chlorophenyl)phthalazin-1(2H)-one (1.2 g), (MS: ESI+ve, 257.12 [M+H]).
¹H NMR: (400 MHz, DMSO) δ: 7.58-7.60 (m, 2H), 7.61-7.64 (m, 2H), 7.65-7.67 (m, 1H), 7.90-7.93 (m, 2H), 8.34-8.36 (m, 1H). 12.93 (s, 1H).

Example 63

2-(4-(3-chlorophenyl)-1-oxophthalazin-2(1H)-yl)-N-methyl-N-(2-methylbenzo[d]oxazol-6-yl)acetamide

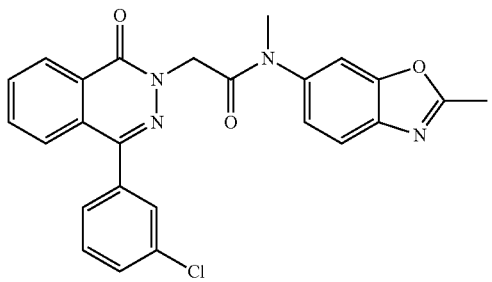

To a solution of 4-(3-chlorophenyl)phthalazin-1(2H)-one (0.5 g, 1.94 mmol) in DMF (20 mL) was added NaH (60%) (0.116 g, 2.91 mmol) portionwise at 0° C. After stirring for 30 min, 2-bromo-N-methyl-N-(2-methylbenzo[d]oxazol-6- yl) acetamide (0.55 g, 1.94 mmol) in DMF (2 mL) was added dropwise and the reaction mixture warmed to rt overnight. The reaction was quenched with water and the solid collected by filtration. The crude was purified by column chromatography (60-70% EtOAc/hexane) to give 2-(4-(3-chlorophenyl)-1-oxophthalazin-2(1H)-yl)-N-methyl-N-(2-methylbenzo[d]oxazol-6-yl)acetamide (0.22 g), (MS: ESI+ve, 459.17 [M+H]). $^1$H NMR: (400 MHz, DMSO) δ: 2.63 (s, 3H), 3.24 (s, 3H), 4.73 (s, 2H), 7.44-7.46 (d, J=8.0, 1H), 7.55-7.66 (m, 4H), 7.69-7.74 (q, 2H), 7.93 (s, 3H), 8.29-8.31 (d, J=7.2, 1H).

Representative compounds of the invention were prepared in a similar manner to example 63 from 4-chlorophthalazin-1(2H)-one, the corresponding boronic acid or ester, and the appropriate alkylating agent (scheme 2).

2,2,2-trifluoro-N-methyl-N-(2-methylbenzo[d]oxazol-6-yl)acetamide

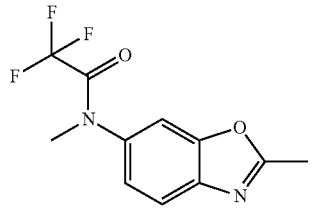

| 64. | 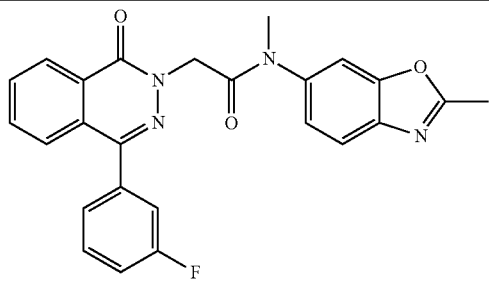 | 2-(4-(3-fluorophenyl)-1-oxophthalazin-2(1H)-yl)-N-methyl-N-(2-methylbenzo[d]oxazol-6-yl)acetamide | 443 [M + H] |
|---|---|---|---|

2-methylbenzo[d]oxazol-6-amine

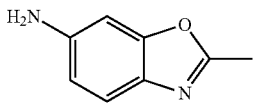

2-Methyl-6-nitrobenzoxazole (10.0 g, 56 mmol) and 10% Pd/C (3.4 g) in MeOH (10 mL) were hydrogenated at rt for 16 h. The reaction mixture was filtered through Celite and wash with MeOH (100 mL). The filtrate was concentrated under vacuum to obtained crude 2-methylbenzo[d]oxazol-6-amine (8.4 g), (MS: ESI+ve, 149.07 [M+H]); $^1$H NMR: (400 MHz, DMSO) δ: 2.47 (s, 3H), 5.24 (s, 2H), 6.56-6.53 (dd, J=2, 1H), 6.70-6.70 (d, J=1.6, 1H), 7.25-7.23 (d, J=8.4, 1H).

2,2,2-trifluoro-N-(2-methylbenzo[d]oxazol-6-yl)acetamide

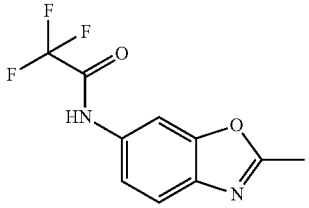 [SMILES: Cc1nc2ccc(NC(=O)C(F)(F)F)cc2o1]

A solution of 2-methylbenzo[d]oxazol-6-amine (8.4 g, 56.7 mmol) in pyridine (80 mL) at 0° C. was treated with TFAA (19.8 mL, 141.0 mmol) and stirred at rt for 4 h. The reaction mixture was diluted with water (100 mL) and the product extracted with EtOAc (3×100 mL). The organics were washed with brine, dried over Na$_2$SO$_4$, and concentrated to obtain the crude 2,2,2-trifluoro-N-(2-methylbenzo[d]oxazol-6-yl)acetamide (15.0 g), (MS: ESI+ve, 245.20 [M−H]); $^1$H NMR: (400 MHz, DMSO) δ: 2.61 (s, 3H), 7.61-7.56 (m, 1H), 7.69-7.67 (d, J=8.4, 1H), 8.04-8.04 (d, J=2, 1H), 11.45 (s, 1H).

A solution of 2,2,2-trifluoro-N-(2-methylbenzo[d]oxazol-6-yl)acetamide (15.0 g, 61.2 mmol) in DMF (100 mL) was treated with K$_2$CO$_3$ (8.448 g, 61.2 mmol) and the reaction mixture was stirred at rt for 1 h, then cooled to 0° C. Iodomethane (3.9 mL, 64.2 mmol) was added dropwise and stirring continued at rt overnight. The reaction mixture was diluted with water (100 mL) and extracted with EtOAc (3×100 mL). The organics were washed with brine, dried over Na$_2$SO$_4$ and concentrated to obtain crude 2,2,2-trifluoro-N-methyl-N-(2-methylbenzo[d]oxazol-6-yl)acetamide (16.5 g), (MS: ESI+ve, 259.26 [M+H]).

N,2-dimethylbenzo[d]oxazol-6-amine

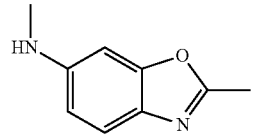

To a solution of crude 2,2,2-trifluoro-N-methyl-N-(2-methylbenzo[d]oxazol-6-yl)acetamide (16.5 g, 63.0 mmol) in MeOH (440 mL) and water (73 mL) was added K$_2$CO$_3$ (35.3 g, 25.5 mmol). The reaction mixture was stirred at reflux for 3 h, then concentrated under vacuum, diluted with water (50 mL), extracted with EtOAc (2×50 mL). The organics were washed with brine, dried over Na$_2$SO$_4$, and concentrated to obtain crude N,2-dimethylbenzo[d]oxazol-6-amine (8.3 g), (MS: ESI+ve, 163.12 [M+H]); $^1$H NMR: (400 MHz, DMSO) δ: 2.51 (s, 3H), 2.56 (s, 3H), 5.87-5.85 (m, 1H), 6.57-6.53 (m, 1H), 6.65-6.64 (d, J=2.4, 1H), 7.31-7.28 (t, 1H).

2-bromo-N-methyl-N-(2-methylbenzo[d]oxazol-6-yl)acetamide

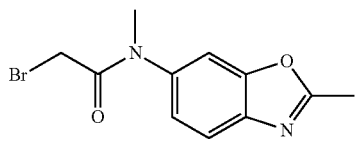 [SMILES: Cc1nc2ccc(N(C)C(=O)CBr)cc2o1]

To a solution of N,2-dimethylbenzo[d]oxazol-6-amine (9.4 g, 58.0 mmol) in DCM (100 mL) was added EDC.HCl (26.6 g, 139 mmol), DMAP (0.354 g, 2.9 mmol) and bromoacetic acid (18.5 g, 133.0 mmol) at 0° C. under $N_2$. The reaction mixture was stirred at rt overnight, then diluted with water (200 mL). The product was extracted with DCM (3×100 mL) and the organics were washed with brine, dried over $Na_2SO_4$ and concentrated to obtain 2-bromo-N-methyl-N-(2-methylbenzo[d]oxazol-6-yl)acetamide (10.0 g, 61%), (MS: ESI+ve, 283.1 [M+H]); $^1$H NMR: (400 MHz, DMSO) δ: 2.59 (s, 3H), 3.23 (s, 3H), 4.04 (s, 2H), 6.76-6.74 (d, J=8.8, 1H), 7.38-7.30 (dd, J=8.8, 1H), 7.73-7.71 (d, J=8, 1H).

1,4-dioxo-1,2,3,4-tetrahydrophthalazine-6-carboxylic acid

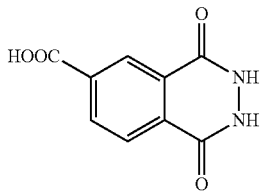 [SMILES: O=C(O)c1ccc2c(=O)[nH][nH]c(=O)c2c1]

To a solution of 1,4-dioxo-1,2,3,4-tetrahydrophthalazine-6-carboxylic acid (20 g, 104 mmol) in iPrOH (250 mL) was added hydrazine hydrate (10.40 g, 208 mmol) and the reaction mixture heated to reflux overnight. Upon cooling, the reaction mixture was filtered and the precipitate washed with iPrOH (100 mL) to obtain 1,4-dioxo-1,2,3,4-tetrahydrophthalazine-6-carboxylic acid (25 g, 100%), (MS: ESI+ve, 205.19 [M+H])$^1$H NMR: (400 MHz, DMSO) δ: 8.00-8.02 (dd, J=1.6, 8.4, 1H), 8.24-8.31 (m, 1H), 8.56 (s, 1H).

1-chloro-4-oxo-3,4-dihydrophthalazine-6-carboxylic acid and 1-chloro-4-oxo-3,4-dihydrophthalazine-7-carboxylic acid

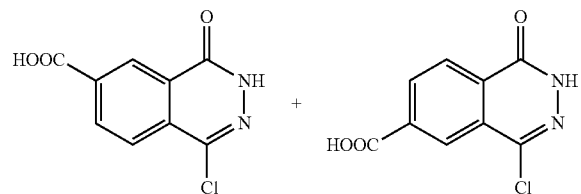 [SMILES: O=C(O)c1ccc2c(Cl)n[nH]c(=O)c2c1 ; O=C(O)c1ccc2c(=O)[nH]nc(Cl)c2c1]

A solution of 1,4-dioxo-1,2,3,4-tetrahydrophthalazine-6-carboxylic acid (2.0 g) in $SO_2Cl_2$ (20 mL) was heated to 90° C. for 3 h. $POCl_3$ (20 mL) was added and heating continued at 110° C. overnight. The solution was concentrated under vacuum and distilled with toluene (3×50 mL) to give crude 1,4-dichlorophthalazine-6-carboxylic acid (1.3 g, 56%), (MS: ESI+ve, 242 [M+H]). This material was dissolved in dioxane (25 mL) and treated dropwise with 2N NaOH (27 mL) at 0° C. The reaction mixture was stirred at 50° C. for 1 h, then cooled to rt and concentrated. Water was added and acidified with 1N HCl. The solid was filtered and dried under vacuum to give a 1:1 isomeric mixture of 1-chloro-4-oxo-3,4-dihydrophthalazine-6-carboxylic acid and 1-chloro-4-oxo-3,4-dihydrophthalazine-7-carboxylic acid (0.7 g, 58%), (MS: ESI+ve, 225 [M+H]).

Ethyl 1-chloro-4-oxo-3,4-dihydrophthalazine-6-carboxylate and ethyl 1-chloro-4-oxo-3,4-dihydrophthalazine-7-carboxylate

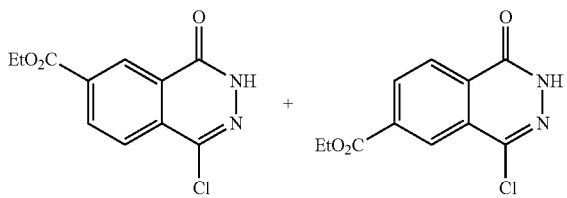 [SMILES: CCOC(=O)c1ccc2c(Cl)n[nH]c(=O)c2c1 ; CCOC(=O)c1ccc2c(=O)[nH]nc(Cl)c2c1]

To a solution of a 1:1 mixture of 1-chloro-4-oxo-3,4-dihydrophthalazine-6-carboxylic acid and 1-chloro-4-oxo-3,4-dihydrophthalazine-7-carboxylic acid (0.7 g) in EtOH (10 mL) was added $H_2SO_4$ (0.7 mL) and the resulting solution stirred at reflux for 16 h. The reaction was concentrated, water (25 mL) added, treated with sat'd $NaHCO_3$ (30 mL), and the product extracted with EtOAc (2×100 mL). The organics were washed with brine, dried over $Na_2SO_4$, and concentrated. The crude product was purified by column chromatography (10-15% EtOAc/hexane) to give a mixture of ethyl 1-chloro-4-oxo-3,4-dihydrophthalazine-6-carboxylate and ethyl 1-chloro-4-oxo-3,4-dihydrophthalazine-7-carboxylate (0.550 g, 70%), (MS: ESI+ve, 252.8 [M+H])

Ethyl 1-(3-chlorophenyl)-4-oxo-3,4-dihydrophthalazine-6-carboxylate and Ethyl 1-(3-chlorophenyl)-4-oxo-3,4-dihydrophthalazine-7-carboxylate

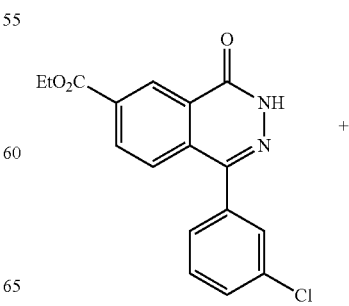

137

-continued

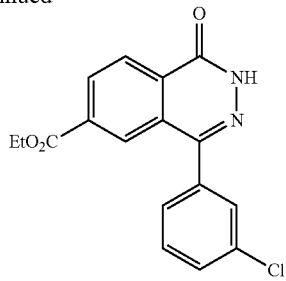

A mixture of ethyl 1-chloro-4-oxo-3,4-dihydrophthalazine-6-carboxylate and ethyl 1-chloro-4-oxo-3,4-dihydrophthalazine-7-carboxylate (0.5 g, 1.98 mmol), (3-chlorophenyl)boronic acid (0.34 g, 2.1 mmol), and $K_2CO_3$ (0.546 g, 3.9 mmol) in dioxane (10 mL) and water (1 mL) was degassed with argon. It was treated with 1,1-bis(diphenylphosphino)ferrocene-palladium(II) dichloride methylene chloride complex (0.16 g, 0.19 mmol). The reaction was heated to reflux for 1 hr, then diluted with water (20 mL) and extracted with EtOAc (2×25 mL). The organics were dried over $Na_2SO_4$ and concentrated to give crude product, which was purified by column chromatography (10-15% EtOAc/hexane) to give a mixture of ethyl 1-(3-chlorophenyl)-4-oxo-3,4-dihydrophthalazine-6-carboxylate and ethyl 1-(3-chlorophenyl)-4-oxo-3,4-dihydrophthalazine-7-carboxylate (0.4 g, 61%), (MS: ESI+ve, 328.86 [M+H]).

Examples 65 and 66

Ethyl 1-(3-chlorophenyl)-3-(2-(methyl(2-methylbenzo[d]oxazol-6-yl)amino)-2-oxoethyl)-4-oxo-3,4-dihydrophthalazine-6-carboxylate and ethyl 1-(3-chlorophenyl)-3-(2-(methyl(2-methylbenzo[d]oxazol-6-yl)amino)-2-oxoethyl)-4-oxo-3,4-dihydrophthalazine-7-carboxylate

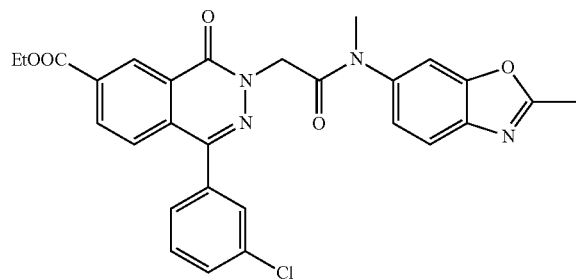

138

-continued

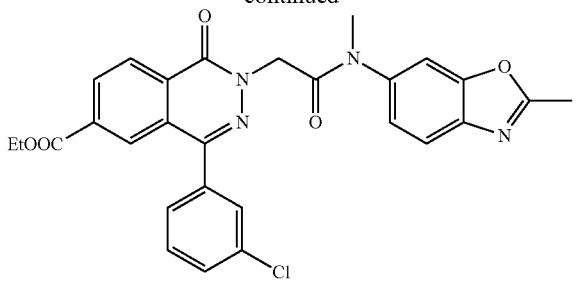

A mixture of ethyl 1-(3-chlorophenyl)-4-oxo-3,4-dihydrophthalazine-6-carboxylate and ethyl 1-(3-chlorophenyl)-4-oxo-3,4-dihydrophthalazine-7-carboxylate (0.7 g, 2.1 mmol) in THF (15 mL) at 0° C. was treated with LiHMDS (1N in THF) (3.2 mL, 3.2 mmol) and stirred for 30 min. 2-Bromo-N-methyl-N-(2-methylbenzo[d]oxazol-6-yl) acetamide (0.6 g, 2.1 mmol) in THF (10 mL) was added dropwise and the reaction warmed to rt overnight. It was quenched with water (100 mL) and product extracted with EtOAc (2×100 mL). The organics were washed with brine (50 mL), dried over $Na_2SO_4$ and concentrated to give crude product, which was purified by preparative HPLC. Example 65: ethyl 1-(3-chlorophenyl)-3-(2-(methyl(2-methylbenzo[d]oxazol-6-yl)amino)-2-oxoethyl)-4-oxo-3,4-dihydrophthalazine-6-carboxylate (0.025 g), (MS: ESI+ve, 530.88 [M+H])$^1$H NMR: (400 MHz, DMSO) δ: 1.36-1.40 (t, 3H), 2.62 (s, 3H), 3.34 (s, 3H), 4.39-4.44 (q, 2H), 4.78 (s, 2H), 7.43-7.45 (d, J=7.2, 1H), 7.56-7.72 (m, 4H), 7.83-7.85 (d, J=8.4, 2H), 7.93 (s, 1H), 8.39-8.41 (t, 1H), 8.77 (s, 1H); Example 66: ethyl 1-(3-chlorophenyl)-3-(2-(methyl(2-methylbenzo[d]oxazol-6-yl)amino)-2-oxoethyl)-4-oxo-3,4-dihydrophthalazine-7-carboxylate (0.014 g), (MS: ESI+ve, 530.88 [M+H]). $^1$H NMR (400 MHz, DMSO) δ: 1.30-1.33 (t, 3H), 2.62 (s, 3H), 3.34 (s, 3H), 4.33-4.38 (q, 2H), 4.76 (s, 2H), 7.44-7.46 (d, J=7.6, 1H), 7.59-7.74 (m, 5H), 7.94 (s, 1H), 8.20 (s, 1H), 8.37-8.43 (q, 2H).

Representative compounds of the invention were prepared in a similar manner to examples 65 and 66 (scheme 2) using the appropriate alkylating agent and commercially available boronic acid or boronic ester.

| Example No | Structure | IUPAC Name | LCMS m/z |
|---|---|---|---|
| 67. | 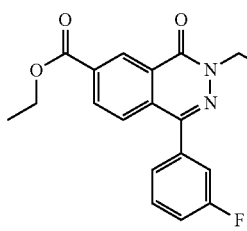 | ethyl 1-(3-fluorophenyl)-3-(2-(methyl(2-methylbenzo[d]oxazol-6-yl)amino)-2-oxoethyl)-4-oxo-3,4-dihydrophthalazine-6-carboxylate | 532 [M + H] |

| Example No | Structure | IUPAC Name | LCMS m/z |
|---|---|---|---|
| 68. | 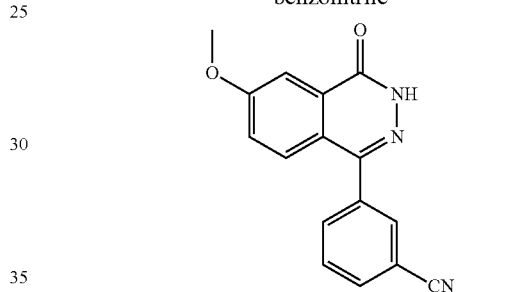 | ethyl 4-(3-fluorophenyl)-2-(2-(methyl(2-methyl-benzo[d]oxazol-6-yl)amino)-2-oxoethyl)-1-oxo-1,2-dihydrophthalazine-6-carboxylate | 532 [M + H] |

3-cyano-N-methoxy-N-methylbenzamide

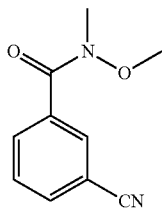

To a 0° C. solution of 3-cyano benzoic acid (5.0 g, 33.9 mmol) in DMF (30 mL) was added triethylamine (14.8 mL, 101.7 mmol) and EDC.HCl (9.77 g, 12.24 mmol). The mixture was stirred at rt for 30 minutes, then cooled again to 0° C. N—O-Dimethylhydroxylamine.HCl (4.97 g, 50.98 mmol) was added and the mixture stirred at rt overnight. The reaction was quenched with water (300 mL) and extracted with EtOAc (2×100 mL). The organic layers was washed with brine, dried over $Na_2SO_4$, and concentrated. The crude product was purified by silica gel chromatography (0-25% EtOAc/hexane) to give 3-cyano-N-methoxy-N-methylbenzamide (3.2 g, 191 [M+H]). $^1$H NMR: (400 MHz, DMSO) δ: 3.28 (s, 3H), 3.55 (s, 3H), 7.65-7.69 (t, 1H), 7.89-7.90 (d, J=2.4, 1H), 7.96-7.97 (d, J=5.6, 1H), 8.03 (s, 1H).

2-(3-cyanobenzoyl)-5-methoxybenzoic acid

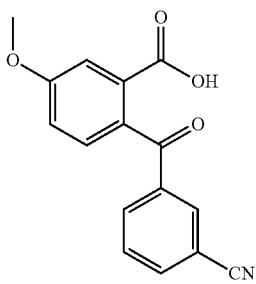 [SMILES: COc1ccc(C(=O)c2cccc(C#N)c2)c(C(=O)O)c1]

To a solution of 2-bromo-5-methoxybenzoic acid (3.69 g, 15.0 mmol) in THF (15 mL) was added n-BuLi (1.6 M in hexane) (21 mL, 33.6 mmol) dropwise at −78° C. The reaction mixture was stirred for 1 h at −78° C., and then a solution of 3-cyano-N-methoxy-N-methylbenzamide (3.2 g, 16.8 mmol) in THF (15 mL) was added dropwise. The reaction was stirred for 1 h at −78° C. and then overnight at rt. The reaction mixture was diluted with water (30 mL) and acidified with 5N HCl solution (10 mL) and extracted with EtOAc (2×100 mL). The organic layer was washed with brine, dried over $Na_2SO_4$, and concentrated to obtain 2-(3-cyanobenzoyl)-5-methoxybenzoic acid (3.8 g, 282 [M+H]). $^1$H NMR: (400 MHz, DMSO) δ: 3.92 (s, 3H), 7.31-7.32 (t, 2H), 7.43-7.45 (t, 2H), 7.56 (s, 1H), 7.71-7.72 (d, J=1.6, 1H), 8.10-8.10 (d, J=1.2, 1H), 12.70 (s, 1H).

3-(6-methoxy-4-oxo-3, 4-dihydrophthalazin-1-yl)benzonitrile

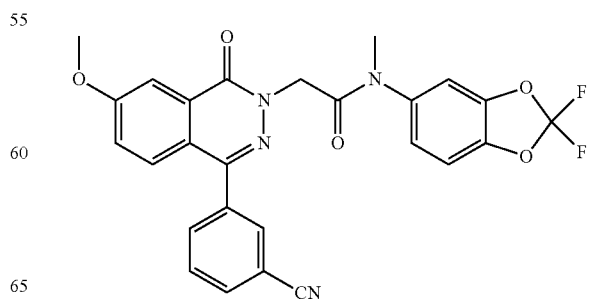

A solution of 2-(3-cyanobenzoyl)-5-methoxybenzoic acid (4.0 g, 14.2 mmol) in hydrazine hydrate (8 mL) and EtOH (40 mL) was heated at 110° C. for 2 hr. The reaction mixture was diluted with water (100 mL), and the precipitate was filtered and dried to yield 3-(6-methoxy-4-oxo-3, 4-dihydrophthalazin-1-yl) benzonitrile (1.1 g, 278 [M+H]). $^1$H NMR: (400 MHz, DMSO) δ: 3.96 (s, 3H), 7.28-7.33 (dd, J=2.0, 1H), 7.60-7.62 (d, J=8.8, 1H), 7.73-7.78 (m, 2H), 7.92-7.94 (d, J=8.0, 1H), 8.01-8.03 (d, J=8.0, 1H), 8.07 (s, 1H), 12.83 (s, 1H).

Example 69

2-(4-(3-cyanophenyl)-7-methoxy-1-oxophthalazin-2(1H)-yl)-N-(2, 2-difluorobenzo[d][1, 3]dioxol-5-yl)-N-methylacetamide To a solution of 3-(6-methoxy-4-oxo-3, 4-dihydrophthalazin-1-yl) benzonitrile (0.1 g, 0.36 mmol) in DMF (10 mL) was added NaH (60%) (0.021 g, 0.36 mmol) portionwise at 0° C. The reaction mixture was stirred for 30 min at 0° C. 2-Bromo-N-(2, 2-difluorobenzo[d][1, 3]dioxol-5-yl-N-methylacetamide (0.111 g, 0.54 mmol) in DMF (2 mL) was added dropwise at 0° C. and the reaction stirred overnight at rt. The reaction mixture was diluted with sat'd NH₄Cl (25 mL) and extracted with EtOAc (2×25 mL). The organics were washed with brine (50 mL), dried over Na₂SO₄, and concentrated to give crude which was purified by column chromatography (0-10% EtOAc/DCM) to yield 2-(4(3-cyanophenyl)-7-methoxy-1-oxophthalazine-2(1H)-yl)-N-(2, 2-difluorobenzo[d][1, 3]dioxol-5-yl)-N-methylacetamide (0.045 g, 505 [M+H]). ¹H NMR: (400 MHz, DMSO) δ: 3.19 (s, 3H), 3.96 (s, 3H), 4.77 (s, 2H), 7.34-7.36 (d, J=7.6, 1H), 7.49-7.52 (m, 2H), 7.64-7.69 (t, 3H), 7.76-7.80 (t, 1H), 7.91-7.93 (d, J=8.0, 1H), 8.03-8.05 (m, 2H).

3-fluoro-N-methoxy-N-methylbenzamide

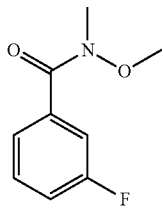

To a solution of 3-fluorobenzoic acid (30 g, 214.1 mmol) in DCM (300 mL) were added EDC.HCl (45 g, 235 mmol) and N,O-dimethylhydroxylamine.HCl (23 g, 235 mmol) at 0° C. under N₂. The reaction mixture was stirred at rt for 3 h, then diluted with water (1000 mL) and extracted with DCM (3×200 mL). The organics were washed with brine, dried over Na₂SO₄, and concentrated to obtain the 3-fluoro-N-methoxy-N-methylbenzamide (24 g, 61%). (183.91 [M+H]) 1H NMR: (400 MHz, CDCl₃) δ: 3.38 (s, 3H), 3.57 (s, 3H), 7.14-7.19 (m, 1H), 7.37-7.43 (m, 2H), 7.48-7.50 (d, J=7.6, 1H).

2-(3-fluorobenzoyl)-5-methoxybenzoic acid

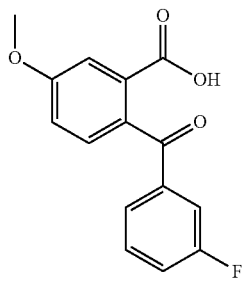 [SMILES: COc1ccc(C(=O)c2cccc(F)c2)c(C(=O)O)c1]

A −78° C. solution of 2-bromo-5-methoxybenzoic acid (26.0 g, 112.5 mmol) in THF (100 mL) was treated with n-BuLi (1.6 M in hexane) (140 mL, 225 mmol) and stirred at −78° C. for 1 h. 3-fluoro-N-methoxy-N-methylbenzamide (15.3 g, 83.8 mmol) in THF (40 mL) was added dropwise then warmed to rt for 16 h. The reaction mixture was diluted with water (100 mL), acidified with 5N HCl (25 mL) and extracted with EtOAc (3×200 mL). The organic layer was washed with brine, dried over Na₂SO₄, and concentrated to obtain 2-(3-fluorobenzoyl)-5-methoxybenzoic acid (21.0 g, 68%) (274.83 [M+H]); ¹H NMR: (400 MHz, DMSO) δ: 3.89 (s, 3H), 7.26-7.29 (m, 1H), 7.37-7.45 (m, 4H), 7.50-7.55 (m, 2H).

4-(3-fluorophenyl)-7-methoxyphthalazin-1(2H)-one

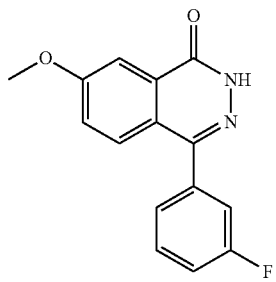 [SMILES: COc1ccc2c(-c3cccc(F)c3)n[nH]c(=O)c2c1]

A solution of 2-(3-fluorobenzoyl)-5-methoxybenzoic acid (21 g, 76.5 mmol) in hydrazine hydrate (4.09 mL, 84.0 mmol) and EtOH (300 mL) was heated overnight at 80° C. The reaction mixture was concentrated, diluted with water (300 mL), and the precipitate was filtered and dried to yield 4-(3-fluorophenyl)-7-methoxyphthalazin-1(2H)-one (7.2 g). (270.85 [M+H])¹H NMR: (400 MHz, DMSO) δ: 3.96 (s, 3H), 7.36-7.43 (m, 3H), 7.46-7.49 (m, 1H), 7.57-7.64 (m, 2H), 7.73-7.73 (d, J=2.8, 1H).

Example 70

2-(4-(3-fluorophenyl)-7-methoxy-1-oxophthalazin-2(1H)-yl)-N-methyl-N-(2-methylbenzo[d]oxazol-6-yl) acetamide

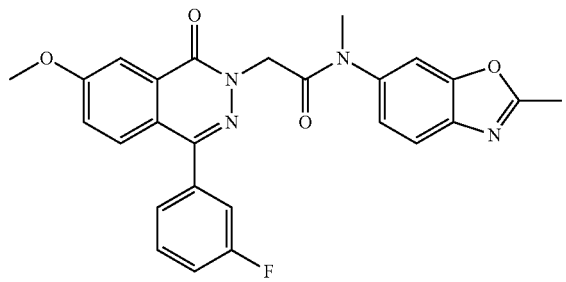

A 0° C. solution of 4-(3-fluorophenyl)-7-methoxyphthalazin-1(2H)-one (7.0 g, 25.9 mmol) in THF (160 mL) was treated with LiHMDS (1M in THF) (38 mL, 38 mmol) and stirred for 30 min. 2-Bromo-N-methyl-N-(2-methylbenzo[d]oxazol-6-yl)acetamide (7.33 g, 25.9 mmol) in THF (40 mL) was added dropwise and stirring was maintained at rt for 16 h. The reaction mixture was diluted with water (200 mL) and the product extracted with EtOAc (3×150 mL). The organics were washed with brine (100 mL), dried over Na₂SO₄, and concentrated. The crude was triturated with MeOH (250 mL) to yield 2-(4-(3-fluorophenyl)-7-methoxy-1-oxophthalazin-2(1H)-yl)-N-methyl-N-(2-methylbenzo[d]oxazol-6-yl)acetamide (9.1 g, 74%). (472.87 [M+H])¹H NMR: (400 MHz, DMSO) δ: 2.62 (s, 3H), 3.33 (s, 3H), 4.95 (s, 3H), 4.73 (s, 2H), 7.37-7.43 (m, 4H), 7.48-7.51 (d, J=2.4, 8.8, 1H), 7.58-7.73 (m, 4H), 7.90 (s, 1H).

Representative compounds of the invention were prepared in a similar manner to example 70 from the corresponding 2-bromobenzoic acid, N-methoxy-N-benzamide and appropriate alkylating agent (scheme 5).

| Example No. | Structure | IUPAC Name | LCMS m/z |
|---|---|---|---|
| 71. | 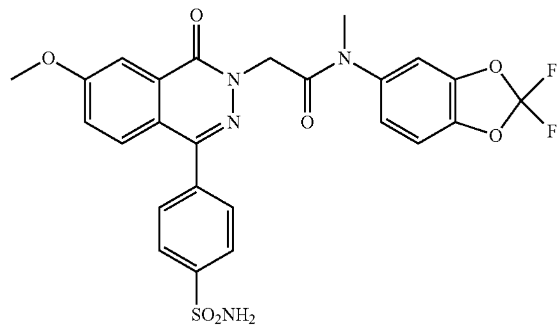 [SMILES: COc1ccc2c(-c3ccc(S(N)(=O)=O)cc3)nn(CC(=O)N(C)c3ccc4c(c3)OC(F)(F)O4)c(=O)c2c1] | N-(2,2-difluorobenzo[d][1,3]dioxol-5-yl)-2-(7-methoxy-1-oxo-4-(4-sulfamoylphenyl)phthalazin-2(1H)-yl)-N-methylacetamide | 559 [M + H] |
| 72. | 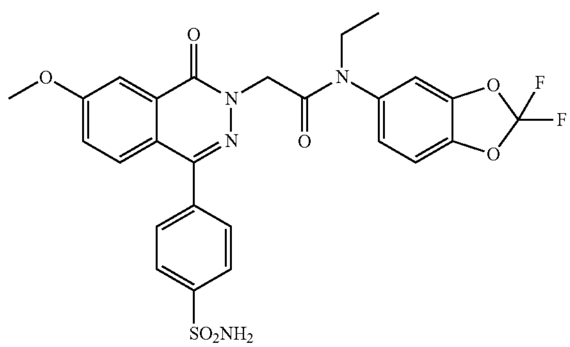 [SMILES: CCN(C(=O)Cn1nc(-c2ccc(S(N)(=O)=O)cc2)c2ccc(OC)cc2c1=O)c1ccc2c(c1)OC(F)(F)O2] | N-(2,2-difluorobenzo[d][1,3]dioxol-5-yl)-N-ethyl-2-(7-methoxy-1-oxo-4-(4-sulfamoylphenyl)phthalazin-2(1H)-yl)-acetamide | 573 [M + H] |
| 73. | 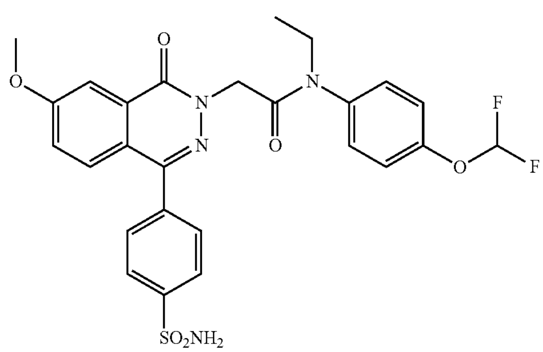 [SMILES: CCN(C(=O)Cn1nc(-c2ccc(S(N)(=O)=O)cc2)c2ccc(OC)cc2c1=O)c1ccc(OC(F)F)cc1] | N-(4-(difluoromethoxy)phenyl)-N-ethyl-2-(7-methoxy-1-oxo-4-(4-sulfamoylphenyl)phthalazin-2(1H)-yl)acetamide | 559 [M + H] |
| 74. | 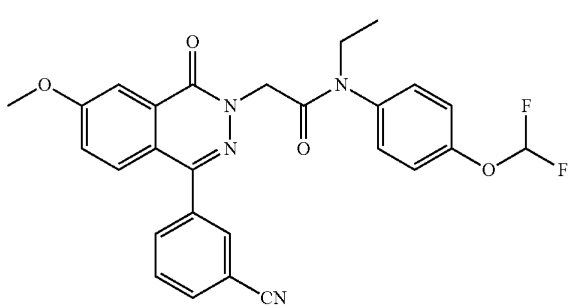 [SMILES: CCN(C(=O)Cn1nc(-c2cccc(C#N)c2)c2ccc(OC)cc2c1=O)c1ccc(OC(F)F)cc1] | 2-(4-(3-cyanophenyl)-7-methoxy-1-oxophthalazin-2(1H)-yl)-N-(4-(difluoromethoxy)phenyl)-N-ethylacetamide | 505 [M + H] |

| Example No. | Structure | IUPAC Name | LCMS m/z |
|---|---|---|---|
| 75. | 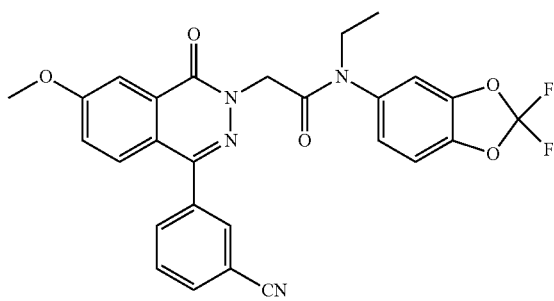 [SMILES: CCN(C(=O)Cn1nc(-c2cccc(C#N)c2)c2ccc(OC)cc2c1=O)c1ccc2c(c1)OC(F)(F)O2] | 2-(4-(3-cyanophenyl)-7-methoxy-1-oxophthalazin-2(1H)-yl)-N-(2,2-difluorobenzo[d][1,3]dioxol-5-yl)-N-ethylacetamide | 519 [M + H] |
| 76. | 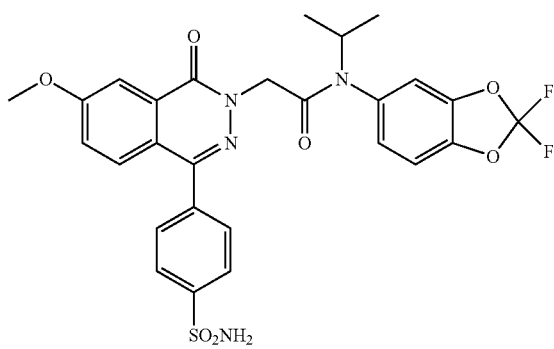 [SMILES: COc1ccc2c(-c3ccc(S(N)(=O)=O)cc3)nn(CC(=O)N(c3ccc4c(c3)OC(F)(F)O4)C(C)C)c(=O)c2c1] | N-(2,2-difluorobenzo[d][1,3]dioxol-5-yl)-N-isopropyl-2-(7-methoxy-1-oxo-4-(4-sulfamoylphenyl)phthalazin-2(1H)-yl)acetamide | 587 [M + H] |
| 77. | 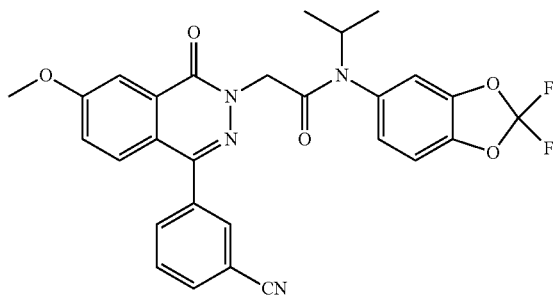 [SMILES: COc1ccc2c(-c3cccc(C#N)c3)nn(CC(=O)N(c3ccc4c(c3)OC(F)(F)O4)C(C)C)c(=O)c2c1] | 2-(4-(3-cyanophenyl)-7-methoxy-1-oxophthalazin-2(1H)-yl)-N-(2,2-difluorobenzo[d][1,3]dioxol-5-yl)-N-isopropylacetamide | 533 [M + H] |
| 78. | 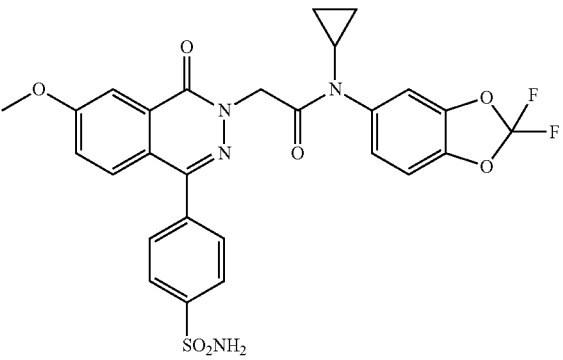 [SMILES: COc1ccc2c(-c3ccc(S(N)(=O)=O)cc3)nn(CC(=O)N(c3ccc4c(c3)OC(F)(F)O4)C3CC3)c(=O)c2c1] | N-cyclopropyl-N-(2,2-difluorobenzo[d][1,3]dioxol-5-yl)-2-(7-methoxy-1-oxo-4-(4-sulfamoylphenyl)phthalazin-2(1H)-yl)acetamide | 585 [M + H] |

-continued

| Example No. | Structure | IUPAC Name | LCMS m/z |
|---|---|---|---|
| 79. | 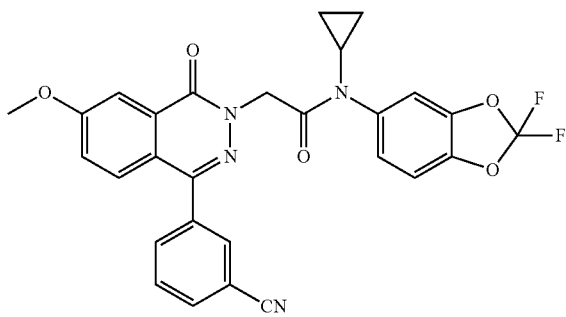 [SMILES: COc1ccc2c(-c3cccc(C#N)c3)nn(CC(=O)N(c3ccc4c(c3)OC(F)(F)O4)C3CC3)c(=O)c2c1] | 2-(4-(3-cyanophenyl)-7-methoxy-1-oxophthalazin-2(1H)-yl)-N-cyclopropyl-N-(2,2-difluorobenzo[d][1,3]dioxol-5-yl)acetamide | 531 [M + H] |
| 80. | 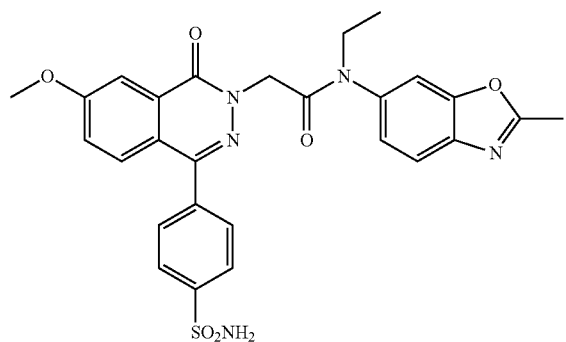 | N-ethyl-2-(7-methoxy-1-oxo-4-(4-sulfamoylphenyl)phthalazin-2(1H)-yl)-N-(2-methylbenzo[d]oxazol-6-yl)acetamide | 548 [M + H] |
| 81. | 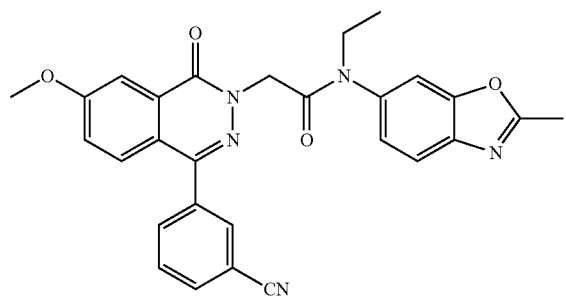 | 2-(4-(3-cyanophenyl)-7-methoxy-1-oxophthalazin-2(1H)-yl)-N-ethyl-N-(2-methylbenzo[d]oxazol-6-yl)acetamide | 494 [M + H] |
| 82. | 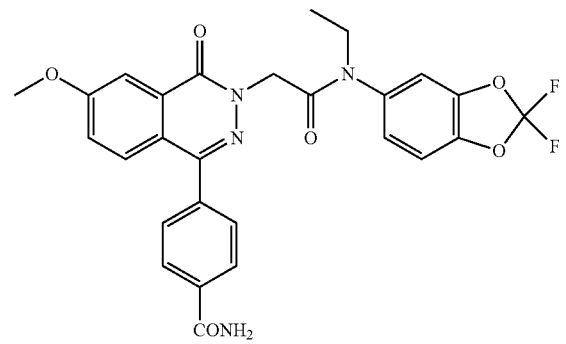 [SMILES: CCN(C(=O)Cn1nc(-c2ccc(C(N)=O)cc2)c2ccc(OC)cc2c1=O)c1ccc2c(c1)OC(F)(F)O2] | 4-(3-(2-((2,2-difluorobenzo[d][1,3]dioxol-5-yl)(ethyl)amino)-2-oxoethyl)-6-methoxy-4-oxo-3,4-dihydrophthalazin-1-yl)benzamide | 537 [M + H] |

| Example No. | Structure | IUPAC Name | LCMS m/z |
|---|---|---|---|
| 83. | 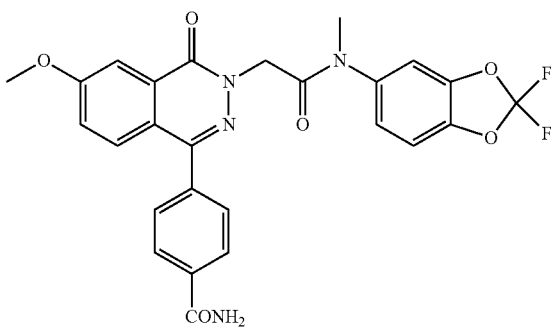 [SMILES: COc1ccc2c(-c3ccc(C(N)=O)cc3)nn(CC(=O)N(C)c3ccc4c(c3)OC(F)(F)O4)c(=O)c2c1] | 4-(3-(2-((2,2-difluorobenzo[d][1,3]dioxol-5-yl)(methyl)amino)-2-oxoethyl)-6-methoxy-4-oxo-3,4-dihydrophthalazin-1-yl)benzamide | 523 [M + H] |
| 84. | 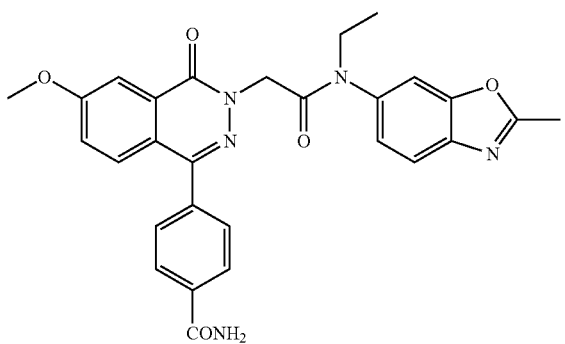 | 4-(3-(2-(ethyl(2-methylbenzo[d]oxazol-6-yl)amino)-2-oxoethyl)-6-methoxy-4-oxo-3,4-dihydrophthalazin-1-yl)benzamide | 512 [M + H] |
| 85. | 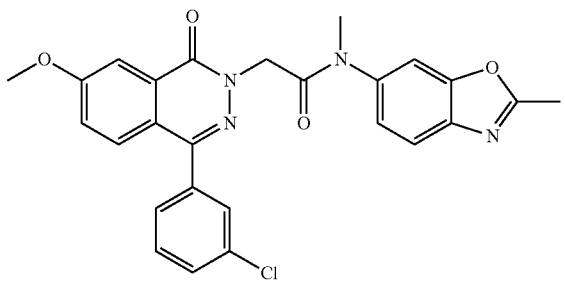 | 2-(4-(3-chlorophenyl)-7-methoxy-1-oxophthalazin-2(1H)-yl)-N-methyl-N-(2-methylbenzo[d]oxazol-6-yl)acetamide | 490 [M + H] |
| 86. | 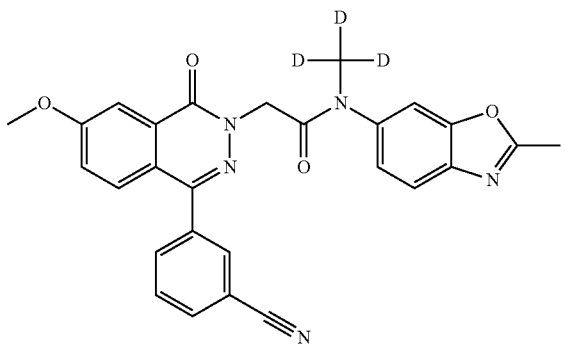 | 2-(4-(3-cyanophenyl)-7-methoxy-1-oxophthalazin-2(1H)-yl)-N-(methyl-d3)-N-(2-methylbenzo[d]oxazol-6-yl)acetamide | 484 [M + H] |

-continued

| Example No. | Structure | IUPAC Name | LCMS m/z |
|---|---|---|---|
| 87. | 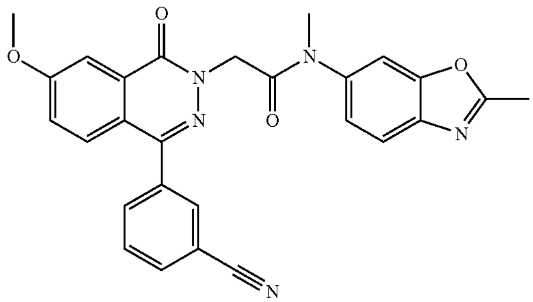 [SMILES: COc1ccc2c(-c3cccc(C#N)c3)nn(CC(=O)N(C)c3ccc4nc(C)oc4c3)c(=O)c2c1] | 2-(4-(3-cyanophenyl)-7-methoxy-1-oxophthalazin-2(1H)-yl)-N-methyl-N-(2-methylbenzo[d]oxazol-6-yl)acetamide | 480 [M + H] |
| 88. | 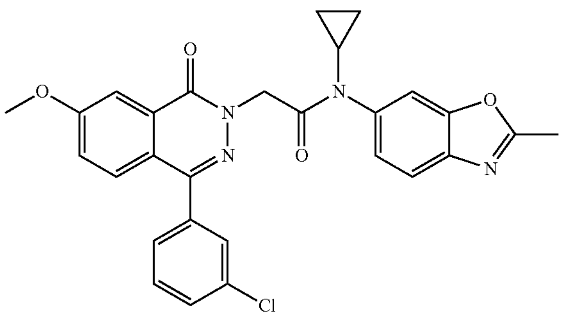 | 2-(4-(3-chlorophenyl)-7-methoxy-1-oxophthalazin-2(1H)-yl)-N-cyclopropyl-N-(2-methylbenzo[d]oxazol-6-yl)acetamide | 516 [M + H] |
| 89. | 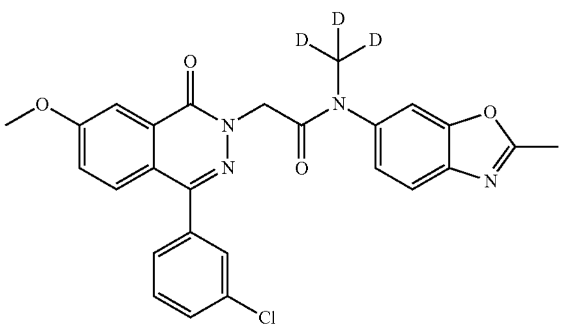 | 2-(4-(3-chlorophenyl)-7-methoxy-1-oxophthalazin-2(1H)-yl)-N-(methyl-d3)-N-(2-methylbenzo[d]oxazol-6-yl)acetamide | 493 [M + H] |
| 90. | 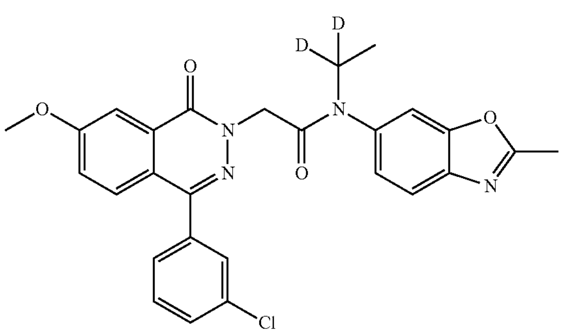 | 2-(4-(3-chlorophenyl)-7-methoxy-1-oxophthalazin-2(1H)-yl)-N-(ethyl-1,1-d2)-N-(2-methylbenzo[d]oxazol-6-yl)acetamide | 506 [M + H] |
| 91. | 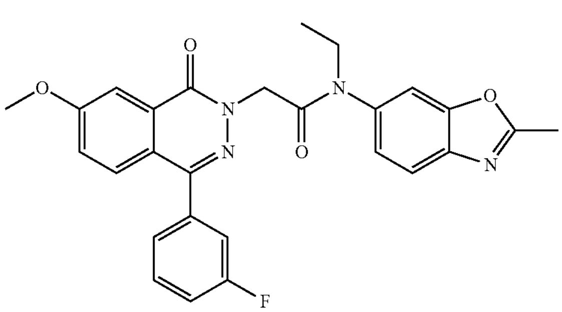 | N-ethyl-2-(4-(3-fluorophenyl)-7-methoxy-1-oxophthalazin-2(1H)-yl)-N-(2-methylbenzo[d]oxazol-6-yl)acetamide | 488 [M + H] |

-continued

| Example No. | Structure | IUPAC Name | LCMS m/z |
|---|---|---|---|
| 92. | 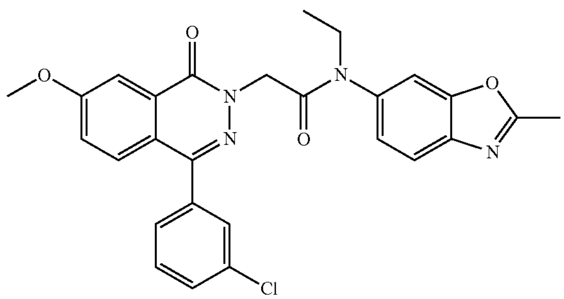 | 2-(4-(3-chlorophenyl)-7-methoxy-1-oxophthalazin-2(1H)-yl)-N-ethyl-N-(2-methylbenzo[d]oxazol-6-yl)acetamide | 504 [M + H] |
| 93. | 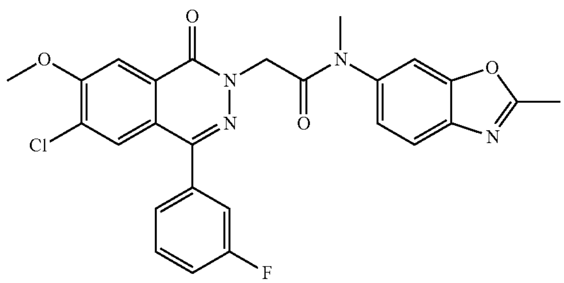 | 2-(6-chloro-4-(3-fluorophenyl)-7-methoxy-1-oxophthalazin-2(1H)-yl)-N-methyl-N-(2-methylbenzo[d]oxazol-6-yl)acetamide | 522 [M + H] |
| 94. | 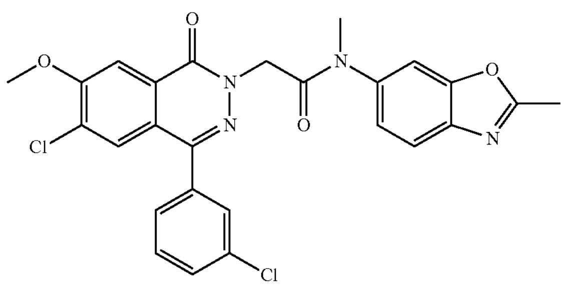 | 2-(6-chloro-4-(3-chlorophenyl)-7-methoxy-1-oxophthalazin-2(1H)-yl)-N-methyl-N-(2-methylbenzo[d]oxazol-6-yl)acetamide | 524 [M + H] |
| 95. | 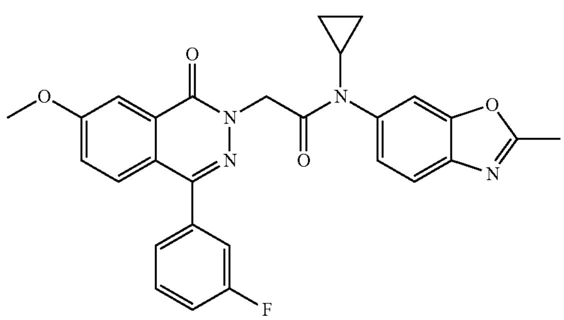 | N-cyclopropyl-2-(4-(3-fluorophenyl)-7-methoxy-1-oxophthalazin-2(1H)-yl)-N-(2-methylbenzo[d]oxazol-6-yl)acetamide | 500 [M + H] |
| 96. | 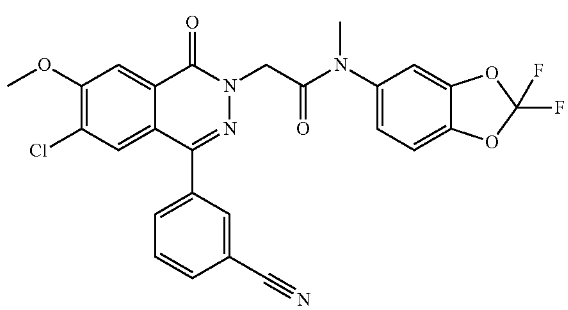 [SMILES: COc1cc2c(=O)n(CC(=O)N(C)c3ccc4c(c3)OC(F)(F)O4)nc(-c3cccc(C#N)c3)c2cc1Cl] | 2-(6-chloro-4-(3-cyanophenyl)-7-methoxy-1-oxophthalazin-2(1H)-yl)-N-(2,2-difluorobenzo[d][1,3]dioxol-5-yl)-N-methylacetamide | 540 [M + H] |

2-bromo-4-chloro-5-methoxybenzoic acid

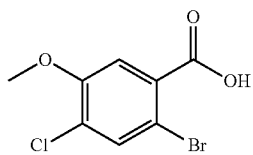

A solution of 4-chloro-3-methoxybenzoic acid (5.0 g, 26.7 mmol) in HOAc (25 mL) and water (25 mL) was treated slowly with Br₂ (1.6 mL 32 mmol). After heating to 60° C. for 2 h, the reaction was stirred cooled to rt overnight. It was quenched with water (300 mL), and the precipitate was filtered and dried to yield 2-bromo-4-chloro-5-methoxybenzoic acid (5.0 g, 70%). (264.87 [M−H])¹H NMR: (400 MHz, DMSO) δ: 3.90 (s, 3H), 7.46 (s, 1H), 7.82 (s, 1H), 13.63 (s, 1H).

4-chloro-2-(3-cyanobenzoyl)-5-methoxybenzoic acid

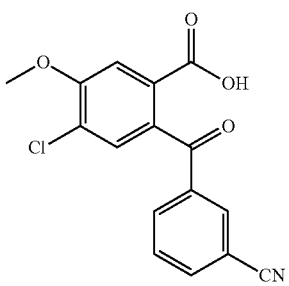 [SMILES: COc1cc(C(=O)O)c(C(=O)c2cccc(C#N)c2)cc1Cl]

A −78° C. solution of 2-bromo-4-chloro-5-methoxybenzoic acid (0.5 g, 1.88 mmol) in THF (15 mL) was treated with n-BuLi (1.6M in hexane) (1.7 ml, 2.82 mmol) and stirred for 1h at −78° C. 3-Cyano-N-methoxy-N-methylbenzamide (0.35 g, 1.88 mmol) in THF (15 mL) was added dropwise and the reaction stirred for 1h at −78° C., then overnight at rt. It was diluted with water (30 mL), acidified with 5N HCl (15 mL), and extracted with EtOAc (2×100 mL). The organic layer was washed with brine, dried over Na₂SO₄, and concentrated to obtain 4-chloro-2-(3-cyanobenzoyl)-5-methoxybenzoic acid (0.5 g, 84%) (316.33 [M−H]).

3-(7-chloro-6-methoxy-4-oxo-3, 4-dihydrophthalazin-1-yl) benzonitrile

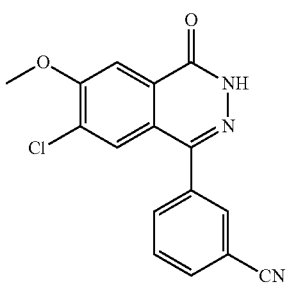 [SMILES: COc1cc2c(=O)[nH]nc(-c3cccc(C#N)c3)c2cc1Cl]

A solution of 4-chloro-2-(3-cyanobenzoyl)-5-methoxybenzoic acid (3.0 g, 9.50 mmol) in hydrazine hydrate (0.6 mL 11.4 mmol) and EtOH (40 mL) was heated at 80° C. for 2h. The reaction mixture was diluted with water (100 mL), and the precipitate was filtered and dried to obtain 3-(7-chloro-6-methoxy-4-oxo-3,4-dihydrophthalazin-1-yl) benzonitrile (0.6 g, 17%) (312.4 [M+H])¹H NMR: (400 MHz, DMSO) δ: 3.96 (s, 3H), 7.64 (s, 1H), 7.79-7.75 (t, 1H), 7.87 (s, 1H), 7.96-7.94 (d, J=8, 1H), 8.04-8.02 (d, J=8, 1H), 8.09 (s, 1H), 13.03 (s, 1H).

Example 97

Synthesis of 2-(4-(3-fluorophenyl)-7-hydroxy-1-oxophthalazin-2(1H)-yl)-N-methyl-N-(2-methylbenzo[d]oxazol-6-yl)acetamide

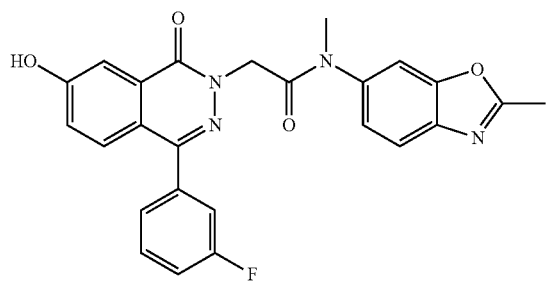 [SMILES: Cc1nc2ccc(N(C)C(=O)Cn3nc(-c4cccc(F)c4)c4ccc(O)cc4c3=O)cc2o1]

To a solution of 2-(4-(3-fluorophenyl)-7-methoxy-1-oxophthalazin-2(1H)-yl)-N-methyl-N-(2-methylbenzo[d]oxazol-6-yl)acetamide (example 70) (4.0 g, 8.469 mmol) in DCM (30 mL) was added BBr₃ (4.8 mL, 50.8 mmol) at 0° C. The reaction mixture was stirred at rt overnight then diluted with water (150 mL), neutralized with NaHCO₃, then extracted with DCM (3×100 mL).

The organic layer was washed with brine (100 mL), dried over Na₂SO₄, and concentrated to yield 2-(4-(3-fluorophenyl)-7-hydroxy-1-oxophthalazin-2(1H)-yl)-N-methyl-N-(2-methylbenzo[d]oxazol-6-yl)acetamide (2.9 g, 74%) (459.36 [M+H]).

Representative compounds of the invention were prepared in a similar manner to example 97 (scheme 6).

| Example No. | Structure | IUPAC Name | LCMS m/z |
|---|---|---|---|
| 98. | 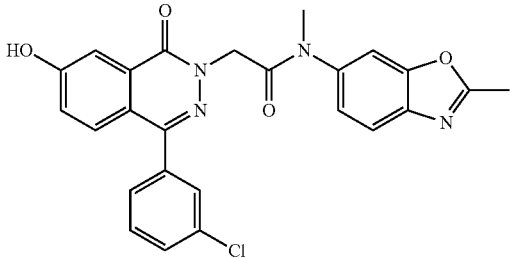 | 2-(4-(3-chlorophenyl)-7-hydroxy-1-oxophthalazin-2(1H)-yl)-N-methyl-N-(2-methylbenzo[d]oxazol-6-yl)acetamide | 459 [M + H] |
| 99. | 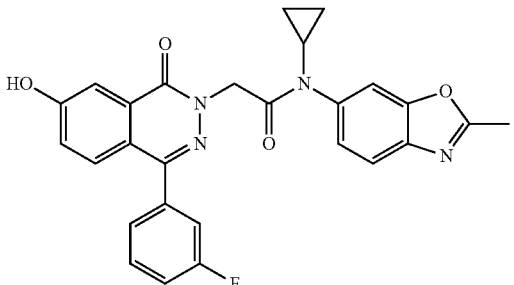 | N-cyclopropyl-2-(4-(3-fluorophenyl)-7-hydroxy-1-oxophthalazin-2(1H)-yl)-N-(2-methylbenzo[d]oxazol-6-yl)acetamide | 485 [M + H] |
| 100. | 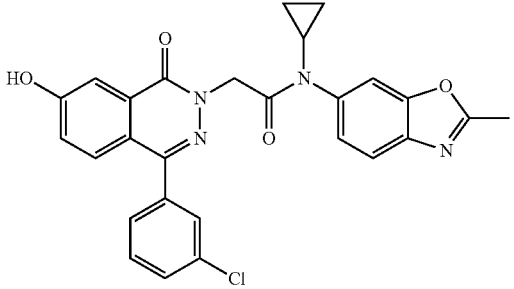 | 2-(4-(3-chlorophenyl)-7-hydroxy-1-oxophthalazin-2(1H)-yl)-N-cyclopropyl-N-(2-methylbenzo[d]oxazol-6-yl)acetamide | 502 [M + H] |
| 101. | 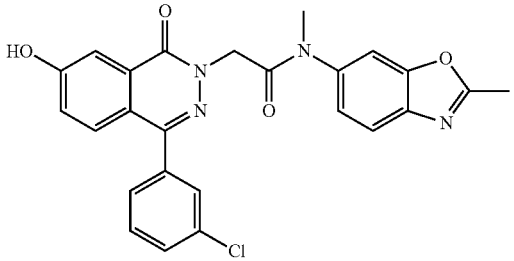 | 2-(4-(3-chlorophenyl)-7-hydroxy-1-oxophthalazin-2(1H)-yl)-N-methyl-N-(2-methylbenzo[d]oxazol-6-yl)acetamide | 476 [M + H] |
| 102. | 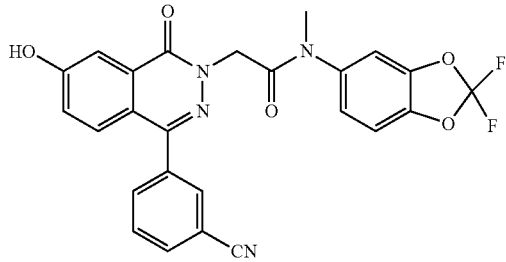 [SMILES: CN(C(=O)Cn1nc(-c2cccc(C#N)c2)c2ccc(O)cc2c1=O)c1ccc2c(c1)OC(F)(F)O2] | 2-(4-(3-cyanophenyl)-7-hydroxy-1-oxophthalazin-2(1H)-yl)-N-(2,2-difluorobenzo[d][1,3]dioxol-5-yl)-N-methylacetamide | 491 [M + H] |

| Example No. | Structure | IUPAC Name | LCMS m/z |
|---|---|---|---|
| 103. | 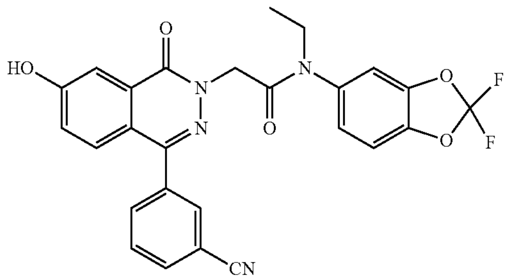 [SMILES: CCN(C(=O)Cn1nc(-c2cccc(C#N)c2)c2ccc(O)cc2c1=O)c1ccc2c(c1)OC(F)(F)O2] | 2-(4-(3-cyanophenyl)-7-hydroxy-1-oxophthalazin-2(1H)-yl)-N-(2,2-difluorobenzo[d][1,3]dioxol-5-yl)-N-ethylacetamide | 505 [M + H] |

Example 104

Synthesis of 2-(7-ethoxy-4-(3-fluorophenyl)-1-oxophthalazin-2(1H)-yl)-N-methyl-N-(2-methylbenzo[d]oxazol-6-yl)acetamide

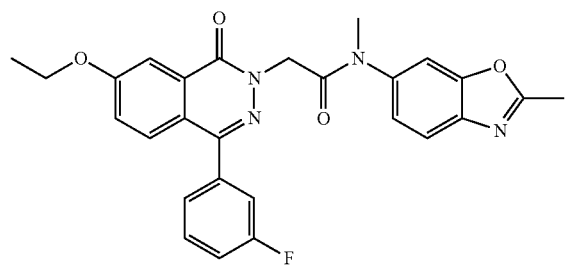

Example 97 (6.5 g, 14.19 mmol) was dissolved in DMF (60 mL), treated with $K_2CO_3$ (3.04 g, 21.2 mmol) and stirred at rt for 30 min. After cooling to 0° C., EtI (1.26 mL, 15.59 mmol) was added dropwise and the reaction was warmed to rt for 1 h. It was diluted with water (20 mL) and extracted with EtOAc (2×15 mL). The organics were washed with brine (300 mL), dried over $Na_2SO_4$, and concentrated to give crude material which was purified by chromatography (40% EtOAc/hexane) to yield 2-(7-ethoxy-4-(3-fluorophenyl)-1-oxophthalazin-2(1H)-yl)-N-methyl-N-(2-methylbenzo[d]oxazol-6-yl)acetamide (3.5 g) (487.52 [M+H]). $^1$H NMR: (400 MHz, DMSO) δ: 1.39-1.42 (t, 3H), 2.62 (s, 3H), 3.24 (s, 3H), 4.22-4.24 (d, J=7.2, 2H), 4.72 (s, 2H), 7.37-7.49 (m, 5H), 7.58-7.65 (m, 3H), 7.71-7.73 (d, J=8.4, 1H), 7.90 (s, 1H).

Representative compounds of the invention were prepared in a similar manner to example 104.

| Example No. | Structure | IUPAC Name | LCMS m/z |
|---|---|---|---|
| 105. | 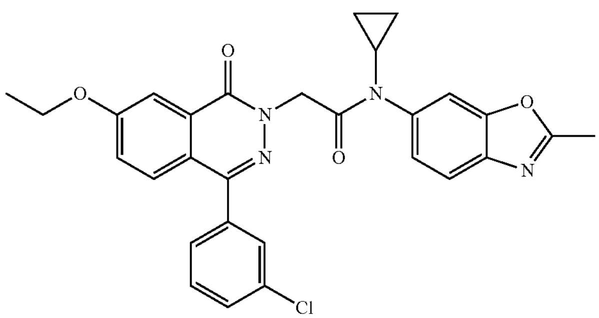 [SMILES: CCOc1ccc2c(-c3cccc(Cl)c3)nn(CC(=O)N(c3ccc4nc(C)oc4c3)C3CC3)c(=O)c2c1] | 2-(4-(3-chlorophenyl)-7-ethoxy-1-oxophthalazin-2(1H)-yl)-N-cyclopropyl-N-(2-methylbenzo[d]oxazol-6-yl)acetamide | 530 [M + H] |
| 106. | 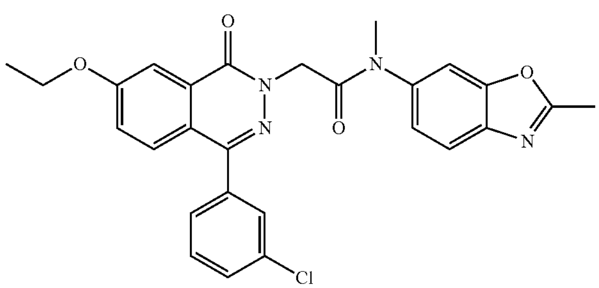 [SMILES: CCOc1ccc2c(-c3cccc(Cl)c3)nn(CC(=O)N(C)c3ccc4nc(C)oc4c3)c(=O)c2c1] | 2-(4-(3-chlorophenyl)-7-ethoxy-1-oxophthalazin-2(1H)-yl)-N-methyl-N-(2-methylbenzo[d]oxazol-6-yl)acetamide | 504 [M + H] |

-continued

| Example No. | Structure | IUPAC Name | LCMS m/z |
|---|---|---|---|
| 107. | 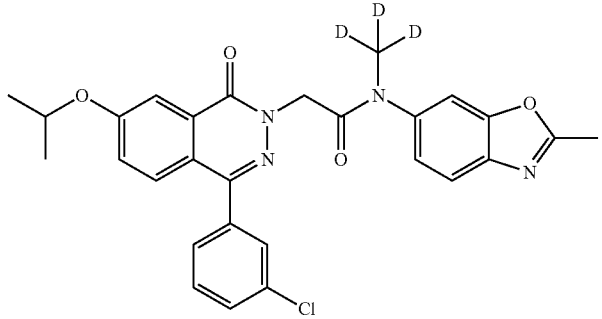 [SMILES: [2H]C([2H])([2H])N(C(=O)Cn1nc(-c2cccc(Cl)c2)c2ccc(OC(C)C)cc2c1=O)c1ccc2nc(C)oc2c1] | 2-(4-(3-chlorophenyl)-7-isopropoxy-1-oxophthalazin-2(1H)-yl)-N-(methyl-d3)-N-(2-methylbenzo[d]oxazol-6-yl)acetamide | 521 [M + H] |
| 108. | 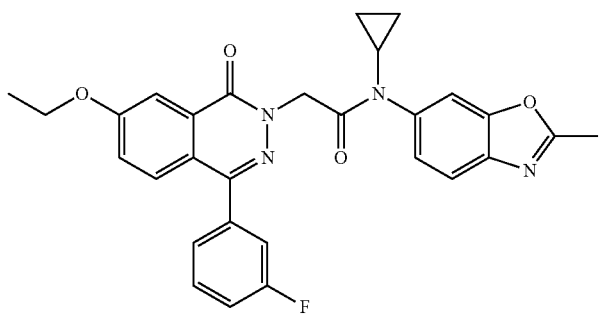 | N-cyclopropyl-2-(7-ethoxy-4-(3-fluorophenyl)-1-oxophthalazin-2(1H)-yl)-N-(2-methylbenzo[d]oxazol-6-yl)acetamide | 514 [M + H] |
| 109. | 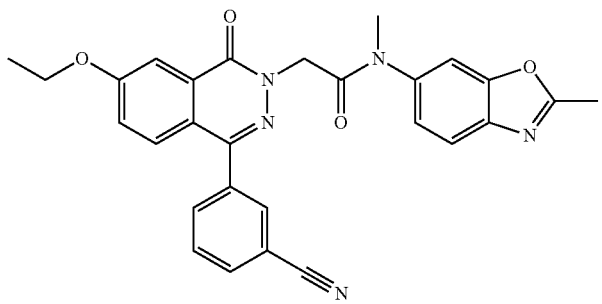 [SMILES: CCOc1ccc2c(-c3cccc(C#N)c3)nn(CC(=O)N(C)c3ccc4nc(C)oc4c3)c(=O)c2c1] | 2-(4-(3-cyanophenyl)-7-ethoxy-1-oxophthalazin-2(1H)-yl)-N-methyl-N-(2-methylbenzo[d]oxazol-6-yl)acetamide | 495 [M + H] |
| 110. | 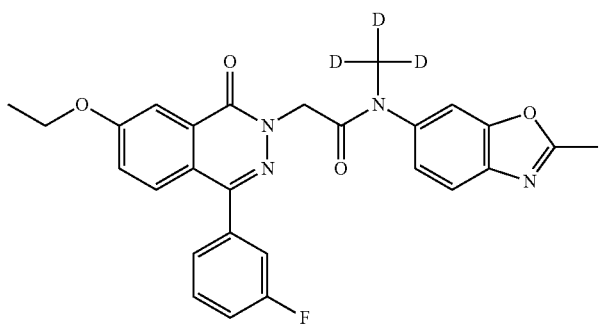 [SMILES: [2H]C([2H])([2H])N(C(=O)Cn1nc(-c2cccc(F)c2)c2ccc(OCC)cc2c1=O)c1ccc2nc(C)oc2c1] | 2-(7-ethoxy-4-(3-fluorophenyl)-1-oxophthalazin-2(1H)-yl)-N-(methyl-d3)-N-(2-methylbenzo[d]oxazol-6-yl)acetamide | 491 [M + H] |

-continued

| Example No. | Structure | IUPAC Name | LCMS m/z |
|---|---|---|---|
| 111. | 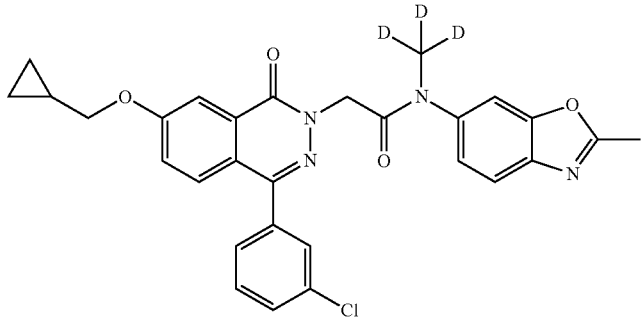 [SMILES: [2H]C([2H])([2H])N(C(=O)Cn1nc(-c2cccc(Cl)c2)c2ccc(OCC3CC3)cc2c1=O)c1ccc2nc(C)oc2c1] | 2-(4-(3-chlorophenyl)-7-(cyclopropylmethoxy)-1-oxophthalazin-2(1H)-yl)-N-(methyl-d3)-N-(2-methylbenzo[d]oxazol-6-yl)acetamide | 533 [M + H] |
| 112. | 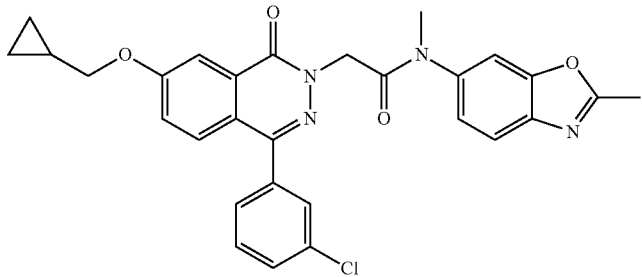 [SMILES: Cc1nc2ccc(N(C)C(=O)Cn3nc(-c4cccc(Cl)c4)c4ccc(OCC5CC5)cc4c3=O)cc2o1] | 2-(4-(3-chlorophenyl)-7-(cyclopropylmethoxy)-1-oxophthalazin-2(1H)-yl)-N-methyl-N-(2-methylbenzo[d]oxazol-6-yl)acetamide | 530 [M + H] |
| 113. | 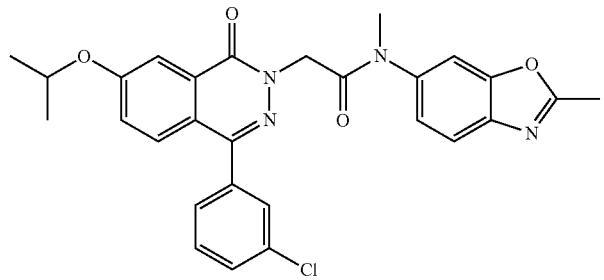 [SMILES: Cc1nc2ccc(N(C)C(=O)Cn3nc(-c4cccc(Cl)c4)c4ccc(OC(C)C)cc4c3=O)cc2o1] | 2-(4-(3-chlorophenyl)-7-isopropoxy-1-oxophthalazin-2(1H)-yl)-N-methyl-N-(2-methylbenzo[d]oxazol-6-yl)acetamide | 518 [M + H] |
| 114. | 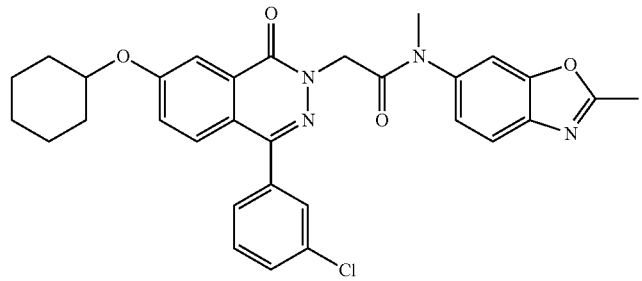 | 2-(4-(3-chlorophenyl)-7-(cyclohexyloxy)-1-oxophthalazin-2(1H)-yl)-N-methyl-N-(2-methylbenzo[d]oxazol-6-yl)acetamide | 558 [M + H] |
| 115. | 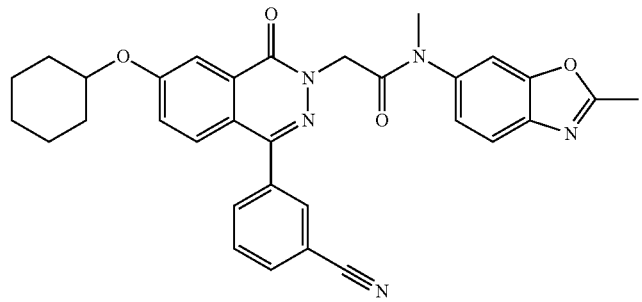 [SMILES: Cc1nc2ccc(N(C)C(=O)Cn3nc(-c4cccc(C#N)c4)c4ccc(OC5CCCCC5)cc4c3=O)cc2o1] | 2-(4-(3-cyanophenyl)-7-(cyclohexyloxy)-1-oxophthalazin-2(1H)-yl)-N-methyl-N-(2-methylbenzo[d]oxazol-6-yl)acetamide | 549 [M + H] |

| Example No. | Structure | IUPAC Name | LCMS m/z |
|---|---|---|---|
| 116. | 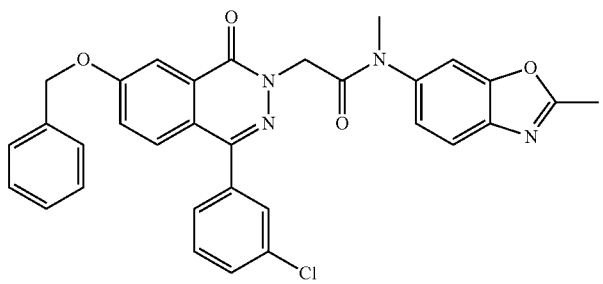 [SMILES: Cc1nc2ccc(N(C)C(=O)Cn3nc(-c4cccc(Cl)c4)c4ccc(OCc5ccccc5)cc4c3=O)cc2o1] | 2-(7-(benzyloxy)-4-(3-chlorophenyl)-1-oxophthalazin-2(1H)-yl)-N-methyl-N-(2-methylbenzo[d]oxazol-6-yl)acetamide | 566 [M + H] |
| 117. | 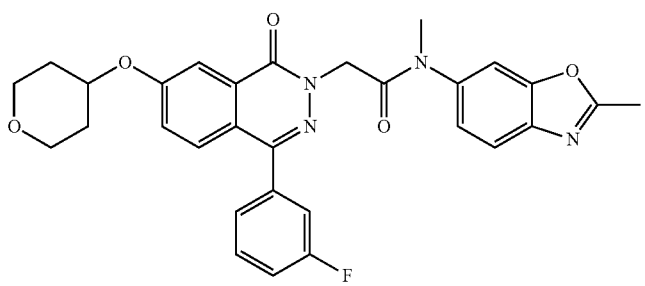 [SMILES: Cc1nc2ccc(N(C)C(=O)Cn3nc(-c4cccc(F)c4)c4ccc(OC5CCOCC5)cc4c3=O)cc2o1] | 2-(4-(3-fluorophenyl)-1-oxo-7-((tetrahydro-2H-pyran-4-yl)oxy)phthalazin-2(1H)-yl)-N-methyl-N-(2-methylbenzo[d]oxazol-6-yl)acetamide | 544 [M + H] |
| 118. | 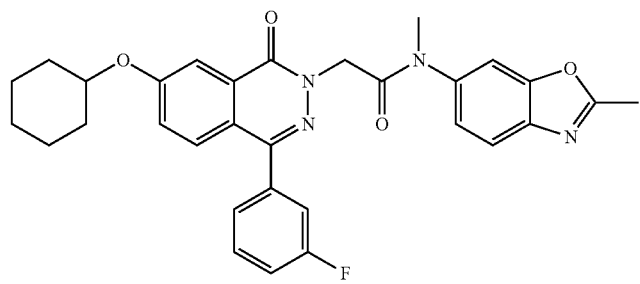 [SMILES: Cc1nc2ccc(N(C)C(=O)Cn3nc(-c4cccc(F)c4)c4ccc(OC5CCCCC5)cc4c3=O)cc2o1] | 2-(7-(cyclohexyloxy)-4-(3-fluorophenyl)-1-oxophthalazin-2(1H)-yl)-N-methyl-N-(2-methylbenzo[d]oxazol-6-yl)acetamide | 542 [M + H] |
| 119. | 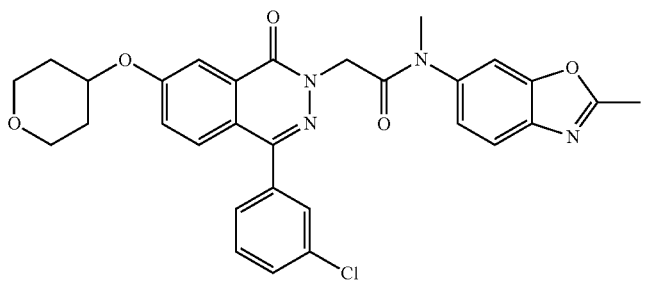 | 2-(4-(3-chlorophenyl)-1-oxo-7-((tetrahydro-2H-pyran-4-yl)oxy)phthalazin-2(1H)-yl)-N-methyl-N-(2-methylbenzo[d]oxazol-6-yl)acetamide | 560 [M + H] |
| 120. | 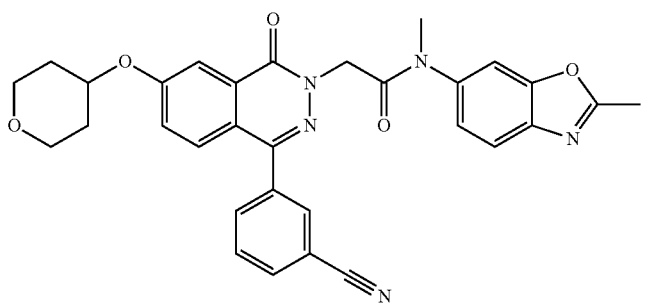 [SMILES: Cc1nc2ccc(N(C)C(=O)Cn3nc(-c4cccc(C#N)c4)c4ccc(OC5CCOCC5)cc4c3=O)cc2o1] | 2-(4-(3-cyanophenyl)-1-oxo-7-((tetrahydro-2H-pyran-4-yl)oxy)phthalazin-2(1H)-yl)-N-methyl-N-(2-methylbenzo[d]oxazol-6-yl)acetamide | 551 [M + H] |

| Example No. | Structure | IUPAC Name | LCMS m/z |
|---|---|---|---|
| 121. | 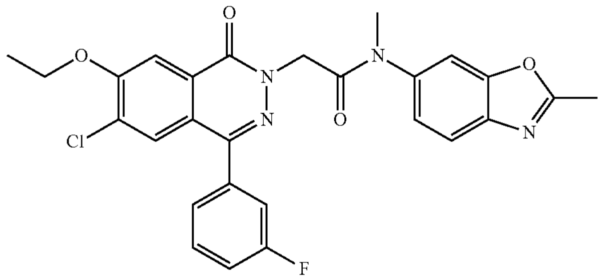 | 2-(6-chloro-7-ethoxy-4-(3-fluorophenyl)-1-oxophthalazin-2(1H)-yl)-N-methyl-N-(2-methylbenzo[d]oxazol-6-yl)acetamide | 508 [M + H] |
| 122. | 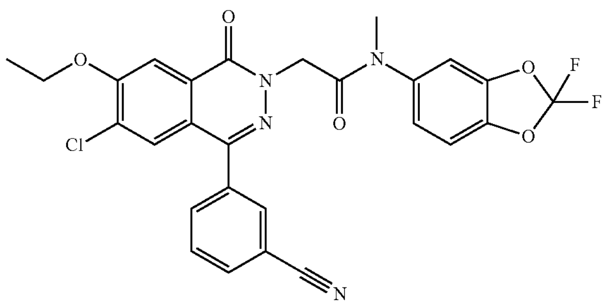 [SMILES: CCOc1cc2c(=O)n(CC(=O)N(C)c3ccc4c(c3)OC(F)(F)O4)nc(-c3cccc(C#N)c3)c2cc1Cl] | 2-(6-chloro-4-(3-cyanophenyl)-7-ethoxy-1-oxophthalazin-2(1H)-yl)-N-(2,2-difluorobenzo[d][1,3]dioxol-5-yl)-N-methylacetamide | 554 [M + H] |
| 123. | 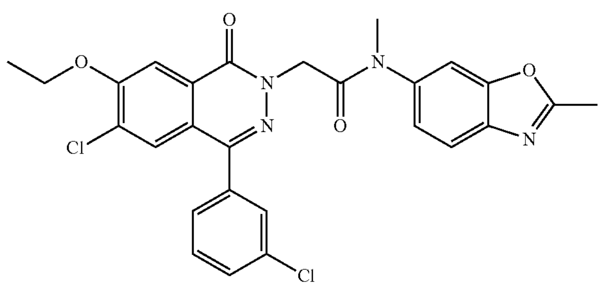 [SMILES: CCOc1cc2c(=O)n(CC(=O)N(C)c3ccc4nc(C)oc4c3)nc(-c3cccc(Cl)c3)c2cc1Cl] | 2-(6-chloro-4-(3-chlorophenyl)-7-ethoxy-1-oxophthalazin-2(1H)-yl)-N-methyl-N-(2-methylbenzo[d]oxazol-6-yl)acetamide | 538 [M + H] |

4-Oxo-3, 4-dihydrophthalazine-1-carboxylic acid:

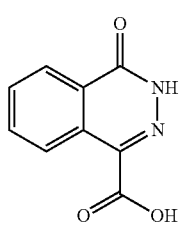 [SMILES: O=C(O)c1n[nH]c(=O)c2ccccc12]

A solution of 2-methyl acetophenone (5.0 g, 37 mmol) in water (70 mL) was treated with $K_2CO_3$ (3.0 g, 22 mmol), then heated to reflux and a solution of $KMnO_4$ (23.5 g, 150 mmol) in water (330 mL) was added dropwise. After stirring overnight at 90° C., the reaction mixture was filtered through Celite and concentrated to half volume. The pH was adjusted 8 by addition of 2N HCl. It was heated to 90° C. and hydrazine sulfate (4.8 g, 37 mmol) and NaOH (1.66 g, 41 mmol) were added and the heating continued overnight. The reaction volume was reduced to half volume and solids filtered. The aqueous layer was acidified with 2N HCl and the resulting white precipitate filtered and dried to give 4-oxo-3, 4-dihydrophthalazine-1-carboxylic acid (1.5 g). $^1$H NMR: (400 MHz, DMSO) δ: 7.42-7.26 (m, 2H), 7.91-7.80 (m, 2H), 8.46 (s, 1H), 12.85 (s, 1H).

Ethyl 4-oxo-3, 4-dihydrophthalazine-1-carboxylate

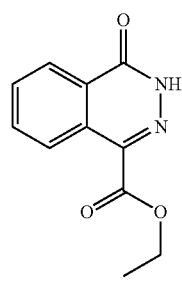 [SMILES: CCOC(=O)c1n[nH]c(=O)c2ccccc12]

To a solution of 4-oxo-3, 4-dihydrophthalazine-1-carboxylic acid (16 g, 84.2 mmol) in EtOH was added con $H_2SO_4$ (40 mL) dropwise. The reaction was heated to 80° C. overnight. The EtOH was distilled off and water (200 mL) added. The solution was neutralized with $NaHCO_3$ and then extracted with EtOAc (3×200 mL). The organic layer was dried over $Na_2SO_4$ and concentrated to give ethyl 4-oxo-3, 4-dihydrophthalazine-1-carboxylate (15 g, 219 [M+H]). $^1$H NMR: (400 MHz, DMSO) δ: 1.37-1.35 (t, 3H), 4.42-4.37 (m, 2H), 7.93-7.88 (m, 1H), 8.02-7.97 (m, 1H), 8.31-8.28 (m, 1H), 8.53-8.51 (m, 1H), 13.18 (s, 1H).

Ethyl 3-(2-((2, 2-difluorobenzo[d][1, 3]dioxol-5-yl)(ethyl)amino)-2-oxoethyl)-4-oxo-3, 4-dihydrophthalazine-1-carboxylate

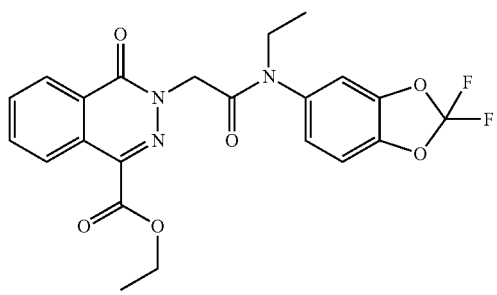 [SMILES: CCOC(=O)c1nn(CC(=O)N(CC)c2ccc3c(c2)OC(F)(F)O3)c(=O)c2ccccc12]

To a solution of ethyl 4-oxo-3, 4-dihydrophthalazine-1-carboxylate (2.0 g, 9.17 mmol) in THF (20 mL) was added NaH (60%) (0.403 g, 10.09 mmol) portionwise at 0° C. The reaction mixture was stirred for 30 min at 0° C., then 2-bromo-N-(2, 2-difluorobenzo[d][1, 3]dioxol-5-yl)-N-ethylacetamide (3.044 g, 9.17 mmol) was added and the mixture stirred overnight at rt. The reaction mixture was diluted with water (100 mL) and extracted with EtOAc (3×25 mL). The organic layer was dried over Na$_2$SO$_4$ and concentrated to give ethyl 3-(2-((2, 2-difluorobenzo[d][1, 3]dioxol-5-yl)(ethyl)amino)-2-oxoethyl)-4-oxo-3, 4-dihydrophthalazine-1-carboxylate (3.4 g, 460[M+H]). $^1$H NMR: (400 MHz, DMSO) δ: 1.21-1.15 (m, 3H), 1.38-1.28 (m, 3H), 4.05-4.00 (q, 2H), 4.45-4.39 (m, 2H), 4.70 (s, 2H), 7.37-7.34 (m, 2H), 7.56-7.49 (m, 2H), 7.69-7.68 (d, J=2 Hz, 1H), 7.99-7.90 (m, 1H), 8.03-8.01 (m, 1H), 8.28-8.8.26 (d, J=7.6 Hz, 1H), 8.459-8.43 (d, J=8.4 Hz, 1H).

3-(2-((2, 2-difluorobenzo[d][1, 3]dioxol-5-yl)(ethyl)amino)-2-oxoethyl)-4-oxo-3, 4-dihydrophthalazine-1-carboxylic acid

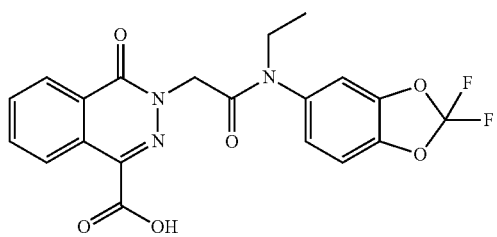 [SMILES: CCN(C(=O)Cn1nc(C(=O)O)c2ccccc2c1=O)c1ccc2c(c1)OC(F)(F)O2]

To a solution of ethyl 3-(2-((2, 2-difluorobenzo[d][1, 3]dioxol-5-yl)(ethyl)amino)-2-oxoethyl)-4-oxo-3, 4-dihydrophthalazine-1-carboxylate (3.4 g, 7.40 mmol) in THF (30 mL) was added 1N NaOH (30 mL, 30 mmol) dropwise at rt. The reaction mixture was stirred at rt overnight, diluted with water (100 mL), neutralized with 2N HCl, and extracted with EtOAc (3×50 mL). The organic layer was dried over Na$_2$SO$_4$ and concentrated to give 3-(2-((2, 2-difluorobenzo[d][1, 3]dioxol-5-yl)(ethyl)amino)-2-oxoethyl)-4-oxo-3, 4-dihydrophthalazine-1-carboxylic acid (2.0 g, 62%). $^1$H NMR: (400 MHz, DMSO) δ: 1.10-1.07 (t, J=6.8 Hz, 3H), 3.70-3.62 (m, 2H), 4.70 (s, 2H), 7.25-7.23 (d, 1H, J=7.6 Hz), 7.36-7.31 (m, 1H), 7.56-7.49 (m, 1H), 8.02-7.90 (m, 2H), 8.28-8.26 (d, J=7.6 Hz, 1H), 8.55-8.53 (d, J=8 Hz, 1H).

Example 124

N-(2-cyanophenyl)-3-(2-((2, 2-difluorobenzo[d][1, 3]dioxol-5-yl)(ethyl)amino)-2-oxoethyl)-4-oxo-3, 4-dihydrophthalazine-1-carboxamide

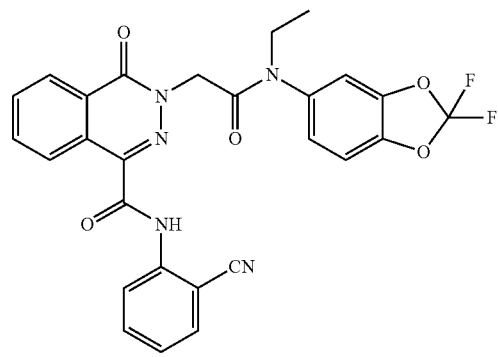 [SMILES: CCN(C(=O)Cn1nc(C(=O)Nc2ccccc2C#N)c2ccccc2c1=O)c1ccc2c(c1)OC(F)(F)O2]

A solution of 3-(2-((2, 2-difluorobenzo[d][1, 3]dioxol-5-yl)(ethyl)amino)-2-oxoethyl)-4-oxo-3, 4-dihydrophthalazine-1-carboxylic acid (0.150 g, 0.34 mmol) and 2-aminobenzonitrile (0.040 g, 0.34 mmol) in DCM (15 mL) was treated at 0° C. with pyridine (1.0 mL) and stirred for 15 min. POCl$_3$ (1.0 mL) was added dropwise and the reaction mixture stirred for 2 hr. The reaction was diluted with water (50 mL), neutralized with sat'd NaHCO$_3$ (10 mL), and then extracted in EtOAc (3×15 mL). The organic layer was dried over Na$_2$SO$_4$ to obtain crude product, which was purified by column chromatography (20-25% EtOAc/hexane) to give N-(2-cyanophenyl)-3-(2-((2, 2-difluorobenzo[d][1, 3]dioxol-5-yl)(ethyl)amino)-2-oxoethyl)-4-oxo-3, 4-dihydrophthalazine-1-carboxamide (71 mg, 532 [M+H]). $^1$H NMR: (400 MHz, DMSO) δ: 1.03-1.06 (t, 3H), 3.68-3.73 (q, 2H), 4.76 (s, 2H), 7.36-7.39 (d, J=8.4 Hz, 1H), 7.46-7.50 (m, 1H), 7.57-7.59 (d, J=8.8 Hz, 1H), 7.70-7.74 (t, 2H), 7.78-7.82 (m, 1H), 7.93-8.05 (m, 3H), 8.31-8.33 (d, J=8 Hz, 1H), 8.71-8.73 (d, J=8.4 Hz, 1H), 10.82 (s, 1H).

Representative compounds of the invention were prepared in a similar manner to example 124 from the corresponding amine and the appropriate side-chain alkylation agent (scheme 6).

| Example No. | Structure | IUPAC Name | LCMS m/z |
|---|---|---|---|
| 125. | 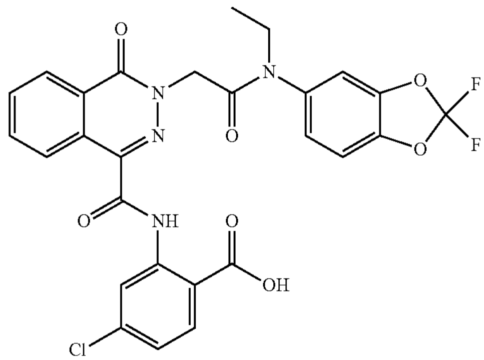 [SMILES: CCN(C(=O)Cn1nc(C(=O)Nc2cc(Cl)ccc2C(=O)O)c2ccccc2c1=O)c1ccc2c(c1)OC(F)(F)O2] | 4-chloro-2-(3-(2-((2,2-difluorobenzo[d][1,3]dioxol-5-yl)ethyl)amino)-2-oxoethyl)-4-oxo-3,4-dihydrophthalazine-1-carboxamido)benzoic acid | 585 [M + H] |
| 126. | 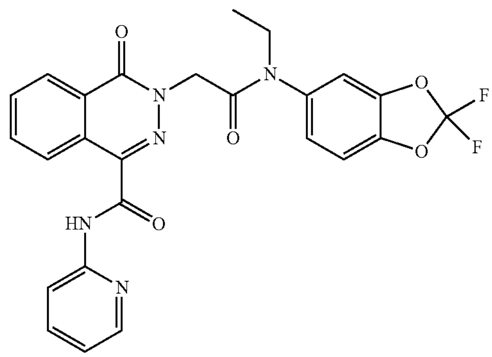 [SMILES: CCN(C(=O)Cn1nc(C(=O)Nc2ccccn2)c2ccccc2c1=O)c1ccc2c(c1)OC(F)(F)O2] | 3-(2-((2,2-difluorobenzo[d][1,3]dioxol-5-yl)(ethyl)amino)-2-oxoethyl)-4-oxo-N-(pyridin-2-yl)-3,4-dihydrophthalazine-1-carboxamide | 508 [M + H] |
| 127. | 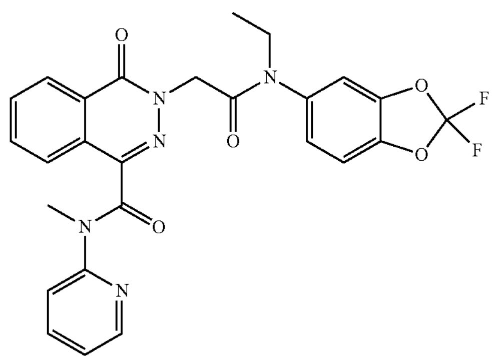 [SMILES: CCN(C(=O)Cn1nc(C(=O)N(C)c2ccccn2)c2ccccc2c1=O)c1ccc2c(c1)OC(F)(F)O2] | 3-(2-((2,2-difluorobenzo[d][1,3]dioxol-5-yl)(ethyl)amino)-2-oxoethyl)-N-methyl-4-oxo-N-(pyridin-2-yl)-3,4-dihydrophthalazine-1-carboxamide | 522 [M + H] |
| 128. | 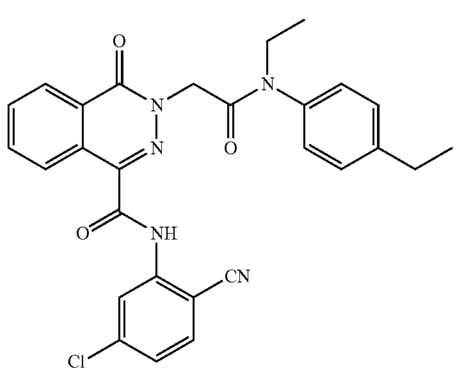 [SMILES: CCc1ccc(N(CC)C(=O)Cn2nc(C(=O)Nc3cc(Cl)ccc3C#N)c3ccccc3c2=O)cc1] | N-(5-chloro-2-cyanophenyl)-3-(2-(ethyl(4-ethylphenyl)amino)-2-oxoethyl)-4-oxo-3,4-dihydrophthalazine-1-carboxamide | 514 [M + H] |

| Example No. | Structure | IUPAC Name | LCMS m/z |
|---|---|---|---|
| 129. | 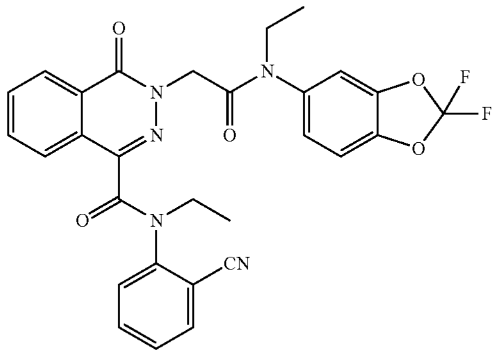 [SMILES: CCN(C(=O)Cn1nc(C(=O)N(CC)c2ccccc2C#N)c2ccccc2c1=O)c1ccc2c(c1)OC(F)(F)O2] | N-(2-cyanophenyl)-3-(2-((2,2-difluorobenzo[d][1,3]dioxol-5-yl)(ethyl)amino)-2-oxoethyl)-N-ethyl-4-oxo-3,4-dihydrophthalazine-1-carboxamide | 560 [M + H] |
| 130. | 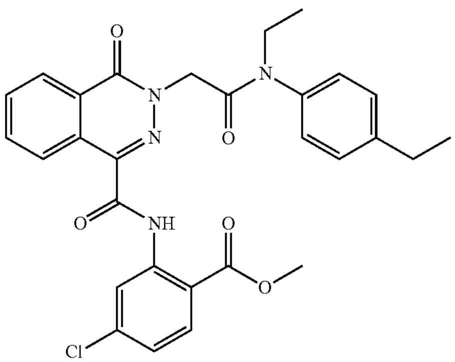 [SMILES: CCc1ccc(N(CC)C(=O)Cn2nc(C(=O)Nc3cc(Cl)ccc3C(=O)OC)c3ccccc3c2=O)cc1] | methyl 4-chloro-2-(3-(2-(ethyl(4-ethylphenyl)amino)-2-oxoethyl)-4-oxo-3,4-dihydrophthalazine-1-carboxamido)benzoate | 548 [M + H] |

5-chloro-4-phenylpyridazin-3(2H)-one

To a solution of 4,5-dichloropyridazone (5.0 g, 30.3 mmol) in THF (100 mL) was added PhMgBr (1M in THF) (91 mL, 91 mmol) dropwise at 15° C., then stirred under N₂ at 15° C. for 30 min and at rt for 2 hr. The reaction mixture was quenched with sat'd NH₄Cl (500 mL) and extracted with EtOAc (2×250 mL). The organics were washed with brine, dried over Na₂SO₄ and concentrated to give 5-chloro-4-phenylpyridazin-3(2H)-one (5.02 g, 207 [M+H]). ¹H NMR: (400 MHz, DMSO) δ: 7.41-7.50 (m, 5H), 8.11 (s, 1H), 13.44 (s, 1H).

2-(4-chloro-6-oxo-5-phenylpyridazin-1(6H)-yl)-N-(2, 2-difluorobenzo[d][1, 3]dioxol-5-yl)-N-ethylacetamide A 0° C. solution of 5-chloro-4-phenylpyridazin-3(2H)-one (3.0 g, 14.5 mmol) in THF (30 mL) was treated with NaH (60%) (0.699 g, 17.4 mmol) and stirred at 0° C. for 30 min. A solution of 2-bromo-N-(2, 2-difluorobenzo[d][1, 3]dioxol-5-yl)-N-ethylacetamide (4.68 g, 14.5 mmol) in THF (5 mL) was added dropwise and the reaction mixture stirred overnight at rt. It was diluted with sat'd NH₄Cl (200 mL) and extracted with EtOAc (2×250 mL). The extract was washed with brine (300 mL), dried over Na₂SO₄ and concentrated to give crude product which was purified by column chromatography (20-25% EtOAc/hexane) to give 2-(4-chloro-6-oxo-5-phenylpyridazin-1(6H)-yl)-N-(2, 2-difluorobenzo[d][1, 3]dioxol-5-yl)-N-ethylacetamide (5.01 g, 448 [M+H]). ¹H NMR: (400 MHz, DMSO) δ: 0.99-1.02 (t, J=6.6 Hz, 3H), 3.65-3.67 (q, J=6.4 Hz, 2H), 4.60 (s, 2H), 7.28-7.30 (d, J=8.4 Hz, 1H), 7.37-7.48 (m, 5H), 7.53-7.55 (d, J=4.8 Hz, 1H), 7.63 (s, 1H), 8.19 (s, 1H).

N-(2, 2-difluorobenzo[d][1, 3]dioxol-5-yl)-N-ethyl-2-(1-oxo-1H-pyridazino[4,5-b]indol-2(5H)-yl)acetamide

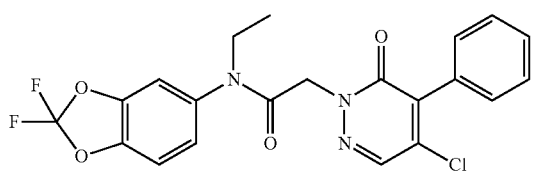 [SMILES: CCN(C(=O)Cn1ncc(Cl)c(-c2ccccc2)c1=O)c1ccc2c(c1)OC(F)(F)O2]

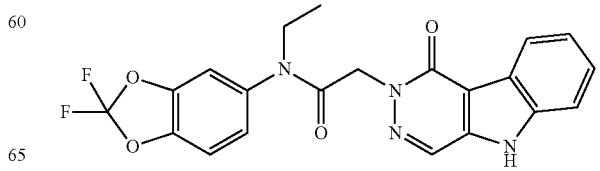

To a solution of 2-(4-chloro-6-oxo-5-phenylpyridazin-1(6H)-yl)-N-(2, 2-difluorobenzo[d][1, 3]dioxol-5-yl)-N-ethylacetamide (5.0 g, 11.2 mmol) in DMF (40 mL) was added NaN₃ (1.45 g, 22.3 mmol). The reaction was stirred overnight at 110° C., then cooled to rt, diluted with water (100 mL), and extracted with EtOAc (2×250 mL). The organics were washed with brine, dried over Na₂SO₄ and concentrated to give a residue which was purified by chromatography (20-25% EtOAc/DCM) to yield N-(2, 2-difluorobenzo[d][1, 3]dioxol-5-yl)-N-ethyl-2-(1-oxo-1H-pyridazino[4, 5-b]indol-2(5H)-yl)acetamide (3.6 g, 427 [M+H]). ¹H NMR: (400 MHz, DMSO) δ: 1.01-1.05 (t, J=7 Hz, 3H), 3.63-3.69 (q, J=7.6 Hz, 2H), 4.71 (s, 2H), 7.26-7.60 (m, 6H), 8.13-8.15 (d, J=8 Hz, 1H), 8.39 (s, 1H), 12.30 (s, 1H).

Example 131

N-(2, 2-difluorobenzo[d][1, 3]dioxol-5-yl)-N-ethyl-2-(1-oxo-5-(pyridin-2-ylmethyl)-1H-pyridazino[4, 5-b]indol-2(5H)-yl)acetamide

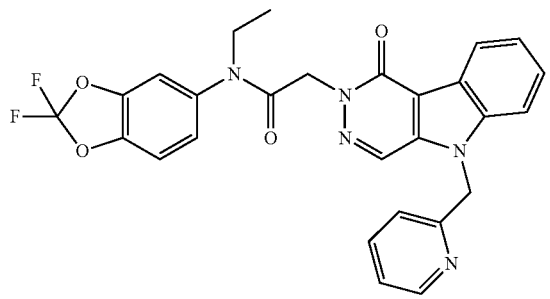 [SMILES: CCN(C(=O)Cn1ncc2c(c1=O)c1ccccc1n2Cc1ccccc1)c1ccc2c(c1)OC(F)(F)O2]

To a solution of N-(2, 2-difluorobenzo[d][1, 3]dioxol-5-yl)-N-ethyl-2-(1-oxo-1H-pyridazino[4, 5-b]indol-2(5H)-yl)acetamide (0.200 g, 0.469 mmol) in THF (10 mL) was added NaH (60%) (0.022 g, 0.56 mmol) portion wise at 0° C. After stirring 30 min at 0° C., 2-(bromomethyl) pyridine. HBr (0.081 g, 0.516 mmol) was added and the reaction stirred overnight at rt. The reaction mixture was diluted with water (20 mL) and extracted with EtOAc (2×25 mL). The organics were washed with brine, dried over Na₂SO₄ and concentrated to give a residue which was purified by chromatography (10-12% EtOAc/DCM) to give N-(2, 2-difluorobenzo[d][1, 3]dioxol-5-yl)-N-ethyl-2-(1-oxo-5-(pyridin-2-ylmethyl)-1H-pyridazino[4, 5-b]indol-2(5H)-yl)acetamide (0.045 g, 519[M+H]). ¹H NMR: (400 MHz, DMSO) δ: 1.02-1.05 (t, J=7, 3H), 3.71-3.65 (qt, J=6.8, 13.6, 2H), 4.73 (s, 2H), 5.89 (s, 2H), 7.31-7.28 (m, 1H), 7.40-7.34 (m, 3H), 7.55-7.48 (m, 2H), 7.700 (s, 1H), 7.81-7.7 (m, 2H), 8.18-8.16 (d, J=7.6, 1H), 8.47-8.46 (dd, J=0.8, 5.2, 1H), 8.73 (s, 1H).

Representative compounds of the invention were prepared in a similar manner to examples 131 (scheme 5).

| Example No. | Structure | IUPAC Name | LCMS m/z |
|---|---|---|---|
| 132. | 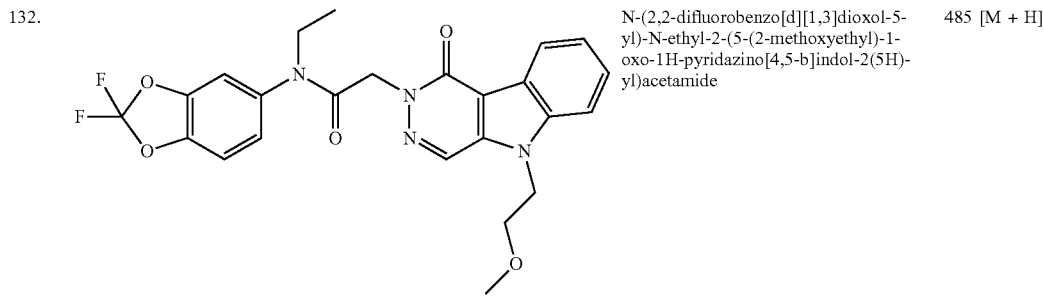 | N-(2,2-difluorobenzo[d][1,3]dioxol-5-yl)-N-ethyl-2-(5-(2-methoxyethyl)-1-oxo-1H-pyridazino[4,5-b]indol-2(5H)-yl)acetamide | 485 [M + H] |
| 133. | 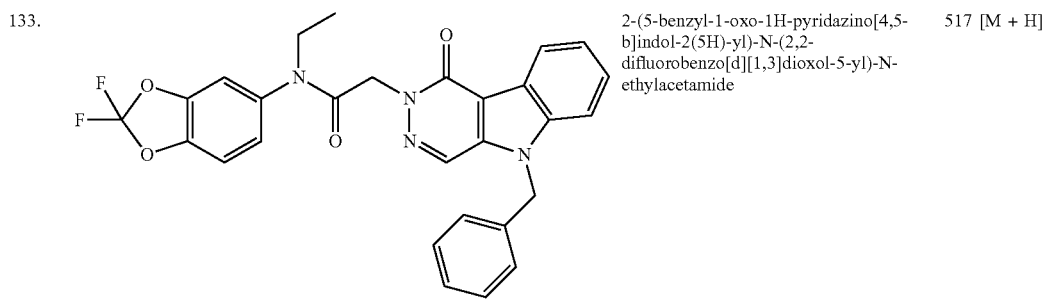 | 2-(5-benzyl-1-oxo-1H-pyridazino[4,5-b]indol-2(5H)-yl)-N-(2,2-difluorobenzo[d][1,3]dioxol-5-yl)-N-ethylacetamide | 517 [M + H] |

-continued

| Example No. | Structure | IUPAC Name | LCMS m/z |
|---|---|---|---|
| 134. | 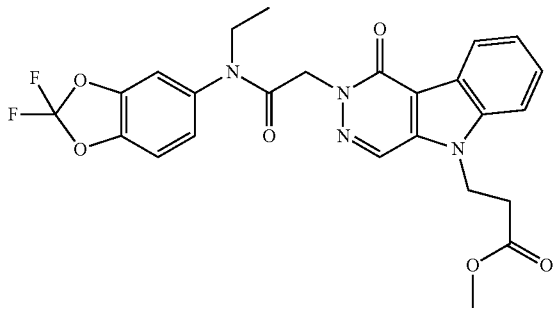 [SMILES: CCN(C(=O)Cn1ncc2c(c1=O)c1ccccc1n2CCC(=O)OC)c1ccc2c(c1)OC(F)(F)O2] | methyl 3-(2-(2-((2,2-difluorobenzo[d][1,3]dioxol-5-yl)(ethyl)amino)-2-oxoethyl)-1-oxo-1H-pyridazino[4,5-b]indol-5(2H)-yl)propanoate | 513 [M + H] |
| 135. | 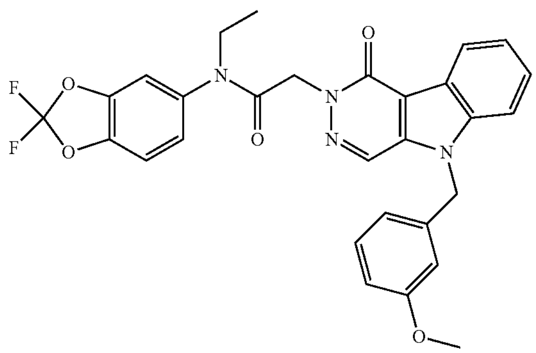 [SMILES: CCN(C(=O)Cn1ncc2c(c1=O)c1ccccc1n2Cc1cccc(OC)c1)c1ccc2c(c1)OC(F)(F)O2] | N-(2,2-difluorobenzo[d][1,3]dioxol-5-yl)-N-ethyl-2-(5-(3-methoxybenzyl)-1-oxo-1H-pyridazino[4,5-b]indol-2(5H)-yl)acetamide | 547 [M + H] |
| 136. | 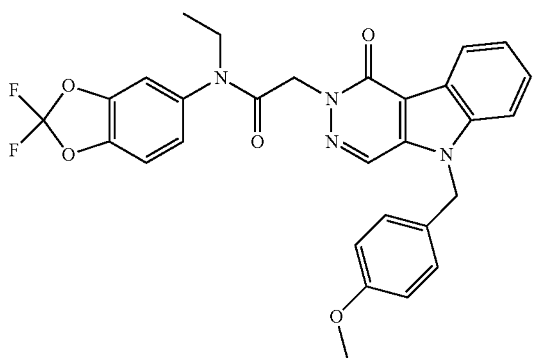 [SMILES: CCN(C(=O)Cn1ncc2c(c1=O)c1ccccc1n2Cc1ccc(OC)cc1)c1ccc2c(c1)OC(F)(F)O2] | N-(2,2-difluorobenzo[d][1,3]dioxol-5-yl)-N-ethyl-2-(5-(4-methoxybenzyl)-1-oxo-1H-pyridazino[4,5-b]indol-2(5H)-yl)acetamide | 547 [M + H] |
| 137. | 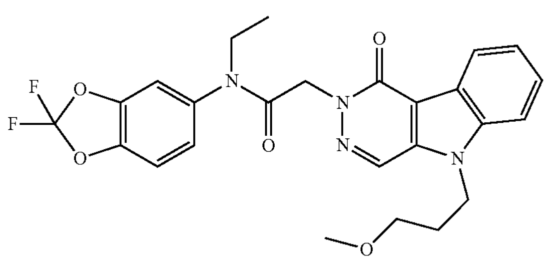 [SMILES: CCN(C(=O)Cn1ncc2c(c1=O)c1ccccc1n2CCCOC)c1ccc2c(c1)OC(F)(F)O2] | N-(2,2-difluorobenzo[d][1,3]dioxol-5-yl)-N-ethyl-2-(5-(3-methoxypropyl)-1-oxo-1H-pyridazino[4,5-b]indol-2(5H)-yl)acetamide | 499 [M + H] |
| 138. | 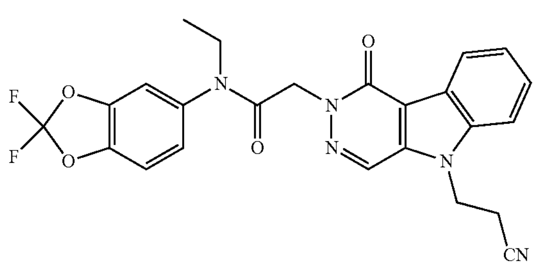 [SMILES: CCN(C(=O)Cn1ncc2c(c1=O)c1ccccc1n2CCC#N)c1ccc2c(c1)OC(F)(F)O2] | 2-(5-(2-cyanoethyl)-1-oxo-1H-pyridazino[4,5-b]indol-2(5H)-yl)-N-(2,2-difluorobenzo[d][1,3]dioxol-5-yl)-N-ethylacetamide | 480 [M + H] |

| Example No. | Structure | IUPAC Name | LCMS m/z |
|---|---|---|---|
| 139. | 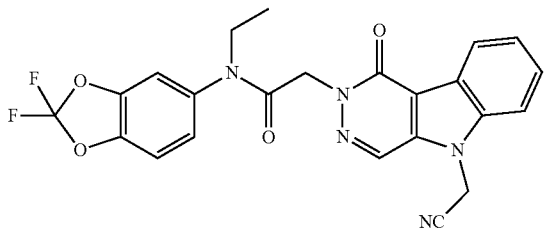 [SMILES: CCN(C(=O)Cn1ncc2c(c1=O)c1ccccc1n2CC#N)c1ccc2c(c1)OC(F)(F)O2] | 2-(5-(cyanomethyl)-1-oxo-1H-pyridazino[4,5-b]indol-2(5H)-yl)-N-(2,2-difluorobenzo[d][1,3]dioxol-5-yl)-N-ethylacetamide | 466 [M + H] |
| 140. | 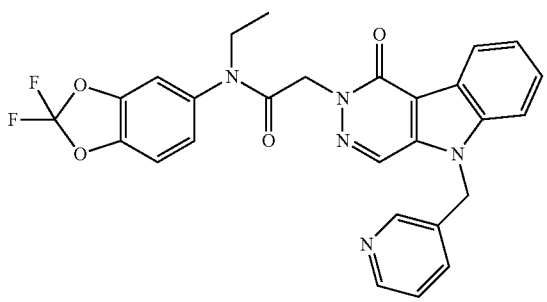 | N-(2,2-difluorobenzo[d][1,3]dioxol-5-yl)-N-ethyl-2-(1-oxo-5-(pyridin-3-ylmethyl)-1H-pyridazino[4,5-b]indol-2(5H)-yl)acetamide | 518 [M + H] |
| 141. | 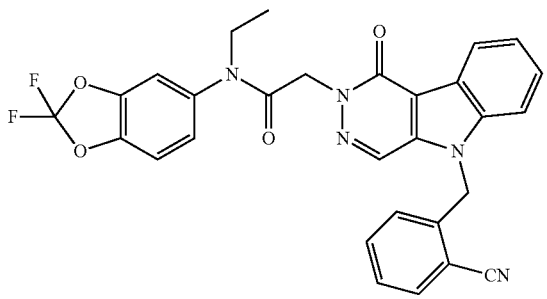 [SMILES: CCN(C(=O)Cn1ncc2c(c1=O)c1ccccc1n2Cc1ccccc1C#N)c1ccc2c(c1)OC(F)(F)O2] | 2-(5-(2-cyanobenzyl)-1-oxo-1H-pyridazino[4,5-b]indol-2(5H)-yl)-N-(2,2-difluorobenzo[d][1,3]dioxol-5-yl)-N-ethylacetamide | 542 [M + H] |
| 142. | 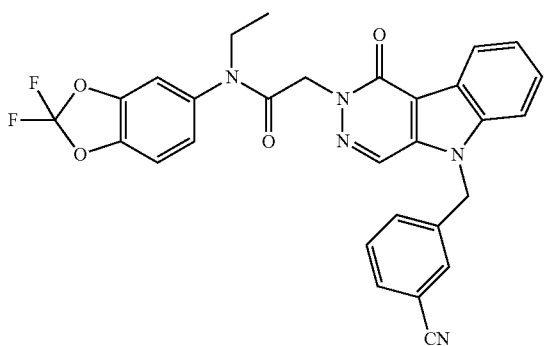 [SMILES: CCN(C(=O)Cn1ncc2c(c1=O)c1ccccc1n2Cc1cccc(C#N)c1)c1ccc2c(c1)OC(F)(F)O2] | 2-(5-(3-cyanobenzyl)-1-oxo-1H-pyridazino[4,5-b]indol-2(5H)-yl)-N-(2,2-difluorobenzo[d][1,3]dioxol-5-yl)-N-ethylacetamide | 542 [M + H] |
| 143. | 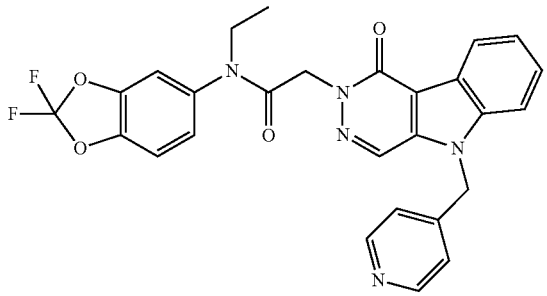 | N-(2,2-difluorobenzo[d][1,3]dioxol-5-yl)-N-ethyl-2-(1-oxo-5-(pyridin-4-ylmethyl)-1H-pyridazino[4,5-b]indol-2(5H)-yl)acetamide | 518 [M + H] |

| Example No. | Structure | IUPAC Name | LCMS m/z |
|---|---|---|---|
| 144. | 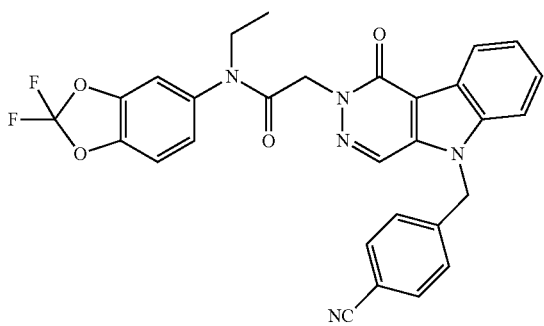 [SMILES: CCN(C(=O)Cn1ncc2c(c1=O)c1ccccc1n2Cc1ccc(C#N)cc1)c1ccc2c(c1)OC(F)(F)O2] | 2-(5-(4-cyanobenzyl)-1-oxo-1H-pyridazino[4,5-b]indol-2(5H)-yl)-N-(2-2-difluorobenzo[d][1,3]dioxol-5-yl)-N-ethylacetamide | 542 [M + H] |
| 145. | 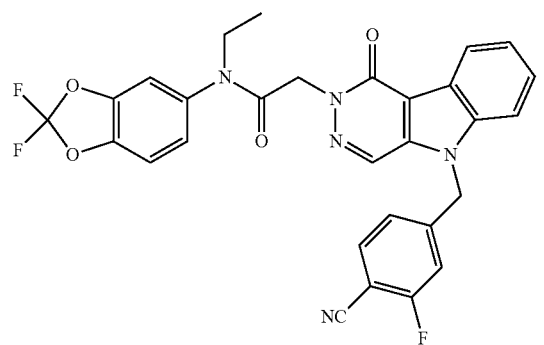 [SMILES: CCN(C(=O)Cn1ncc2c(c1=O)c1ccccc1n2Cc1ccc(C#N)c(F)c1)c1ccc2c(c1)OC(F)(F)O2] | 2-(5-(4-cyano-3-fluorobenzyl)-1-oxo-1H-pyridazino[4,5-b]indol-2(5H)-yl)-N-(2,2-difluorobenzo[d][1,3]dioxol-5-yl)-N-ethylacetamide | 560 [M + H] |
| 146. | 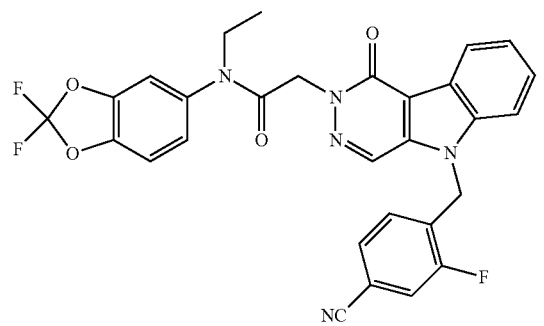 [SMILES: CCN(C(=O)Cn1ncc2c(c1=O)c1ccccc1n2Cc1ccc(C#N)cc1F)c1ccc2c(c1)OC(F)(F)O2] | 2-(5-(4-cyano-2-fluorobenzyl)-1-oxo-1H-pyridazino[4,5-b]indol-2(5H)-yl)-N-(2,2-difluorobenzo[d][1,3]dioxol-5-yl)-N-ethylacetamide | 560 [M + H] |
| 147. | 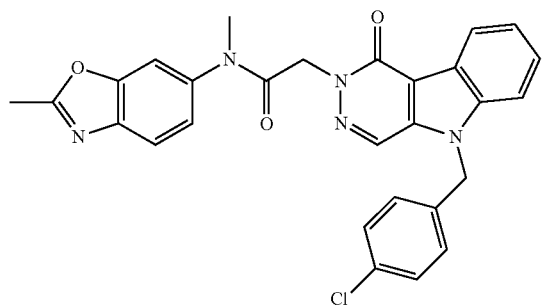 [SMILES: Cc1nc2ccc(N(C)C(=O)Cn3ncc4c(c3=O)c3ccccc3n4Cc3ccc(Cl)cc3)cc2o1] | 2-(5-(4-chlorobenzyl)-1-oxo-1,5-dihydro-2H-pyridazino[4,5-b]indol-2-yl)-N-methyl-N-(2-methylbenzo[d]oxazol-6-yl)acetamide | 513 [M + H] |

| Example No. | Structure | IUPAC Name | LCMS m/z |
|---|---|---|---|
| 148. | 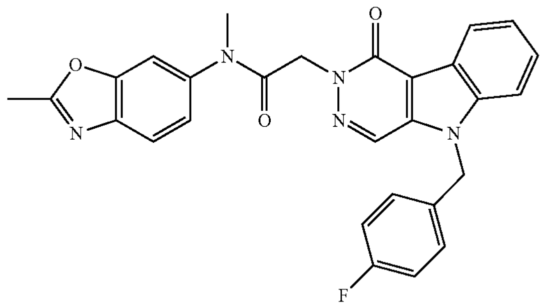 [SMILES: Cc1nc2ccc(N(C)C(=O)Cn3ncc4c(c3=O)c3ccccc3n4Cc3ccc(F)cc3)cc2o1] | 2-(5-(4-fluorobenzyl)-1-oxo-1,5-dihydro-2H-pyridazino[4,5-b]indol-2-yl)-N-methyl-N-(2-methylbenzo[d]oxazol-6-yl)acetamide | 496 [M + H] |
| 149. | 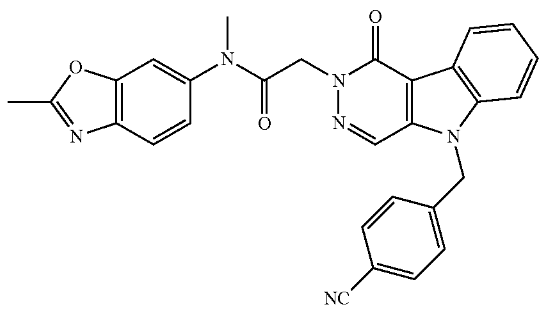 [SMILES: Cc1nc2ccc(N(C)C(=O)Cn3ncc4c(c3=O)c3ccccc3n4Cc3ccc(C#N)cc3)cc2o1] | 2-(5-(4-cyanobenzyl)-1-oxo-1,5-dihydro-2H-pyridazino[4,5-b]indol-2-yl)-N-methyl-N-(2-methylbenzo[d]oxazol-6-yl)acetamide | 504 [M + H] |

Example 150

Synthesis of 5-methyl-1-(piperidine-1-carbonyl)-3-p-tolyl-3H-pyridazino [4, 5-b]indol-4(5H)-one

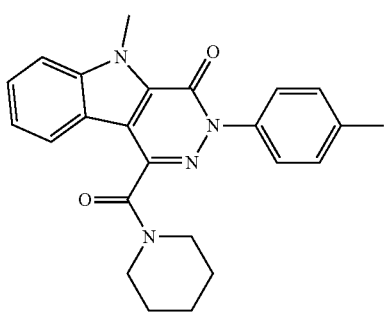 [SMILES: Cc1ccc(-n2nc(C(=O)N3CCCCC3)c3c4ccccc4n(C)c3c2=O)cc1]

Ethyl 1-methyl-1H-indole-2-carboxylate

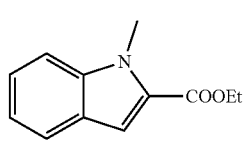

Ethyl 1H-indole-2-carboxylate (5.0 g, 26.45 mmol) was dissolved in DMF (40 mL), then NaH (60%) (1.58 g, 39.68 mmol) was added at 0° C. After stirring for 20 min at this temperature, iodomethane (8.27 mL, 13.22 mmol) was added dropwise and the reaction stirred at rt overnight. It was partitioned between sat'd NH₄Cl (100 mL) and diethyl ether (100 mL), and the aqueous layer was further extracted with diethyl ether (2×50 mL). The organic layers were combined and dried (Na₂SO₄), then the solvent was removed in vacuo to obtain ethyl 1-methyl-1H-indole-2-carboxylate (4.0 g, 74%).

Ethyl 3-(2-ethoxy-2-oxoacetyl)-1-methyl-1H-indole-2-carboxylate

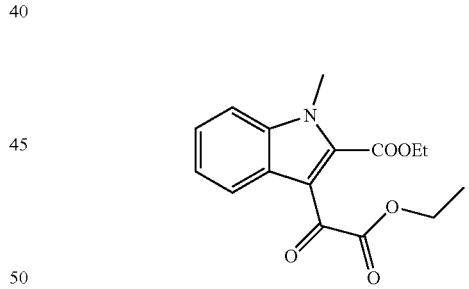

To a solution of ethyl chloro oxoacetate (0.60 mL, 5.41 mmol) in DCE (30 mL) was added TiCl₄ (0.59 mL, 5.41 mmol) at rt, and the reaction stirred for 30 min at rt. Ethyl 1-methyl-1H-indole-2-carboxylate (1.0 g, 4.92 mmol) in DCE was added dropwise and the reaction stirred for 3 hr at rt. The reaction was quenched with sat'd NH₄Cl solution (50 mL) and extracted with DCM (25 mL×3). The organic layer was dried over Na₂SO₄ and concentrated to give ethyl 3-(2-ethoxy-2-oxoacetyl)-1-methyl-1H-indole-2-carboxylate (1.0 g). MS: ESI+ve, 304.6 [M+H].

5-Methyl-4-oxo-3-p-tolyl-4, 5-dihydro-3H-pyridazino[4, 5-b]indole-1-carboxylate

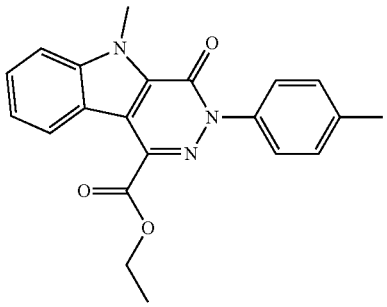 [SMILES: CCOC(=O)c1nn(-c2ccc(C)cc2)c(=O)c2c1c1ccccc1n2C]

To a solution of ethyl 3-(2-ethoxy-2-oxoacetyl)-1-methyl-1H-indole-2-carboxylate (0.9 g, 3.11 mmol) in HOAc (20 mL) was added p-tolylhydrazine hydrochloride (0.6 g, 3.92 mmol). The reaction mixture was heated at 100° C. overnight, then the reaction was quenched with water (5 mL) and neutralized with sat'd NaHCO$_3$ (10 mL). The aqueous layered was extracted with EtOAc (3×30 mL), and the combined organic layers dried with Na$_2$SO$_4$, then concentrated. The crude product was purified by column chromatography (10-50% EtOAc/hexane) to give ethyl 5-methyl-4-oxo-3-p-tolyl-4, 5-dihydro-3H-pyridazino[4, 5-b]indole-1-carboxylate (0.33 g). MS: ESI+ve, 348.69 [M+H].

Example 150 of 5-methyl-1-(piperidine-1-carbonyl)-3-p-tolyl-3H-pyridazino [4, 5-b]indol-one

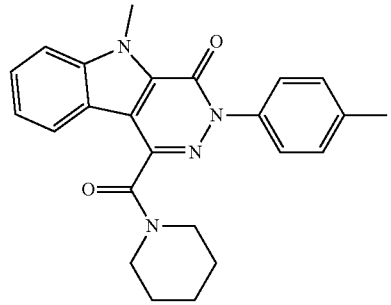 [SMILES: Cc1ccc(-n2nc(C(=O)N3CCCCC3)c3c4ccccc4n(C)c3c2=O)cc1]

Me$_3$Al (2M in toluene, 1.05 mL, 2.07 mmol) was added dropwise to a stirred solution of piperidine (0.107 g, 1.24 mmol) in toluene (5 mL). After stirring the mixture for 2 hr at rt, ethyl 5-methyl-4-oxo-3-p-tolyl-4, 5-dihydro-3H-pyridazino[4, 5-b]indole-1-carboxylate (0.150 g, 0.41 mmol) was added and the reaction heated to 110° C. for 2 h. The reaction was quenched with water (15 mL) and extracted with EtOAc (3×20 mL). The organic layer was dried over Na$_2$SO$_4$, then concentrated to obtain crude material, which was purified by column chromatography (5-50% EtOAc/hexane) to yield 5-methyl-1-(piperidine-1-carbonyl)-3-p-tolyl-3H-pyridazino [4, 5-b]indol-4(5H)-one (0.036 g); MS: ESI+ve, 401.34 [M+H]. $^1$H NMR (DMSO-d$_6$) δ 7.84 (m, 2H), 7.64 (m, 1H), 7.45 (m, 3H), 7.33 (m, 2H), 4.34 (s, 3H), 3.77 (m, 2H), 3.43 (q, 2H), 2.40 (s, 3H), 1.65 (m, 4H), 1.37 (m, 2H).

Representative compounds of the invention were prepared in a similar manner to example 150 (scheme7).

| Example No. | Structure | IUPAC Name | LCMS m/z |
|---|---|---|---|
| 151. | 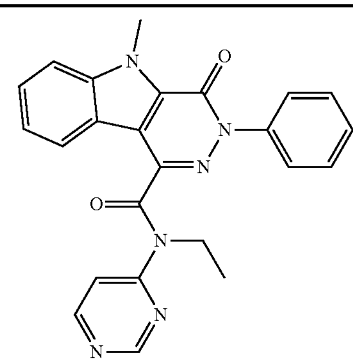 | N-ethyl-5-methyl-4-oxo-3-phenyl-N-(pyrimidin-4-yl)-4,5-dihydro-3H-pyridazino[4,5-b]indole-1-carboxamide | 439 [M + H] |
| 152. | 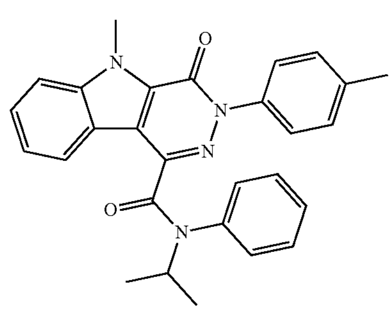 [SMILES: Cc1ccc(-n2nc(C(=O)N(c3ccccc3)C(C)C)c3c4ccccc4n(C)c3c2=O)cc1] | N-isopropyl-5-methyl-4-oxo-N-phenyl-3-(p-tolyl)-4,5-dihydro-3H-pyridazino[4,5-b]indole-1-carboxamide | 451 [M + H] |

-continued

| Example No. | Structure | IUPAC Name | LCMS m/z |
|---|---|---|---|
| 153. | 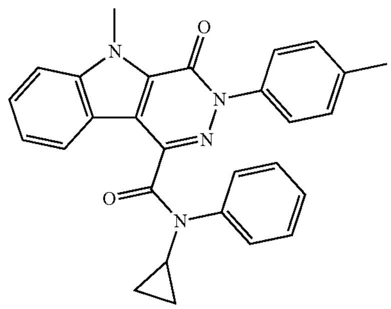 [SMILES: Cc1ccc(-n2nc(C(=O)N(c3ccccc3)C3CC3)c3c4ccccc4n(C)c3c2=O)cc1] | N-cyclopropyl-5-methyl-4-oxo-N-phenyl-3-(p-tolyl)-4,5-dihydro-3H-pyridazino[4,5-b]indole-1-carboxamide | 449 [M + H] |
| 154. | 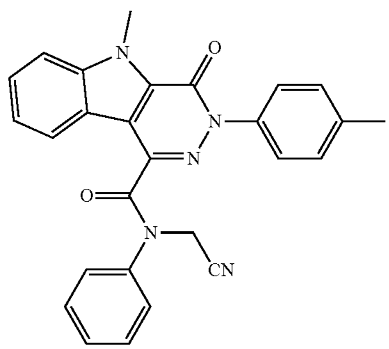 [SMILES: Cc1ccc(-n2nc(C(=O)N(CC#N)c3ccccc3)c3c4ccccc4n(C)c3c2=O)cc1] | N-(cyanomethyl)-5-methyl-4-oxo-N-phenyl-3-(p-tolyl)-4,5-dihydro-3H-pyridazino[4,5-b]indole-1-carboxamide | 448 [M + H] |
| 155. | 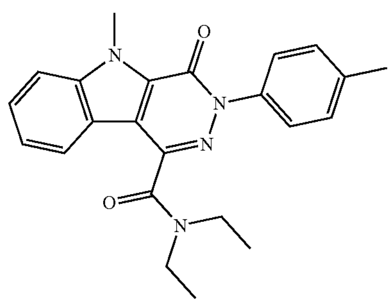 [SMILES: CCN(CC)C(=O)c1nn(-c2ccc(C)cc2)c(=O)c2c1c1ccccc1n2C] | N,N-diethyl-5-methyl-4-oxo-3-(p-tolyl)-4,5-dihydro-3H-pyridazino[4,5-b]indole-1-carboxamide | 389 [M + H] |
| 156. | 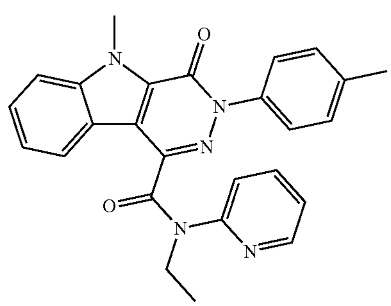 [SMILES: CCN(C(=O)c1nn(-c2ccc(C)cc2)c(=O)c2c1c1ccccc1n2C)c1ccccn1] | N-ethyl-5-methyl-4-oxo-N-(pyridin-2-yl)-3-(p-tolyl)-4,5-dihydro-3H-pyridazino[4,5-b]indole-1-carboxamide | 438 [M + H] |
| 157. | 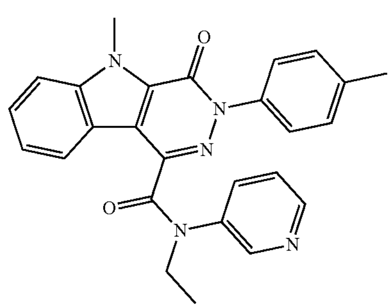 [SMILES: CCN(C(=O)c1nn(-c2ccc(C)cc2)c(=O)c2c1c1ccccc1n2C)c1cccnc1] | N-ethyl-5-methyl-4-oxo-N-(pyridin-3-yl)-3-(p-tolyl)-4,5-dihydro-3H-pyridazino[4,5-b]indole-1-carboxamide | 438 [M + H] |

-continued

| Example No. | Structure | IUPAC Name | LCMS m/z |
|---|---|---|---|
| 158. | 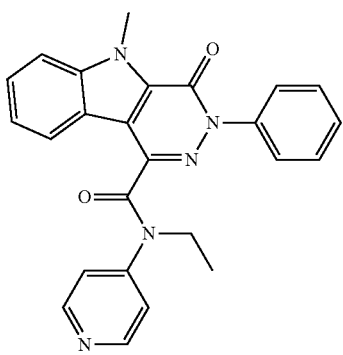 | N-ethyl-5-methyl-4-oxo-3-phenyl-N-(pyridin-4-yl)-4,5-dihydro-3H-pyridazino[4,5-b]indole-1-carboxamide | 438 [M + H] |
| 159. | 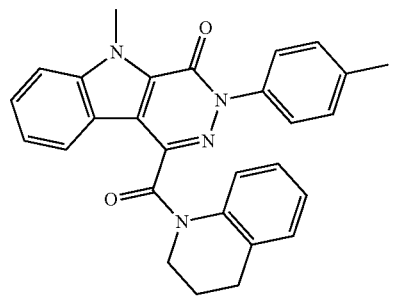 [SMILES: Cc1ccc(-n2nc(C(=O)N3CCCc4ccccc43)c3c4ccccc4n(C)c3c2=O)cc1] | 5-methyl-1-(1,2,3,4-tetrahydroquinoline-1-carbonyl)-3-(p-tolyl)-3H-pyridazino[4,5-b]indol-4(5H)-one | 449 [M + H] |
| 160. | 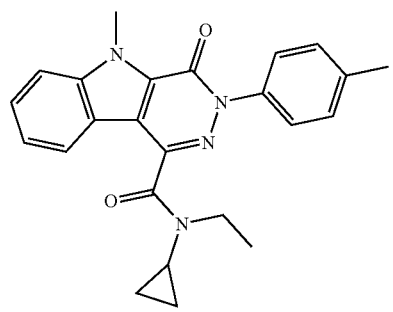 [SMILES: CCN(C(=O)c1nn(-c2ccc(C)cc2)c(=O)c2c1c1ccccc1n2C)C1CC1] | N-cyclopropyl-N-ethyl-5-methyl-4-oxo-3-(p-tolyl)-4,5-dihydro-3H-pyridazino[4,5-b]indole-1-carboxamide | 401 [M + H] |
| 161. | 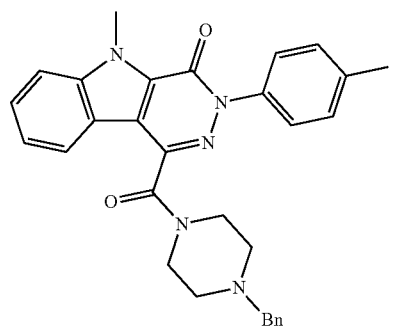 [SMILES: Cc1ccc(-n2nc(C(=O)N3CCN(Cc4ccccc4)CC3)c3c4ccccc4n(C)c3c2=O)cc1] | 1-(4-benzylpiperazine-1-carbonyl)-5-methyl-3-(p-tolyl)-3H-pyridazino[4,5-b]indol-4(5H)-one | 492 [M + H] |

| Example No. | Structure | IUPAC Name | LCMS m/z |
|---|---|---|---|
| 162. | 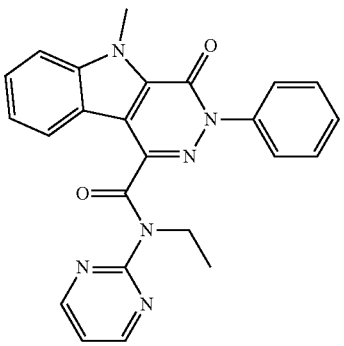 | N-ethyl-5-methyl-4-oxo-3-phenyl-N-(pyrimidin-2-yl)-4,5-dihydro-3H-pyridazino[4,5-b]indole-1-carboxamide | 439 [M + H] |
| 163. | 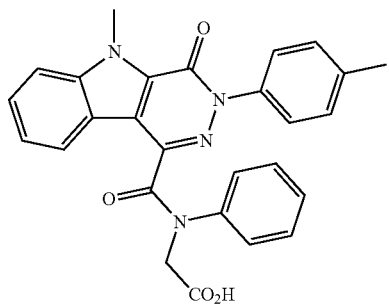 [SMILES: Cc1ccc(-n2nc(C(=O)N(CC(=O)O)c3ccccc3)c3c4ccccc4n(C)c3c2=O)cc1] | 2-(5-methyl-4-oxo-N-phenyl-3-(p-tolyl)-4,5-dihydro-3H-pyridazino[4,5-b]indole-1-carboxamido)acetic acid | 467 [M + H] |
| 164. | 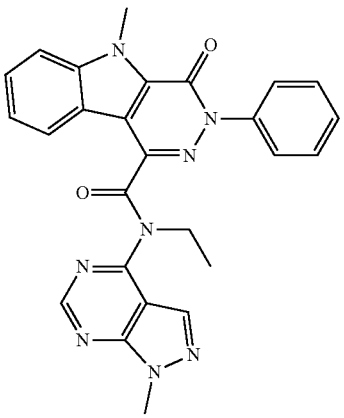 | N-ethyl-5-methyl-N-(1-methyl-1H-pyrazolo[3,4-d]pyrimidin-4-yl)-4-oxo-3-phenyl-4,5-dihydro-3H-pyridazino[4,5-b]indole-1-carboxamide | 493 [M + H] |
| 165. | 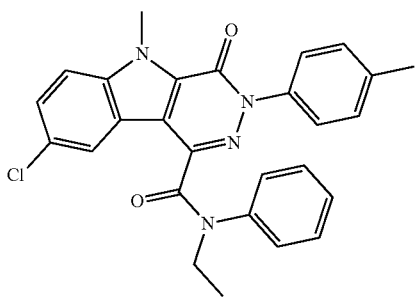 [SMILES: CCN(C(=O)c1nn(-c2ccc(C)cc2)c(=O)c2c1c1cc(Cl)ccc1n2C)c1ccccc1] | 8-chloro-N-ethyl-5-methyl-4-oxo-N-phenyl-3-(p-tolyl)-4,5-dihydro-3H-pyridazino[4,5-b]indole-1-carboxamide | 472 [M + H] |

| Example No. | Structure | IUPAC Name | LCMS m/z |
|---|---|---|---|
| 166. | 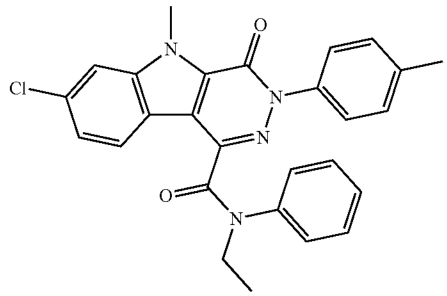 [SMILES: CCN(C(=O)c1nn(-c2ccc(C)cc2)c(=O)c2c1c1ccc(Cl)cc1n2C)c1ccccc1] | 7-chloro-N-ethyl-5-methyl-4-oxo-N-phenyl-3-(p-tolyl)-4,5-dihydro-3H-pyridazino[4,5-b]indole-1-carboxamide | 472 [M + H] |
| 167. | 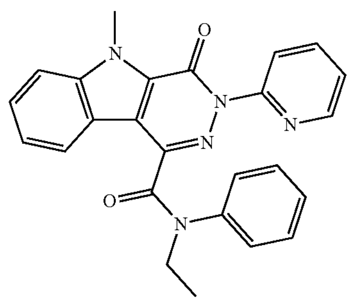 [SMILES: CCN(C(=O)c1nn(-c2ccccn2)c(=O)c2c1c1ccccc1n2C)c1ccccc1] | N-ethyl-5-methyl-4-oxo-N-phenyl-3-(pyridin-2-yl)-4,5-dihydro-3H-pyridazino[4,5-b]indole-1-carboxamide | 424 [M + H] |
| 168. | 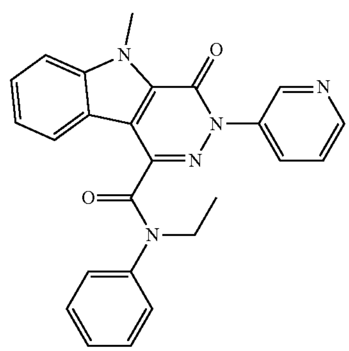 [SMILES: CCN(C(=O)c1nn(-c2cccnc2)c(=O)c2c1c1ccccc1n2C)c1ccccc1] | 3-benzyl-N-ethyl-5-methyl-4-oxo-N-phenyl-4,5-dihydro-3H-pyridazino[4,5-b]indole-1-carboxamide | 424 [M + H] |
| 169. | 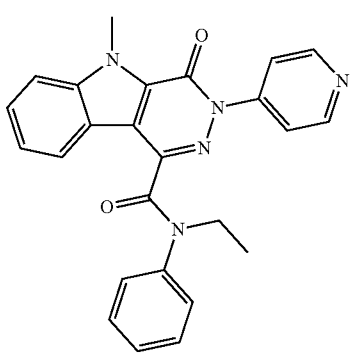 [SMILES: CCN(C(=O)c1nn(-c2ccncc2)c(=O)c2c1c1ccccc1n2C)c1ccccc1] | N-ethyl-5-methyl-4-oxo-N-phenyl-3-(pyridin-4-yl)-4,5-dihydro-3H-pyridazino[4,5-b]indole-1-carboxamide | 424 [M + H] |

-continued

| Example No. | Structure | IUPAC Name | LCMS m/z |
|---|---|---|---|
| 170. | 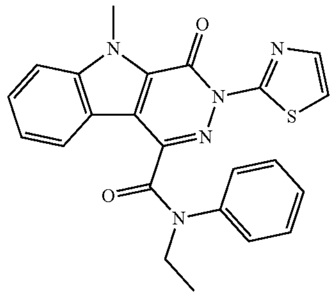 [SMILES: CCN(C(=O)c1nn(-c2nccs2)c(=O)c2c1c1ccccc1n2C)c1ccccc1] | N-ethyl-5-methyl-4-oxo-N-phenyl-3-(thiazol-2-yl)-4,5-dihydro-3H-pyridazino[4,5-b]indole-1-carboxamide | 430 [M + H] |
| 171. | 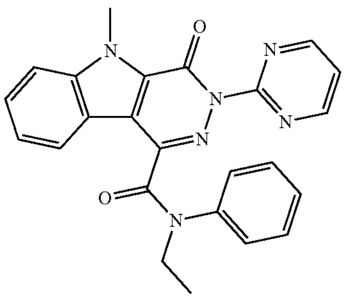 [SMILES: CCN(C(=O)c1nn(-c2ncccn2)c(=O)c2c1c1ccccc1n2C)c1ccccc1] | N-ethyl-5-methyl-4-oxo-N-phenyl-3-(pyrimidin-2-yl)-4,5-dihydro-3H-pyridazino[4,5-b]indole-1-carboxamide | 425 [M + H] |
| 172. | 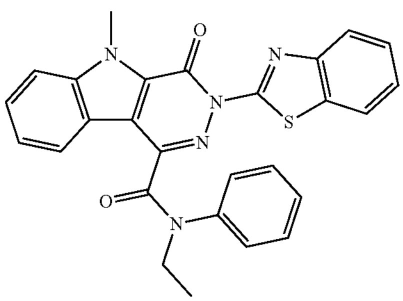 [SMILES: CCN(C(=O)c1nn(-c2nc3ccccc3s2)c(=O)c2c1c1ccccc1n2C)c1ccccc1] | 3-(benzo[d]thiazol-2-yl)-N-ethyl-5-methyl-4-oxo-N-phenyl-4,5-dihydro-3H-pyridazino[4,5-b]indole-1-carboxamide | 480 [M + H] |
| 173. | 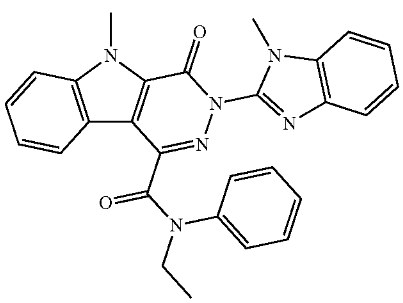 [SMILES: CCN(C(=O)c1nn(-c2nc3ccccc3n2C)c(=O)c2c1c1ccccc1n2C)c1ccccc1] | N-ethyl-5-methyl-3-(1-methyl-1H-benzo[d]imidazol-2-yl)-4-oxo-N-phenyl-4,5-dihydro-3H-pyridazino[4,5-b]indole-1-carboxamide | 477 [M + H] |
| 174. | 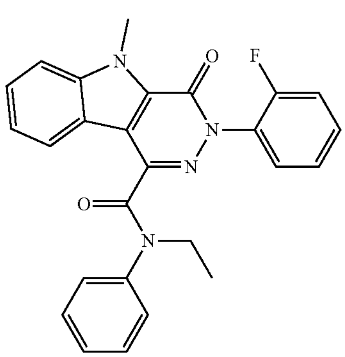 [SMILES: CCN(C(=O)c1nn(-c2ccccc2F)c(=O)c2c1c1ccccc1n2C)c1ccccc1] | N-ethyl-3-(2-fluorophenyl)-5-methyl-4-oxo-N-phenyl-4,5-dihydro-3H-pyridazino[4,5-b]indole-1-carboxamide | 441 [M + H] |

| Example No. | Structure | IUPAC Name | LCMS m/z |
|---|---|---|---|
| 175. | 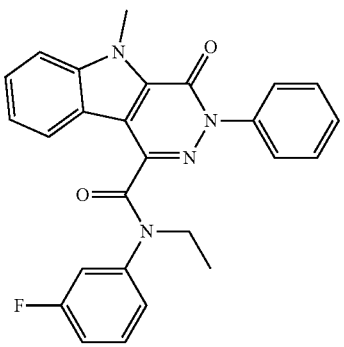 [SMILES: CCN(C(=O)c1nn(-c2ccccc2)c(=O)c2c1c1ccccc1n2C)c1cccc(F)c1] | N-ethyl-N-(3-fluorophenyl)-5-methyl-4-oxo-3-phenyl-4,5-dihydro-3H-pyridazino[4,5-b]indole-1-carboxamide | 442 [M + H] |
| 176. | 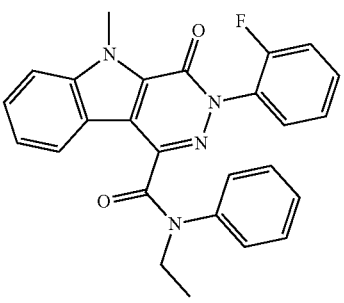 [SMILES: CCN(C(=O)c1nn(-c2ccccc2F)c(=O)c2c1c1ccccc1n2C)c1ccccc1] | N-ethyl-3-(2-fluorophenyl)-5-methyl-4-oxo-N-phenyl-4,5-dihydro-3H-pyridazino[4,5-b]indole-1-carboxamide | 441 [M + H] |
| 177. | 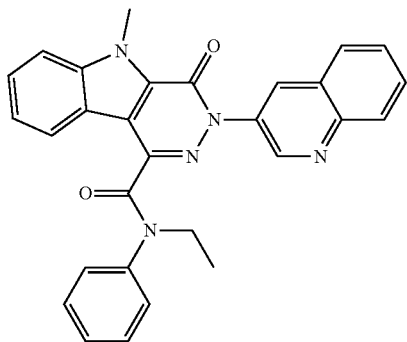 [SMILES: CCN(C(=O)c1nn(-c2cnc3ccccc3c2)c(=O)c2c1c1ccccc1n2C)c1ccccc1] | N-ethyl-5-methyl-4-oxo-N-phenyl-3-(quinolin-3-yl)-4,5-dihydro-3H-pyridazino[4,5-b]indole-1-carboxamide | 474 [M + H] |
| 178. | 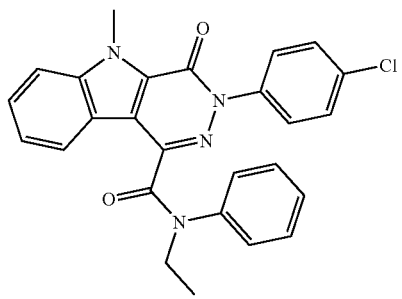 [SMILES: CCN(C(=O)c1nn(-c2ccc(Cl)cc2)c(=O)c2c1c1ccccc1n2C)c1ccccc1] | 3-(4-chlorophenyl)-N-ethyl-5-methyl-4-oxo-N-phenyl-4,5-dihydro-3H-pyridazino[4,5-b]indole-1-carboxamide | 457 [M + H] |

| Example No. | Structure | IUPAC Name | LCMS m/z |
|---|---|---|---|
| 179. | 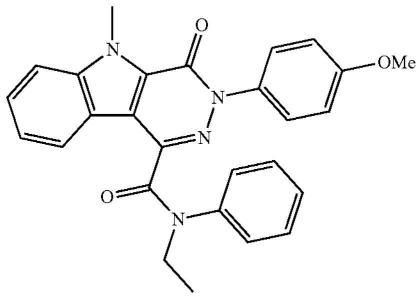 [SMILES: CCN(C(=O)c1nn(-c2ccc(OC)cc2)c(=O)c2c1c1ccccc1n2C)c1ccccc1] | N-ethyl-3-(4-methoxyphenyl)-5-methyl-4-oxo-N-phenyl-4,5-dihydro-3H-pyridazino[4,5-b]indole-1-carboxamide | 453 [M + H] |
| 180. | 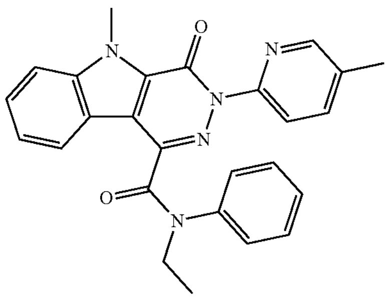 [SMILES: CCN(C(=O)c1nn(-c2ccc(C)cn2)c(=O)c2c1c1ccccc1n2C)c1ccccc1] | N-ethyl-5-methyl-3-(5-methylpyridin-2-yl)-4-oxo-N-phenyl-4,5-dihydro-3H-pyridazino[4,5-b]indole-1-carboxamide | 438 [M + H] |
| 181. | 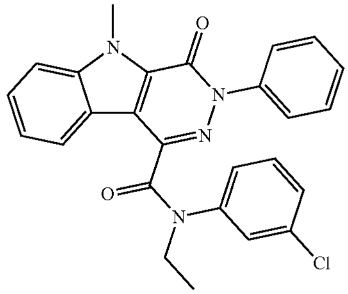 [SMILES: CCN(C(=O)c1nn(-c2ccccc2)c(=O)c2c1c1ccccc1n2C)c1cccc(Cl)c1] | N-(3-chlorophenyl)-N-ethyl-5-methyl-4-oxo-3-phenyl-4,5-dihydro-3H-pyridazino[4,5-b]indole-1-carboxamide | 457 [M + H] |
| 182. | 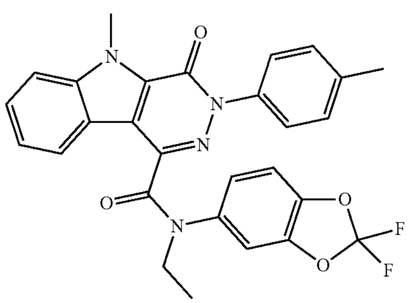 [SMILES: CCN(C(=O)c1nn(-c2ccc(C)cc2)c(=O)c2c1c1ccccc1n2C)c1ccc2c(c1)OC(F)(F)O2] | N-(2,2-difluorobenzo[d][1,3]dioxol-5-yl)-N-ethyl-5-methyl-4-oxo-3-(p-tolyl)-4,5-dihydro-3H-pyridazino[4,5-b]indole-1-carboxamide | 517 [M + H] |
| 183. | 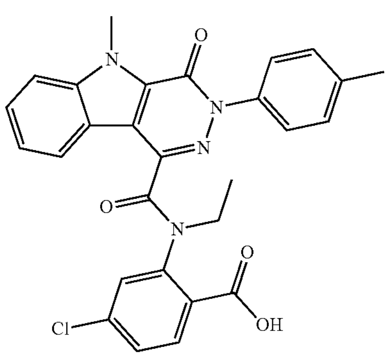 [SMILES: CCN(C(=O)c1nn(-c2ccc(C)cc2)c(=O)c2c1c1ccccc1n2C)c1cc(Cl)ccc1C(=O)O] | 4-chloro-2-(N-ethyl-5-methyl-4-oxo-3-(p-tolyl)-4,5-dihydro-3H-pyridazino[4,5-b]indole-1-carboxamido)benzoic acid | 515 [M + H] |

-continued

| Example No. | Structure | IUPAC Name | LCMS m/z |
|---|---|---|---|
| 184. | 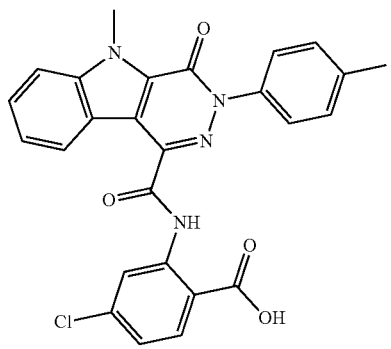 [SMILES: Cc1ccc(-n2nc(C(=O)Nc3cc(Cl)ccc3C(=O)O)c3c4ccccc4n(C)c3c2=O)cc1] | 4-chloro-2-(5-methyl-4-oxo-3-(p-tolyl)-4,5-dihydro-3H-pyridazino[4,5-b]indole-1-carboxamido)benzoic acid | 487 [M + H] |
| 185. | 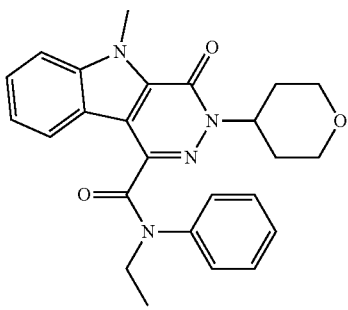 [SMILES: CCN(C(=O)c1nn(C2CCOCC2)c(=O)c2c1c1ccccc1n2C)c1ccccc1] | N-ethyl-5-methyl-4-oxo-N-phenyl-3-(tetrahydro-2H-pyran-4-yl)-4,5-dihydro-3H-pyridazino[4,5-b]indole-1-carboxamide | 431 [M + H] |
| 186. | 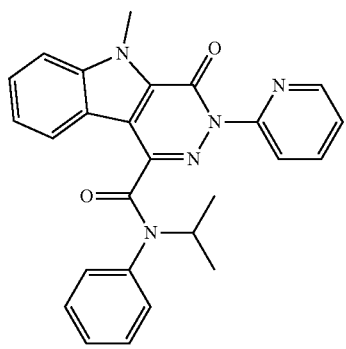 [SMILES: CC(C)N(C(=O)c1nn(-c2ccccn2)c(=O)c2c1c1ccccc1n2C)c1ccccc1] | N-isopropyl-5-methyl-4-oxo-N-phenyl-3-(pyridin-2-yl)-4,5-dihydro-3H-pyridazino[4,5-b]indole-1-carboxamide | 438 [M + H] |
| 187. | 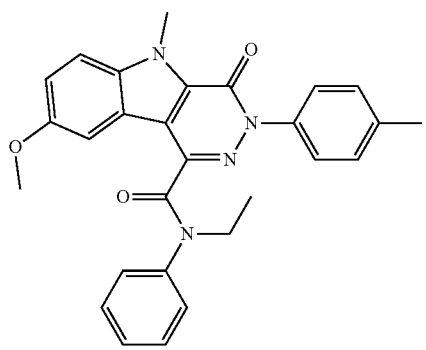 [SMILES: CCN(C(=O)c1nn(-c2ccc(C)cc2)c(=O)c2c1c1cc(OC)ccc1n2C)c1ccccc1] | N-ethyl-8-methoxy-5-methyl-4-oxo-N-phenyl-3-(p-tolyl)-4,5-dihydro-3H-pyridazino[4,5-b]indole-1-carboxamide | 467 [M + H] |

| Example No. | Structure | IUPAC Name | LCMS m/z |
|---|---|---|---|
| 188. | 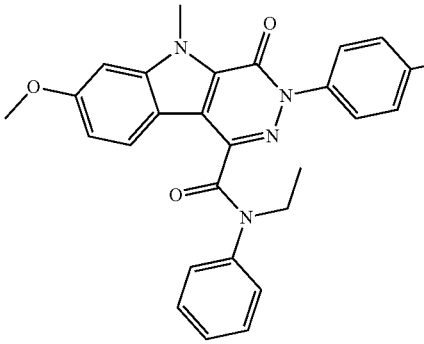 | N-ethyl-7-methoxy-5-methyl-4-oxo-N-phenyl-3-(p-tolyl)-4,5-dihydro-3H-pyridazino[4,5-b]indole-1-carboxamide | 467 [M + H] |
| 189. | 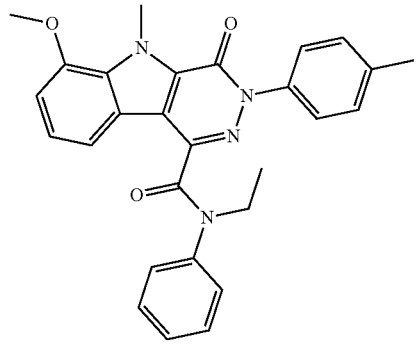 | N-ethyl-6-methoxy-5-methyl-4-oxo-N-phenyl-3-(p-tolyl)-4,5-dihydro-3H-pyridazino[4,5-b]indole-1-carboxamide | 467 [M + H] |
| 190. | 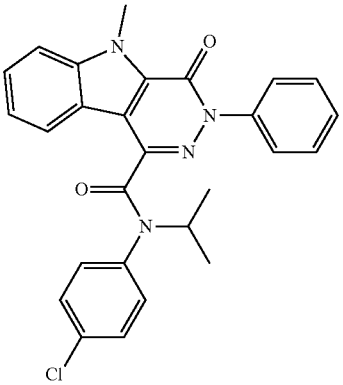 [SMILES: CC(C)N(C(=O)c1nn(-c2ccccc2)c(=O)c2c1c1ccccc1n2C)c1ccc(Cl)cc1] | N-(4-chlorophenyl)-N-isopropyl-5-methyl-4-oxo-3-phenyl-4,5-dihydro-3H-pyridazino[4,5-b]indole-1-carboxamide | 471 [M + H] |
| 191. | 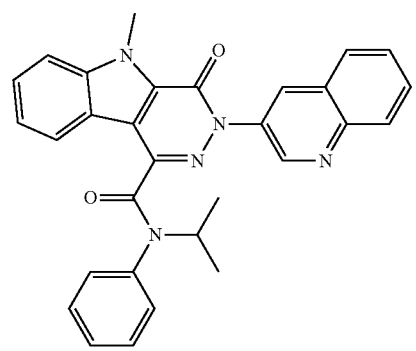 [SMILES: CC(C)N(C(=O)c1nn(-c2cnc3ccccc3c2)c(=O)c2c1c1ccccc1n2C)c1ccccc1] | N-isopropyl-5-methyl-4-oxo-N-phenyl-3-(quinolin-3-yl)-4,5-dihydro-3H-pyridazino[4,5-b]indole-1-carboxamide | 488 [M + H] |

-continued

| Example No. | Structure | IUPAC Name | LCMS m/z |
|---|---|---|---|
| 192. | 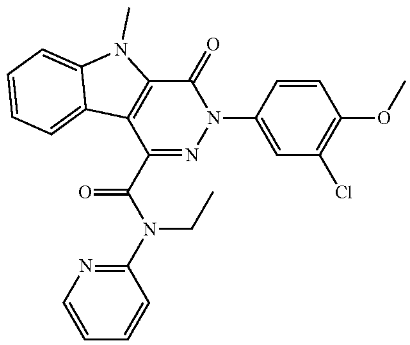 [SMILES: CCN(C(=O)c1nn(-c2ccc(OC)c(Cl)c2)c(=O)c2c1c1ccccc1n2C)c1ccccn1] | 3-(3-chloro-4-methoxyphenyl)-N-ethyl-5-methyl-4-oxo-N-(pyridin-2-yl)-4,5-dihydro-3H-pyridazino[4,5-b]indole-1-carboxamide | 488 [M + H] |
| 193. | 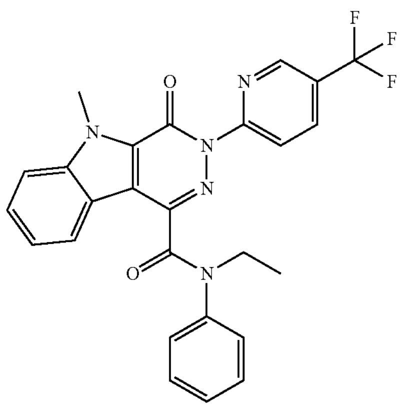 [SMILES: CCN(C(=O)c1nn(-c2ccc(C(F)(F)F)cn2)c(=O)c2c1c1ccccc1n2C)c1ccccc1] | N-ethyl-5-methyl-4-oxo-N-phenyl-3-(5-(trifluoromethyl)pyridin-2-yl)-4,5-dihydro-3H-pyridazino[4,5-b]indole-1-carboxamide | 492 [M + H] |
| 194. | 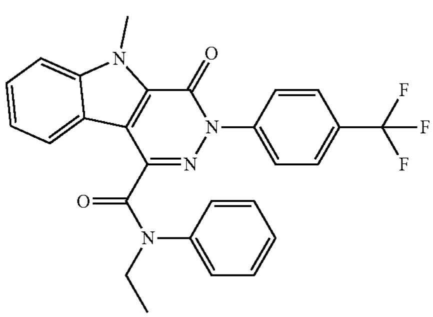 [SMILES: CCN(C(=O)c1nn(-c2ccc(C(F)(F)F)cc2)c(=O)c2c1c1ccccc1n2C)c1ccccc1] | N-ethyl-5-methyl-4-oxo-N-phenyl-3-(4-(trifluoromethyl)phenyl)-4,5-dihydro-3H-pyridazino[4,5-b]indole-1-carboxamide | 491 [M + H] |
| 195. | 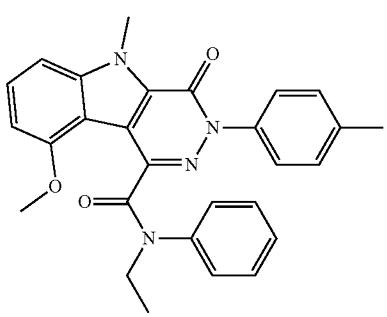 [SMILES: CCN(C(=O)c1nn(-c2ccc(C)cc2)c(=O)c2c1c1c(OC)cccc1n2C)c1ccccc1] | N-ethyl-9-methoxy-5-methyl-4-oxo-N-phenyl-3-(p-tolyl)-4,5-dihydro-3H-pyridazino[4,5-b]indole-1-carboxamide | 467 [M + H] |

| Example No. | Structure | IUPAC Name | LCMS m/z |
|---|---|---|---|
| 196. | 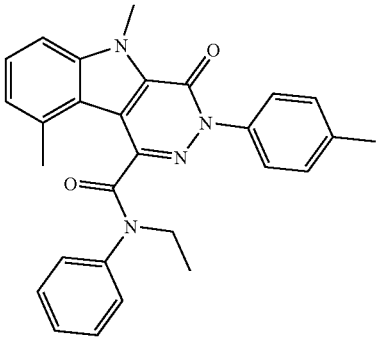 [SMILES: CCN(C(=O)c1nn(-c2ccc(C)cc2)c(=O)c2c1c1c(C)cccc1n2C)c1ccccc1] | N-ethyl-5,9-dimethyl-4-oxo-N-phenyl-3-(p-tolyl)-4,5-dihydro-3H-pyridazino[4,5-b]indole-1-carboxamide | 451 [M + H] |

Example 197

Synthesis of 3-benzyl-N-ethyl-5-methyl-4-oxo-N-phenyl-4, 5-dihydro-3H-pyridazino[4, 5-b]indole-1-carboxamide

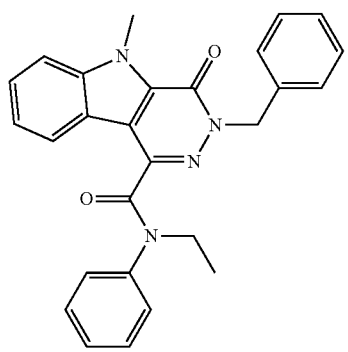 [SMILES: CCN(C(=O)c1nn(Cc2ccccc2)c(=O)c2c1c1ccccc1n2C)c1ccccc1]

5-Methyl-4-oxo-4, 5-dihydro-3H-pyridazino[4, 5-b]indole-1-carboxylate

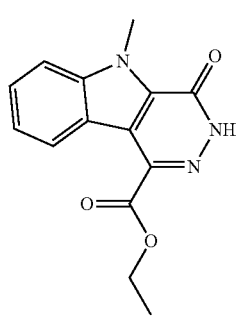 [SMILES: CCOC(=O)c1n[nH]c(=O)c2c1c1ccccc1n2C]

To a solution of ethyl 3-(2-ethoxy-2-oxoacetyl)-1-methyl-1H-indole-2-carboxylate (0.5 g, 1.65 mmol) in HOAc (6.0 mL) was added hydrazine hydrate (0.123 g, 2.47 mmol) and the reaction stirred at 110° C. overnight. The reaction was quenched with water (50 mL) and the precipitate collected and dried to give ethyl 5-methyl-4-oxo-4, 5-dihydro-3H-pyridazino[4, 5-b]indole-1-carboxylate (0.33 g) as solid. MS: ESI+ve, 273.18 [M+H].

Ethyl 3-benzyl-5-methyl-4-oxo-4, 5-dihydro-3H-pyridazino[4, 5-b]indole-1-carboxylate

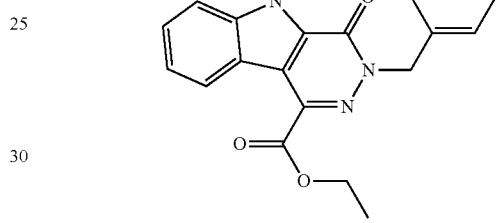

NaH (60%) (0.062 g, 1.54 mmol) was added a solution of ethyl 5-methyl-4-oxo-4, 5-dihydro-3H-pyridazino[4, 5-b]indole-1-carboxylate (0.35 g, 1.29 mmol) in THF (5 mL) at 0° C. and stirred at rt for 30 min. The reaction was cooled to 0° C. again, then Bn-Br (0.17 mL, 1.42 mmol) added and the mixture stirred at rt for 12 hr. The reaction was quenched with water (20 mL) and extracted with EtOAc (3×20 mL). The combined organic layers were dried over Na₂SO₄, and concentrated. The crude product was purified by column chromatography (20% EtOAc/hexane) to give ethyl 3-benzyl-5-methyl-4-oxo-4, 5-dihydro-3H-pyridazino[4, 5-b]indole-1-carboxylate (0.25 g, 53%) as a solid. MS: ESI+ve, 362.24 [M+H].

Example 197

3-benzyl-N-ethyl-5-methyl-4-oxo-N-phenyl-4, 5-dihydro-3H-pyridazino[4, 5-b]indole-1-carboxamide

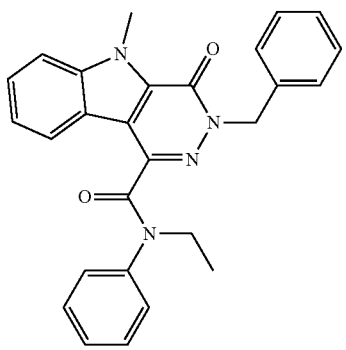 [SMILES: CCN(C(=O)c1nn(Cc2ccccc2)c(=O)c2c1c1ccccc1n2C)c1ccccc1]

Me₃Al (2M in toluene, 1.05 mL, 2.07 mmol) was added dropwise to a stirred solution of N-ethyl aniline (0.15 g, 1.24 mmol) in toluene (5 mL). After stirring the mixture for 2 hr at rt, ethyl 3-benzyl-5-methyl-4-oxo-4, 5-dihydro-3H-pyridazino[4, 5-b]indole-1-carboxylate (0.150 g, 0.42 mmol) was added and the reaction heated to 110° C. for 2 h. The reaction was quenched with water (20 mL), neutralized with a satd. solution of NaHCO₃ (15 mL) and extracted with EtOAc (3×25 mL). The organic layer was dried over Na₂SO₄, concentrated, and purified by column chromatography (0-30% EtOAc/hexane) to yield 3-benzyl-N-ethyl-5-methyl-4-oxo-N-phenyl-4, 5-dihydro-3H-pyridazino[4, 5-b]indole-1-carboxamide (0.060 g). MS: ESI+ve, 437.31 [M+H]. ¹H NMR (DMSO-d₆) δ 8.02 (d, J=8 Hz, 1 H), 7.80 (m, 1 H), 7.68 (m, 1H), 7.49 (m, 1H), 7.24 (m, 3 H), 7.19 (m, 3 H), 7.05 (m, 2 H), 6.85 (m, 2 H), 5.14 (s, 2 H), 4.23 (s, 3 H), 4.05 (q, J=7 Hz, 2 H), 1.23 (t, J=7 Hz, 3 H).

Representative compounds of the invention were prepared in a similar manner to example 197 (scheme 8).

| Example No. | Structure | IUPAC Name | LCMS m/z |
|---|---|---|---|
| 198. | 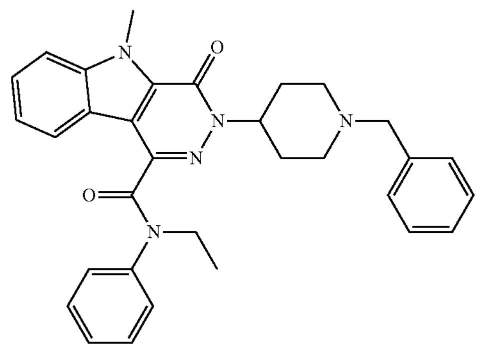 [SMILES: CCN(C(=O)c1nn(C2CCN(Cc3ccccc3)CC2)c(=O)c2c1c1ccccc1n2C)c1ccccc1] | 3-(1-benzylpiperidin-4-yl)-N-ethyl-5-methyl-4-oxo-N-phenyl-4,5-dihydro-3H-pyridazino[4,5-b]indole-1-carboxamide | 520 [M + H] |
| 199. | 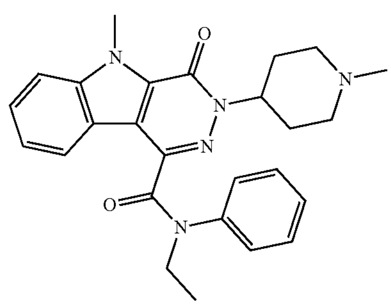 [SMILES: CCN(C(=O)c1nn(C2CCN(C)CC2)c(=O)c2c1c1ccccc1n2C)c1ccccc1] | N-ethyl-5-methyl-3-(1-methylpiperidin-4-yl)-4-oxo-N-phenyl-4,5-dihydro-3H-pyridazino[4,5-b]indole-1-carboxamide | 444 [M + H] |
| 200. | 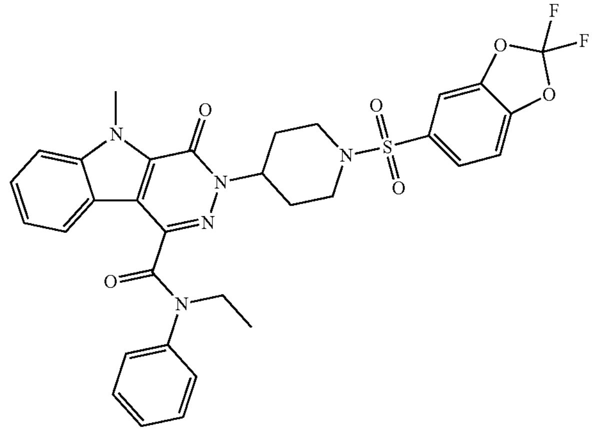 [SMILES: CCN(C(=O)c1nn(C2CCN(S(=O)(=O)c3ccc4c(c3)OC(F)(F)O4)CC2)c(=O)c2c1c1ccccc1n2C)c1ccccc1] | 3-(1-((2,2-difluorobenzo[d][1,3]dioxol-5-yl)sulfonyl)piperidin-4-yl)-N-ethyl-5-methyl-4-oxo-N-phenyl-4,5-dihydro-3H-pyridazino[4,5-b]indole-1-carboxamide | 650 [M + H] |

| Example No. | Structure | IUPAC Name | LCMS m/z |
|---|---|---|---|
| 201. | 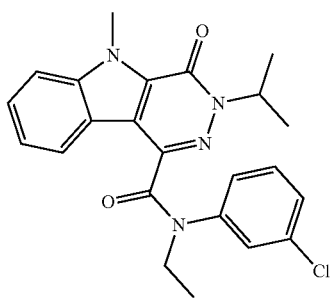 [SMILES: CCN(C(=O)c1nn(C(C)C)c(=O)c2c1c1ccccc1n2C)c1cccc(Cl)c1] | N-(3-chlorophenyl)-N-ethyl-3-isopropyl-5-methyl-4-oxo-4,5-dihydro-3H-pyridazino[4,5-b]indole-1-carboxamide | 423 [M + H] |
| 202. | 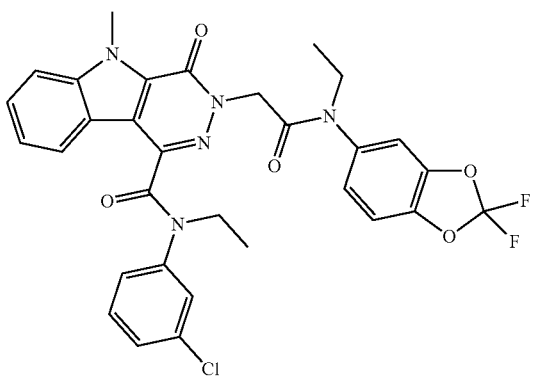 [SMILES: CCN(C(=O)Cn1nc(C(=O)N(CC)c2cccc(Cl)c2)c2c3ccccc3n(C)c2c1=O)c1ccc2c(c1)OC(F)(F)O2] | N-(3-chlorophenyl)-3-(2-((2,2-difluorobenzo[d][1,3]dioxol-5-yl)(ethyl)amino)-2-oxoethyl)-N-ethyl-5-methyl-4-oxo-4,5-dihydro-3H-pyridazino[4,5-b]indole-1-carboxamide | 623 [M + H] |
| 203. | 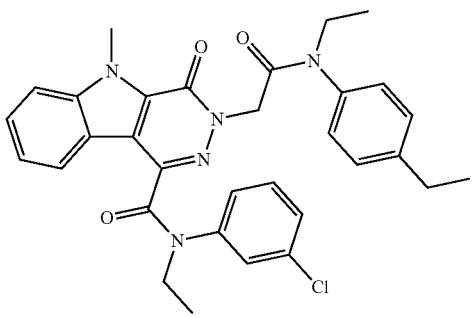 [SMILES: CCc1ccc(N(CC)C(=O)Cn2nc(C(=O)N(CC)c3cccc(Cl)c3)c3c4ccccc4n(C)c3c2=O)cc1] | N-(3-chlorophenyl)-N-ethyl-3-(2-(ethyl(4-ethylphenyl)amino)-2-oxoethyl)-5-methyl-4-oxo-4,5-dihydro-3H-pyridazino[4,5-b]indole-1-carboxamide | 571 [M + H] |
| 204. | 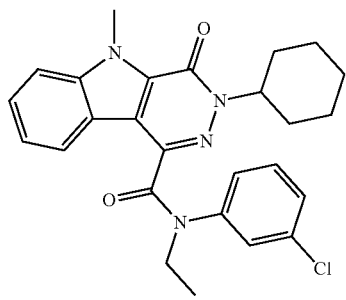 [SMILES: CCN(C(=O)c1nn(C2CCCCC2)c(=O)c2c1c1ccccc1n2C)c1cccc(Cl)c1] | N-(3-chlorophenyl)-3-cyclohexyl-N-ethyl-5-methyl-4-oxo-4,5-dihydro-3H-pyridazino[4,5-b]indole-1-carboxamide | 463 [M + H] |

| Example No. | Structure | IUPAC Name | LCMS m/z |
|---|---|---|---|
| 205. | 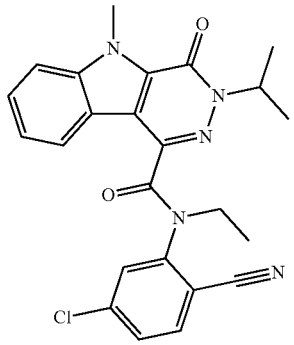 [SMILES: CCN(C(=O)c1nn(C(C)C)c(=O)c2c1c1ccccc1n2C)c1cc(Cl)ccc1C#N] | N-(5-chloro-2-cyanophenyl)-N-ethyl-3-isopropyl-5-methyl-4-oxo-4,5-dihydro-3H-pyridazino[4,5-b]indole-1-carboxamide | 448 [M + H] |
| 206. | 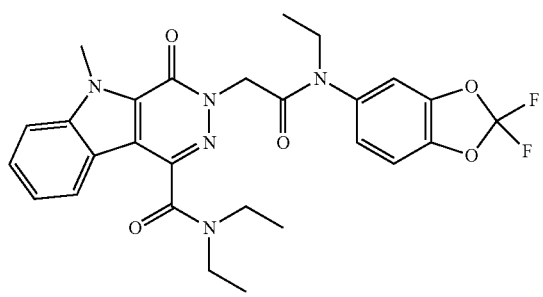 [SMILES: CCN(CC)C(=O)c1nn(CC(=O)N(CC)c2ccc3c(c2)OC(F)(F)O3)c(=O)c2c1c1ccccc1n2C] | 3-(2-((2,2-difluorobenzo[d][1,3]dioxol-5-yl)(ethyl)amino)-2-oxoethyl)-N,N-diethyl-5-methyl-4-oxo-4,5-dihydro-3H-pyridazino[4,5-b]indole-1-carboxamide | 540 [M + H] |
| 207. | 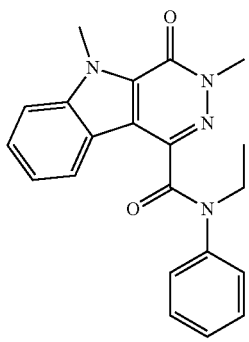 [SMILES: CCN(C(=O)c1nn(C)c(=O)c2c1c1ccccc1n2C)c1ccccc1] | N-ethyl-3,5-dimethyl-4-oxo-N-phenyl-4,5-dihydro-3H-pyridazino[4,5-b]indole-1-carboxamide | 361 [M + H] |
| 208. | 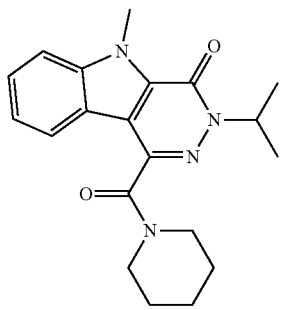 [SMILES: CC(C)n1nc(C(=O)N2CCCCC2)c2c3ccccc3n(C)c2c1=O] | 3-isopropyl-5-methyl-1-(piperidine-1-carbonyl)-3,5-dihydro-4H-pyridazino[4,5-b]indol-4-one | 353 [M + H] |

| Example No. | Structure | IUPAC Name | LCMS m/z |
|---|---|---|---|
| 209. | 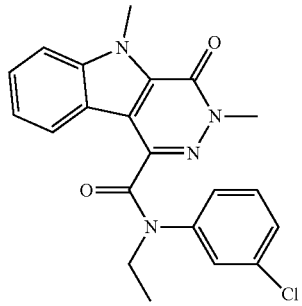 [SMILES: CCN(C(=O)c1nn(C)c(=O)c2c1c1ccccc1n2C)c1cccc(Cl)c1] | N-(3-chlorophenyl)-N-ethyl-3,5-dimethyl-4-oxo-4,5-dihydro-3H-pyridazino[4,5-b]indole-1-carboxamide | 395 [M + H] |
| 210. | 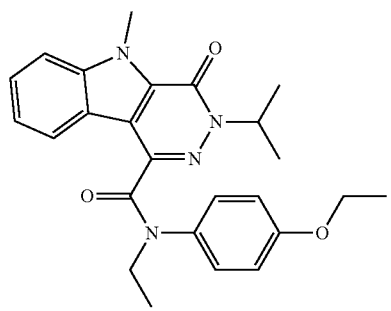 [SMILES: CCOc1ccc(N(CC)C(=O)c2nn(C(C)C)c(=O)c3c2c2ccccc2n3C)cc1] | N-(4-ethoxyphenyl)-N-ethyl-3-isopropyl-5-methyl-4-oxo-4,5-dihydro-3H-pyridazino[4,5-b]indole-1-carboxamide | 433 [M + H] |
| 211. | 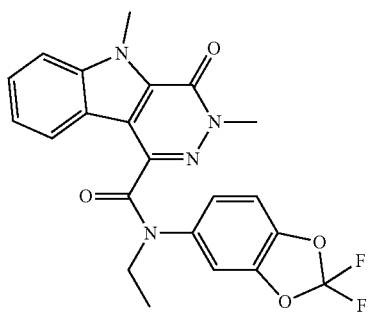 [SMILES: CCN(C(=O)c1nn(C)c(=O)c2c1c1ccccc1n2C)c1ccc2c(c1)OC(F)(F)O2] | N-(2,2-difluorobenzo[d][1,3]dioxol-5-yl)-N-ethyl-3,5-dimethyl-4-oxo-4,5-dihydro-3H-pyridazino[4,5-b]indole-1-carboxamide | 441 [M + H] |
| 212. | 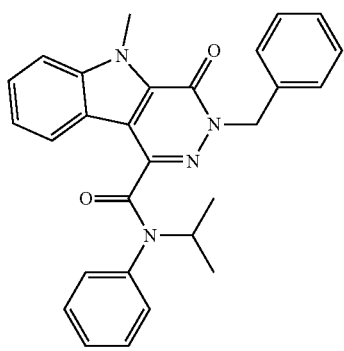 [SMILES: CC(C)N(C(=O)c1nn(Cc2ccccc2)c(=O)c2c1c1ccccc1n2C)c1ccccc1] | 3-benzyl-N-isopropyl-5-methyl-4-oxo-N-phenyl-4,5-dihydro-3H-pyridazino[4,5-b]indole-1-carboxamide | 451 [M + H] |

| Example No. | Structure | IUPAC Name | LCMS m/z |
|---|---|---|---|
| 213. | 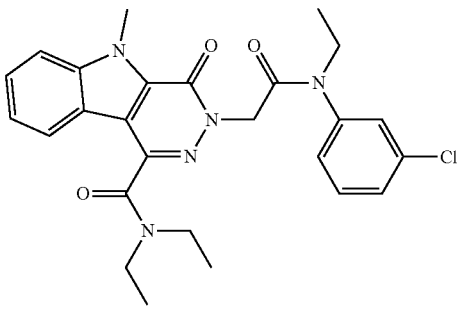 [SMILES: CCN(CC)C(=O)c1nn(CC(=O)N(CC)c2cccc(Cl)c2)c(=O)c2c1c1ccccc1n2C] | 3-(2-((3-chlorophenyl)(ethyl)amino)-2-oxoethyl)-N,N-diethyl-5-methyl-4-oxo-4,5-dihydro-3H-pyridazino[4,5-b]indole-1-carboxamide | 494 [M + H] |
| 214. | 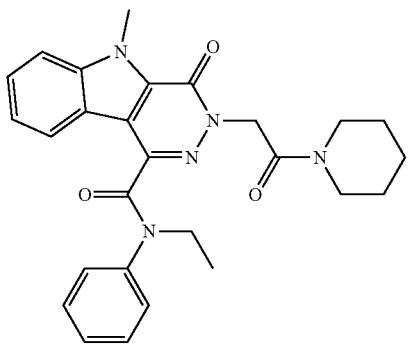 [SMILES: CCN(C(=O)c1nn(CC(=O)N2CCCCC2)c(=O)c2c1c1ccccc1n2C)c1ccccc1] | N-ethyl-5-methyl-4-oxo-3-(2-oxo-2-(piperidin-1-yl)ethyl)-N-phenyl-4,5-dihydro-3H-pyridazino[4,5-b]indole-1-carboxamide | 472 [M + H] |
| 215. | 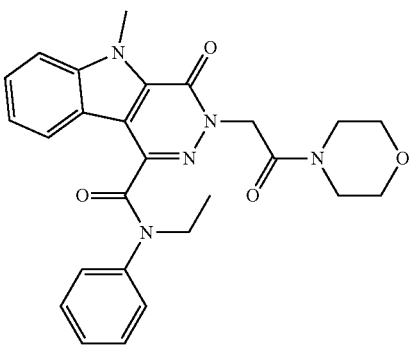 [SMILES: CCN(C(=O)c1nn(CC(=O)N2CCOCC2)c(=O)c2c1c1ccccc1n2C)c1ccccc1] | N-ethyl-5-methyl-3-(2-morpholino-2-oxoethyl)-4-oxo-N-phenyl-4,5-dihydro-3H-pyridazino[4,5-b]indole-1-carboxamide | 474 [M + H] |
| 216. | 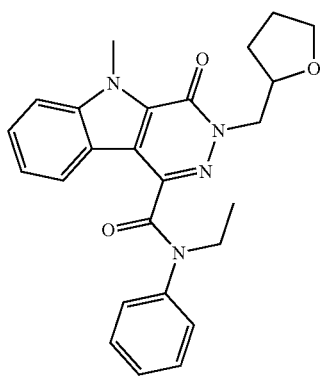 [SMILES: CCN(C(=O)c1nn(CC2CCCO2)c(=O)c2c1c1ccccc1n2C)c1ccccc1] | N-ethyl-5-methyl-4-oxo-N-phenyl-3-((THF-2-yl)methyl)-4,5-dihydro-3H-pyridazino[4,5-b]indole-1-carboxamide | 431 [M + H] |

| Example No. | Structure | IUPAC Name | LCMS m/z |
|---|---|---|---|
| 217. | 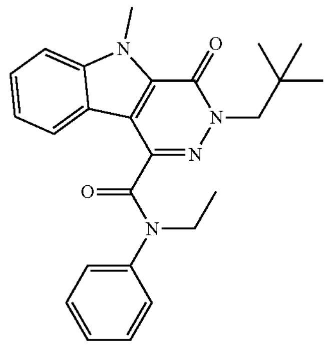 [SMILES: CCN(C(=O)c1nn(CC(C)(C)C)c(=O)c2c1c1ccccc1n2C)c1ccccc1] | N-ethyl-5-methyl-3-neopentyl-4-oxo-N-phenyl-4,5-dihydro-3H-pyridazino[4,5-b]indole-1-carboxamide | 417 [M + H] |
| 218. | 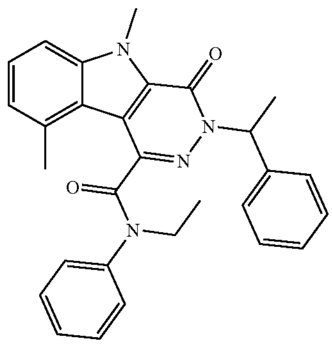 [SMILES: CCN(C(=O)c1nn(C(C)c2ccccc2)c(=O)c2c1c1c(C)cccc1n2C)c1ccccc1] | N-ethyl-5,9-dimethyl-4-oxo-N-phenyl-3-(1-phenylethyl)-4,5-dihydro-3H-pyridazino[4,5-b]indole-1-carboxamide | 465 [M + H] |

Example 219

5-cyclobutyl-N-ethyl-4-oxo-N-phenyl-3-p-tolyl-4,5-dihydro-3H-pyridazino[4, 5-b]indole-1-carboxamide

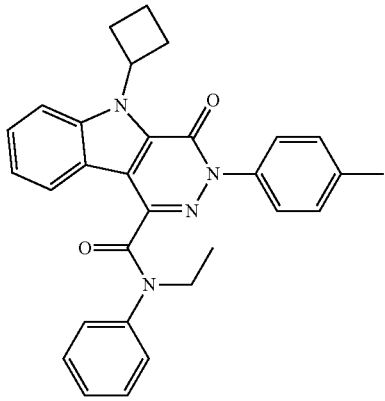 [SMILES: CCN(C(=O)c1nn(-c2ccc(C)cc2)c(=O)c2c1c1ccccc1n2C1CCC1)c1ccccc1]

Ethyl 3-(2-ethoxy-2-oxoacetyl)-1H-indole-2-carboxylate

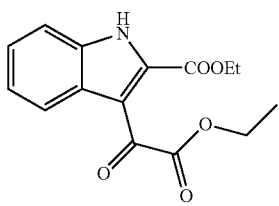 [SMILES: CCOC(=O)C(=O)c1c(C(=O)OCC)[nH]c2ccccc12]

TiCl₄ (1.3 mL, 11.6 mmol) was added to a solution of ethyl chloro oxoacetate (1.3 mL, 11.6 mmol) in DCE (40 mL) and the reaction stirred for 30 min at rt. A solution of ethyl 1H-indole-2-carboxylate (2.0 g, 10.5 mmol) in DCE was added dropwise and stirring was continued for 2 hr. The reaction was quenched with water (100 mL) and extracted with DCM (3×100 mL). The combined organic layers were dried over Na₂SO₄ and concentrated to give ethyl 3-(2-ethoxy-2-oxoacetyl)-1H-indole-2-carboxylate (2.64 g). MS: ESI+ve, 289.94 [M+H].

Ethyl 4-oxo-3-p-tolyl-4, 5-dihydro-3H-pyridazino[4, 5-b]indole-1-carboxylate

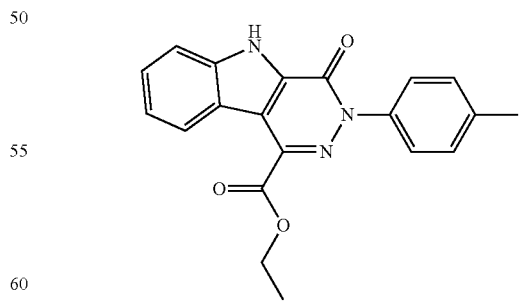

To a solution ethyl 3-(2-ethoxy-2-oxoacetyl)-1H-indole-2-carboxylate (2.64 g, 9.13 mmol) in HOAc (40 mL) was added p-tolylhydrazine hydrochloride (1.82 g, 11.5 mmol), and reaction was heat at 100° C. overnight. The reaction was quenched with water (50 mL), and the solid product collected by filtration to yield ethyl 4-oxo-3-p-tolyl-4, 5-di-hydro-3H-pyridazino[4, 5-b]indole-1-carboxylate (2.5 g). MS: ESI+ve, 347.98 [M+H].

Example 220: N-Ethyl-4-oxo-N-phenyl-3-p-tolyl-4, 5-dihydro-3H-pyridazino[4, 5-b]indole-1-carboxamide

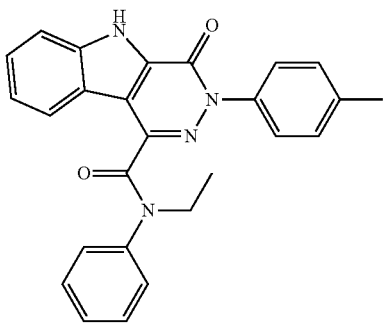 [SMILES: CCN(C(=O)c1nn(-c2ccc(C)cc2)c(=O)c2[nH]c3ccccc3c12)c1ccccc1]

Me$_3$Al (2.0 M in toluene, 7.2 mL, 14.4 mmol) was added dropwise to a stirred solution of N-ethyl aniline (1.04 g, 8.64 mmol) in toluene (20 mL). After stirring the mixture for 2 hr at rt, ethyl 4-oxo-3-p-tolyl-4, 5-dihydro-3H-pyridazino[4, 5-b]indole-1-carboxylate (1.0 g, 2.88 mmol) was added and the reaction heated to 100° C. for 2 h. The reaction was quenched with water (50 mL), neutralized with a satd. solution of NaHCO$_3$ (100 mL) and extracted with EtOAc (3×75 mL). The organic layer was dried over Na$_2$SO$_4$, then concentrated, and purified by column chromatography (40% EtOAc/hexane) to give N-ethyl-4-oxo-N-phenyl-3-p-tolyl-4, 5-dihydro-3H-pyridazino[4, 5-b]indole-1-carboxamide (0.4 g). MS: ESI+ve, 423.68 [M+H]. $^1$H NMR (DMSO-d$_6$) δ 13.1 (s, 1 H), 8.08 (d, J=8 Hz, 1 H), 7.68-7.22 (m, 8 H), 7.08 (m, 2 H), 6.91 (m, 2 H), 4.05 (q, 2 H), 1.25 (t, J=7 Hz, 3 H).

Example 219

5-cyclobutyl-N-ethyl-4-oxo-N-phenyl-3-p-tolyl-4, 5-dihydro-3H-pyridazino[4, 5-b]indole-1-carboxamide

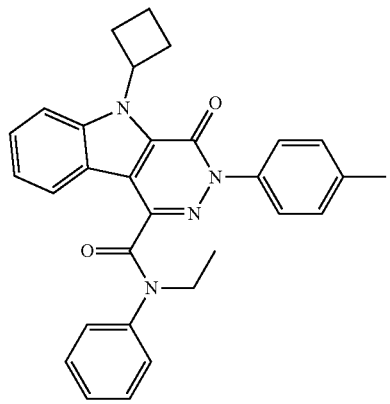 [SMILES: CCN(C(=O)c1nn(-c2ccc(C)cc2)c(=O)c2c1c1ccccc1n2C1CCC1)c1ccccc1]

K$_2$CO$_3$ (0.122 g, 0.88 mmol) was added to a solution of N-ethyl-4-oxo-N-phenyl-3-p-tolyl-4, 5-dihydro-3H-pyridazino[4, 5-b]indole-1-carboxamide (0.25 g, 0.59 mmol) in acetonitrile (5.0 mL) at rt. After stirring for 30 min, bromo cyclobutane (0.48 g, 3.55 mmol) was added and the reaction heated to reflux overnight. The reaction was quenched with water (50 mL) and extracted with EtOAc (3×40 mL). The organic layer was dried over Na$_2$SO$_4$, then concentrated to obtain crude product, which was purified by column chromatography (15% EtOAc/hexane) to give 5-cyclobutyl-N-ethyl-4-oxo-N-phenyl-3-p-tolyl-4, 5-dihydro-3H-pyridazino[4, 5-b]indole-1-carboxamide (11.5 mg). MS: ESI+ve, 477.34 [M+H]. $^1$H NMR (CD$_3$CN) δ 8.18 (m, 1 H), 8.12 (m, 1 H), 7.66 (m, 1 H), 7.50 (m, 1 H), 7.24 (m, 5 H), 7.08 (m, 2 H), 6.97 (m, 2 H), 6.47 (m, 1 H), 4.09 (q, J=7 Hz, 2 H), 3.13 (m, 2 H), 2.47 (m, 2 H), 2.41 (s, 3 H), 2.10 (m, 2 H), 1.32 (t, J=7 Hz, 3 H).

Representative compounds of the invention were prepared in a similar manner to example 219 (scheme 9).

| Example No. | Structure | IUPAC Name | LCMS m/z |
|---|---|---|---|
| 221. | 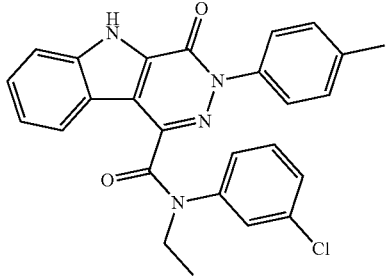 [SMILES: CCN(C(=O)c1nn(-c2ccc(C)cc2)c(=O)c2[nH]c3ccccc3c12)c1cccc(Cl)c1] | N-(3-chlorophenyl)-N-ethyl-4-oxo-3-(p-tolyl)-4,5-dihydro-3H-pyridazino[4,5-b]indole-1-carboxamide | 457 [M + H] |

-continued

| Example No. | Structure | IUPAC Name | LCMS m/z |
|---|---|---|---|
| 222. | 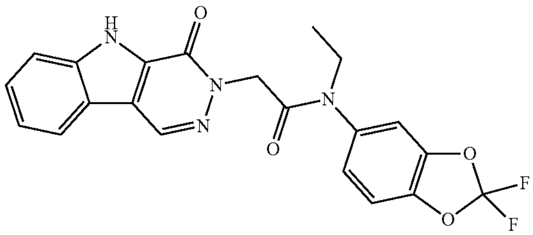 [SMILES: CCN(C(=O)Cn1ncc2c([nH]c3ccccc32)c1=O)c1ccc2c(c1)OC(F)(F)O2] | N-(2,2-difluorobenzo[d][1,3]dioxol-5-yl)-N-ethyl-2-(4-oxo-4,5-dihydro-3H-pyridazino[4,5-b]indol-3-yl)acetamide | 427 [M + H] |
| 223. | 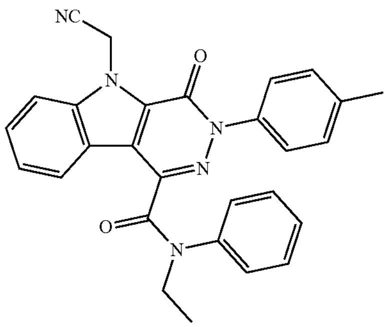 [SMILES: CCN(C(=O)c1nn(-c2ccc(C)cc2)c(=O)c2c1c1ccccc1n2CC#N)c1ccccc1] | 5-(cyanomethyl)-N-ethyl-4-oxo-N-phenyl-3-(p-tolyl)-4,5-dihydro-3H-pyridazino[4,5-b]indole-1-carboxamide | 462 [M + H] |
| 224. | 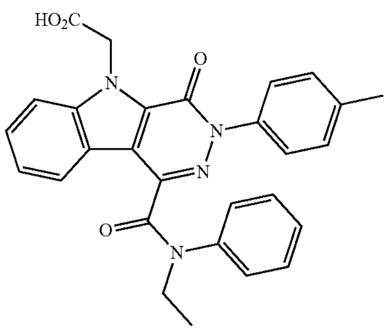 [SMILES: CCN(C(=O)c1nn(-c2ccc(C)cc2)c(=O)c2c1c1ccccc1n2CC(=O)O)c1ccccc1] | 2-(1-(ethyl(phenyl)carbamoyl)-4-oxo-3-(p-tolyl)-3H-pyridazino[4,5-b]indol-5(4H)-yl)acetic acid | 481 [M + H] |
| 225. | 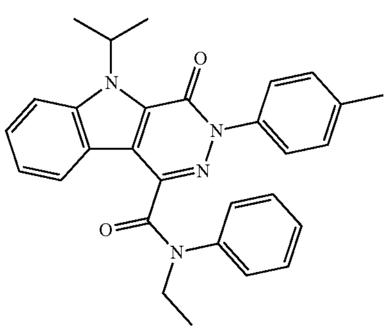 [SMILES: CCN(C(=O)c1nn(-c2ccc(C)cc2)c(=O)c2c1c1ccccc1n2C(C)C)c1ccccc1] | N-ethyl-5-isopropyl-4-oxo-N-phenyl-3-(p-tolyl)-4,5-dihydro-3H-pyridazino[4,5-b]indole-1-carboxamide | 465 [M + H] |

-continued

| Example No. | Structure | IUPAC Name | LCMS m/z |
|---|---|---|---|
| 226. | 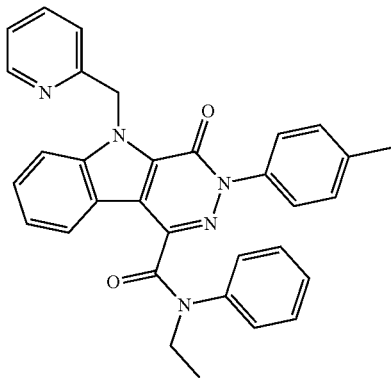 [SMILES: CCN(C(=O)c1nn(-c2ccc(C)cc2)c(=O)c2c1c1ccccc1n2Cc1ccccn1)c1ccccc1] | N-ethyl-4-oxo-N-phenyl-5-(pyridin-2-ylmethyl)-3-(p-tolyl)-4,5-dihydro-3H-pyridazino[4,5-b]indole-1-carboxamide | 514 [M + H] |
| 227. | 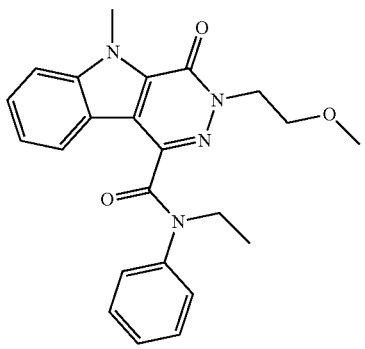 [SMILES: CCN(C(=O)c1nn(CCOC)c(=O)c2c1c1ccccc1n2C)c1ccccc1] | N-ethyl-3-(2-methoxyethyl)-5-methyl-4-oxo-N-phenyl-4,5-dihydro-3H-pyridazino[4,5-b]indole-1-carboxamide | 405 [M + H] |
| 228. | 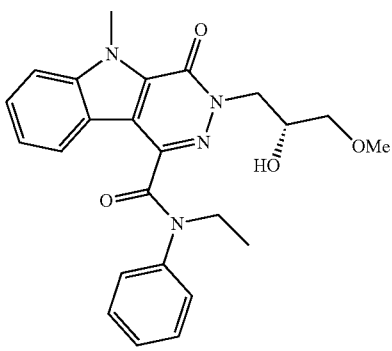 [SMILES: CCN(C(=O)c1nn(C[C@@H](O)COC)c(=O)c2c1c1ccccc1n2C)c1ccccc1] | (R)-N-ethyl-3-(2-hydroxy-3-methoxypropyl)-5-methyl-4-oxo-N-phenyl-4,5-dihydro-3H-pyridazino[4,5-b]indole-1-carboxamide | 435 [M + H] |
| 229. | 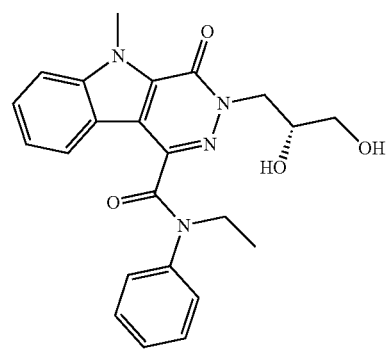 [SMILES: CCN(C(=O)c1nn(C[C@@H](O)CO)c(=O)c2c1c1ccccc1n2C)c1ccccc1] | (R)-3-(2,3-dihydroxypropyl)-N-ethyl-5-methyl-4-oxo-N-phenyl-4,5-dihydro-3H-pyridazino[4,5-b]indole-1-carboxamide | 421 [M + H] |

-continued

| Example No. | Structure | IUPAC Name | LCMS m/z |
|---|---|---|---|
| 230. | 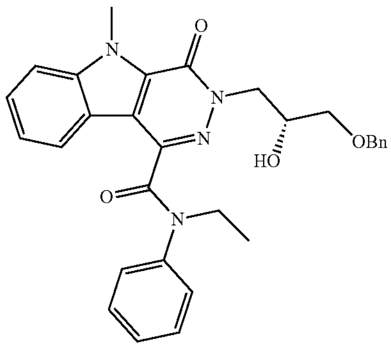 [SMILES: CCN(C(=O)c1nn(C[C@@H](O)COCc2ccccc2)c(=O)c2c1c1ccccc1n2C)c1ccccc1] | (R)-3-(3-(benzyloxy)-2-hydroxypropyl)-N-ethyl-5-methyl-4-oxo-N-phenyl-4,5-dihydro-3H-pyridazino[4,5-b]indole-1-carboxamide | 511 [M + H] |
| 231. | 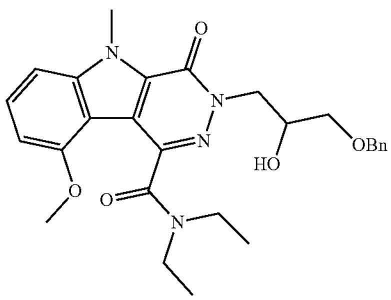 [SMILES: CCN(CC)C(=O)c1nn(CC(O)COCc2ccccc2)c(=O)c2c1c1c(OC)cccc1n2C] | 3-(3-(benzyloxy)-2-hydroxypropyl)-N,N-diethyl-9-methoxy-5-methyl-4-oxo-4,5-dihydro-3H-pyridazino[4,5-b]indole-1-carboxamide | 493 [M + H] |
| 232. | 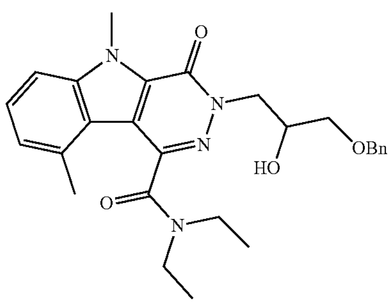 [SMILES: CCN(CC)C(=O)c1nn(CC(O)COCc2ccccc2)c(=O)c2c1c1c(C)cccc1n2C] | 3-(3-(benzyloxy)-2-hydroxypropyl)-N,N-diethyl-5,9-dimethyl-4-oxo-4,5-dihydro-3H-pyridazino[4,5-b]indole-1-carboxamide | 477 [M + H] |
| 233. | 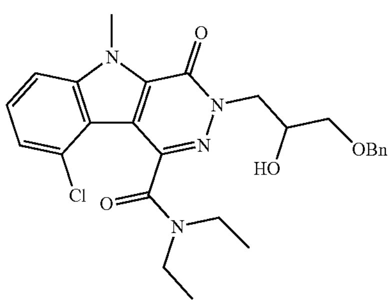 [SMILES: CCN(CC)C(=O)c1nn(CC(O)COCc2ccccc2)c(=O)c2c1c1c(F)cccc1n2C] | 3-(3-(benzyloxy)-2-hydroxypropyl)-9-chloro-N,N-diethyl-5-methyl-4-oxo-4,5-dihydro-3H-pyridazino[4,5-b]indole-1-carboxamide | 498 [M + H] |
| 234. | 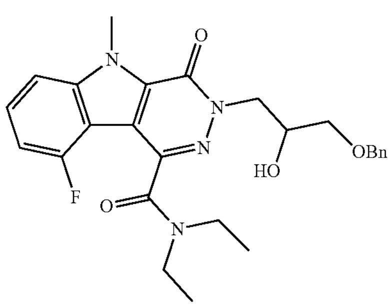 | 3-(3-(benzyloxy)-2-hydroxypropyl)-N,N-diethyl-9-fluoro-5-methyl-4-oxo-4,5-dihydro-3H-pyridazino[4,5-b]indole-1-carboxamide | 481 [M + H] |

Example 235

Synthesis of 1, 3-diphenyl-3H-pyridazino[4,5-b]indol-4(5H)-one

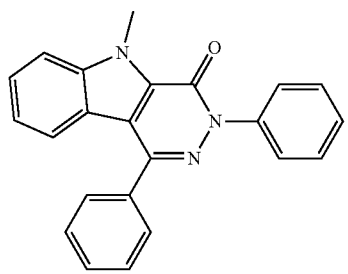 [SMILES: Cn1c2ccccc2c2c(-c3ccccc3)nn(-c3ccccc3)c(=O)c21]

3-Benzoyl-1-methyl-1H-indole-2-carboxylate

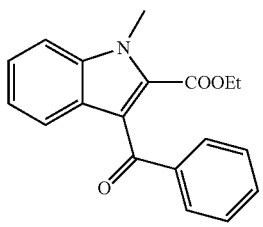 [SMILES: CCOC(=O)c1c(C(=O)c2ccccc2)c2ccccc2n1C]

AlCl$_3$ (0.65 g, 0.49 mmol) was added to a stirred solution of ethyl 1-methyl-1H-indole-2-carboxylate (1.0 g, 0.49 mmol) in DCE (10.0 mL), followed by benzoyl chloride (0.57 mL, 0.49 mmol). The reaction was heated to reflux overnight, then quenched with water (50 mL), neutralized with a satd. solution of NaHCO$_3$ (100 mL), and extracted with EtOAc (3×100 mL). The combined organic layers were dried over Na$_2$SO$_4$ and concentrated to obtained crude product, which was purified by column chromatography (7% EtOAc/hexane) to yield ethyl 3-benzoyl-1-methyl-1H-indole-2-carboxylate (0.5 g). MS: ESI+ve, 309.25 [M+H].

1, 3-Diphenyl-3H-pyridazino[4, 5-b]indol-4(5H)-one (Example 235)

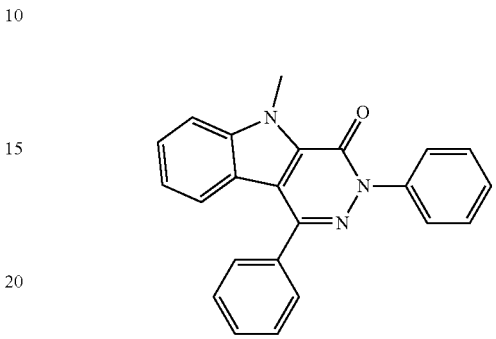

Phenyl hydrazine (0.105 g, 0.97 mmol) was added to a stirred solution of ethyl 3-benzoyl-1-methyl-1H-indole-2-carboxylate (0.2 g, 0.65 mmol) in HOAc (6.0 mL) and the reaction refluxed overnight. The reaction was quenched with water (10 mL), neutralized with satd. NaHCO$_3$ (20 mL) and extracted with EtOAc (3×30 mL). The combined organic layers were dried with Na$_2$SO$_4$ and concentrated to obtained crude product, which was purified by column chromatography (10% EtOAc/hexane) to yield 1, 3-diphenyl-3H-pyridazino[4, 5-b]indol-4(5H)-one (0.02 g). MS: ESI+ve, 352.27 [M+H]. $^1$H NMR (DMSO-d$_6$) δ 7.85 (d, J=8 Hz, 1 H), 7.76-7.68 (m, 4 H), 7.62-7.60 (m, 4 H), 7.58 (m, 2 H), 7.46-7.40 (m, 2 H), 7.26 (m, 1H), 4.38 (s, 3 H).

Representative compounds of the invention were prepared in a similar manner to example 235 (scheme 10).

| Example No. | Structure | IUPAC Name | LCMS m/z |
|---|---|---|---|
| 236. | 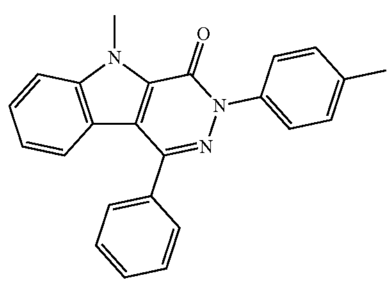 [SMILES: Cc1ccc(-n2nc(-c3ccccc3)c3c4ccccc4n(C)c3c2=O)cc1] | 5-methyl-1-phenyl-3-(p-tolyl)-3H-pyridazino[4,5-b]indol-4(5H)-one | 366 [M + H] |
| 237. | 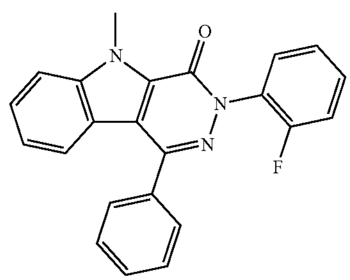 [SMILES: Cn1c2ccccc2c2c(-c3ccccc3)nn(-c3ccccc3F)c(=O)c21] | 3-(2-fluorophenyl)-5-methyl-1-phenyl-3H-pyridazino[4,5-b]indol-4(5H)-one | 370 [M + H] |

| Example No. | Structure | IUPAC Name | LCMS m/z |
|---|---|---|---|
| 238. | 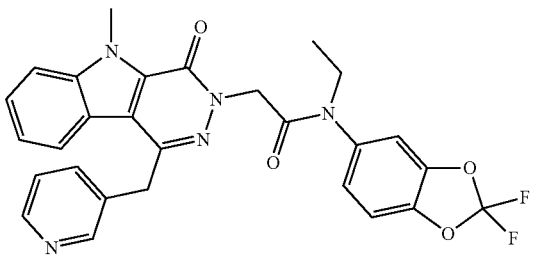 [SMILES: CCN(C(=O)Cn1nc(Cc2cccnc2)c2c3ccccc3n(C)c2c1=O)c1ccc2c(c1)OC(F)(F)O2] | N-(2,2-difluorobenzo[d][1,3]dioxol-5-yl)-N-ethyl-2-(5-methyl-4-oxo-1-(pyridin-3-ylmethyl)-4,5-dihydro-3H-pyridazino[4,5-b]indol-3-yl)acetamide | 532 [M + H] |
| 239. | 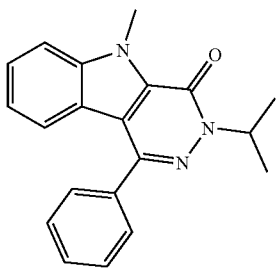 [SMILES: CC(C)n1nc(-c2ccccc2)c2c3ccccc3n(C)c2c1=O] | 3-isopropyl-5-methyl-1-phenyl-3,5-dihydro-4H-pyridazino[4,5-b]indol-4-one | 318 [M + H] |
| 240. | 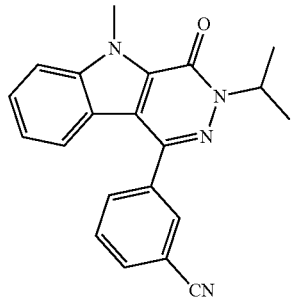 [SMILES: CC(C)n1nc(-c2cccc(C#N)c2)c2c3ccccc3n(C)c2c1=O] | 3-(3-isopropyl-5-methyl-4-oxo-4,5-dihydro-3H-pyridazino[4,5-b]indol-1-yl)benzonitrile | 341 [M + H] |
| 241. | 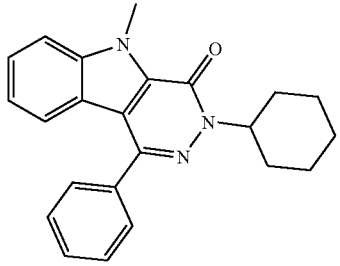 [SMILES: Cn1c2ccccc2c2c(-c3ccccc3)nn(C3CCCCC3)c(=O)c21] | 3-cyclohexyl-5-methyl-1-phenyl-3,5-dihydro-4H-pyridazino[4,5-b]indol-4-one | 358 [M + H] |
| 242. | 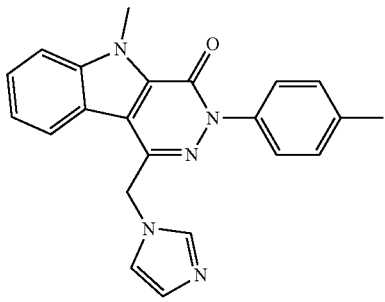 [SMILES: Cc1ccc(-n2nc(Cn3ccnc3)c3c4ccccc4n(C)c3c2=O)cc1] | 1-((1H-imidazol-1-yl)methyl)-5-methyl-3-(p-tolyl)-3,5-dihydro-4H-pyridazino[4,5-b]indol-4-one | 370 [M + H] |

| Example No. | Structure | IUPAC Name | LCMS m/z |
|---|---|---|---|
| 243. | 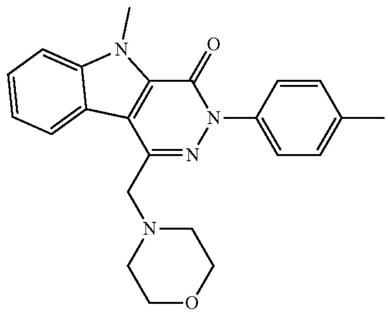 [SMILES: Cc1ccc(-n2nc(CN3CCOCC3)c3c4ccccc4n(C)c3c2=O)cc1] | 5-methyl-1-(morpholinomethyl)-3-(p-tolyl)-3,5-dihydro-4H-pyridazino[4,5-b]indol-4-one | 389 [M + H] |
| 244. | 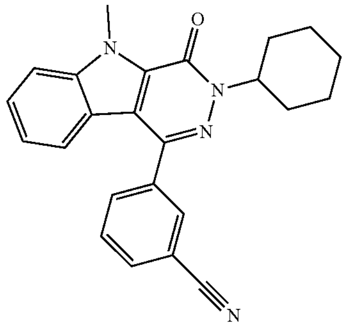 [SMILES: Cn1c2ccccc2c2c(-c3cccc(C#N)c3)nn(C3CCCCC3)c(=O)c21] | 3-(3-cyclohexyl-5-methyl-4-oxo-4,5-dihydro-3H-pyridazino[4,5-b]indol-1-yl)benzonitrile | 383 [M + H] |

Example 245

N-ethyl-2,4-dimethyl-5-oxo-N-phenyl-6-(p-tolyl)-5,6-dihydro-4H-thieno[2',3':4,5]pyrrolo[2,3-d]pyridazine-8-carboxamide

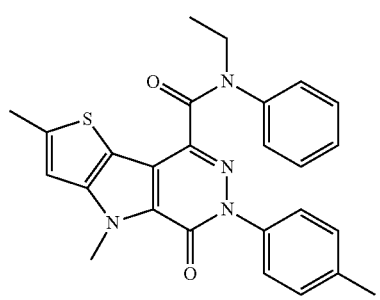

Ethyl (Z)-2-azido-3-(5-methylthiophen-2-yl) acrylate

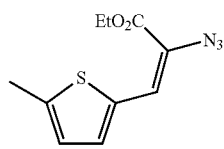 [SMILES: CCOC(=O)/C(=C\c1ccc(C)s1)N=[N+]=[N-]]

A 0° C. solution of 5-methylthiophene-2-carbaldehyde (1.0 g, 7.92 mmol) in EtOH (40 mL) was treated with ethyl azido acetate (2.0 g, 15.85 mmol). After stirring for 10 min, NaOEt (1.07 g, 15.85 mmol) in EtOH (40 mL) was added dropwise, and the reaction stirred at rt for 5 hrs. The reaction was quenched with NH₄Cl solution (100 mL) at which time a precipitate formed. The solid was collected and dried to yield ethyl (Z)-2-azido-3-(5-methylthiophen-2-yl) acrylate (0.60 g).

Ethyl 2-methyl-4H-thieno[3,2-b]pyrrole-5-carboxylate

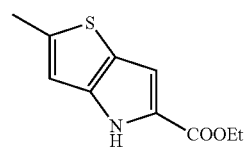

A solution of ethyl (Z)-2-azido-3-(5-methylthiophen-2-yl)acrylate (0.60 g, 2.53 mmol) in toluene (20 mL) was heated at reflux for 30 min. The solvent was evaporated to give ethyl 2-methyl-4H-thieno [3,2-b]pyrrole-5-carboxylate (0.50 g).

Ethyl 2,4-dimethyl-4H-thieno[3,2-b]pyrrole-5-carboxylate

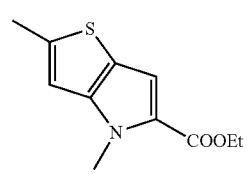

Ethyl 2-methyl-4H-thieno [3,2-b]pyrrole-5-carboxylate

Ethyl 2-methyl-4H-thieno [3,2-b]pyrrole-5-carboxylate (0.50 g, 2.39 mmol) was dissolved in DMF (20 mL), cooled to 0° C., and treated with NaH (60%) (0.143 g, 3.58 mmol). After 30 min, MeI (0.73 mL, 11.95 mmol) was added dropwise, and the reaction was stirred at rt overnight. The reaction was quenched with NH$_4$Cl solution (100 mL) and extracted with EtOAc (2×100 mL). The combined organic layers were dried with Na$_2$SO$_4$ and concentrated to give ethyl 2,4-dimethyl-4H-thieno[3,2-b]pyrrole-5-carboxylate (0.5 g).

Ethyl 6-(2-ethoxy-2-oxoacetyl)-2,4-dimethyl-4H-thieno[3,2-b]pyrrole-5-carboxylate

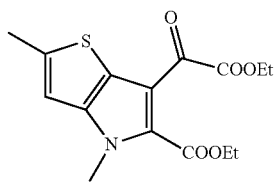 [SMILES: CCOC(=O)C(=O)c1c(C(=O)OCC)n(C)c2cc(C)sc12]

A 0° C. solution of ethyl chloro oxoacetate (1.54 mL, 13.8 mmol) in DCE (50 mL) was treated with TiCl$_4$ (1.51 mL, 13.81 mmol) and stirred for 30 min at rt. Ethyl 2,4-dimethyl-4H-thieno[3,2-b]pyrrole-5-carboxylate (2.80 g, 12.5 mmol) in DCE (10 mL) was added dropwise and the reaction stirred for 3 hrs. It was diluted with water (100 mL) and extracted with DCM (3×50 mL). The combined organic layers were dried with Na$_2$SO$_4$ and concentrated to give ethyl 6-(2-ethoxy-2-oxoacetyl)-2,4-dimethyl-4H-thieno[3,2-b]pyrrole-5-carboxylate (2.3 g). MS: ESI+ve, 324.1 [M+H].

Ethyl 2,4-dimethyl-5-oxo-6-(p-tolyl)-5,6-dihydro-4H-thieno[2',3':4,5]pyrrolo[2,3-d]pyridazine-8-carboxylate

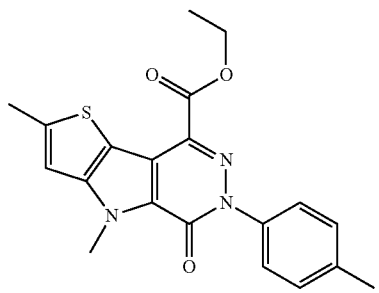

A solution of ethyl 6-(2-ethoxy-2-oxoacetyl)-2,4-dimethyl-4H-thieno[3,2-b]pyrrole-5-carboxylate (1.00 g, 3.09 mmol) in HOAc (15 ml) was treated with p-tolylhydrazine HCl (0.73 g, 4.6 mmol) and heated to reflux overnight. It was diluted with water (100 mL) and extracted with EtOAc (3×50 mL). The combined organic layers were dried with Na$_2$SO$_4$ and concentrated to give ethyl 2,4-dimethyl-5-oxo-6-(p-tolyl)-5,6-dihydro-4H-thieno[2',3':4,5]pyrrolo[2,3-d]pyridazine-8-carboxylate (1.12 g).

2,4-dimethyl-5-oxo-6-(p-tolyl)-5,6-dihydro-4H-thieno[2',3':4,5]pyrrolo[2,3-d]pyridazine-8-carboxylic acid

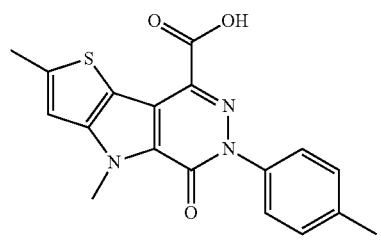

A solution of ethyl 2,4-dimethyl-5-oxo-6-(p-tolyl)-5,6-dihydro-4H-thieno[2',3':4,5]pyrrolo[2,3-d]pyridazine-8-carboxylate (0.175 g, 0.45 mmol) in THF (6.0 ml) was treated with NaOH (0.033 g, 1.37 mmol) in water (4 mL) and stirred at rt overnight. The reaction was concentrated, then treated with water (20 mL) and acidified with 1N HCl. The precipitate was collected and dried to yield 2,4-dimethyl-5-oxo-6-(p-tolyl)-5,6-dihydro-4H-thieno[2',3':4,5]pyrrolo[2,3-d]pyridazine-8-carboxylic acid (0.15 g). MS: ESI+ve, 354[M+H].

Example 245

N-ethyl-2,4-dimethyl-5-oxo-N-phenyl-6-(p-tolyl)-5,6-dihydro-4H-thieno[2',3':4,5]pyrrolo[2,3-d]pyridazine-8-carboxamide

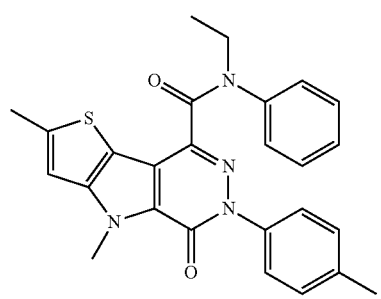

A solution of 2,4-dimethyl-5-oxo-6-(p-tolyl)-5,6-dihydro-4H-thieno[2',3':4,5]pyrrolo[2,3-d]pyridazine-8-carboxylic acid (0.170 g, 0.48 mmol) in DMF (5 mL) was treated with HATU (0.274 g 0.72 mmol) at 0° C. and stirred for 30 minutes. N-Ethyl aniline (0.058 g 0.48 mmol) and DiEA (0.18 g, 1.44 mmol) were added and stirred at rt overnight. The reaction was diluted with water (50 mL) and crude product collected by filtration. It was purified by chromatography (silica gel, 15% EtOAc in hexane) to yield N-ethyl-2,4-dimethyl-5-oxo-N-phenyl-6-(p-tolyl)-5,6-dihydro-4H-thieno[2',3':4,5]pyrrolo[2,3-d]pyridazine-8-carboxamide (0.060 g). MS: ESI+ve, 357[M+H], $^1$H NMR (DMSO-d$_6$) δ: 7.4 (m, 4H), 7.3 (s, 1H), 7.2 (m, 3H), 6.6 (s, 2H), 4.2 (s, 3H), 3.9 (q, 2H), 2.6 (s, 3H), 2.3 (s, 3H), 1.2 (t, 3H).

Representative compounds of the invention were prepared in a similar manner to example 245 (scheme 10).

| Example No. | Structure | IUPAC Name | LCMC m/z |
|---|---|---|---|
| 246. | 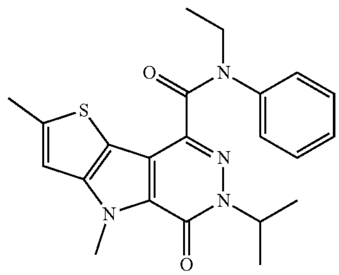 [SMILES: CCN(C(=O)c1nn(C(C)C)c(=O)c2c1c1sc(C)cc1n2C)c1ccccc1] | N-ethyl-6-isopropyl-2,4-dimethyl-5-oxo-N-phenyl-5,6-dihydro-4H-thieno[2',3':4,5]pyrrolo[2,3-d]pyridazine-8-carboxamide | 409 [M + H] |
| 247. | 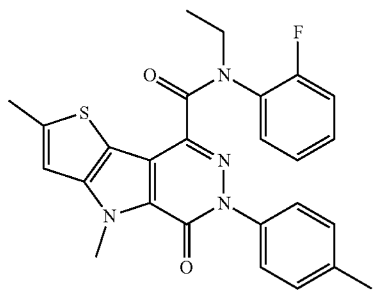 | N-ethyl-N-(2-fluorophenyl)-2,4-dimethyl-5-oxo-6-(p-tolyl)-5,6-dihydro-4H-thieno[2',3':4,5]pyrrolo[2,3-d]pyridazine-8-carboxamide | 475 [M + H] |

Example 248

N-isopropyl-7-oxo-N,3-diphenyl-6-(p-tolyl)-6,7-dihydroisoxazolo[3,4-d]pyridazine-4-carboxamide

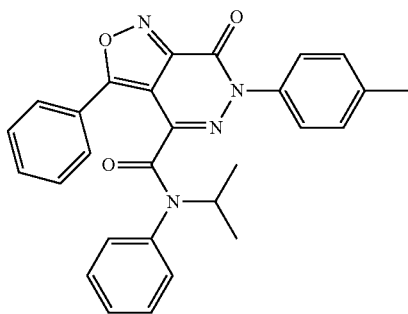 [SMILES: Cc1ccc(-n2nc(C(=O)N(c3ccccc3)C(C)C)c3c(-c4ccccc4)onc3c2=O)cc1]

Ethyl 4-(2-ethoxy-2-oxoacetyl)-5-phenylisoxazole-3-carboxylate

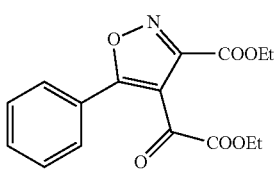 [SMILES: CCOC(=O)C(=O)c1c(C(=O)OCC)noc1-c1ccccc1]

Ethyl 2,4-dioxo-4-phenylbutanoate (1.0 g, 4.54 mmol) was added at 0° C. to a solution of NaOEt (0.376 g, 5.52 mmol) in EtOH (20 mL). After 10 min, ethyl (Z)-2-chloro-2-(hydroxyimino)acetate (0.84 g, 5.54 mmol) solution in EtOH (20 mL) was added dropwise and stirred at 25° C. overnight. The reaction was diluted with water (25 mL) and extracted with EtOAc (3×25 mL). The combined organic layers were dried with $Na_2SO_4$ and concentrated to give ethyl 4-(2-ethoxy-2-oxoacetyl)-5-phenylisoxazole-3-carboxylate (0.85 g). MS: ESI+ve, 318.2 [M+H].

Ethyl 2-oxo-2-(7-oxo-3-phenyl-6-(p-tolyl)-6,7-dihydroisoxazolo[3,4-d]pyridazin-4-yl)acetate

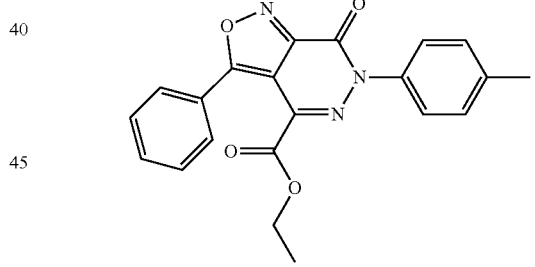

p-Tolylhydrazine hydrochloride (0.30 g, 1.89 mmol) was added to a stirred solution of ethyl 4-(2-ethoxy-2-oxoacetyl)-5-phenylisoxazole-3-carboxylate (0.50 g, 1.58 mmol) in HOAc (10 mL), then heated to reflux overnight. The reaction was diluted with water (25 mL) and extracted with EtOAc (3×25 mL). The combined organic layers were dried with $Na_2SO_4$ and concentrated to give crude product, which was purified by chromatography (silica gel, 10% EtOAc in hexane) to yield ethyl 2-oxo-2-(7-oxo-3-phenyl-6-(p-tolyl)-6,7-dihydroisoxazolo[3,4-d]pyridazin-4-yl)acetate (0.27 g). MS: ESI+ve, 376.3 [M+H].

2-Oxo-2-(7-oxo-3-phenyl-6-(p-tolyl)-6,7-dihydroisoxazolo[3,4-d]pyridazin-4-yl)acetic acid

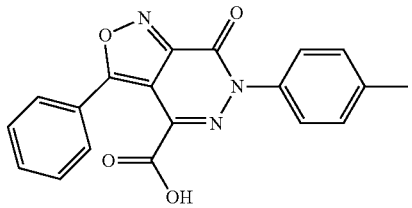 [SMILES: Cc1ccc(-n2nc(C(=O)O)c3c(-c4ccccc4)onc3c2=O)cc1]

NaOH (55 mg, 1.38 mmol) in water (4 mL) was added to a stirred solution of 2-oxo-2-(7-oxo-3-phenyl-6-(p-tolyl)-6,7-dihydroisoxazolo[3,4-d]pyridazin-4-yl)acetate (0.26 g, 0.69 mmol) in THF (8 mL). After stirring at rt overnight, the reaction was concentrated, then treated with water (20 mL) and acidified with 1N HCl. The precipitate was collected and dried to yield 2-oxo-2-(7-oxo-3-phenyl-6-(p-tolyl)-6,7-dihydroisoxazolo[3,4-d]pyridazin-4-yl)acetic acid (0.20 g). MS: ESI+ve, 366.2 [M+18].

Example 248

N-isopropyl-7-oxo-N,3-diphenyl-6-(p-tolyl)-6,7-dihydroisoxazolo[3,4-d]pyridazine-4-carboxamide

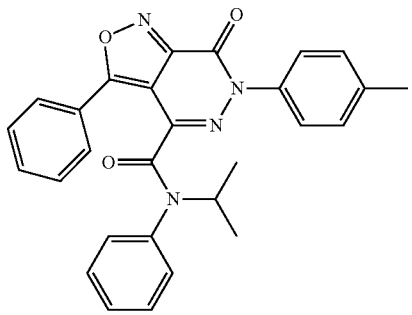 [SMILES: Cc1ccc(-n2nc(C(=O)N(c3ccccc3)C(C)C)c3c(-c4ccccc4)onc3c2=O)cc1]

A solution of 2-oxo-2-(7-oxo-3-phenyl-6-(p-tolyl)-6,7-dihydroisoxazolo[3,4-d]pyridazin-4-yl)acetic acid (0.18 g, 0.51 mmol) in DCM (10 mL) was treated with N-isopropyl aniline (0.07 g, 0.51 mmol) and pyridine (0.6 mL). The reaction was then cooled to 0° C. and treated with POCl$_3$ (0.6 mL). After stirring for 1 hr, the reaction was diluted with a NaHCO$_3$ solution (30 mL), then extracted with EtOAc (2×30 mL). The combined organics were washed with brine (25 mL), dried with Na$_2$SO$_4$ and concentrated to give crude product, which was purified by chromatography (silica gel, 20% EtOAc/hexane) to yield N-isopropyl-7-oxo-N,3-diphenyl-6-(p-tolyl)-6,7-dihydroisoxazolo[3,4-d]pyridazine-4-carboxamide (0.020 g). MS: ESI+ve, 465.0 [M+H]; $^1$H NMR (CDCl$_3$) δ: 7.99 (d, 2H), 7.7 (m, 3H), 7.2 (m, 7H), 6.73 (d, 2H), 5.00 (m, 1H), 2.4 (s, 3H), 1.0 (d, 6H).

Example 249

4-(3-chlorophenyl)-2-(2-(1-(2,2-difluorobenzo[d][1,3]dioxol-5-yl)cyclopropyl)-2-oxoethyl)-7-methoxyphthalazin-1(2H)-one

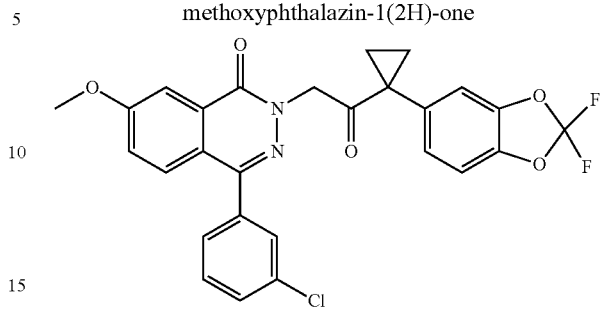

2-bromo-1-(1-(2,2-difluorobenzo[d][1,3]dioxol-5-yl)cyclopropyl)ethan-1-one

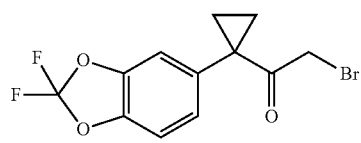 [SMILES: O=C(CBr)C1(c2ccc3c(c2)OC(F)(F)O3)CC1]

A 0° C. solution of 1-(2,2-difluorobenzo[d][1,3]dioxol-5-yl)cyclopropane-1-carboxylic acid (1.0 g, 4.13 mmol) in DCM (20 mL) was treated with a DMF (0.1 mL) and oxalylchloride (0.8 mL, 6.9 mmol). After stirring at rt for 2 h, the reaction concentrated to dryness. The residue was dissolved in THF (10 mL) and acetonitrile (10 mL), cooled to 0° C., and treated dropwise with trimethylsilyl diazomethane (0.6 M in hexane) (5.37 mmol, 6 mL). The reaction was stirred for 2 h at rt, diluted with water (25 mL) and sat'd NaHCO$_3$ (25 mL), and extracted with EtOAc (2×50 mL). The organics were washed with brine, dried with Na$_2$SO$_4$ and concentrated. The residue at 0° C. was treated slowly with a solution of HBr/HOAc (30%, 6 mL), and the reaction stirred for 0.5 h at rt. It was diluted with ice-water (50 mL) and extracted with EtOAc (2×50 mL). The organics were washed with sat'd NaHCO$_3$, brine, dried with Na$_2$SO$_4$ and concentrated. The crude product was purified by chromatography (0-5% EtOAc/hexane) to yield 2-bromo-1-(1-(2,2-difluorobenzo[d][1,3]dioxol-5-yl)cyclopropyl)ethan-1-one (0.3 g, 23%); $^1$H NMR (CDCl$_3$) δ: 2.21-2.30 (m, 1H), 2.51-2.60 (m, 1H), 3.14-3.20 (m, 1H), 3.39-3.45 (m, 1H), 3.84-3.81 (d, 1H), 3.97-3.94 (d, 1H), 7.03-7.01 (m, 2H), 7.10-7.07 (m, 1H).

Example 249

4-(3-chlorophenyl)-2-(2-(1-(2,2-difluorobenzo[d][1,3]dioxol-5-yl)cyclopropyl)-2-oxoethyl)-7-methoxyphthalazin-1(2H)-one

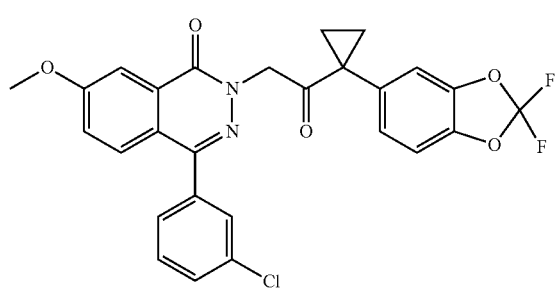 [SMILES: COc1ccc2c(-c3cccc(Cl)c3)nn(CC(=O)C3(c4ccc5c(c4)OC(F)(F)O5)CC3)c(=O)c2c1]

A 0° C. solution of 4-(3-chlorophenyl)-7-methoxyphthalazin-1(2H)-one (0.1 g, 0.34 mmol) in DMF (2 mL) was treated with NaH (60%) (0.012 g, 0.54 mmol) and stirred for 30 min. A solution of 2-bromo-1-(1-(2,2-difluorobenzo[d][1,3]dioxol-5-yl)cyclopropyl)ethan-1-one (0.121 g, 0.384 mmol) in DMF (2 mL) was added dropwise and the reaction stirred overnight at rt. It was diluted with water (30 mL) and extracted with EtOAc (2×30 mL). The organics were washed with brine, dried with Na$_2$SO$_4$ and concentrated to give crude material which was purified by chromatography (30% EtOAc/hexane) to yield 4-(3-chlorophenyl)-2-(2-(1-(2,2-difluorobenzo[d][1,3]dioxol-5-yl)cyclopropyl)-2-oxoethyl)-7-methoxyphthalazin-1(2H)-one (0.026 g, 16%). (ESI+ve, 524.93 [M+H]); $^1$H NMR (DMSO) δ: 1.33-1.36 (q, 2H), 1.59-1.62 (q, 2H), 3.95 (s, 3H), 4.94 (s, 2H), 7.33-7.35 (dd, J=1.8, 1H), 7.38-7.40 (d, J=8.4, 1H), 7.49-7.54 (m, 2H), 7.56-7.60 (m, 3H), 7.61-7.65 (m, 2H), 7.67-7.68 (d, J=2.8, 1H).

Representative compounds of the invention were prepared in a similar manner to example 249.

Example 253

4-(3-chlorophenyl)-2-(2-(1-(2,2-difluorobenzo[d][1,3]dioxol-5-yl)cyclopropyl)-2-oxoethyl)-7-hydroxyphthalazin-1(2H)-one

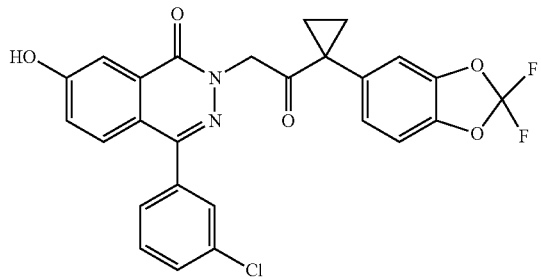

| Example No. | Structure | IUPAC Name | LCMS m/z |
|---|---|---|---|
| 250. | 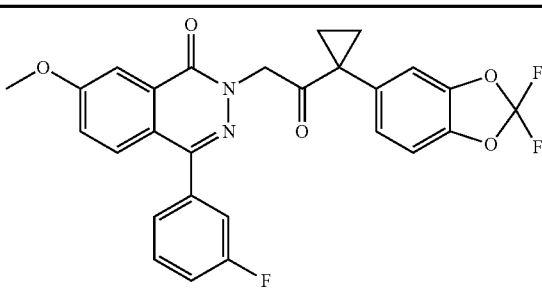 | 2-(2-(1-(2,2-difluorobenzo[d][1,3]dioxol-5-yl)cyclopropyl)-2-oxoethyl)-4-(3-fluorophenyl)-7-methoxyphthalazin-1(2H)-one | [M + H] |
| 251. | 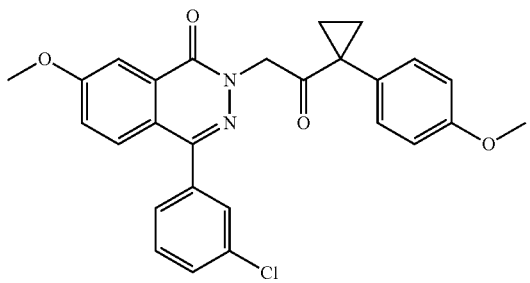 | 4-(3-chlorophenyl)-7-methoxy-2-(2-(1-(4-methoxyphenyl)cyclopropyl)-2-oxoethyl)phthalazin-1(2H)-one | 477 [M + H] |
| 252. | 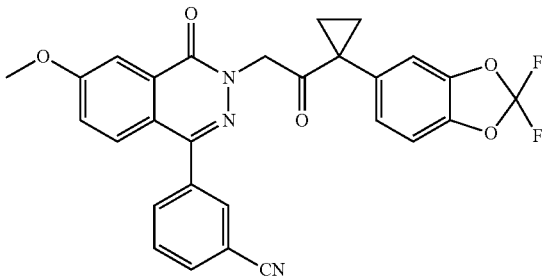 | 3-(3-(2-(1-(2,2-difluorobenzo[d][1,3]dioxol-5-yl)cyclopropyl)-2-oxoethyl)-6-methoxy-4-oxo-3,4-dihydrophthalazin-1-yl)benzonitrile | 516 [M + H] |

5-(benzyloxy)-2-bromobenzaldehyde

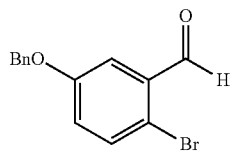

1-Bromo-5-hydroxybenzaldehyde (5.00 g, 24.9 mmol) in DMF (50 mL) was treated with Cs$_2$CO$_3$ (12.1 g, 37.3 mmol) and stirred at 0° C. for 15 minutes. Benzyl bromide (6.38 g, 37.3 mmol) was added and the reaction heated to 100° C. 4 h. After cooling to rt, it was diluted with water (100 mL) and extracted with EtOAc (2×50 mL). The organics were washed with brine, dried with Na$_2$SO$_4$ and concentrated to give crude material which was purified by chromatography (10-15% EtOAc/hexane) to yield 5-(benzyloxy)-2-bromobenzaldehyde (6.8 g, 94%). (ESI+ve, 292.94 [M+H]); $^1$H NMR (DMSO) δ: 5.20 (s, 2H), 7.29-7.36 (m, 2H), 7.42-7.47 (m, 5H), 7.70-7.72 (d, J=8.8, 1H), 10.17 (s, 1H).

5-(benzyloxy)-2-bromobenzoic acid

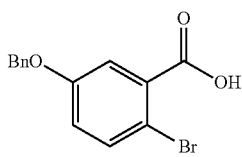 [SMILES: O=C(O)c1cc(OCc2ccccc2)ccc1Br]

5-(Benzyloxy)-2-bromobenzaldehyde (1.00 g, 3.42 mmol) in dioxane/water (1:1, 20 mL) was treated with KOH (0.383 g, 6.84 mmol) and KMnO$_4$ (0.811 g, 5.13 mmol), then stirred overnight. The reaction mixture was filtered, washed with water, and dioxane distilled away. The aqueous solution was acidified with 1N HCl (25 mL) to yield a precipitate which was filtered, washed with water, and dried to yield 5-(benzyloxy)-2-bromobenzoic acid (0.715 g, 68%). (ESI+ve, 307.18 [M+H]); $^1$H NMR (DMSO) δ: 5.15 (s, 2H), 7.09-7.12 (m, 1H), 7.34-7.46 (m, 6H), 7.59-7.61 (d, J=8.8, 1H), 13.45 (s, 1H).

3-chloro-N-methoxy-N-methylbenzamide

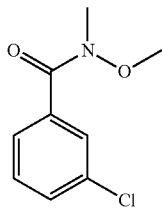

3-Chloro benzoic acid (20.0 g, 128 mmol) in DMF (200 mL) at 0° C. was treated with TEA (20 mL, 134 mmol) and EDC.HCl (25.7 g, 134 mmol) and stirred under N$_2$ for 30 min at rt. N—O-dimethylhydroxylamine. HCl (13.7 g, 140 mmol) was added and the reaction stirred overnight at rt. It was diluted with water (300 mL) and extracted with EtOAc (3×200 mL). The organics were washed with brine, dried with Na$_2$SO$_4$ and concentrated to give crude material which was purified by chromatography (0-25% EtOAc/hexane) to yield 3-chloro-N-methoxy-N-methylbenzamide (16.0 g, 62%). (ESI+ve, 200.19 [M+H]); $^1$H NMR (DMSO) δ: 3.26 (s, 3H), 3.54 (s, 3H), 7.47-7.50 (t, 1H), 7.53-7.58 (qt, 2H), 7.59-7.61 (d, J=9.2, 1H).

5-(benzyloxy)-2-(3-chlorobenzoyl)benzoic acid

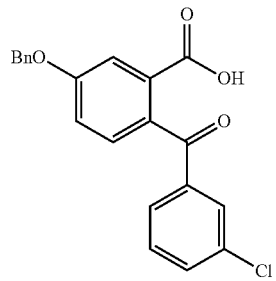 [SMILES: O=C(O)c1cc(OCc2ccccc2)ccc1C(=O)c1cccc(Cl)c1]

5-(Benzyloxy)-2-bromobenzoic acid (5.0 g, 10.2 mmol) in THF (50 mL) at −78° C. was treated with nBuLi (1.6 M in hexane) (12.8 mL, 20.6 mmol) and stirred for 1 h. 3-Chloro-N-methoxy-N-methylbenzamide (2.26 g, 11.3 mmol) in THF (15 ml) was added, and the reaction mixture stirred for 1 h, then overnight at rt. It was diluted with water (50 mL), acidified with 5N HCl, and extracted with EtOAc (2×100 mL). The organics were washed with brine, dried with Na$_2$SO$_4$ and concentrated to give 5-(benzyloxy)-2-(3-chlorobenzoyl)benzoic acid (3.2 g, 53%). (ESI+ve, 367.1 [M+H]).

7-(benzyloxy)-4-(3-chlorophenyl)phthalazin-1(2H)-one

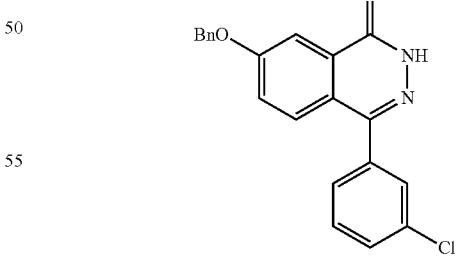

5-(Benzyloxy)-2-(3-chlorobenzoyl)benzoic acid (3.2 g, 8.7 mmol) and hydrazine hydrate (0.5 mL, 9.5 mmol) in EtOH (30 mL) were heated overnight at reflux. The EtOH was removed in vacuo, and the residue suspended in water. The solid was filtered and dried to give crude 7-(benzyloxy)-4-(3-chlorophenyl)phthalazin-1(2H)-one (0.65 g, 20%). (ESI+ve, 363.03 [M+H]).

245

7-(benzyloxy)-4-(3-chlorophenyl)-2-(2-(1-(2,2-difluorobenzo[d][1,3]dioxol-5-yl)cyclopropyl)-2-oxoethyl)phthalazin-1(2H)-one

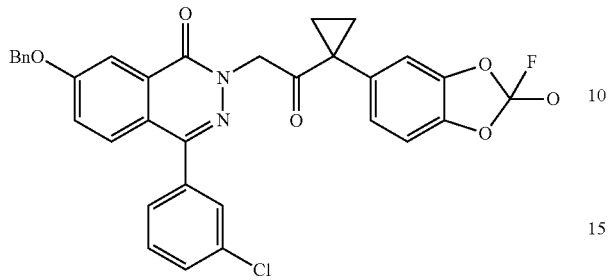

7-(Benzyloxy)-4-(3-chlorophenyl)phthalazin-1(2H)-one (0.25 g, 0.687 mmol) in DMF (10 mL) at 0° C. was treated with NaH (60%) (0.024 g 1.03 mmol) and stirred for 30 m. 2-Bromo-1-(1-(2,2-difluorobenzo[d][1,3]dioxol-5-yl)cyclopropyl)ethan-1-one (0.239 g, 0.75 mmol) in DMF (2 mL) was added and the reaction stirred overnight at rt. It was diluted with water (30 mL) and extracted with EtOAc (2×30 mL). The organics were washed with brine, dried with Na$_2$SO$_4$ and concentrated to give crude material which was purified by chromatography (10% EtOAc/hexane) to yield 7-(benzyloxy)-4-(3-chlorophenyl)-2-(2-(1-(2,2-difluorobenzo[d][1,3]dioxol-5-yl)cyclopropyl)-2-oxoethyl)phthalazin-1(2H)-one (0.16 g, 38%). (ESI+ve, 601.08 [M+H]).

246

Example 253

4-(3-chlorophenyl)-2-(2-(1-(2,2-difluorobenzo[d][1,3]dioxol-5-yl)cyclopropyl)-2-oxoethyl)-7-hydroxyphthalazin-1(2H)-one 7-(Benzyloxy)-4-(3-chlorophenyl)-2-(2-(1-(2,2-difluorobenzo[d][1,3]dioxol-5-yl)cyclopropyl)-2-oxoethyl)phthalazin-1(2H)-one (0.16 g, 0.27 mmol), Pd(OAc)$_2$ (0.04 g, 0.178 mmol), and triethylsilane (0.062 g, 0.53 mmol) in DMC (20 mL) were stirred together at rt overnight. The reaction was diluted with water (30 mL) and extracted with DCM (2×30 mL). The organics were washed with brine, dried with Na$_2$SO$_4$ and concentrated to give crude material which was purified by preparative HPLC to yield 4-(3-chlorophenyl)-2-(2-(1-(2,2-difluorobenzo[d][1,3]dioxol-5-yl)cyclopropyl)-2-oxoethyl)-7-hydroxyphthalazin-1(2H)-one (0.012 g, 8%). (ESI+ve, 510.83 [M+H]); $^1$H NMR (DMSO) δ:1.33-1.34 (d, 2H), 1.59-1.60 (d, 2H), 4.91 (s, 2H), 7.32-7.41 (m, 3H), 7.50-7.62 (m, 7H), 10.91-10.93 (d, 1H).

Representative compounds of the invention were prepared in a similar manner to example 253.

| Example No. | Structure | IUPAC Name | LCMS m/z |
|---|---|---|---|
| 254. | 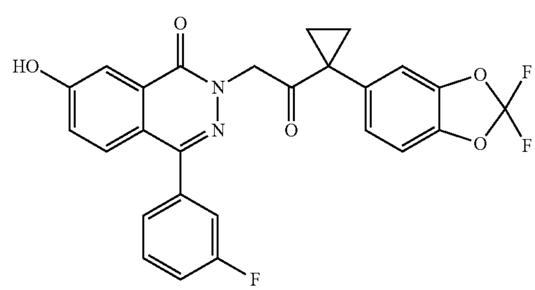 [SMILES: O=C(Cn1nc(-c2cccc(F)c2)c2ccc(O)cc2c1=O)C1(c2ccc3c(c2)OC(F)(F)O3)CC1] | 2-(2-(1-(2,2-difluorobenzo[d][1,3]dioxol-5-yl)cyclopropyl)-2-oxoethyl)-4-(3-fluorophenyl)-7-hydroxyphthalazin-1(2H)-one | 595 [M + H] |
| 255. | 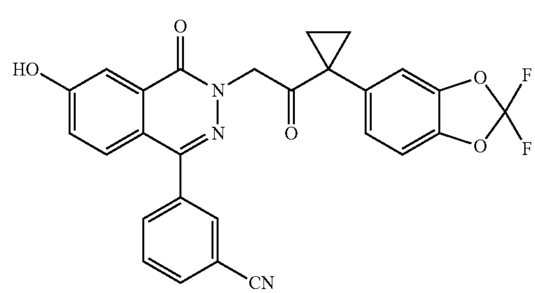 [SMILES: N#Cc1cccc(-c2nn(CC(=O)C3(c4ccc5c(c4)OC(F)(F)O5)CC3)c(=O)c3cc(O)ccc23)c1] | 3-(3-(2-(1-(2,2-difluorobenzo[d][1,3]dioxol-5-yl)cyclopropyl)-2-oxoethyl)-6-hydroxy-4-oxo-3,4-dihydrophthalazin-1-yl)benzonitrile | 500 [M + H] |

Example 256

4-(3-chlorophenyl)-2-(2-(1-(2,2-difluorobenzo[d][1,3]dioxol-5-yl)cyclopropyl)-2-oxoethyl)-7-ethoxyphthalazin-1(2H)-one

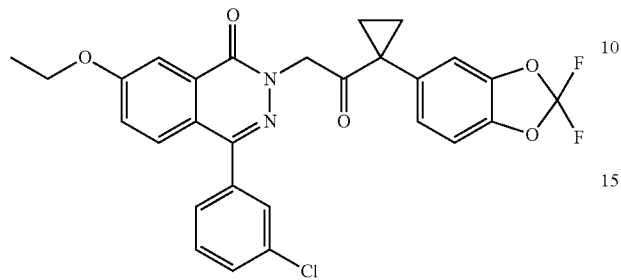

Example 253 (0.10 g, 0.19 mmol) in DMF (3 mL) at 0° C. was treated with K₂CO₃ (0.04 g, 0.29 mmol) for 30 min, then EtI (0.033 g, 0.21 mmol) was added and stirred overnight at rt. The reaction was diluted with water (30 mL) and extracted with EtOAc (2×20 mL). The organics were washed with brine, dried with Na₂SO₄ and concentrated to give crude material which was purified by preparative HPLC to yield 4-(3-chlorophenyl)-2-(2-(1-(2,2-difluorobenzo[d][1,3]dioxol-5-yl)cyclopropyl)-2-oxoethyl)-7-ethoxyphthalazin-1 (2H)-one (0.024 g, 23%). (ESI+ve, 538.9 [M+H]); ¹H NMR (DMSO) δ:1.33-1.35 (t, 2H), 1.38-1.41 (t, 3H), 1.59-1.62 (m, 2H), 4.40-4.26 (q, 2H), 4.94 (s, 2H), 7.33-7.40 (m, 2H), 7.48-7.54 (m, 2H), 7.56-7.64 (m, 6H).

Representative compounds of the invention were prepared in a similar manner to example 256.

Example 259

2-(5-(4-cyanobenzyl)-8-methoxy-1-oxo-1,5-dihydro-2H-pyridazino[4,5-b]indol-2-yl)-N-methyl-N-(2-methylbenzo[d]oxazol-6-yl)acetamide

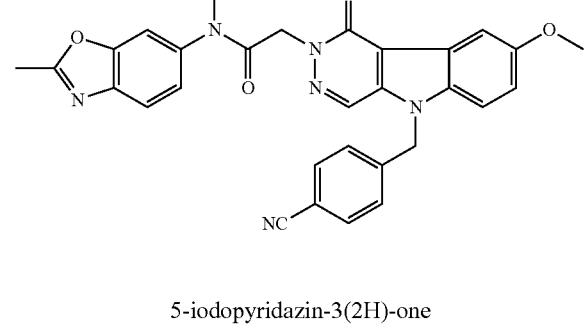

5-iodopyridazin-3(2H)-one

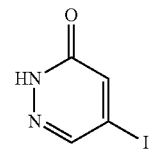

A stirred solution of 4,5-dichloropyridazin-3(2H)-one (1.0 g, 6.74 mmol) in con HI (10 mL) was heated at 120° C. for 16 h. The reaction was diluted with water (50 mL) and extracted with EtOAc (3×100 mL). The organics were washed with sodium thiosulfate (Na₂S₂O₃) and brine, dried with Na₂SO₄ and concentrated to give crude 5-iodopyridazin-3(2H)-one (0.8 g, 222.79 [M–H]). ¹H NMR (DMSO) δ: 7.54-7.54 (s, 1H), 8.00 (s, 1H), 13.27 (s, 1H).

| Example No. | Structure | IUPAC Name | LCMS m/z |
|---|---|---|---|
| 257. | 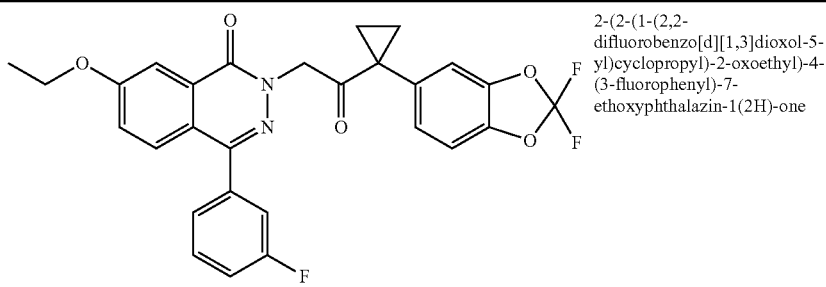 | 2-(2-(1-(2,2-difluorobenzo[d][1,3]dioxol-5-yl)cyclopropyl)-2-oxoethyl)-4-(3-fluorophenyl)-7-ethoxyphthalazin-1(2H)-one | 523 [M + H] |
| 258. | 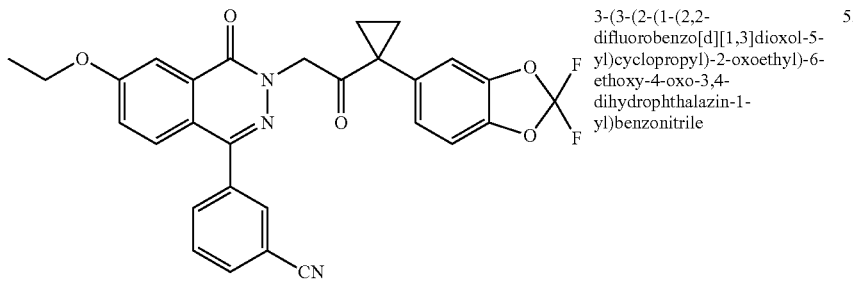 | 3-(3-(2-(1-(2,2-difluorobenzo[d][1,3]dioxol-5-yl)cyclopropyl)-2-oxoethyl)-6-ethoxy-4-oxo-3,4-dihydrophthalazin-1-yl)benzonitrile | 530 [M + H] |

2-(4-iodo-6-oxopyridazin-1 (6H)-yl)-N-methyl-N-(2-methylbenzo[d]oxazol-6-yl) acetamide

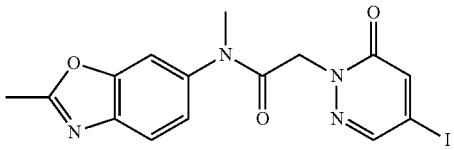 [SMILES: Cc1nc2ccc(N(C)C(=O)Cn3ncc(I)cc3=O)cc2o1]

To a stirred solution of 5-iodopyridazin-3(2H)-one (0.8 g, 3.61 mmol) in THF (10 mL) was added LiHMDS (1M in THF) (5.4 mL, 5.4 mmol) dropwise at 0° C. and the reaction stirred for 30 min. 2-Bromo-N-methyl-N-(2-methylbenzo[d]oxazol-6-yl)acetamide (1.0 g, 3.61 mmol) in THF (10 mL) was added dropwise at 0° C., and the reaction mixture stirred overnight at rt. The reaction was diluted with water (50 mL) and brine solution (50 mL), and a solid precipitated. The solid was filtered and washed with MeOH to obtain 2-(4-iodo-6-oxopyridazin-1(6H)-yl)-N-methyl-N-(2-methylbenzo[d]oxazol-6-yl) acetamide (0.6 g, 425.30 [M+H]).

2-(4-((2-bromo-4-methoxyphenyl)amino)-6-oxopyridazin-1(6H)-yl)-N-methyl-N-(2-methylbenzo[d]oxazol-6-yl)acetamide

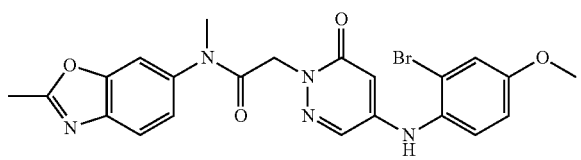

Pd(OAc)$_2$ (0.01 g, 0.04 mmol) and BINAP (0.029 g 0.04 mmol) in toluene (10 mL) were degassed with argon for 15 min, then treated with 2-bromo-4-methoxyaniline (0.30 g 1.48 mmol), Cs$_2$CO$_3$ (1.5 g 4.45 mmol) and 2-(4-iodo-6-oxopyridazin-1(6H)-yl)-N-methyl-N-(2-methylbenzo[d]oxazol-6-yl) acetamide (0.78 g 1.85 mmol). The reaction was heated to 120° C. overnight. It was filtered through Celite, washed with DCM (50 mL) and concentrated to give crude product, which was purified by chromatography (0-2% MeOH/DCM) to yield 2-(4-((2-bromo-4-methoxyphenyl)amino)-6-oxopyridazin-1(6H)-yl)-N-methyl-N-(2-methylbenzo[d]oxazol-6-yl)acetamide (0.3 g, 498.3 [M+H]).

2-(8-methoxy-1-oxo-1,5-dihydro-2H-pyridazino[4,5-b]indol-2-yl)-N-methyl-N-(methylbenzo[d]oxazol-6-yl)acetamide

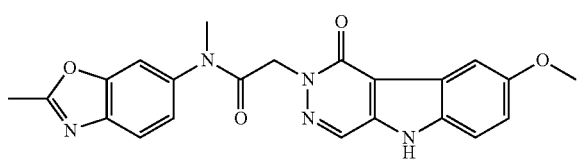

2-(4-((2-Bromo-4-methoxyphenyl)amino)-6-oxopyridazin-1(6H)-yl)-N-methyl-N-(2-methylbenzo[d]oxazol-6-yl)acetamide (0.30 g, 0.60 mmol) and NaOAc (0.12 g, 1.50 mmol) in DMA (5 mL) were degassed with argon for 15 min. Dichlorobis(triphenyl phosphine)palladium (0.004 g 0.0006 mmol) was added and the reaction heated at 180° C. for 10 minutes in a microwave. The reaction mixture was diluted with water (100 mL) and extracted with DCM (3×50 mL). The organics were washed with brine (50 mL), dried with Na$_2$SO$_4$ and concentrated, to give crude product, which was purified by column-chromatography (0-2% MeOH/DCM) to afford 2-(8-methoxy-1-oxo-1,5-dihydro-2H-pyridazino[4, 5-b]indol-2-yl)-N-methyl-N-(methylbenzo[d]oxazol-6-yl)acetamide (0.2 g, 417.90 [M+H]).

Example 259

2-(5-(4-cyanobenzyl)-8-methoxy-1-oxo-1,5-dihydro-2H-pyridazino[4,5-b]indol-2-yl)-N-methyl-N-(2-methylbenzo[d]oxazol-6-yl)acetamide

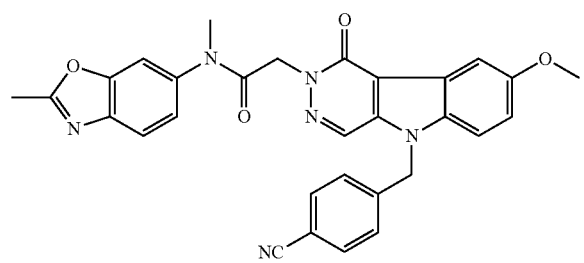

2-(8-Methoxy-1-oxo-1,5-dihydro-2H-pyridazino[4, 5-b]indol-2-yl)-N-methyl-N-(2-methylbenzo[d]oxazol-6-yl)acetamide (0.17 g, 0.40 mmol) in THF (8 mL) at 0° C. was treated with LiHMDS (1M in THF) (0.8 mL, 0.81 mmol) and stirred for 30 min. 4-Cyanobenzyl bromide (0.08 g, 0.40 mmol) in THF (10 mL) was added dropwise at 0° C., and the resulting mixture was stirred overnight at rt. It was diluted with water (100 mL) and extracted with EtOAc (3×50 mL). The organics were washed with brine (50 mL), dried with Na$_2$SO$_4$ and concentrated to give crude product, which was purified by preparative HPLC to yield 2-(5-(4-cyanobenzyl)-8-methoxy-1-oxo-1,5-dihydro-2H-pyridazino[4,5-b]indol-2-yl)-N-methyl-N-(2-methylbenzo[d]oxazol-6-yl)acetamide (0.03 g, 553.30 [M+H]). $^1$H NMR: (400 MHz, DMSO) δ: 2.63 (s, 3H), 3.18 (s, 3H), 3.85 (s, 3H), 4.73 (s, 2H), 5.89 (s, 2H), 7.15-7.18 (dd, J=2.8, 8.8, 1H), 7.30-7.32 (d, J=8.4, 2H), 7.47-7.48 (d, J=7.2, 1H), 7.63-7.66 (q, 2H), 7.76-7.81 (t, 3H), 7.93 (s, 1H), 8.68 (s, 1H).

Example 260

2-(5-(4-fluorobenzyl)-8-methoxy-1-oxo-1,5-dihydro-2H-pyridazino[4,5-b]indol-2-yl)-N-methyl-N-(2-methylbenzo[d]oxazol-6-yl)acetamide

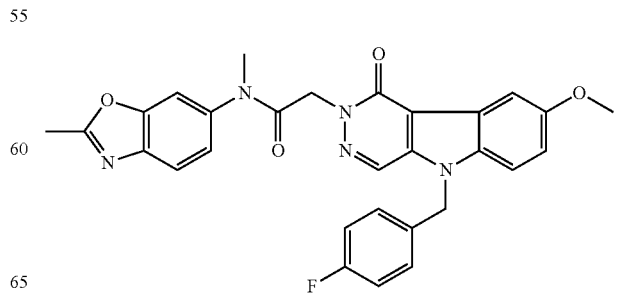

2-(8-Methoxy-1-oxo-1,5-dihydro-2H-pyridazino[4, 5-b]indol-2-yl)-N-methyl-N-(2-methylbenzo[d]oxazol-6-yl)acetamide (0.30 g, 0.71 mmol) in THF (8 mL) at 0° C. was treated with LiHMDS (1M in THF) (1.4 mL, 1.4 mmol) and stirred for 30 min. 4-Fluorobenzyl bromide (0.08 g, 0.71 mmol) in THF (10 mL) was added dropwise at 0° C., and the resulting mixture was stirred overnight at rt. It was diluted with water (100 mL) and extracted with EtOAc (3×50 mL). The organics were washed with brine (50 mL), dried with $Na_2SO_4$ and concentrated to give crude product, which was purified by preparative HPLC to yield 2-(5-(4-fluorobenzyl)-8-methoxy-1-oxo-1,5-dihydro-2H-pyridazino[4,5-b]indol-2-yl)-N-methyl-N-(2-methylbenzo[d]oxazol-6-yl)acetamide (0.03 g, 526.53 [M+H]). $^1$H NMR: (400 MHz, DMSO) δ: 2.63 (s, 3H), 3.25 (s, 3H), 3.84 (s, 3H), 4.73 (s, 2H), 5.75 (s, 2H), 7.13-7.18 (q, 3H), 7.25-7.29 (q, 2H), 7.46-7.48 (d, J=7.6, 1H), 7.61-7.62 (d, J=2, 1H), 7.70-7.77 (q, 2H), 7.93 (s, 1H), 8.71 (s, 1H).

Assays for Detecting and Measuring the Effect of Compounds on F508del-CFTR Channels CFTR-YFP High Throughput Assay-CFTR Corrector Protocol:

This protocol is designed to selectively screen small molecule compounds for F508del CFTR corrector activities in the HTS YFP (yellow fluorescent protein) flux assay. In this protocol, the cells are incubated with testing compounds for 24 hours, washed with PBS, stimulated with forskolin and a standard potentiator, and fluorescence in each plate well is measured kinetically read on a 384-well HTS plate reader, such as the Hamamatsu FDSS-6000.

YFP fluorescence intensity values are acquired at high speed before and after iodide buffer is injected to the assay cells. Iodide enters the cells via active CFTR channels in the plasma membrane, and quenches the YFP fluorescence. The rate of fluorescence quenching is proportionate to the total CFTR activity in the cell membrane. F508del CFTR correctors increase the number of CFTR molecules in the testing cell plasma membrane, and thereby accelerate YFP quenching.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human F508del CFTR and a halide-sensitive yellow fluorescent protein (YFP-H148Q/I152L 25,22) (Galietta et al. Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 g/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 µM in either a 2-fold or 3-fold dilution series. Cells were incubated in a cell culture incubator at 37° C. with 5% $CO_2$ for 24-26 h. Assay plates were washed with DPBS media (Thermo, cat# SH30028.02) to remove unbound cells and compound. Stimulation media (25 µL) containing 20 µM Forskolin & 30 µM P3 [6-(Ethyl-phenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

CFTR-YFP High Throughput Assay-CFTR Potentiator Protocol:

This protocol is designed to selectively screen small molecule compounds for F508del CFTR potentiator activities in the HTS YFP flux assay. Such compounds act acutely to stimulate CFTR already expressed on the membrane surface. In this protocol, the cells are incubated at 27° C. for 24 hours to homogeneously boost F508del CFTR expression in the cell membrane (low temperature correction), washed with PBS, treated with test compound, and CFTR activity is stimulated with forskolin for 1-2 hr. Measurement of ion flux is initiated by addition of iodide-containing buffer, and YFP quenching is kinetically recorded using a 384-well HTS plate reader, such as the Hamamatsu FDSS-6000.

YFP fluorescence intensity values are acquired at high speed over a 1 min time course before and after iodide buffer is injected to the assay cells. Iodide enters the cells via active CFTR channels in the plasma membrane, and quenches the YFP fluorescence. The rate of fluorescence quenching is proportionate to total CFTR activity in the cell membrane. F508del-CFTR potentiators increase CFTR open probability or CFTR-mediated ion conductivity, and this enhanced CFTR mediated iodide flux in the test cell plasma membrane accelerates YFP quenching.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human F508del CFTR and a halide-sensitive yellow fluorescent protein (YFP-H148Q/I152L 25,22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 g/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat# SH30028.02) to remove unbound cells. Test compound was applied to the cells at varying concentrations ranging from 2 nM-40 µM in either a 2-fold or 3-fold dilution series in DPBS and stimulated with 20 µM Forskolin (final concentration) in Hams F-12 coon's modified media. Plates were incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

REFERENCES

Galietta, L. J., Jayaraman, S., and Verkman, A. S. Cell-based assay for high-throughput quantitative screening of CFTR chloride transport agonists. Am. J. Physiol Cell Physiol 281(5), C1734, 2001.

Sui J, Cotard S, Andersen J, Zhu P, Staunton J, Lee M, Lin S. (2010) Optimization of a Yellow fluorescent proteinbased iodide influx high-throughput screening assay for cystic fibrosis transmembrane conductance regulator (CFTR) modulators. Assay Drug Dev Technol. 2010 December; 8(6):656-68.

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay, test compounds were applied to the basolateral surface of the cells at various test concentrations (n=3 or n=4 replicates per test condition).

Ussing Assay

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage were stabilized and adjusted before application of voltage clamp.

Compounds were added in the following order.

| Step | Chamber |
|---|---|
| 3.0 uM Benzamil for 20 minutes | apical addition only |
| 10 uM Forskolin for 20 minutes | apical + basolateral addition |
| 10 uM Genestein for 20 minutes | apical + basolateral addition |
| 10 uM CFTR-172 for 20 minutes | apical + basolateral addition |
| 20 uM Bumetanide for 30 minutes | basolateral addition only |

The short circuit current and transepithelial resistances (typically >300 Ω-cm2) from each chamber was recorded every 10 seconds on stored on a PC using Acquire and Analyze (Physiologic Instruments).

Analysis

Efficacy of test compounds was compared using the average of the forskolin response and the CFTR-172 inhibited current response of the test compound divided by the average of the forskolin response and the CFTR-172 inhibited current elicited by the positive control. Normalized scores were tabulated for all compounds and concentrations.

TABLE I

CFTR-YFP High Throughput Assay; The following meanings apply: % Efficacy is reported as the EMax normalized to the positive control. "+++" refers to EMax > 80%, "++" refers to a range of 80%-30%, "+" refers to a range of 30%-10%. $EC_{50}$: "+++" refers to $EC_{50}$ < 10 µM, "++" refers to $EC_{50}$ range of between 10-20 µM, "+" refers to $EC_{50}$ > 20 µM.

| Example | % Efficacy | $EC_{50}$ |
|---|---|---|
| 1. | + | ++ |
| 2. | + | +++ |
| 3. | ++ | + |
| 4. | ++ | + |
| 5. | ++ | ++ |
| 6. | ++ | +++ |
| 7. | ++ | + |
| 8. | ++ | +++ |
| 9. | + | +++ |
| 10. | + | + |
| 11. | ++ | ++ |
| 12. | ++ | + |
| 13. | ++ | ++ |
| 14. | ++ | + |
| 15. | + | + |
| 16. | ++ | +++ |
| 17. | ++ | +++ |
| 18. | +++ | ++ |
| 19. | +++ | ++ |
| 20. | ++ | + |
| 21. | +++ | +++ |
| 22. | +++ | +++ |
| 23. | +++ | +++ |
| 24. | ++ | +++ |
| 25. | ++ | ++ |
| 26. | ++ | +++ |
| 27. | ++ | +++ |
| 28. | ++ | +++ |
| 29. | ++ | +++ |
| 30. | ++ | +++ |
| 31. | ++ | +++ |
| 32. | + | +++ |
| 33. | ++ | +++ |
| 34. | ++ | +++ |
| 35. | ++ | +++ |
| 36. | ++ | +++ |
| 37. | ++ | +++ |
| 38. | ++ | +++ |
| 39. | ++ | + |
| 40. | ++ | +++ |
| 41. | ++ | +++ |
| 42. | + | + |
| 43. | + | + |
| 44. | ++ | ++ |
| 45. | +++ | +++ |
| 46. | ++ | +++ |
| 47. | ++ | +++ |
| 48. | ++ | +++ |
| 49. | +++ | +++ |
| 50. | +++ | +++ |
| 51. | ++ | +++ |
| 52. | ++ | +++ |
| 53. | ++ | +++ |
| 54. | ++ | +++ |
| 55. | ++ | +++ |
| 56. | ++ | +++ |
| 57. | ++ | +++ |
| 58. | ++ | +++ |
| 59. | ++ | ++ |
| 60. | ++ | +++ |
| 61. | ++ | +++ |
| 62. | ++ | +++ |
| 63. | +++ | +++ |
| 64. | ++ | +++ |
| 65. | +++ | +++ |
| 66. | +++ | +++ |
| 67. | ++ | +++ |
| 68. | ++ | +++ |
| 69. | +++ | +++ |
| 70. | ++ | +++ |
| 71. | ++ | +++ |
| 72. | +++ | +++ |
| 73. | ++ | +++ |
| 74. | ++ | +++ |
| 75. | +++ | +++ |
| 76. | +++ | +++ |
| 77. | +++ | ++ |
| 78. | ++ | +++ |
| 79. | +++ | +++ |
| 80. | ++ | ++ |
| 81. | +++ | +++ |

TABLE I-continued

CFTR-YFP High Throughput Assay; The following meanings apply: % Efficacy is reported as the EMax normalized to the positive control. "+++" refers to EMax > 80%, "++" refers to a range of 80%-30%, "+" refers to a range of 30%-10%. $EC_{50}$: "+++" refers to $EC_{50}$ < 10 μM, "++" refers to $EC_{50}$ range of between 10-20 μM, "+" refers to $EC_{50}$ > 20 μM.

| Example | % Efficacy | $EC_{50}$ |
|---|---|---|
| 82. | ++ | +++ |
| 83. | ++ | +++ |
| 84. | ++ | +++ |
| 85. | +++ | +++ |
| 86. | +++ | +++ |
| 87. | +++ | +++ |
| 88. | +++ | +++ |
| 89. | +++ | +++ |
| 90. | +++ | +++ |
| 91. | +++ | +++ |
| 92. | +++ | +++ |
| 93. | +++ | +++ |
| 94. | +++ | +++ |
| 95. | +++ | +++ |
| 96. | +++ | +++ |
| 97. | +++ | +++ |
| 98. | +++ | +++ |
| 99. | +++ | +++ |
| 100. | +++ | +++ |
| 101. | +++ | +++ |
| 102. | +++ | +++ |
| 103. | +++ | +++ |
| 104. | +++ | +++ |
| 105. | +++ | +++ |
| 106. | +++ | +++ |
| 107. | +++ | +++ |
| 108. | +++ | +++ |
| 109. | +++ | +++ |
| 110. | +++ | +++ |
| 111. | +++ | +++ |
| 112. | +++ | +++ |
| 113. | +++ | +++ |
| 114. | +++ | +++ |
| 115. | +++ | +++ |
| 116. | +++ | +++ |
| 117. | +++ | +++ |
| 118. | +++ | +++ |
| 119. | +++ | +++ |
| 120. | +++ | +++ |
| 121. | +++ | +++ |
| 122. | +++ | +++ |
| 123. | +++ | +++ |
| 124. | ++ | ++ |
| 125. | ++ | +++ |
| 126. | ++ | +++ |
| 127. | ++ | +++ |
| 128. | ++ | ++ |
| 129. | ++ | ++ |
| 130. | ++ | ++ |
| 131. | ++ | +++ |
| 132. | ++ | +++ |
| 133. | ++ | +++ |
| 134. | ++ | +++ |
| 135. | ++ | +++ |
| 136. | ++ | +++ |
| 137. | ++ | +++ |
| 138. | + | + |
| 139. | ++ | ++ |
| 140. | ++ | +++ |
| 141. | ++ | +++ |
| 142. | ++ | +++ |
| 143. | ++ | +++ |
| 144. | +++ | ++ |
| 145. | ++ | +++ |
| 146. | ++ | +++ |
| 147. | ++ | +++ |
| 148. | ++ | +++ |
| 149. | ++ | +++ |
| 150. | ++ | +++ |
| 151. | ++ | +++ |
| 152. | ++ | +++ |
| 153. | ++ | +++ |
| 154. | ++ | +++ |
| 155. | ++ | +++ |
| 156. | ++ | +++ |
| 157. | ++ | +++ |
| 158. | ++ | +++ |
| 159. | ++ | +++ |
| 160. | ++ | +++ |
| 161. | ++ | +++ |
| 162. | ++ | + |
| 163. | ++ | + |
| 164. | ++ | + |
| 165. | ++ | +++ |
| 166. | ++ | +++ |
| 167. | ++ | +++ |
| 168. | ++ | +++ |
| 169. | ++ | +++ |
| 170. | ++ | +++ |
| 171. | + | + |
| 172. | + | ++ |
| 173. | + | + |
| 174. | ++ | +++ |
| 175. | ++ | + |
| 176. | ++ | +++ |
| 177. | ++ | +++ |
| 178. | ++ | +++ |
| 179. | ++ | + |
| 180. | + | +++ |
| 181. | ++ | +++ |
| 182. | ++ | +++ |
| 183. | ++ | +++ |
| 184. | ++ | + |
| 185. | ++ | +++ |
| 186. | + | +++ |
| 187. | ++ | + |
| 188. | ++ | + |
| 189. | ++ | + |
| 190. | ++ | +++ |
| 191. | ++ | + |
| 192. | ++ | +++ |
| 193. | ++ | +++ |
| 194. | ++ | + |
| 195. | ++ | +++ |
| 196. | +++ | + |
| 197. | ++ | + |
| 198. | ++ | +++ |
| 199. | + | + |
| 200. | ++ | +++ |
| 201. | ++ | +++ |
| 202. | ++ | +++ |
| 203. | ++ | +++ |
| 204. | ++ | +++ |
| 205. | ++ | +++ |
| 206. | ++ | +++ |
| 207. | ++ | +++ |
| 208. | + | +++ |
| 209. | ++ | +++ |
| 210. | ++ | +++ |
| 211. | ++ | +++ |
| 212. | ++ | +++ |
| 213. | ++ | +++ |
| 214. | ++ | +++ |
| 215. | ++ | +++ |
| 216. | ++ | +++ |
| 217. | + | + |
| 218. | +++ | +++ |
| 219. | + | ++ |
| 220. | ++ | +++ |
| 221. | ++ | +++ |
| 222. | ++ | + |
| 223. | ++ | + |

TABLE I-continued

CFTR-YFP High Throughput Assay; The following meanings apply: % Efficacy is reported as the EMax normalized to the positive control. "+++" refers to EMax > 80%, "++" refers to a range of 80%-30%, "+" refers to a range of 30%-10%. EC$_{50}$: "+++" refers to EC$_{50}$ < 10 µM, "++" refers to EC$_{50}$ range of between 10-20 µM, "+" refers to EC$_{50}$ > 20 µM.

| Example | % Efficacy | EC$_{50}$ |
|---|---|---|
| 224. | ++ | + |
| 225. | ++ | + |
| 226. | ++ | + |
| 227. | ++ | +++ |
| 228. | ++ | +++ |
| 229. | ++ | +++ |
| 230. | ++ | +++ |
| 231. | ++ | +++ |
| 232. | ++ | +++ |
| 233. | ++ | +++ |
| 234. | ++ | +++ |
| 235. | + | + |
| 236. | + | + |
| 237. | + | + |
| 238. | ++ | +++ |
| 239. | ++ | + |
| 240. | ++ | + |
| 241. | ++ | +++ |
| 242. | ++ | + |
| 243. | ++ | +++ |
| 244. | ++ | +++ |
| 245. | + | +++ |
| 246. | ++ | + |
| 247. | ++ | + |
| 248. | + | +++ |
| 249. | +++ | +++ |
| 250. | ++ | +++ |
| 251. | ++ | +++ |
| 252. | +++ | +++ |
| 253. | | |
| 254. | | |
| 255. | | |
| 256. | | |
| 257. | | |
| 258. | | |
| 259. | +++ | +++ |
| 260. | +++ | +++ |

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed:
1. A compound of Formula II:

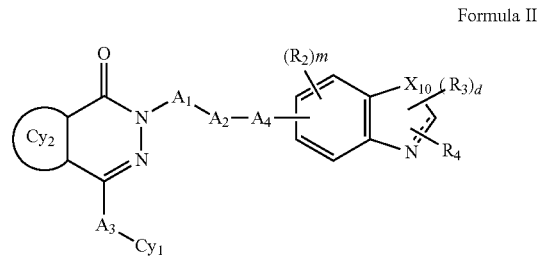

Formula II or a pharmaceutically acceptable salt thereof;
Wherein ===== represents a single or double bond;
m is 0, 1, 2, 3 or 4;
d is 0, 1 or 2;
$X_{10}$ is CH, CH$_2$, S or O;
$Cy_1$ is absent, an aryl, substituted aryl, carbocycle, substituted carbocycle, heterocyclyl, substituted heterocyclyl, heteroaryl, or substituted heteroaryl group having one, two or three rings;
$Cy_2$ is an aryl, substituted aryl, carbocycle, substituted carbocycle, heterocyclyl, substituted heterocyclyl, heteroaryl, or substituted heteroaryl group having one, two or three rings;
$A_1$ is absent, —[C(R$_{100}$)(R$_{101}$)]$_n$—, —C(O)—, —C(S), —S(O)—, —C(O)N(R$_{100}$)—, —S(O)$_2$N(R$_{100}$)—, —S(O)$_2$—, —[C(R$_{25}$)(R$_{26}$)]n-, —[C(R$_{25}$)(R$_{26}$)]n-C=C—[C(R$_{27}$)(R$_{28}$)]p, or —[C(R$_{25}$)(R$_{26}$)]n-C≡C—[C(R$_{27}$)(R$_{28}$)]p, carbocycle, substituted carbocycle, heterocycle, substituted heterocycle, aromatic, substituted aromatic, heteroaromatic or substituted heteroaromatic; wherein n is 0, 1, 2, 3, 4, 5, 6 or 7;
wherein each R$_{100}$ and R$_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —OR$_{200}$, —SR$_{200}$, —C(O)R$_{200}$, —C(O)N(R$_{200}$)$_2$, —NC(O)R$_{200}$, —S(O)$_2$R$_{200}$ wherein R$_{200}$ is hydrogen, C$_1$-C$_6$ alkyl, C$_2$-C$_6$ alkenyl, or C$_2$-C$_6$ alkynyl; alternatively two of R$_{100}$ and R$_{101}$ groups together with the atoms to which they are attached and any intervening atoms may form an additional optionally substituted, 3, 4, 5, 6 or 7 membered ring;
$A_2$ is absent or —[C(R$_{100}$)(R$_{101}$)]n-, —C(O)—, —C(S)—, —S(O)—, —C(O)N(R$_{100}$)—, —C(O)N(R$_{100}$)(R$_{101}$), N(R$_{100}$)(R$_{101}$), —S(O)$_2$—, —S(O)$_2$R$_{100}$, —S(O)$_2$N(R$_{100}$)(R$_{101}$),—[C(R$_{25}$)(R$_{26}$)]n-, —[C(R$_{25}$)(R$_{26}$)]n-C=C—[C(R$_{27}$)(R$_{28}$)]p, or —[C(R$_{25}$)(R$_{26}$)]n-C≡C—[C(R$_{27}$)(R$_{28}$)]p;
$A_3$ is absent or —[C(R$_{100}$)(R$_{101}$)]n-, —C(O)—, —C(S)—, —S(O)—, —C(O)N(R$_{100}$)—, —C(O)N(R$_{100}$)(R$_{101}$), N(R$_{100}$)(R$_{101}$), —S(O)$_2$—, S(O)$_2$R$_{100}$, S(O)R$_{100}$, S(O)$_2$N(R$_{100}$)(R$_{101}$), —[C(R$_{25}$)(R$_{26}$)]n-, —[C(R$_{25}$)(R$_{26}$)]n-C=C—[C(R$_{27}$)(R$_{28}$)]p, or —[C(R$_{25}$)(R$_{26}$)]n-C≡C—[C(R$_{27}$)(R$_{28}$)]p;
$A_4$ is absent or —[C(R$_{25}$)(R$_{26}$)]n-, —[C(R$_{25}$)(R$_{26}$)]n-C=C—[C(R$_{27}$)(R$_{28}$)]p, or —[C(R$_{25}$)(R$_{26}$)]n-C≡C—[C(R$_{27}$)(R$_{28}$)]p;
wherein each R$_{25}$, R$_{26}$, R$_{27}$ and R$_{28}$ is independently selected hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl, substituted aryl, —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)

$R_{101}$, $-S(O)_2R_{100}$, $-S(O)R_{100}$, $-SR_{100}$, $-S(O)_2N(R_{100})R_{101}$, $-CF_3$, $-CN$, $-NO_2$, and $-N_3$; alternatively two of $R_{25}$, $R_{26}$, $R_{27}$ and $R_{28}$ groups together with the atoms to which they are attached and any intervening atoms may form an additional optionally substituted, 3, 4, 5, 6 or 7 membered ring;

p is 0, 1, 2, 3, 4, 5, 6, or 7;

$R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$;

alternatively two $R_2$ together with the atoms to which they are attached may form an optionally substituted 3, 4, 5, 6 or 7 membered ring; and, each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$.

2. The compound of claim 1, wherein $Cy_2$ is selected from the group consisting of:

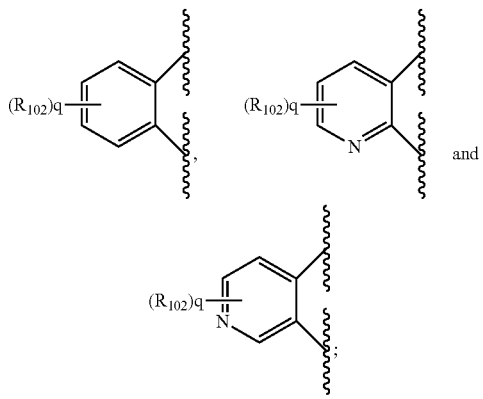

wherein q is 0, 1, 2, 3, 4 or 5;

each $R_{102}$ is independently hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$; alternatively two of $R_{102}$ groups together with the atoms to which they are attached and any intervening atoms may form an additional optionally substituted 3, 4, 5, 6 or 7 membered ring.

3. The compound of claim 1, wherein $Cy_1$ is selected from the group consisting of:

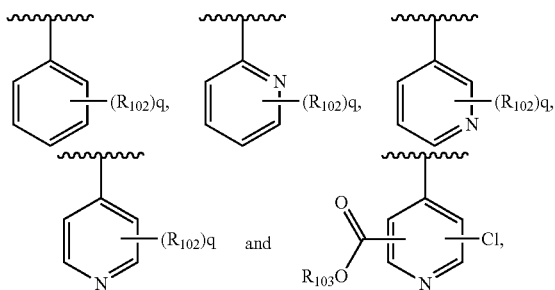

wherein;

q is 0, 1, 2, 3, or 4;

each $R_{102}$ is hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$; alternatively two $R_{102}$ groups together with the atoms to which they are attached and any intervening atoms form an additional optionally substituted 3, 4, 5, 6 or 7 membered ring; and $R_{103}$ is hydrogen, deuterium, alkyl, substituted alkyl, alkenyl, substituted alkenyl, alkynyl, substituted alkynyl, aliphatic, substituted aliphatic, aryl and substituted aryl.

4. The compound of claim 1, wherein $Cy_1$ is selected from the group consisting of:

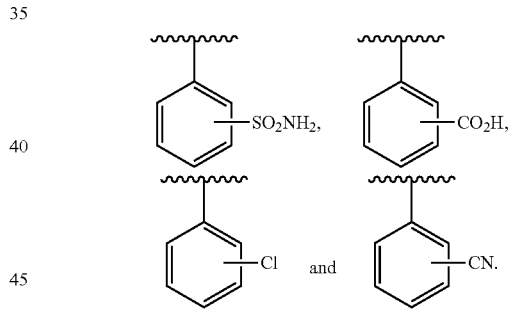

5. The compound of claim 1, wherein ===== represents a double bond and d is 0.

6. The compound of claim 1 represented by Formula IIA,

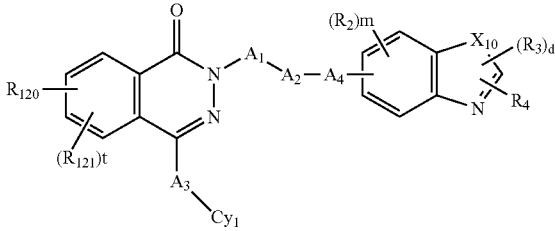

Formula IIA or a pharmaceutically acceptable salt thereof, wherein t is 0, 1, 2 or 3;

$R_{120}$ is selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; and each $R_{121}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, and —$N_3$.

7. The compound of claim 1, wherein $A_1$ is $C(R_{100})(R_{101})$ and $A_2$ is —$C(O)N(R_{100})$—.

8. The compound of claim 6, wherein $A_4$ is absent.

9. The compound of claim 1, wherein $A_3$ is absent, —$[C(R_{100})(R_{101})]_n$—, —C(O)—, or —$C(O)N(R_{100})$—.

10. The compound of claim 9, wherein $A_3$ is absent.

11. A pharmaceutical composition comprising a compound of claim 1 and a pharmaceutically acceptable carrier or excipient.

* * * * *

UNITED STATES PATENT AND TRADEMARK OFFICE
CERTIFICATE OF CORRECTION

PATENT NO. : 10,370,366 B2  
APPLICATION NO. : 15/726813  
DATED : August 6, 2019  
INVENTOR(S) : Bridget M. Cole et al.

Page 1 of 1

It is certified that error appears in the above-identified patent and that said Letters Patent is hereby corrected as shown below:

In the Claims

Column 258, Claim 1, Line 48: after "-S(O)$_2$R$_{100}$," please insert -- -S(O)R$_{100}$, --; and Column 260, Claim 3, Line 10, please delete " 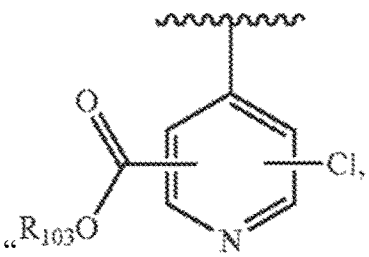 " and replace with

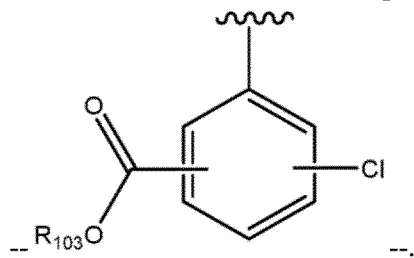 --.

Signed and Sealed this  
Twelfth Day of November, 2019

Andrei Iancu  
*Director of the United States Patent and Trademark Office*